United States Patent
Chen et al.

(10) Patent No.: US 11,384,353 B2
(45) Date of Patent: Jul. 12, 2022

(54) INHIBITION OF UNINTENDED MUTATIONS IN GENE EDITING

(71) Applicant: ShanghaiTech University, Shanghai (CN)

(72) Inventors: Jia Chen, Shanghai (CN); Bei Yang, Shanghai (CN); Li Yang, Shanghai (CN); Xingxu Huang, Shanghai (CN); Lijie Wang, Shanghai (CN)

(73) Assignee: ShanghaiTech University, Shanghai (CN)

( * ) Notice: Subject to any disclaimer, the term of this patent is extended or adjusted under 35 U.S.C. 154(b) by 0 days.

(21) Appl. No.: 17/427,040

(22) PCT Filed: Feb. 3, 2020

(86) PCT No.: PCT/CN2020/074218
§ 371 (c)(1),
(2) Date: Jul. 29, 2021

(87) PCT Pub. No.: WO2020/156575
PCT Pub. Date: Aug. 6, 2020

(65) Prior Publication Data
US 2022/0064626 A1     Mar. 3, 2022

(30) Foreign Application Priority Data
Feb. 2, 2019   (WO) ................ PCT/CN2019/074577

(51) Int. Cl.
| | |
|---|---|
| *C12N 15/10* | (2006.01) |
| *C12N 9/22* | (2006.01) |
| *C12N 9/50* | (2006.01) |
| *C12N 15/11* | (2006.01) |
| *C12N 9/78* | (2006.01) |

(52) U.S. Cl.
CPC ............ *C12N 15/102* (2013.01); *C12N 9/22* (2013.01); *C12N 9/506* (2013.01); *C12N 9/78* (2013.01); *C12N 15/111* (2013.01); *C07K 2319/50* (2013.01); *C07K 2319/85* (2013.01); *C12N 2310/20* (2017.05); *C12Y 304/22044* (2013.01); *C12Y 305/04004* (2013.01); *C12Y 305/04005* (2013.01)

(58) Field of Classification Search
None
See application file for complete search history.

(56) References Cited

U.S. PATENT DOCUMENTS

2009/0260090 A1   10/2009  Wain-Hobson
2017/0121693 A1*  5/2017   Liu ........................ A61P 31/12

FOREIGN PATENT DOCUMENTS

| | | |
|---|---|---|
| CN | 105886498 A | 8/2016 |
| CN | 108342387 A | 7/2018 |
| CN | 109136272 A | 1/2019 |
| EP | 0287128 A1 | 10/1987 |

OTHER PUBLICATIONS

Mouse Apobec3 sequence from UniProt, retrieved Mar. 21, 2022 < https://www.uniprot.org/uniprot/B5TOI9 >.*
Human Apobec3B sequence from UniProt, retrieved Mar. 21, 2022 < https://www.uniprot.org/uniprot/Q9UH17 >.*
Results from ExPasy Protease Peptide Cutter with Mouse Apobec3 sequence from UniProt B5TOI9, retrieved Mar. 21, 2022 < https://www.expasy.org/search/peptide%20cutter >.*
Results from ExPasy Protease Peptide Cutter with Human Apobec3B sequence from UniProt Q9UH17, retrieved Mar. 21, 2022 < https://www.expasy.org/search/peptide%20cutter >.*
Siriwardena et al., "Characterization of the Catalytic Domain of Human APOBEC3B and the Critical Structural Role for a Conserved Methionine", J. Mol. Biology, 2015, 427: 3042-3055. dx.doi.org/10.1016/j.jmb.2015.08.006.*
Hache et al., "The Retroviral Hypermutation Specificity of APOBEC3F and APOBEC3G Is Governed by the C-terminal DNA cytosine Deaminase Domain", JBC, 2005, 280(12): 10920-10924. DOI 10.1074/jbc.M500382200.*
Results from ExPasy Protease Peptide Cutter with the sequence FVYS, retrieved Mar. 21, 2022 < https://www.expasy.org/search/peptide%20cutter >.*
International Search Report, dated Apr. 29, 2020, (3 pages).
Yang, Y.Z. et al.: "Research Advances in Gene Editing and Plant-virus Interaction and Their Application in Breeding Virus-resistant Crops", Biotechnology Bulletin, vol. 34, No. 8, Dec. 31, 2018 (Dec. 31, 2018), pp. 8-16.
Amitai, G et al.: "CRISPR-Cas adaptation: insights into the mechanism of action", Nature Reviesws Microbiology, vol. 14, No. 2, Jan. 11, 2016 (Jan. 11, 2016), pp. 67-76, XP055726947.
Written Opinion of the International Searching Authority, dated Apr. 29, 2020, (4 pages).
Li, M. et al. "First-In-Class Small Molecule Inhibitors of the Single-Strand DNA Cytosine Deaminase APOBEC3G" ACS Chem Biol. Mar. 16, 2012; 7(3): 506-517. doi:10.1021/cb200440y (18 pages).

* cited by examiner

*Primary Examiner* — Suzanne M Noakes
(74) *Attorney, Agent, or Firm* — Sheppard Mullin Richter & Hampton LLP

(57) ABSTRACT

Provided are fusion proteins and related molecules useful for conducting base editing with reduced or no off-target mutations. The fusion proteins may include a first fragment comprising a nucleobase deaminase or a catalytic domain thereof, a second fragment comprising a nucleobase deaminase inhibitory domain, and a protease cleavage site between the first fragment and the second fragment. Also provided are improved prime editing systems, including prime editing guide RNA with improved stability.

14 Claims, 52 Drawing Sheets
Specification includes a Sequence Listing.

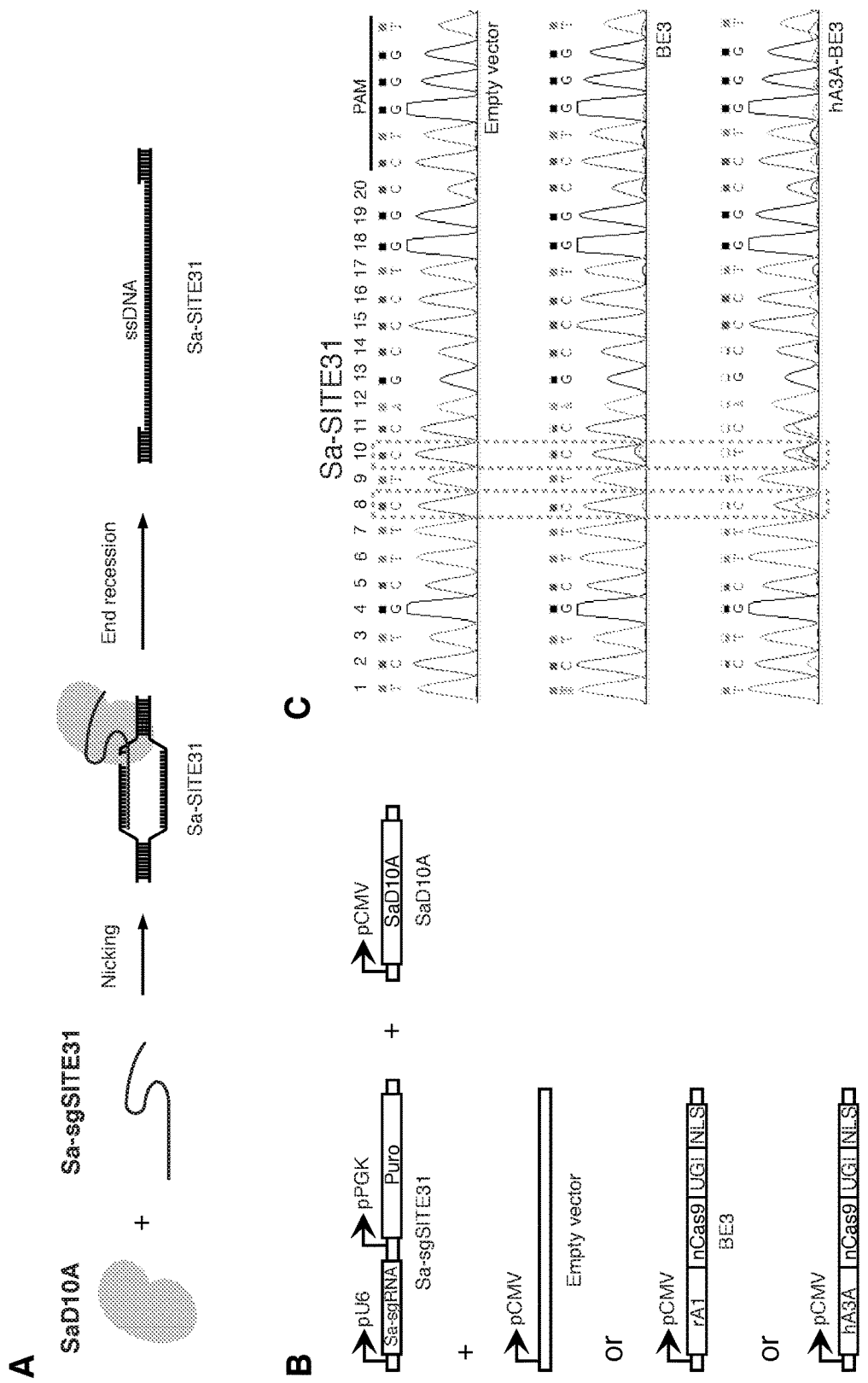
FIG. 1A-C

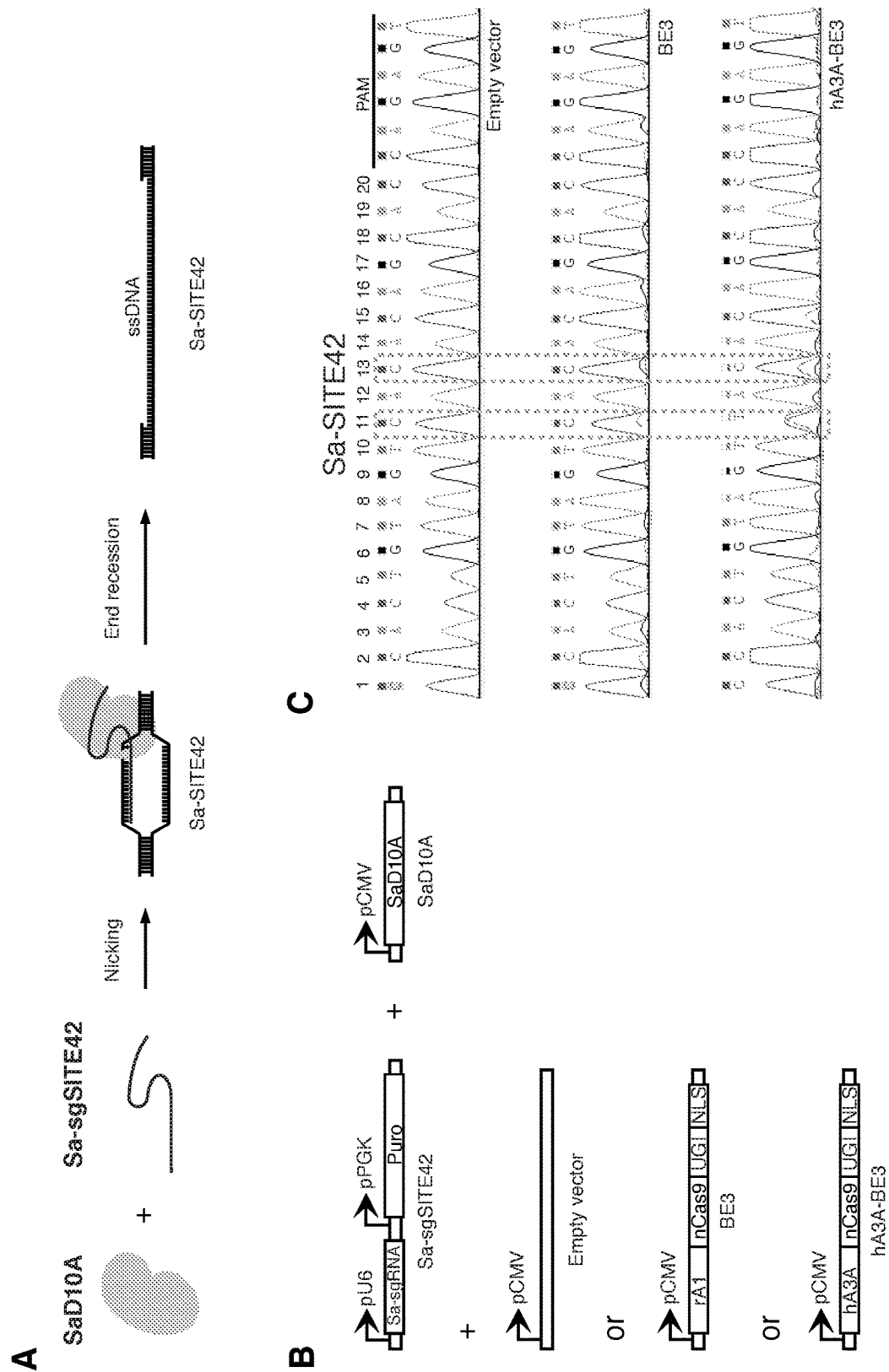
FIG. 2A-C

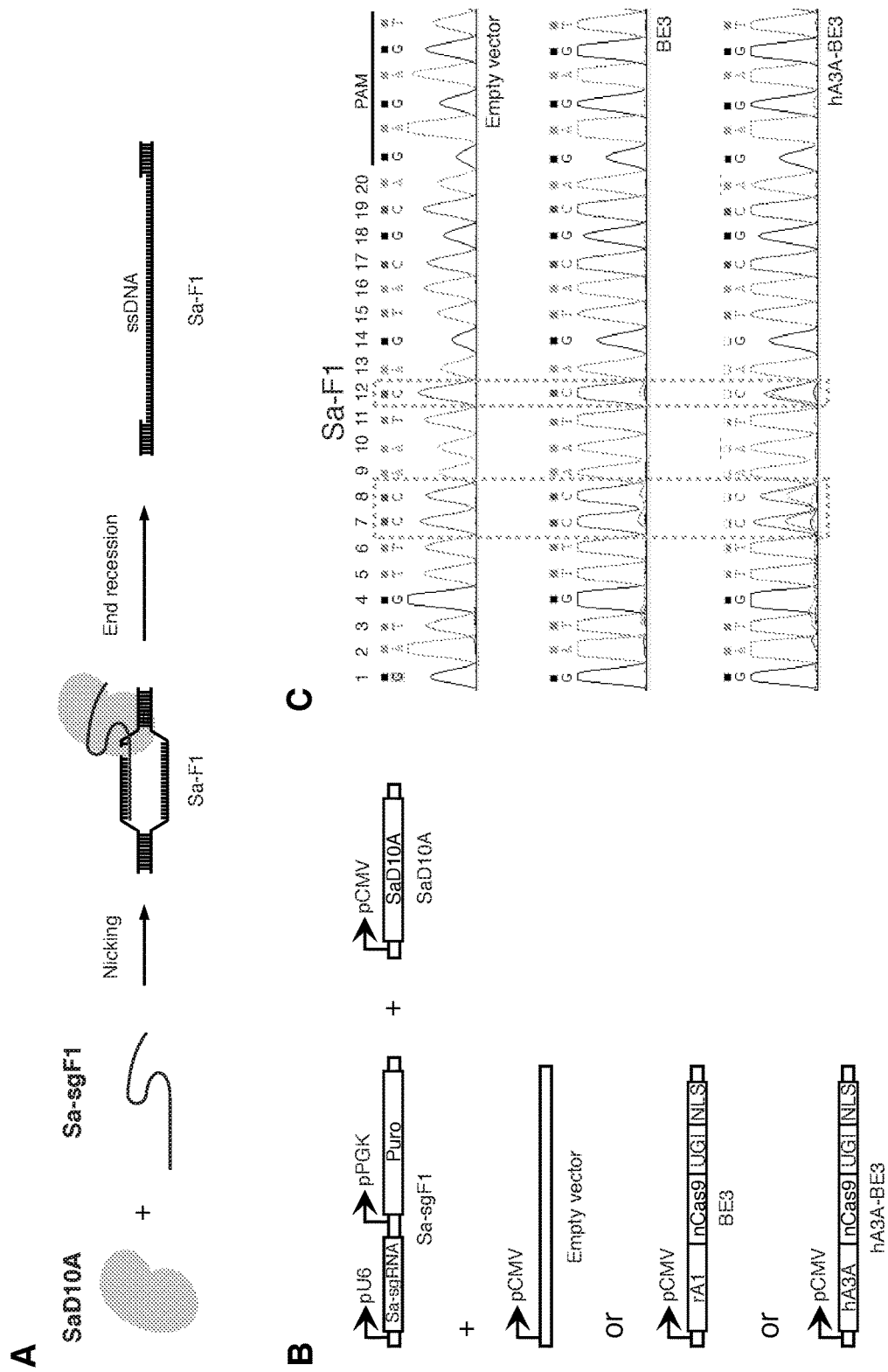
FIG. 3A-C

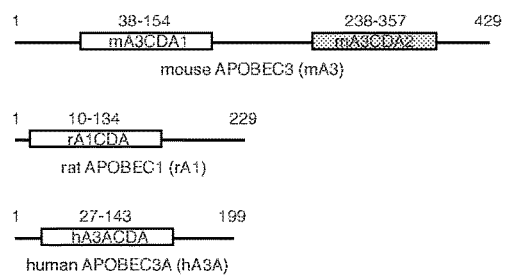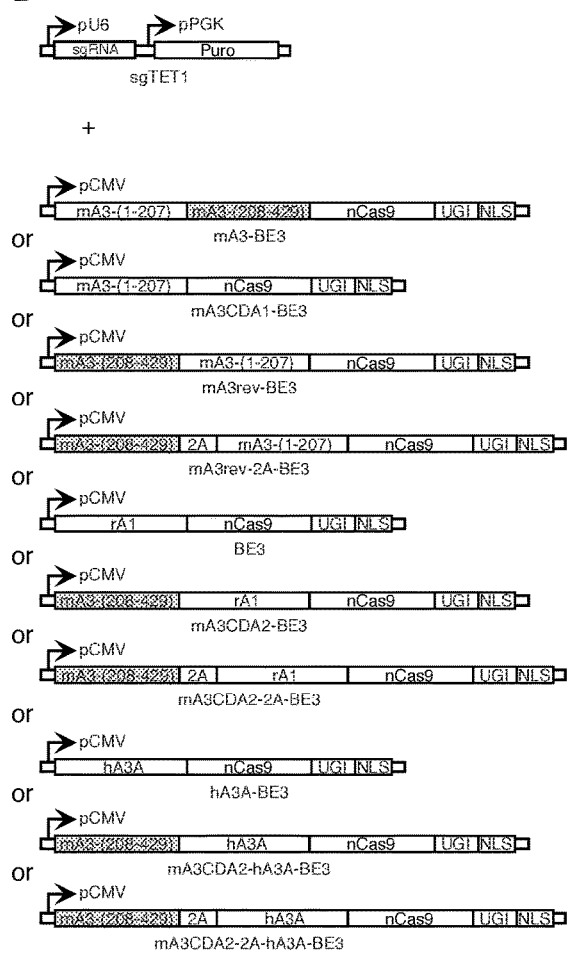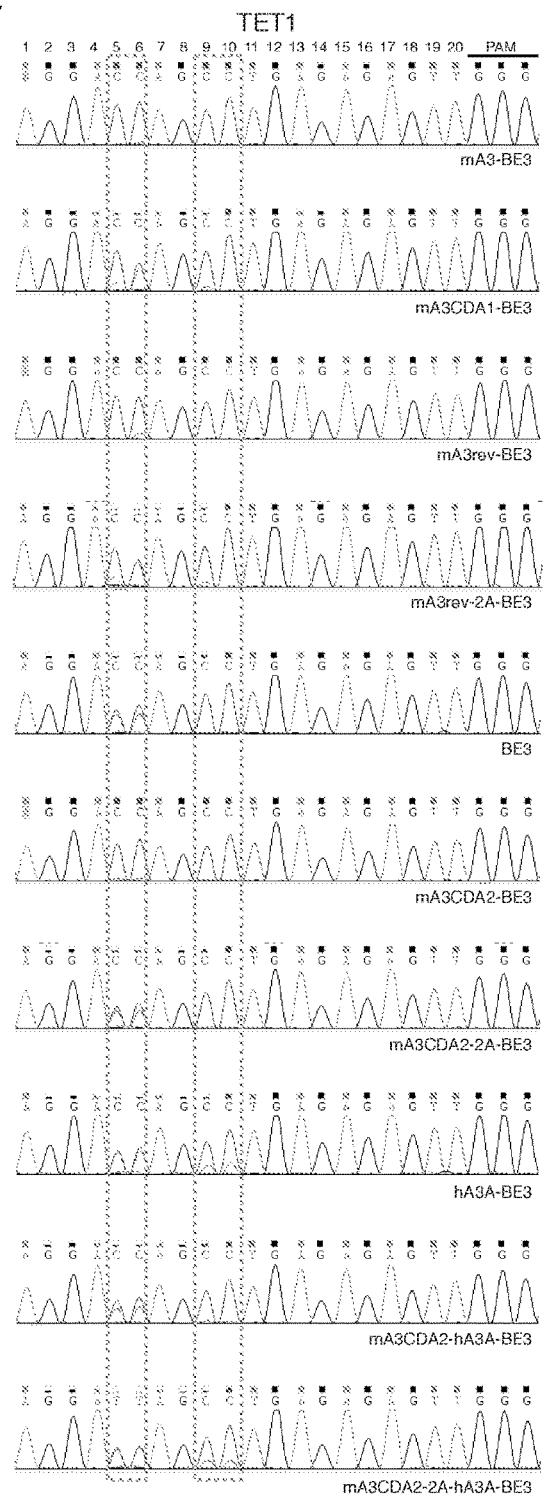
FIG. 4A-C

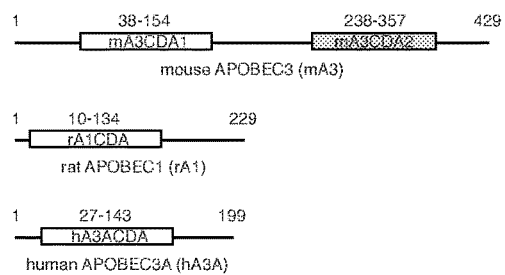
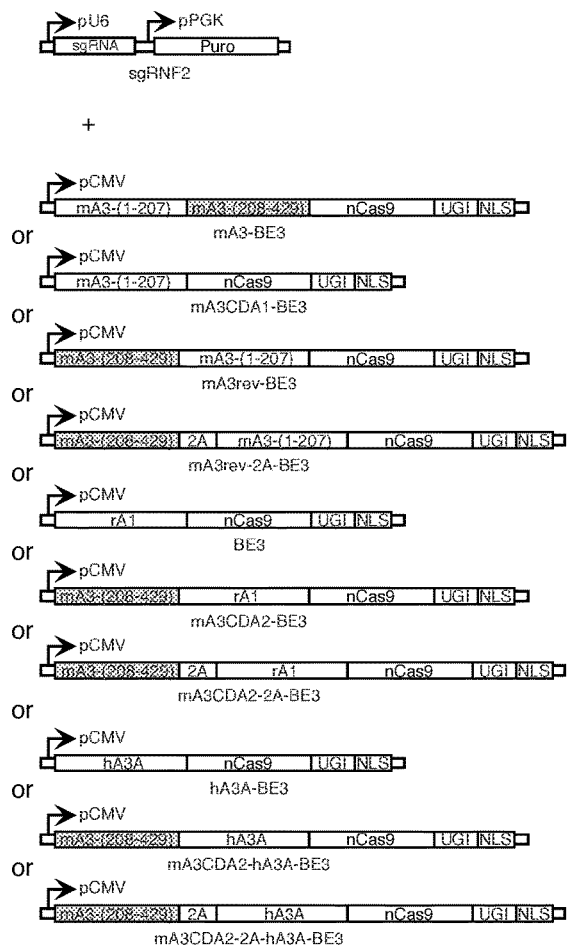
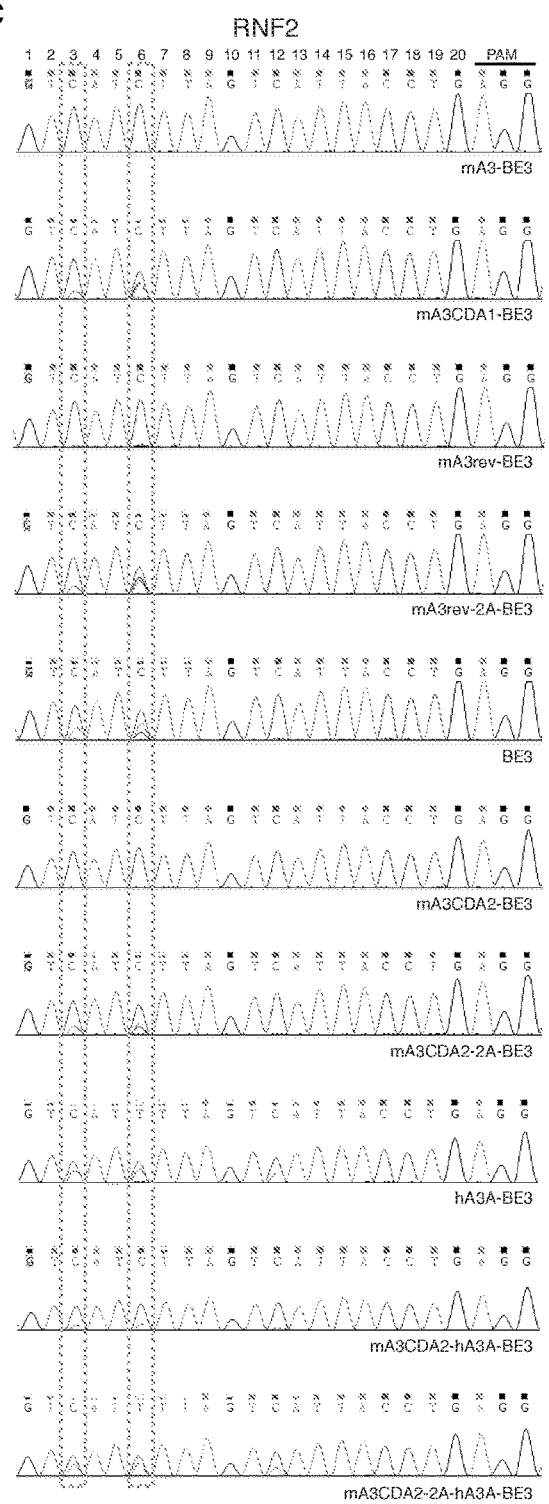
FIG. 5A-C

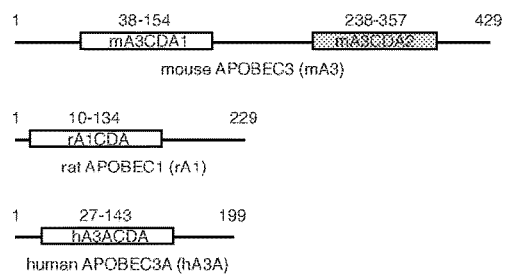
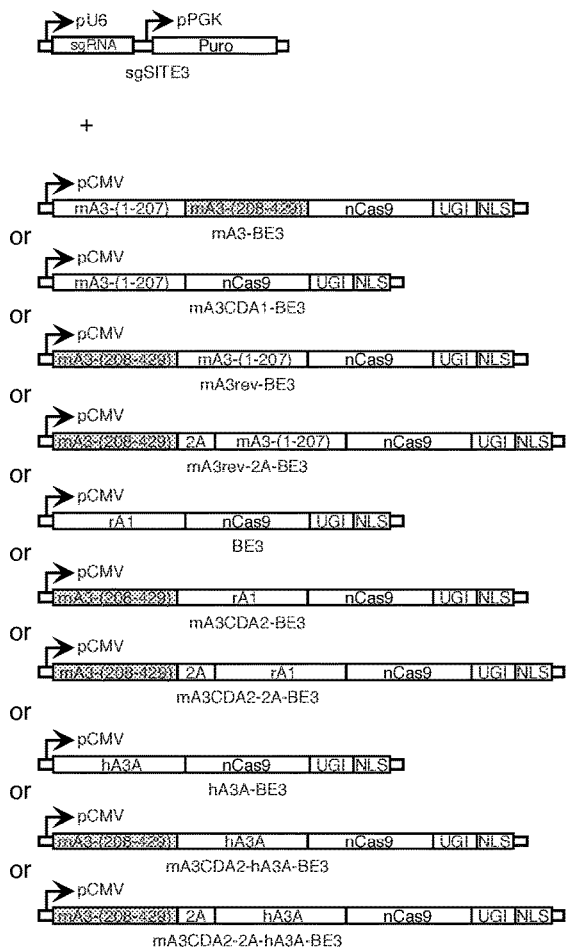
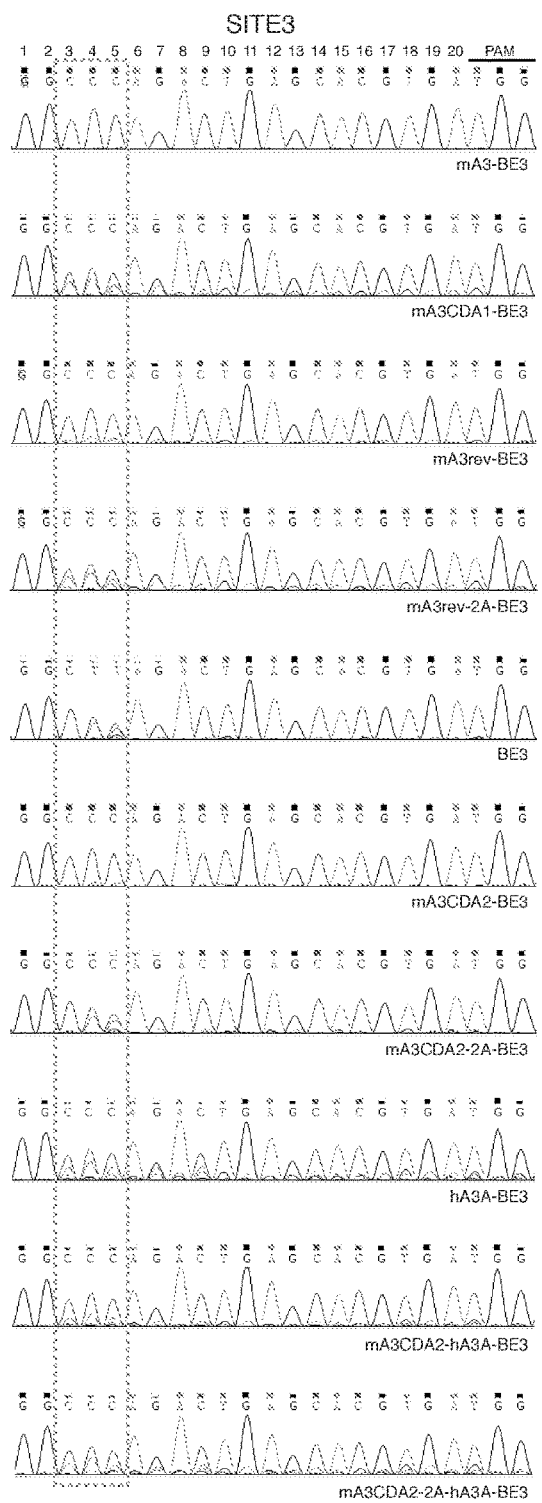
FIG. 6A-C

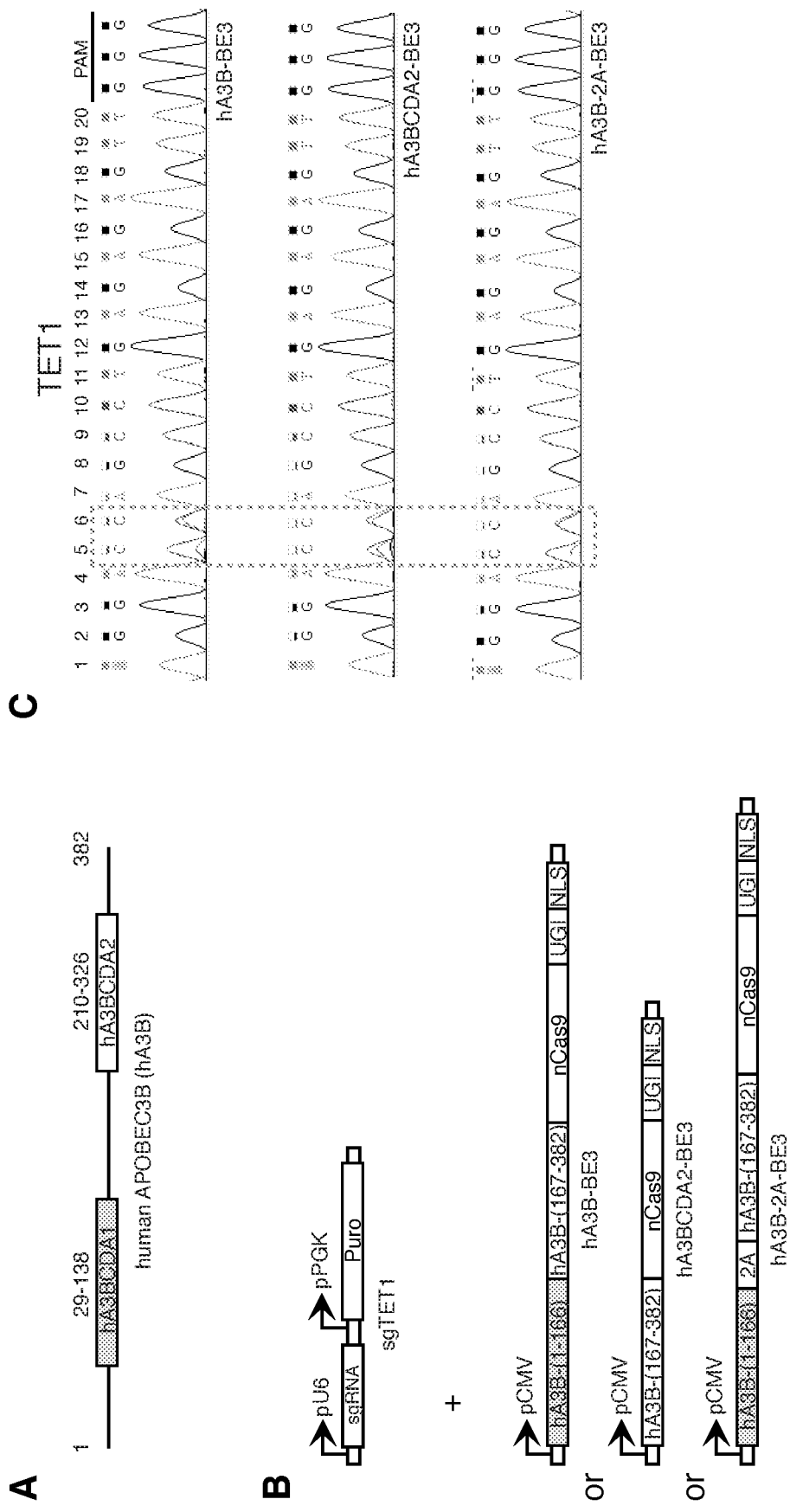
FIG. 7A-C

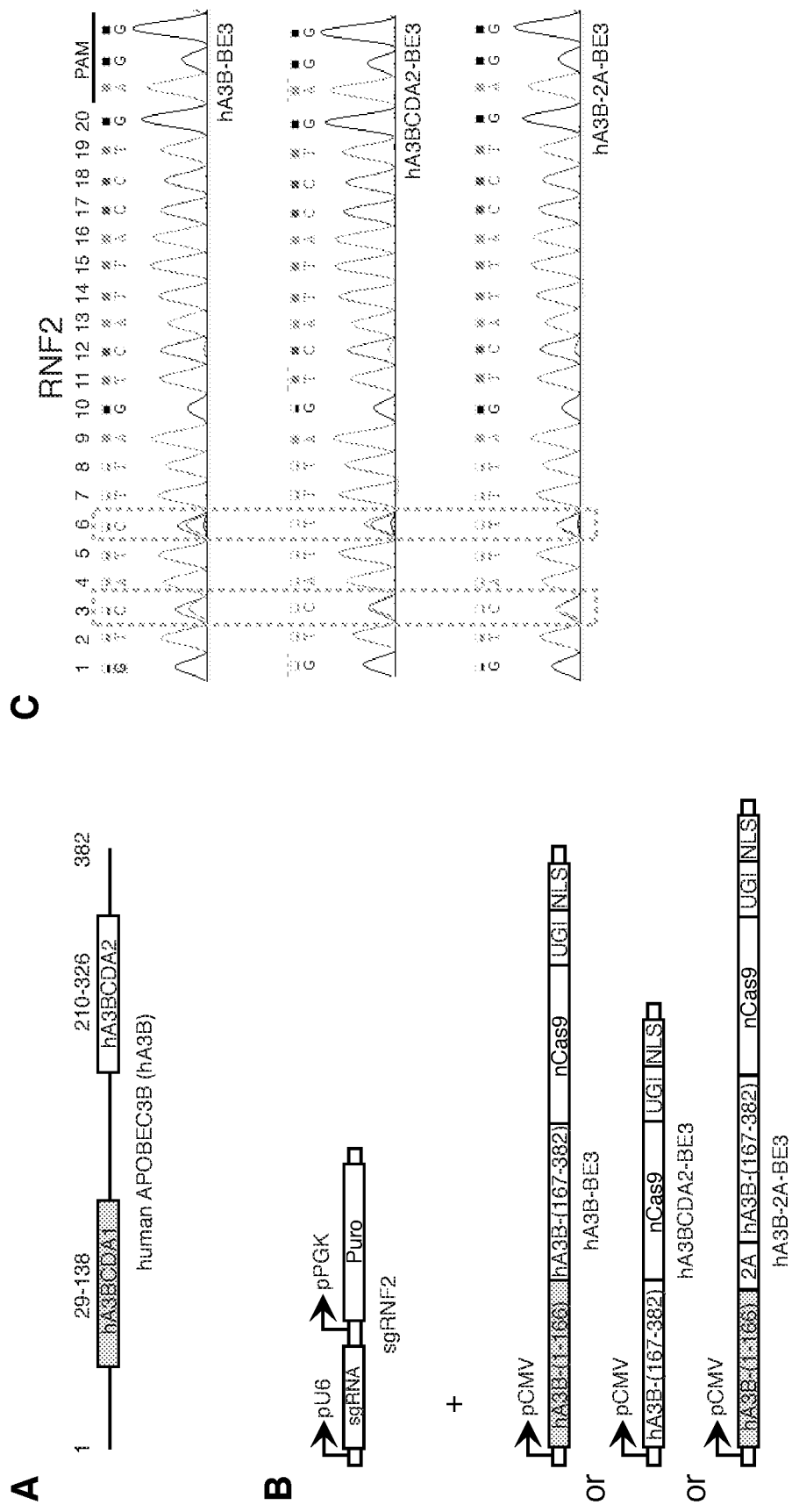
FIG. 8A-C

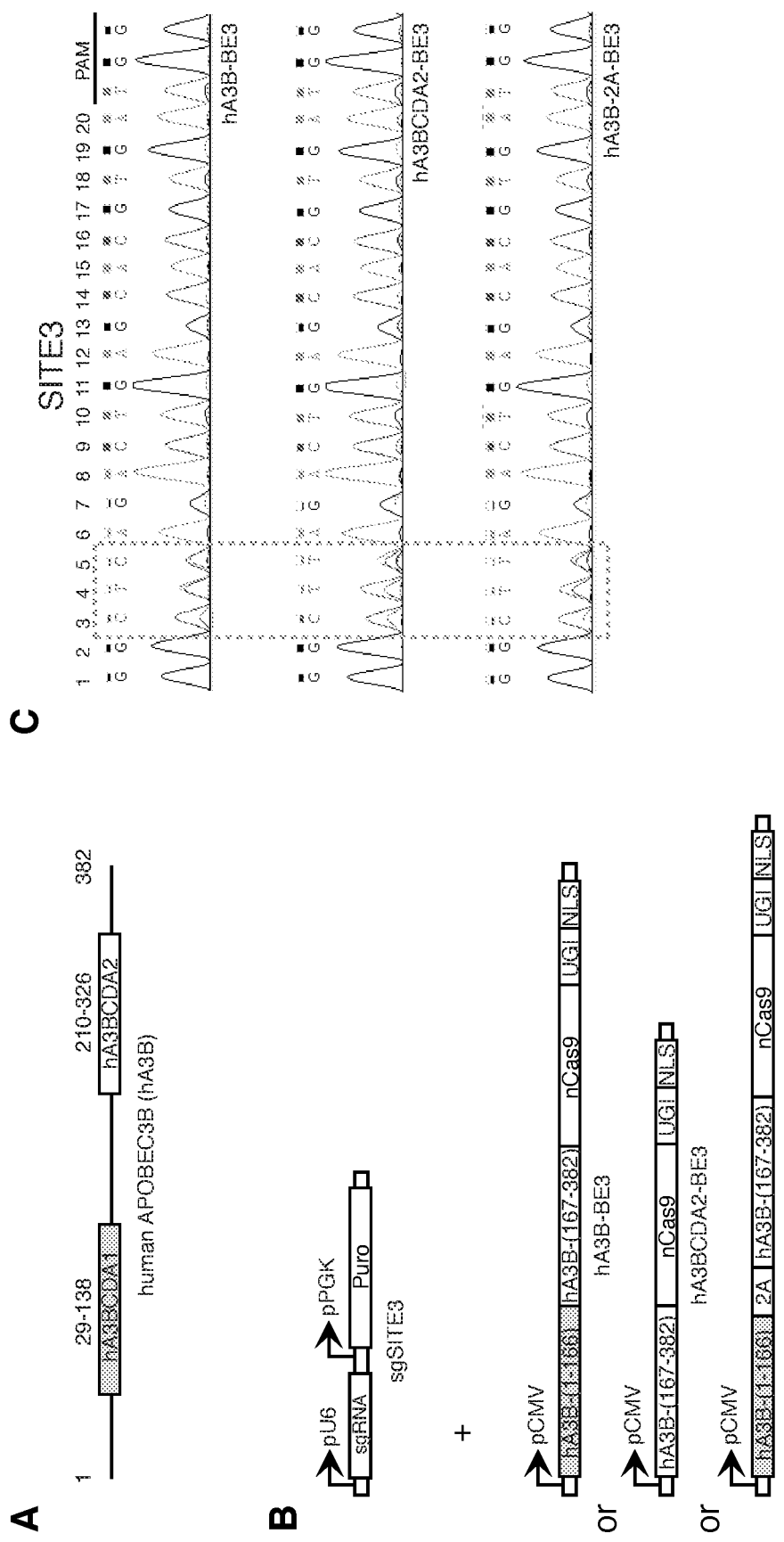
FIG. 9A-C

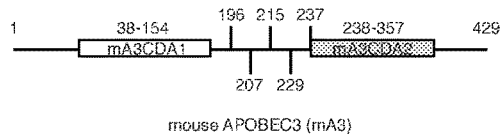
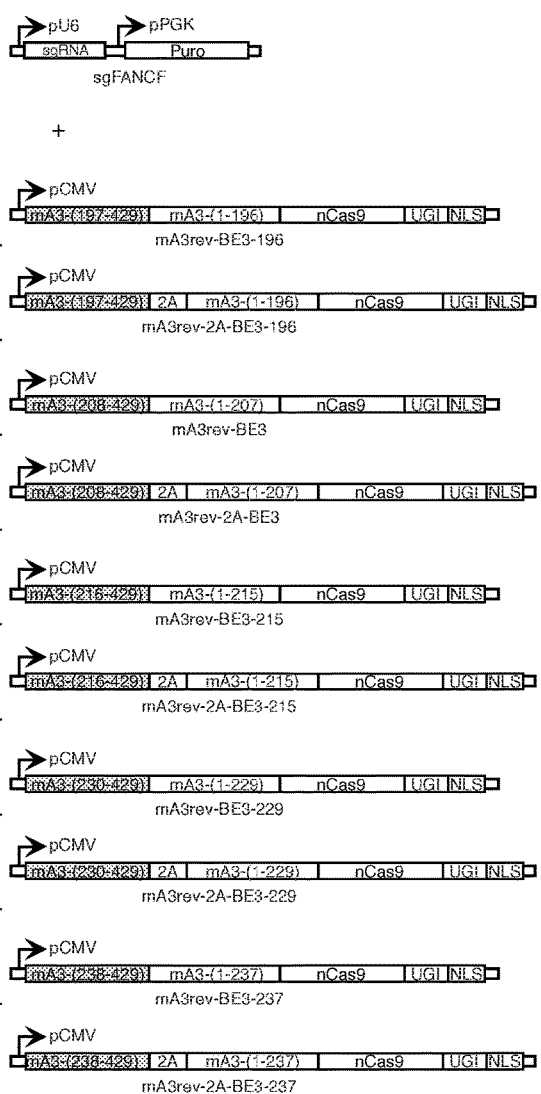
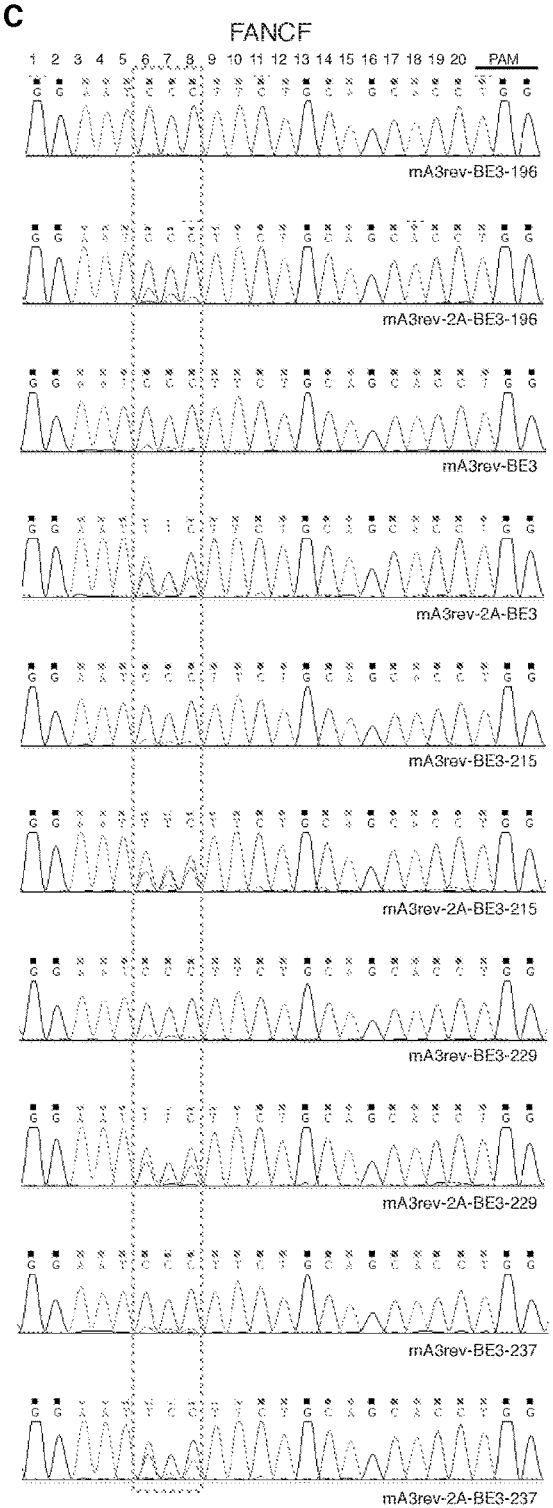
FIG. 10A-C

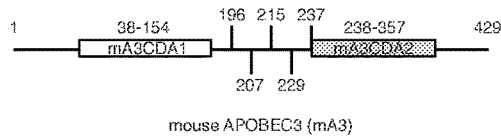
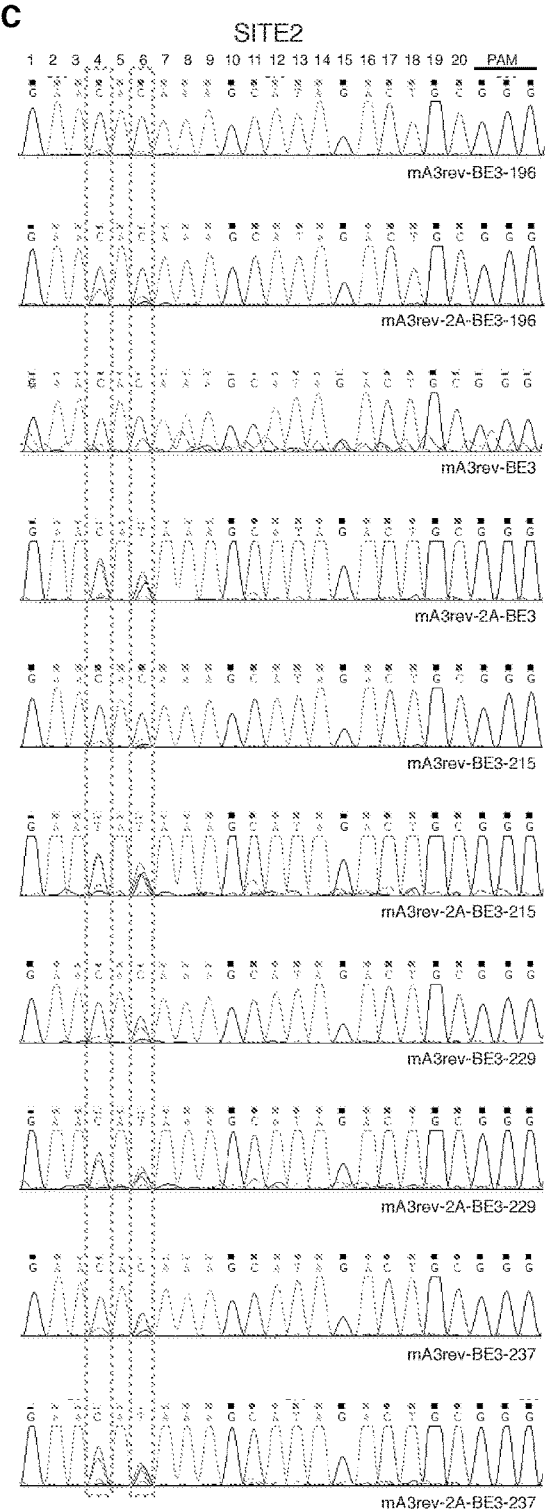
FIG. 11A-C

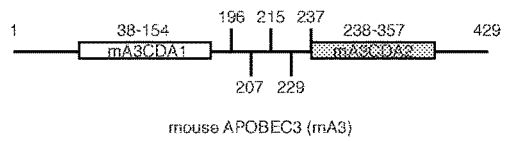
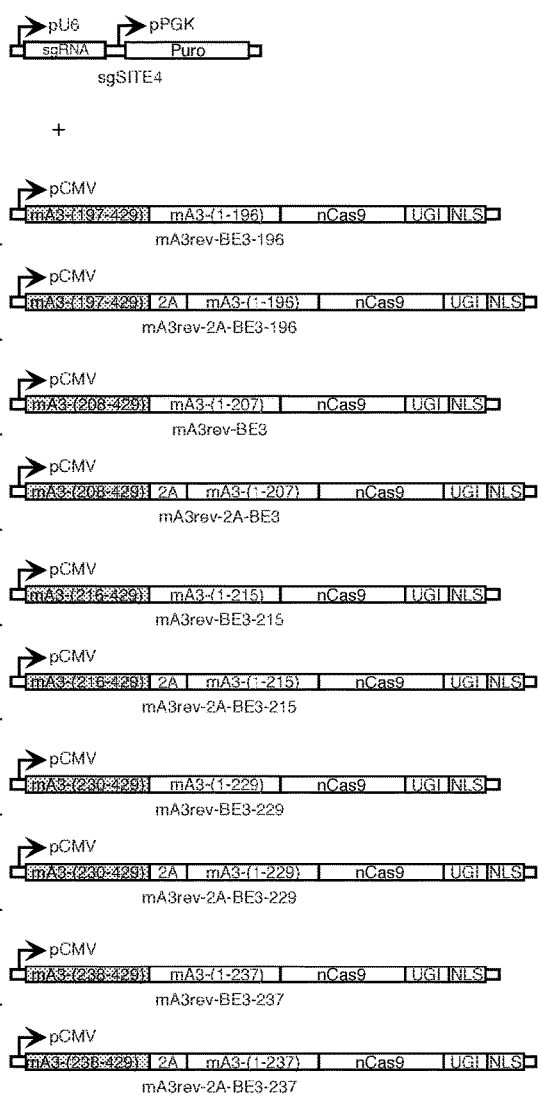
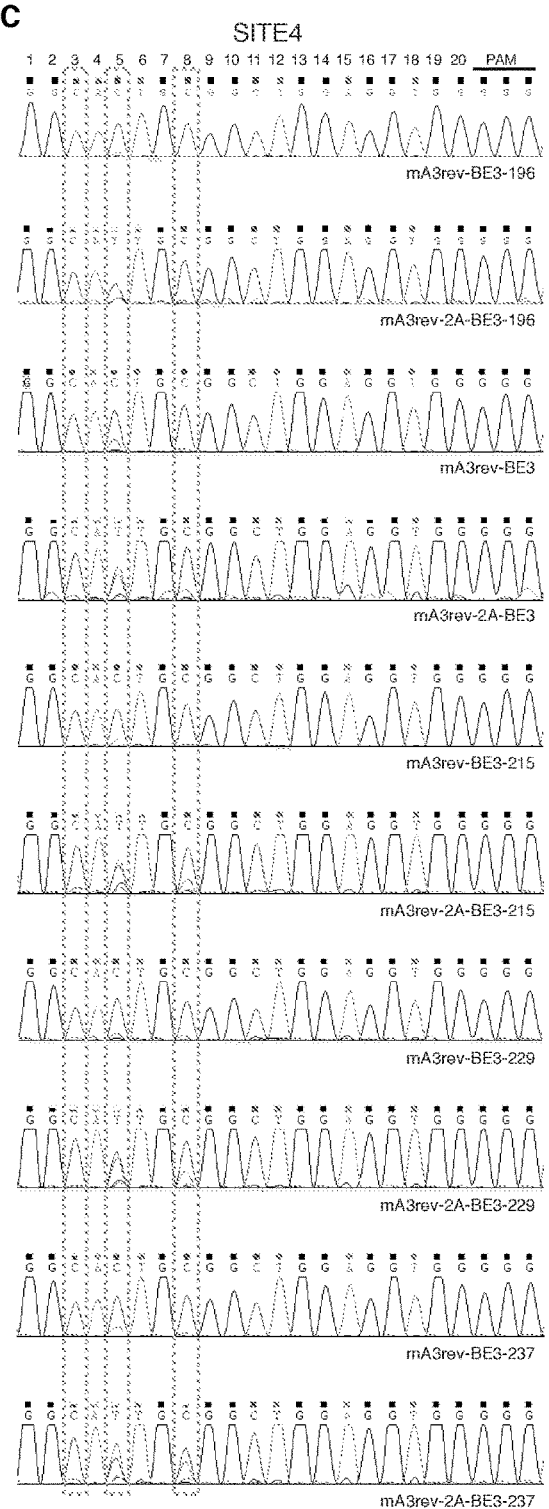
FIG. 12A-C

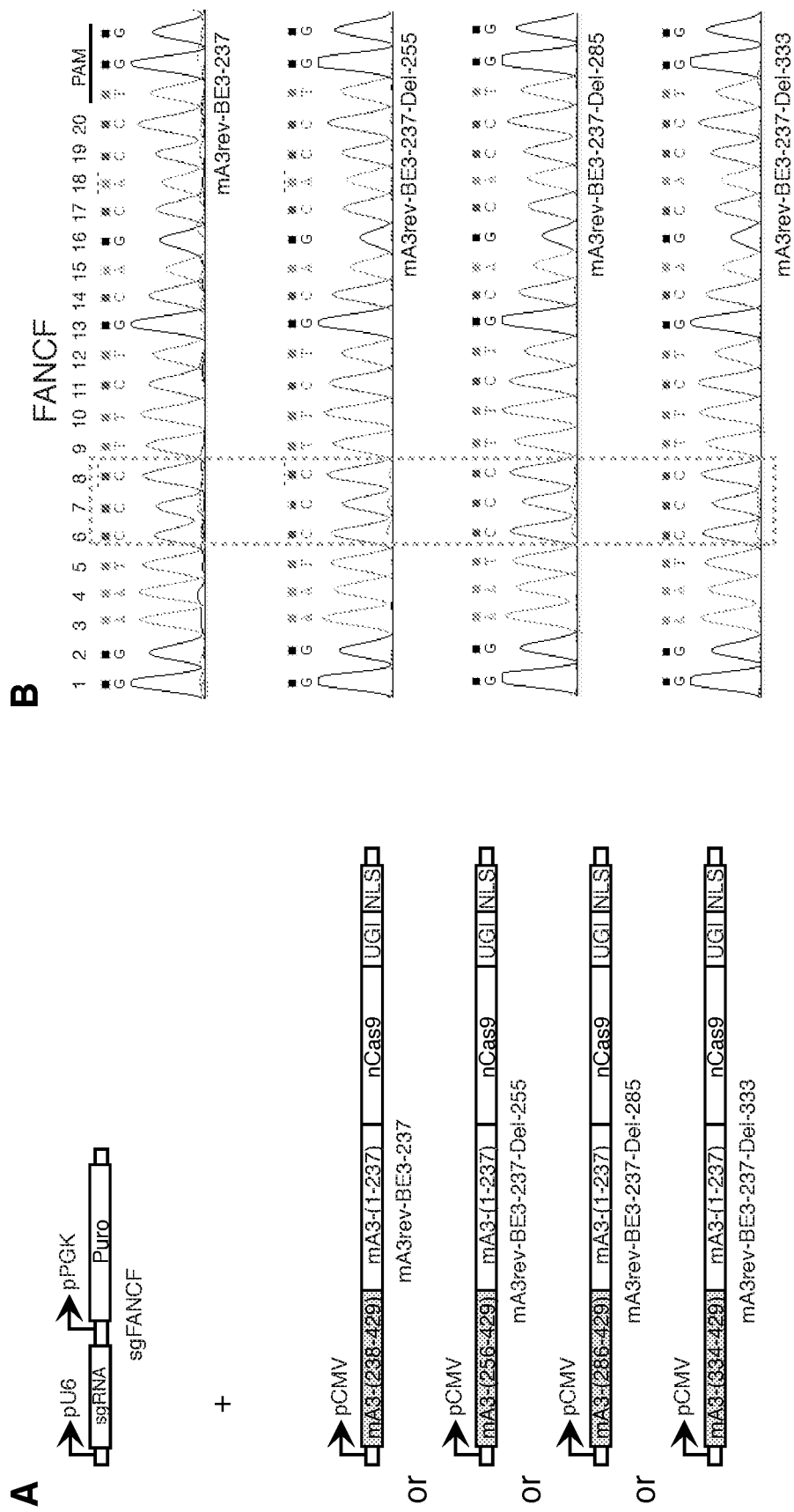
FIG. 13A-B

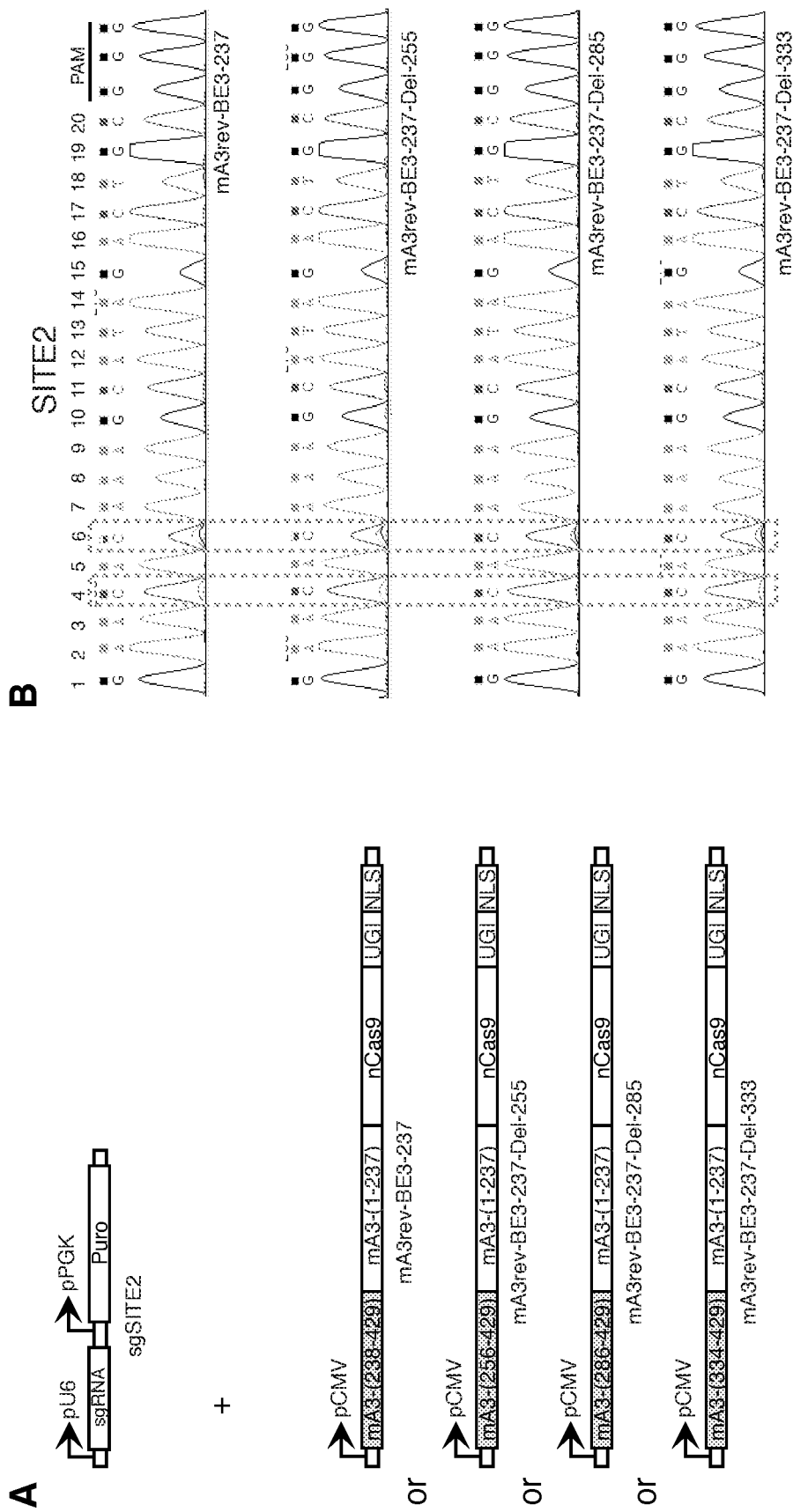
FIG. 14A-B

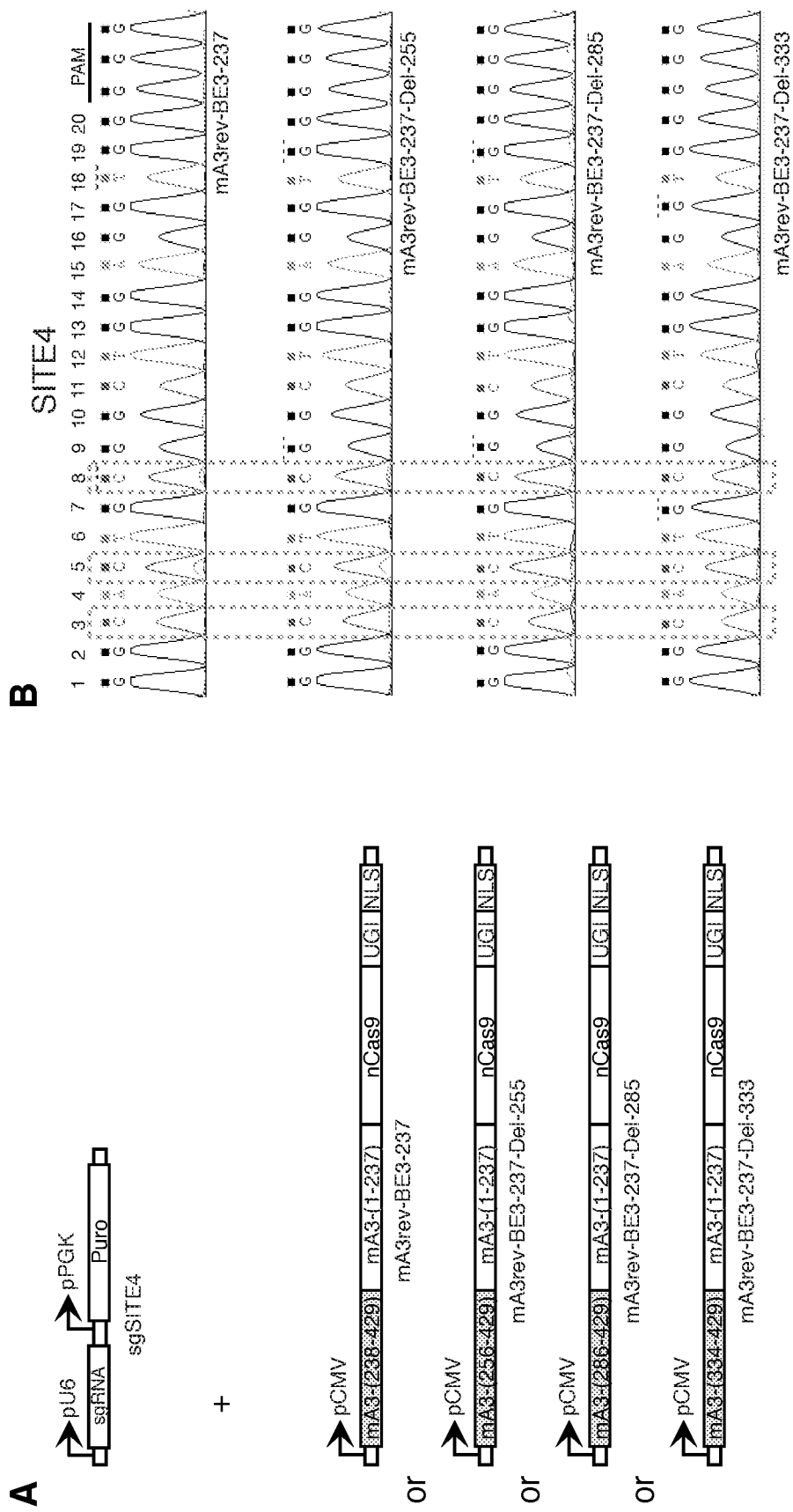
FIG. 15A-B

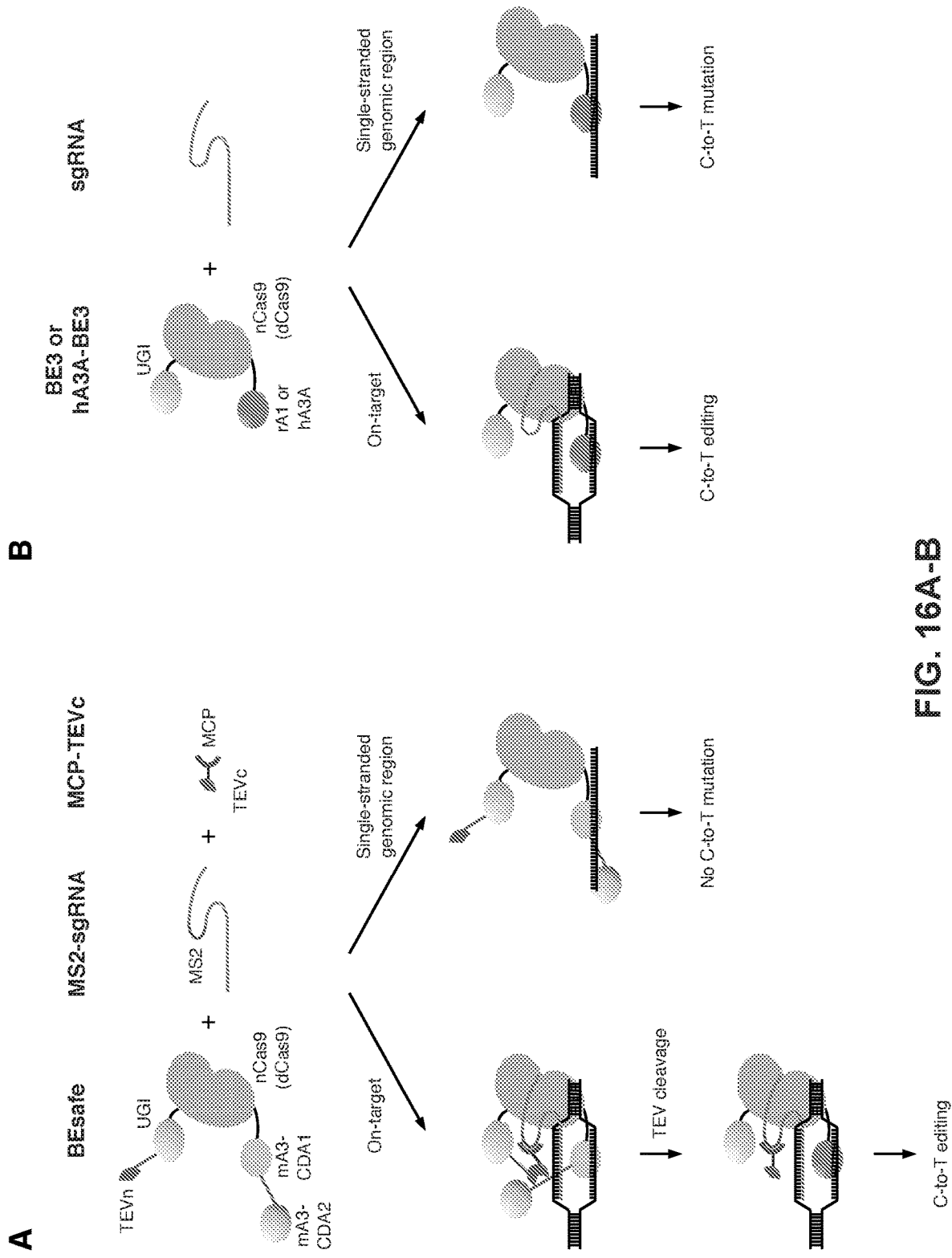
FIG. 16A-B

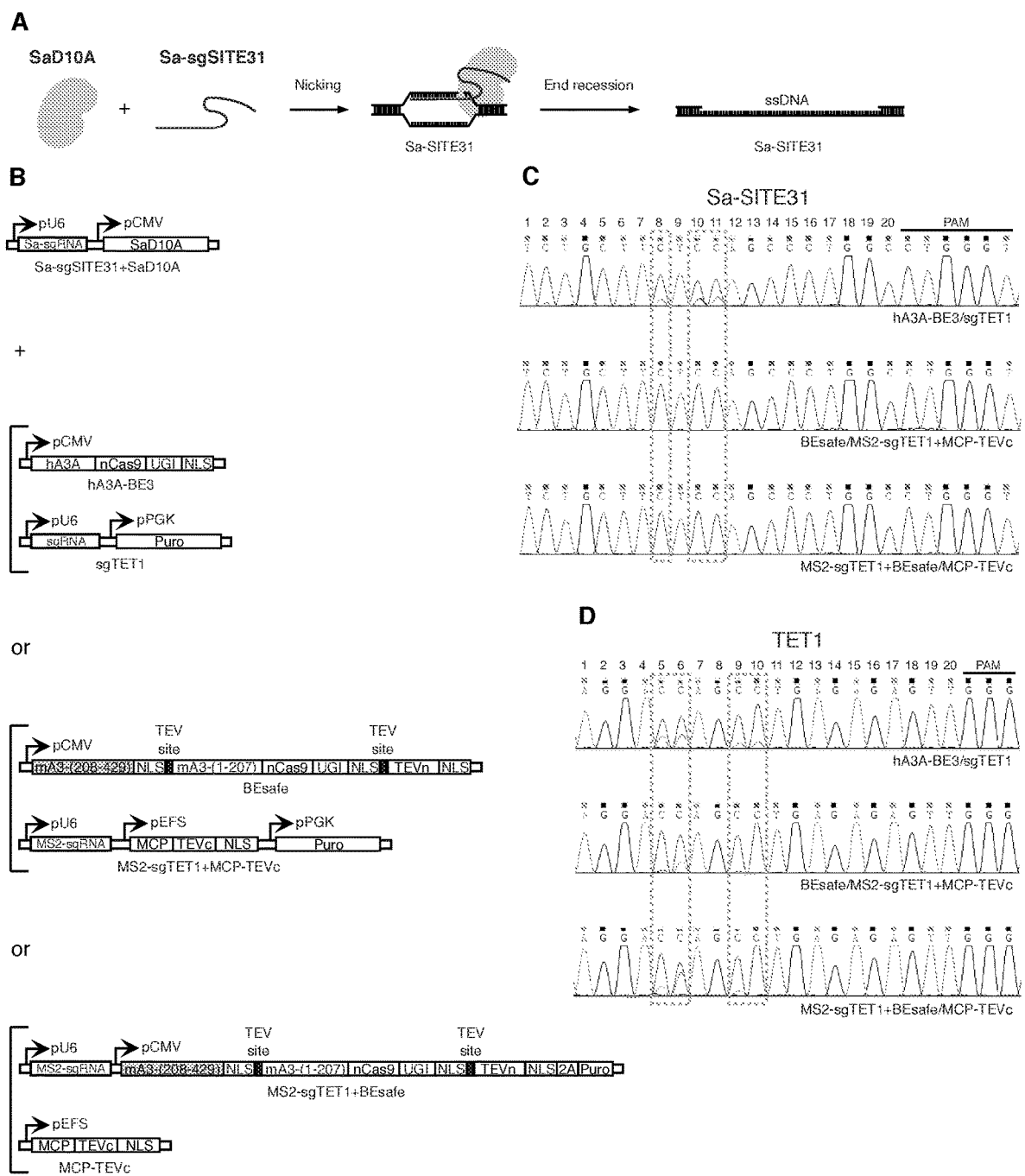
FIG. 17A-D

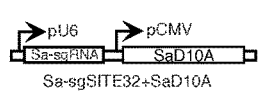
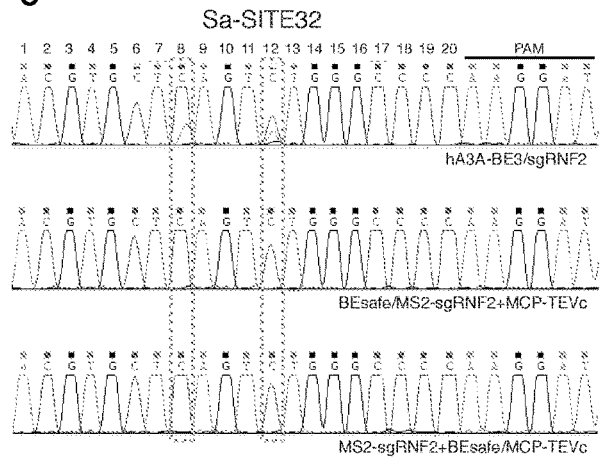
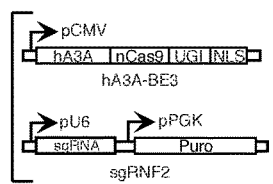
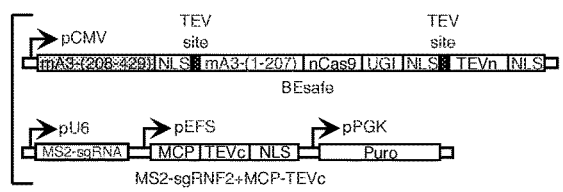
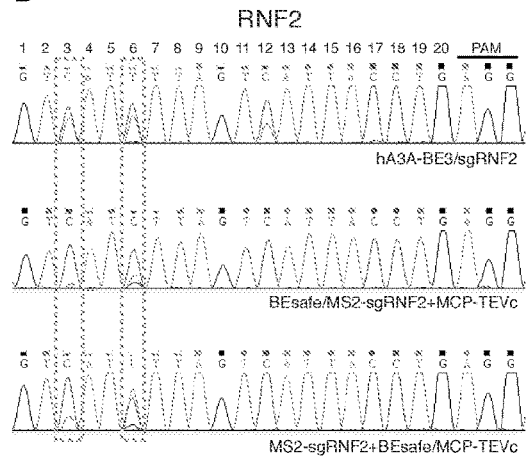
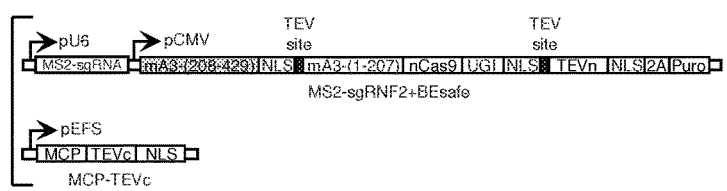
FIG. 18A-D

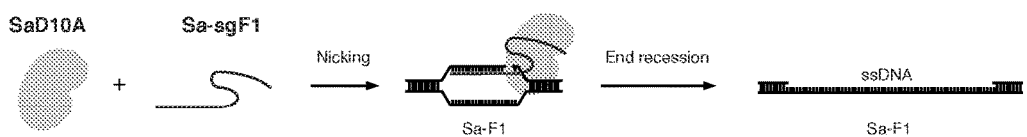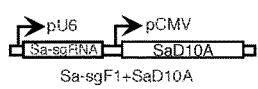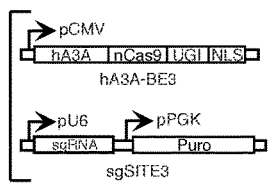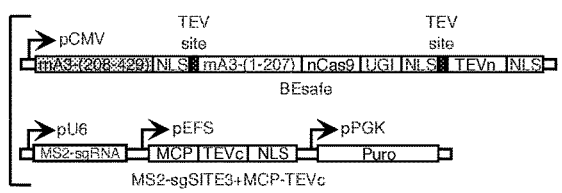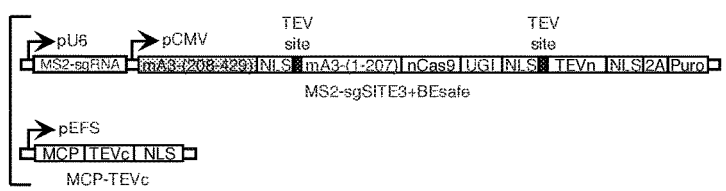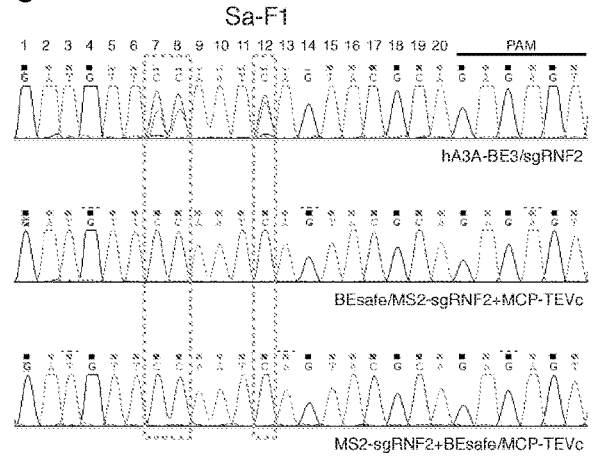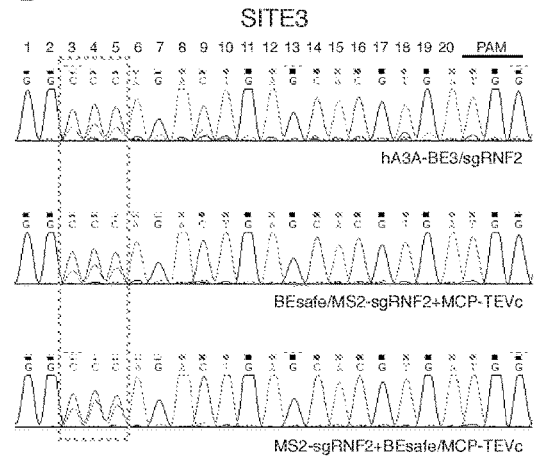
FIG. 19A-D

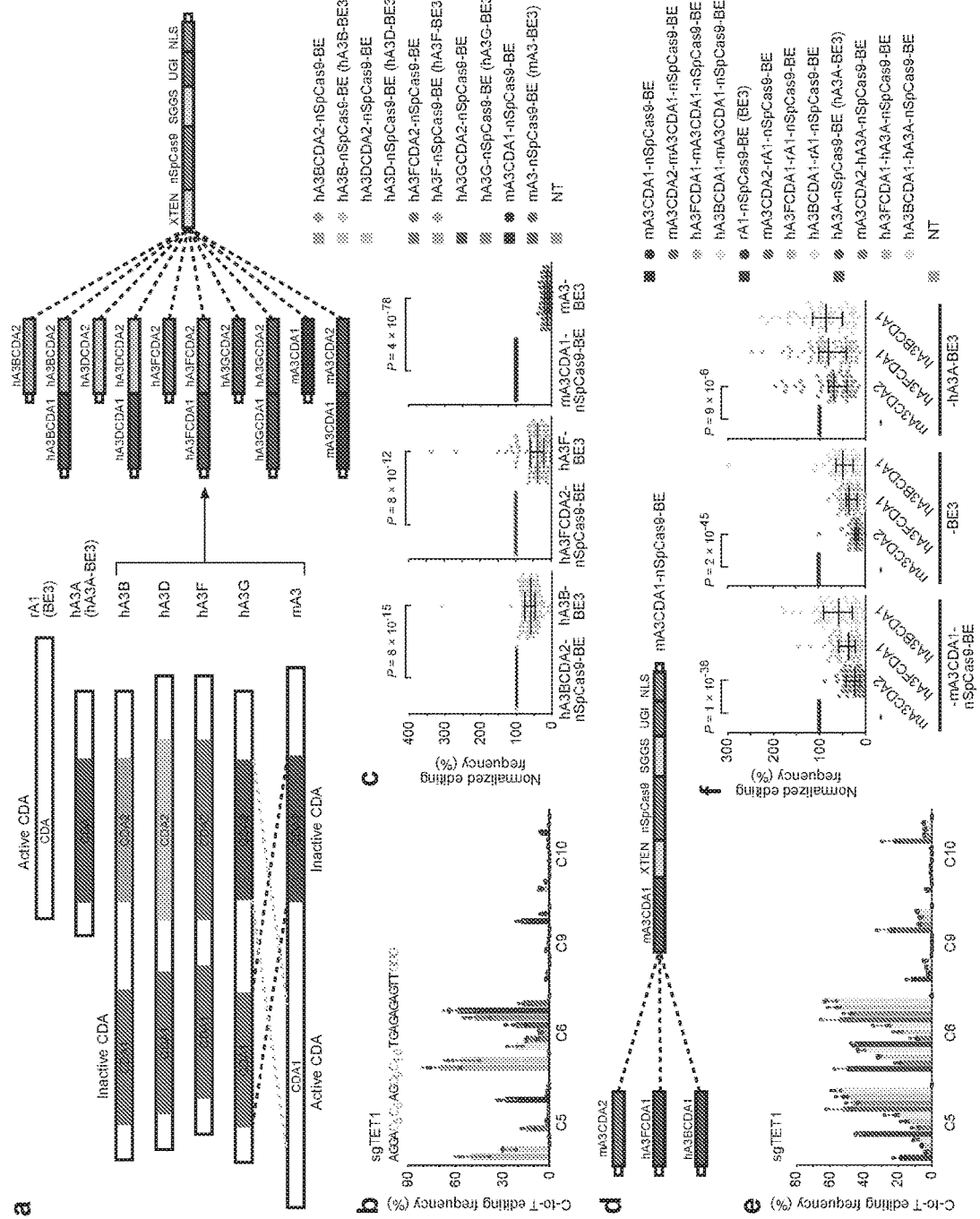
FIG. 20a-f

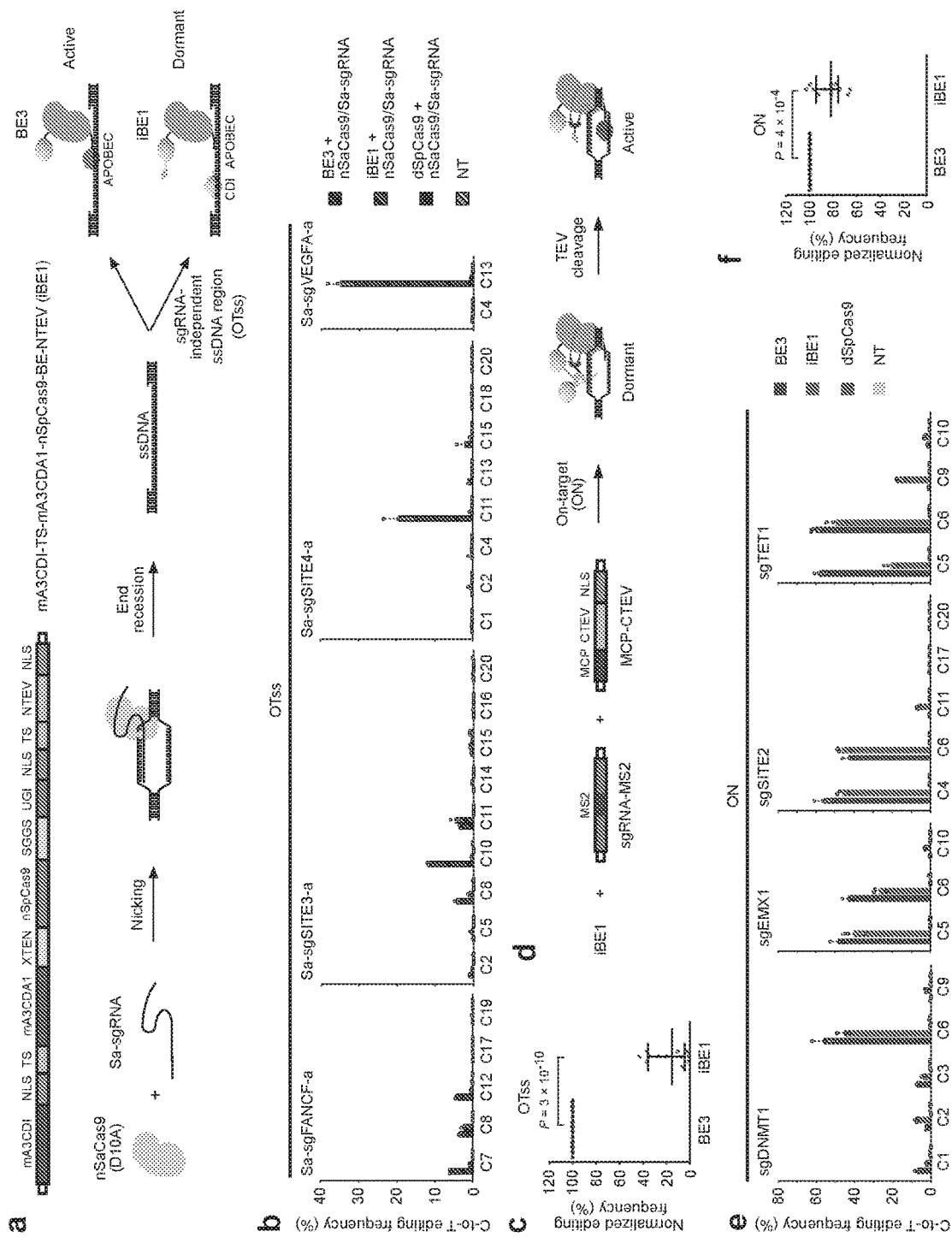
FIG. 21a-f

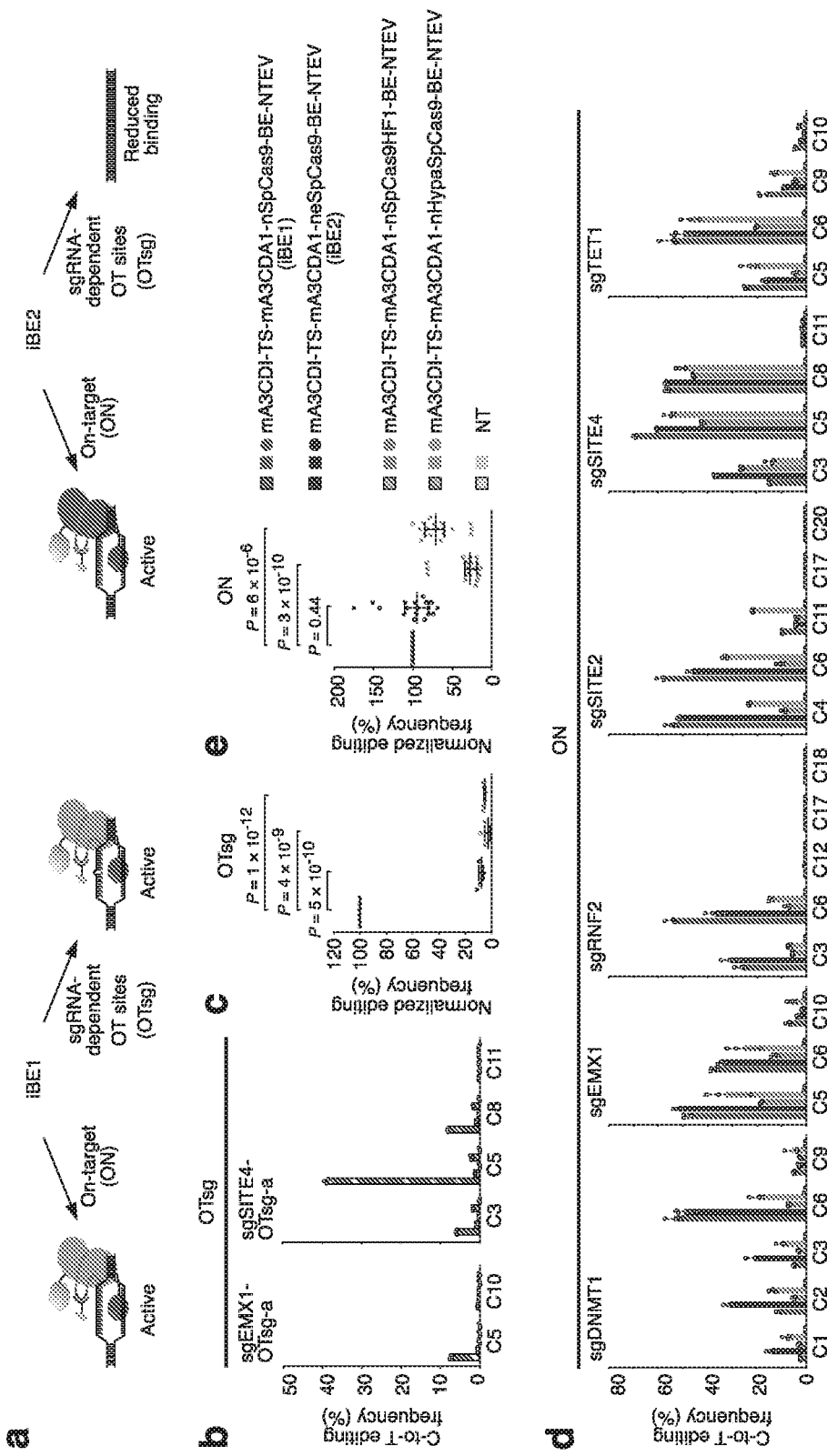
FIG. 22a-e

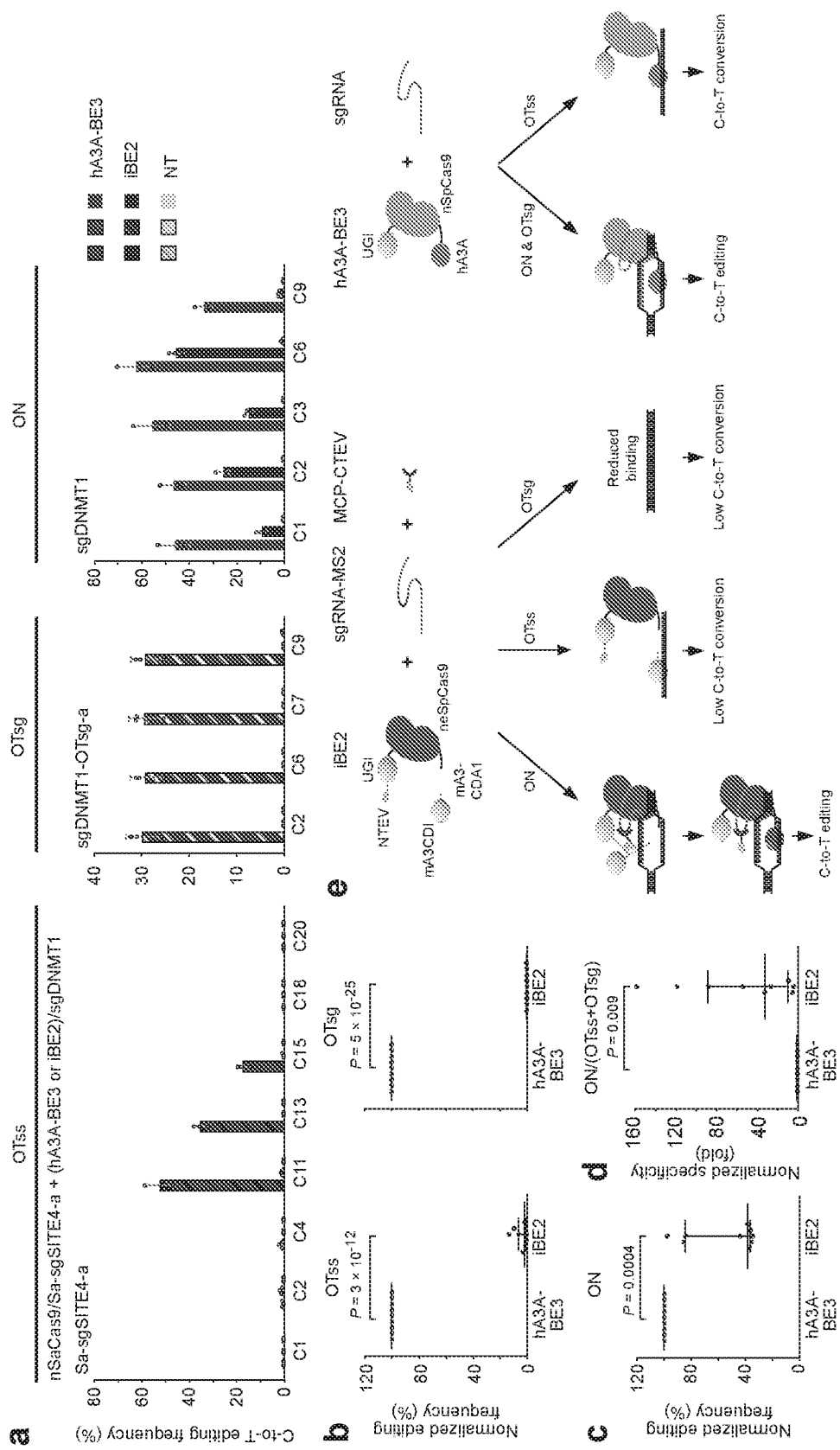
FIG. 23a-e

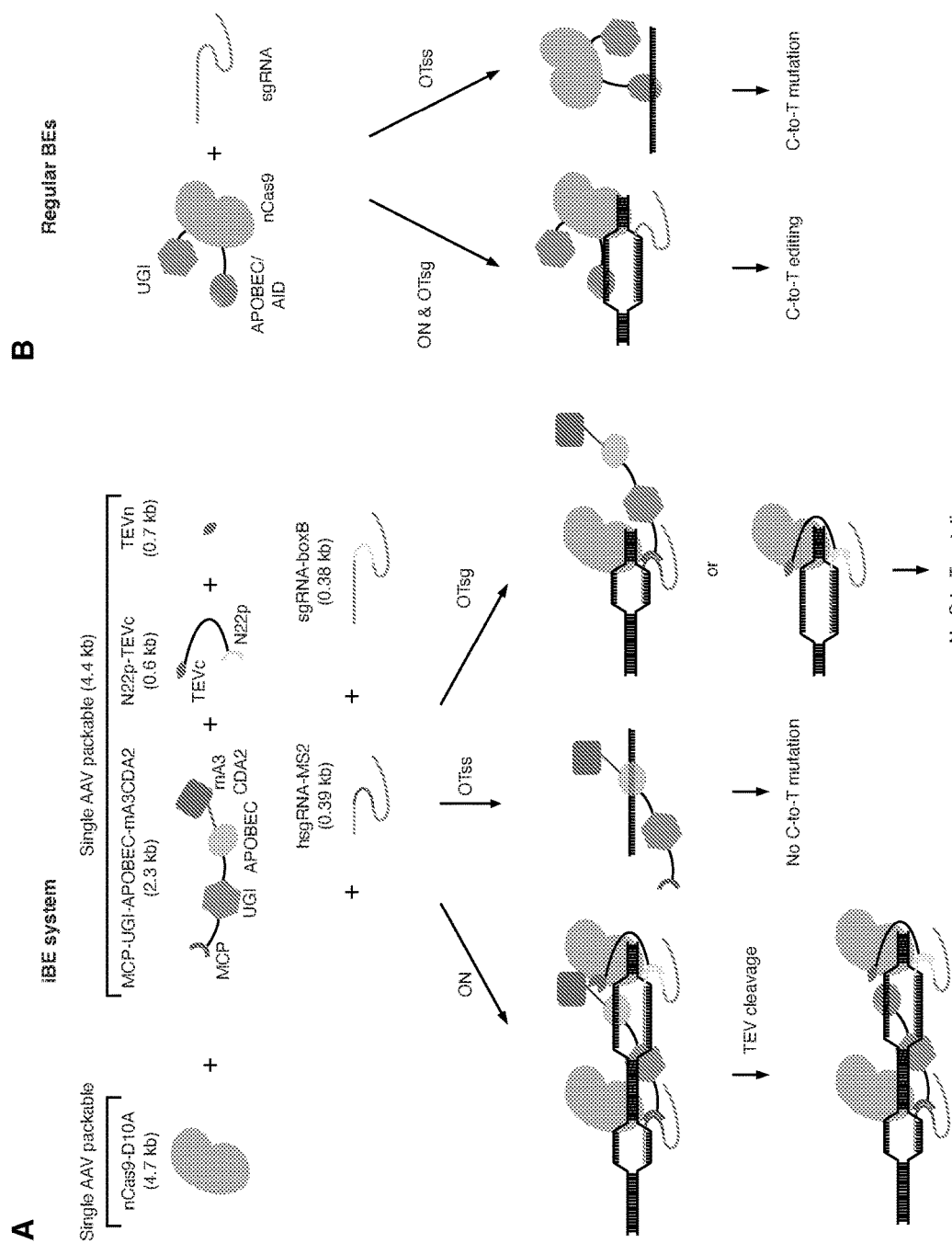
FIG. 24A-B

A

To generate OTss

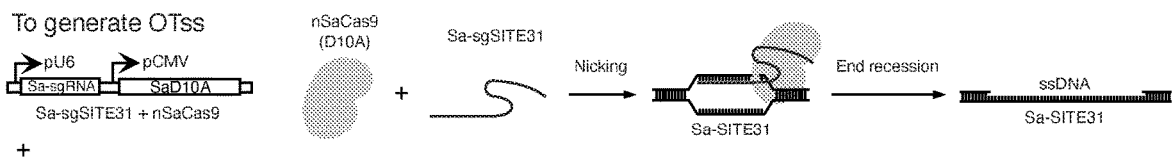

Sa-sgSITE31 + nSaCas9

+

To induce on-target editing

Pair 1
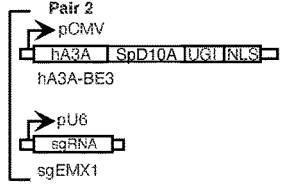
BE3
sgEMX1 or Pair 2
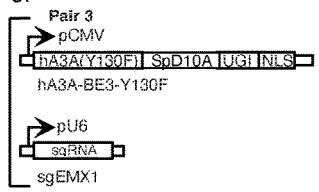
hA3A-BE3
sgEMX1 or Pair 3
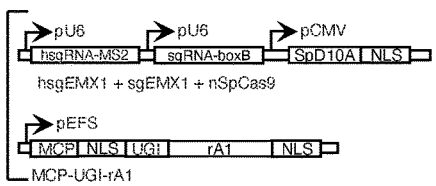
hA3A-BE3-Y130F
sgEMX1 or Pair 4
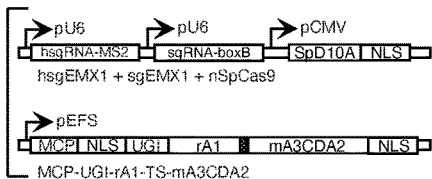
MCP-UGI-rA1 or Pair 5
hsgEMX1 + sgEMX1 + nSpCas9
MCP-UGI-rA1-TS-mA3CDA2 or Pair 6
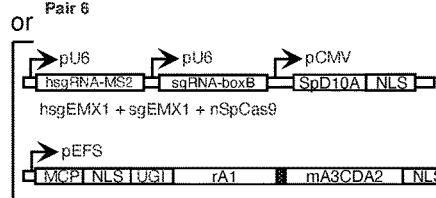
hsgEMX1 + sgEMX1 + nSpCas9
MCP-UGI-rA1-TS-mA3CDA2-2A-TEV

■ TEV site or Pair 7
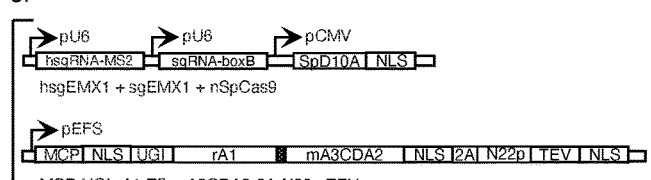
hsgEMX1 + sgEMX1 + nSpCas9
MCP-UGI-rA1-TS-mA3CDA2-2A-N22p-TEV or Pair 8
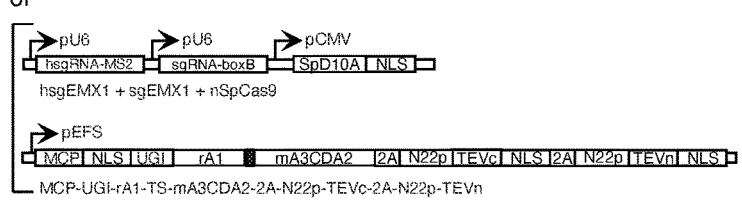
hsgEMX1 + sgEMX1 + nSpCas9
MCP-UGI-rA1-TS-mA3CDA2-2A-N22p-TEVc-2A-N22p-TEVn or Pair 9
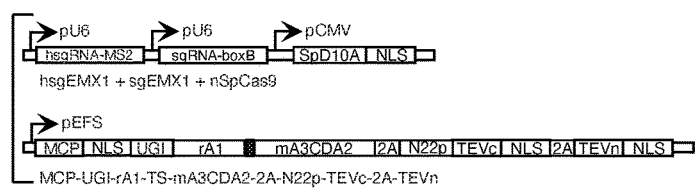
hsgEMX1 + sgEMX1 + nSpCas9
MCP-UGI-rA1-TS-mA3CDA2-2A-N22p-TEVc-2A-TEVn or Pair 10
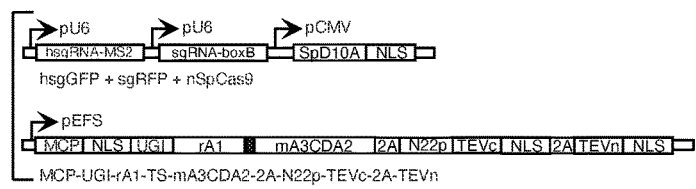
hsgGFP + sgRFP + nSpCas9
MCP-UGI-rA1-TS-mA3CDA2-2A-N22p-TEVc-2A-TEVn

FIG. 26A

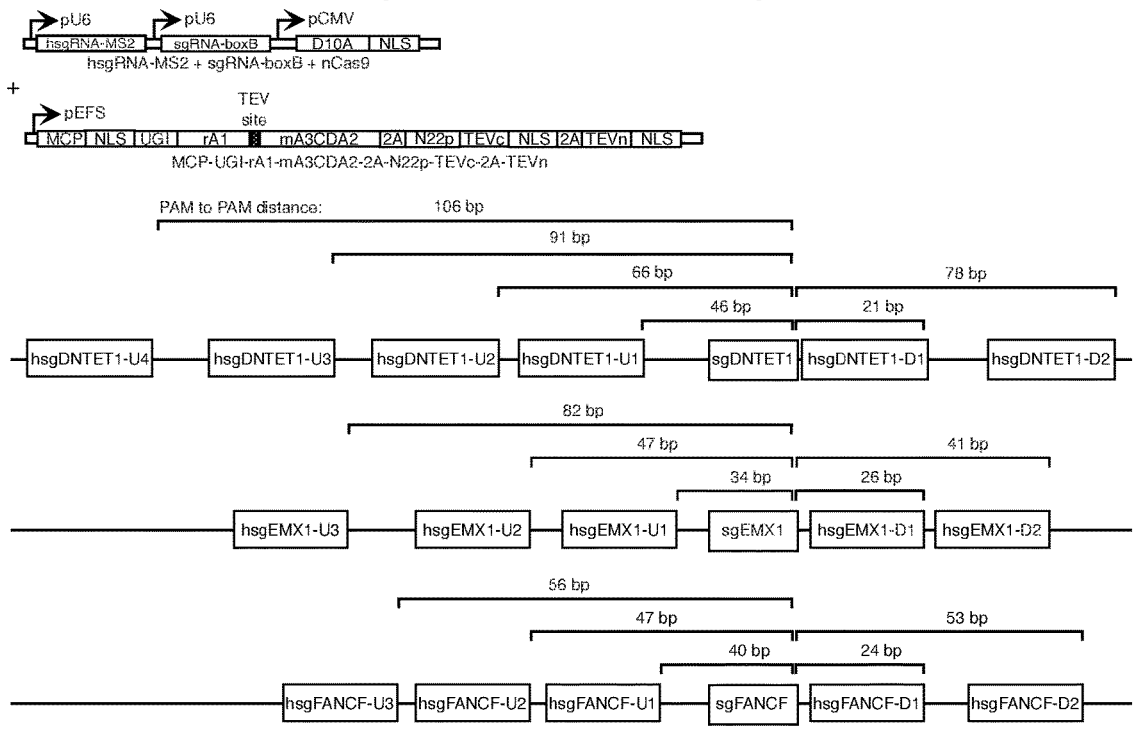
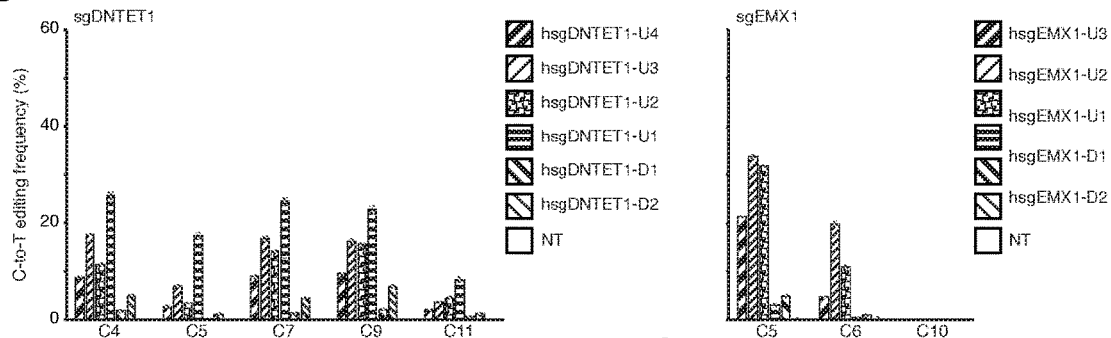
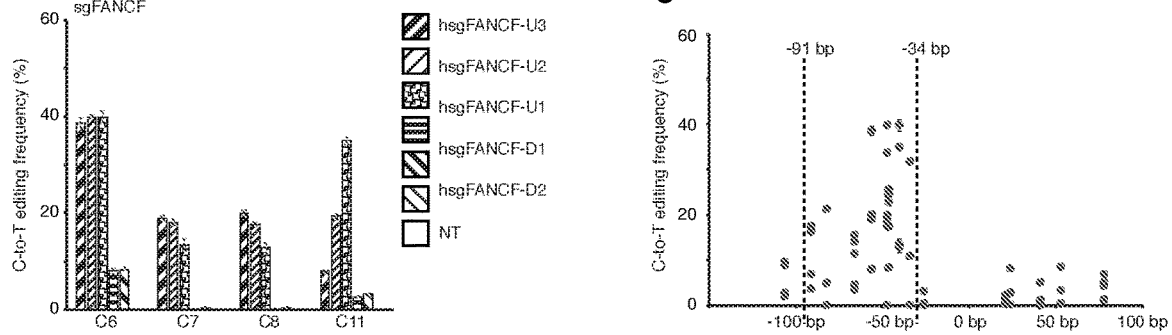
FIG. 29A-C

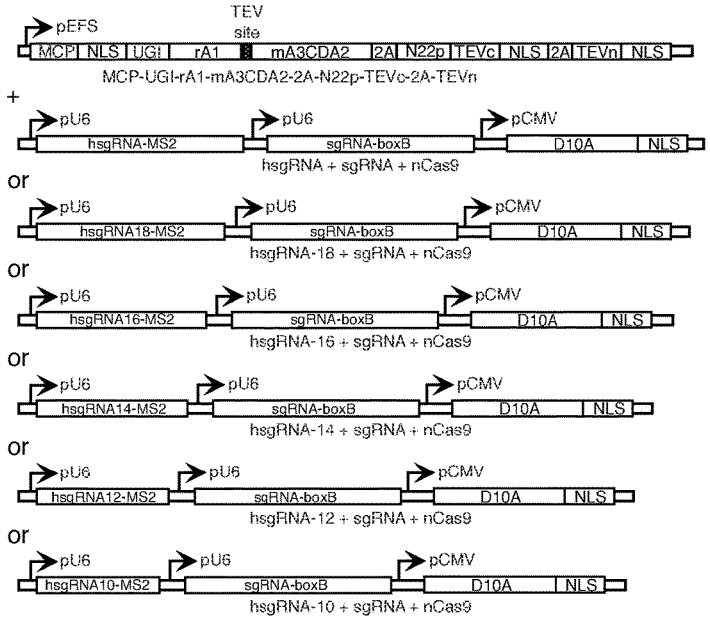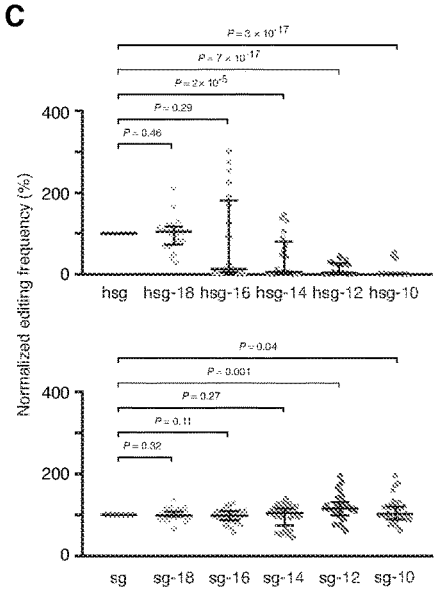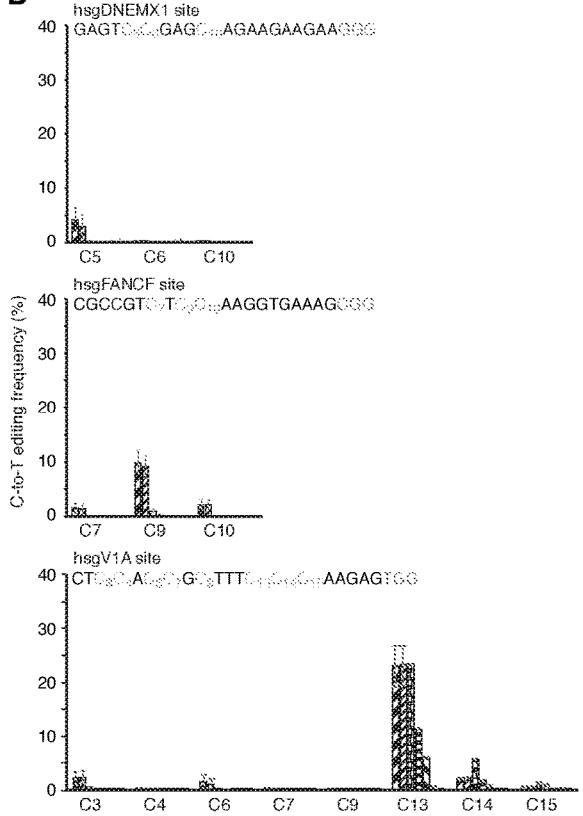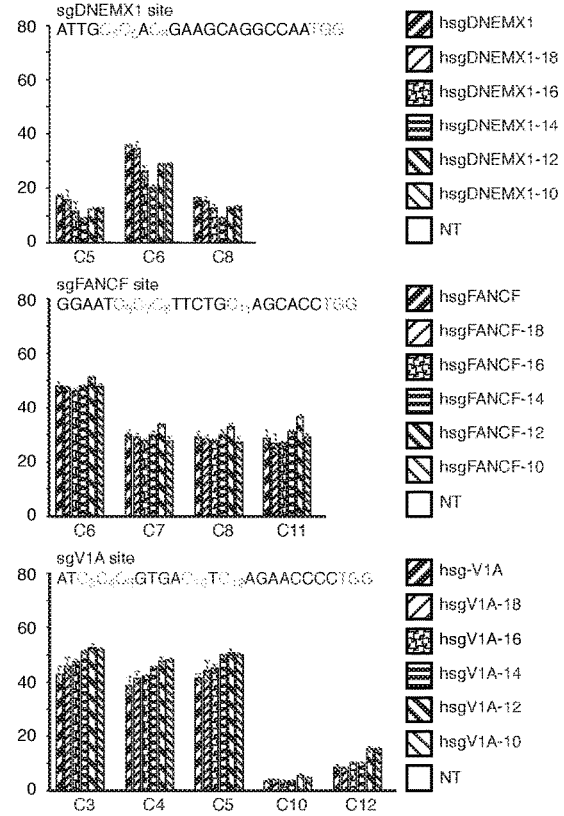
FIG. 30A-C

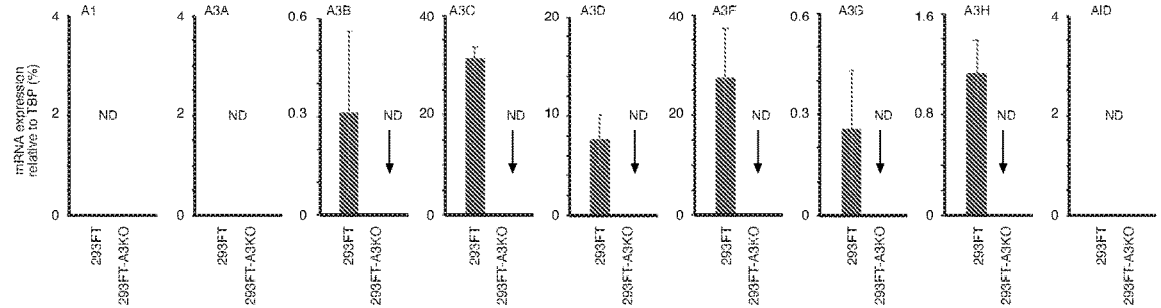
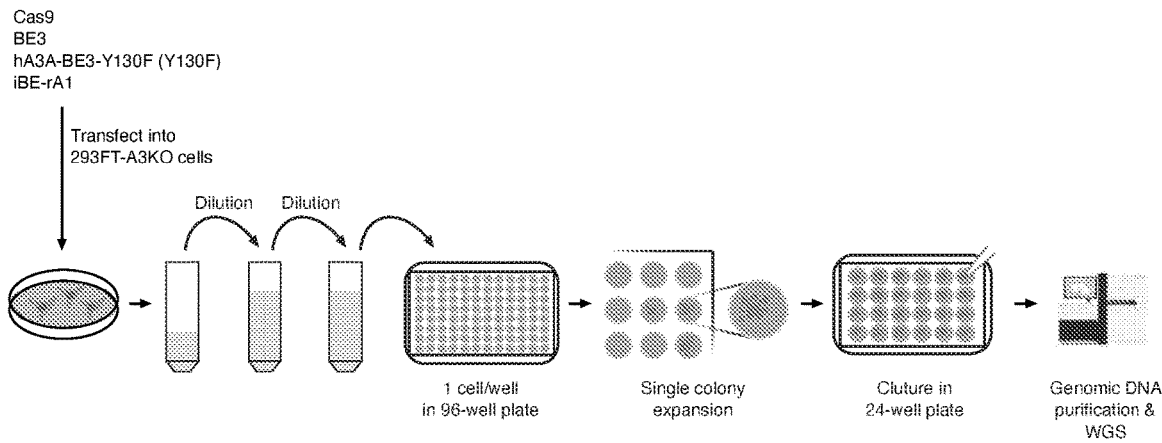
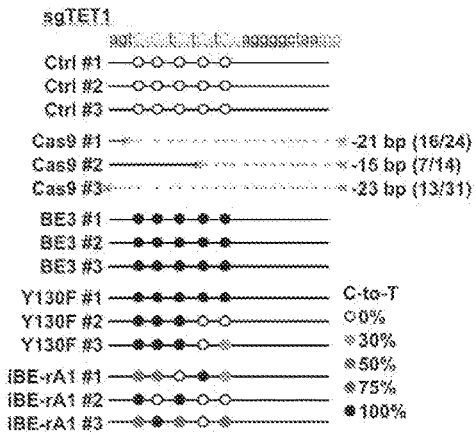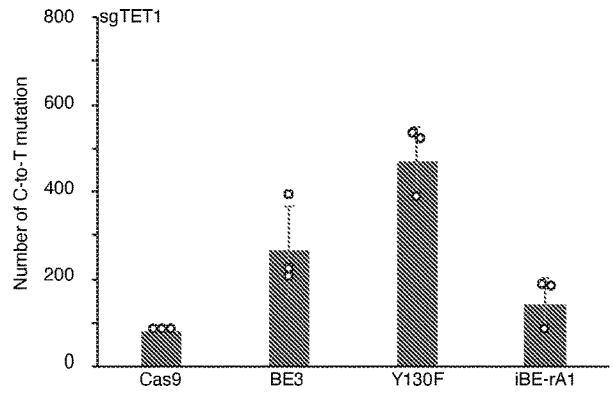
FIG. 32A-C

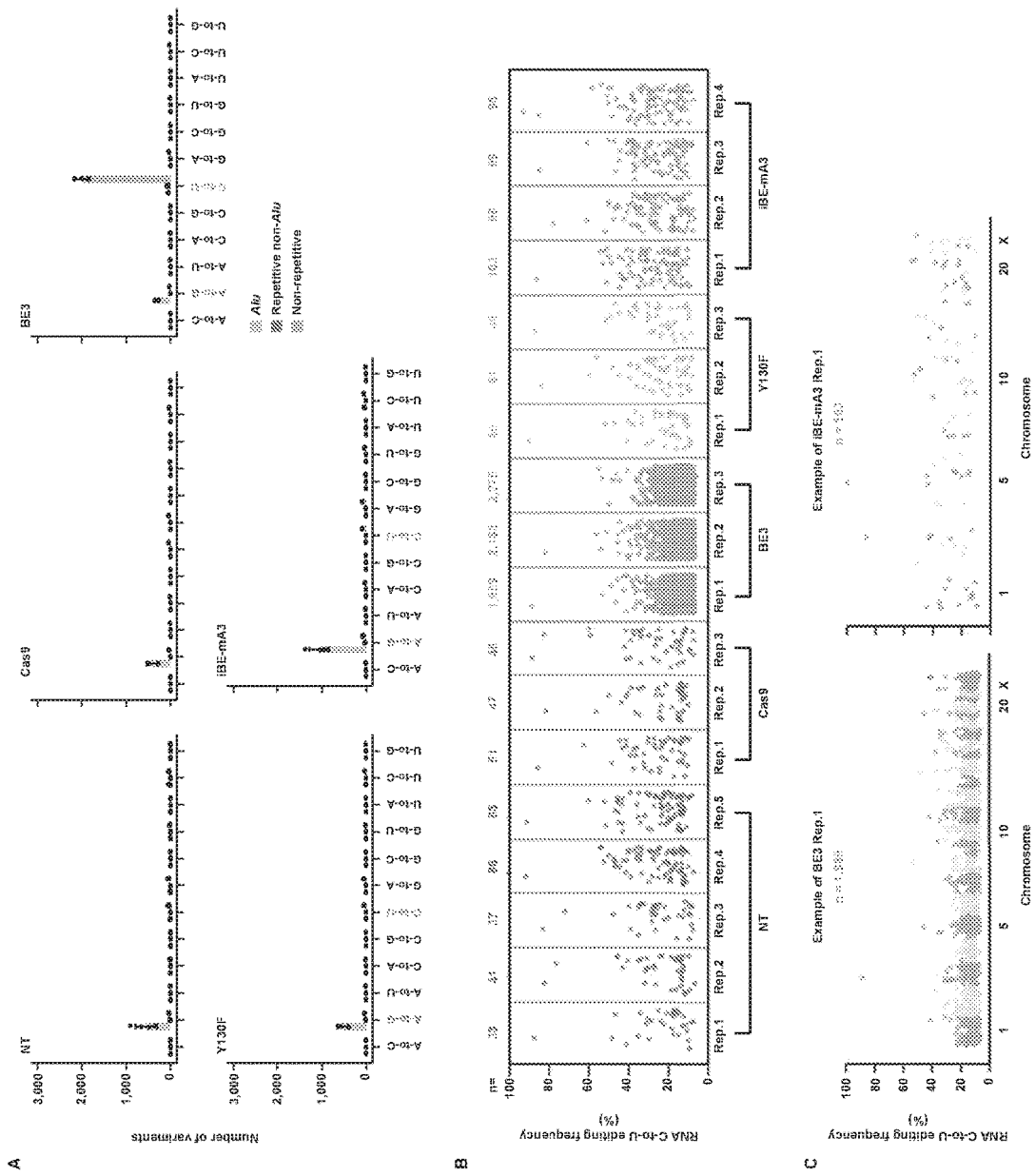
FIG. 33A-C

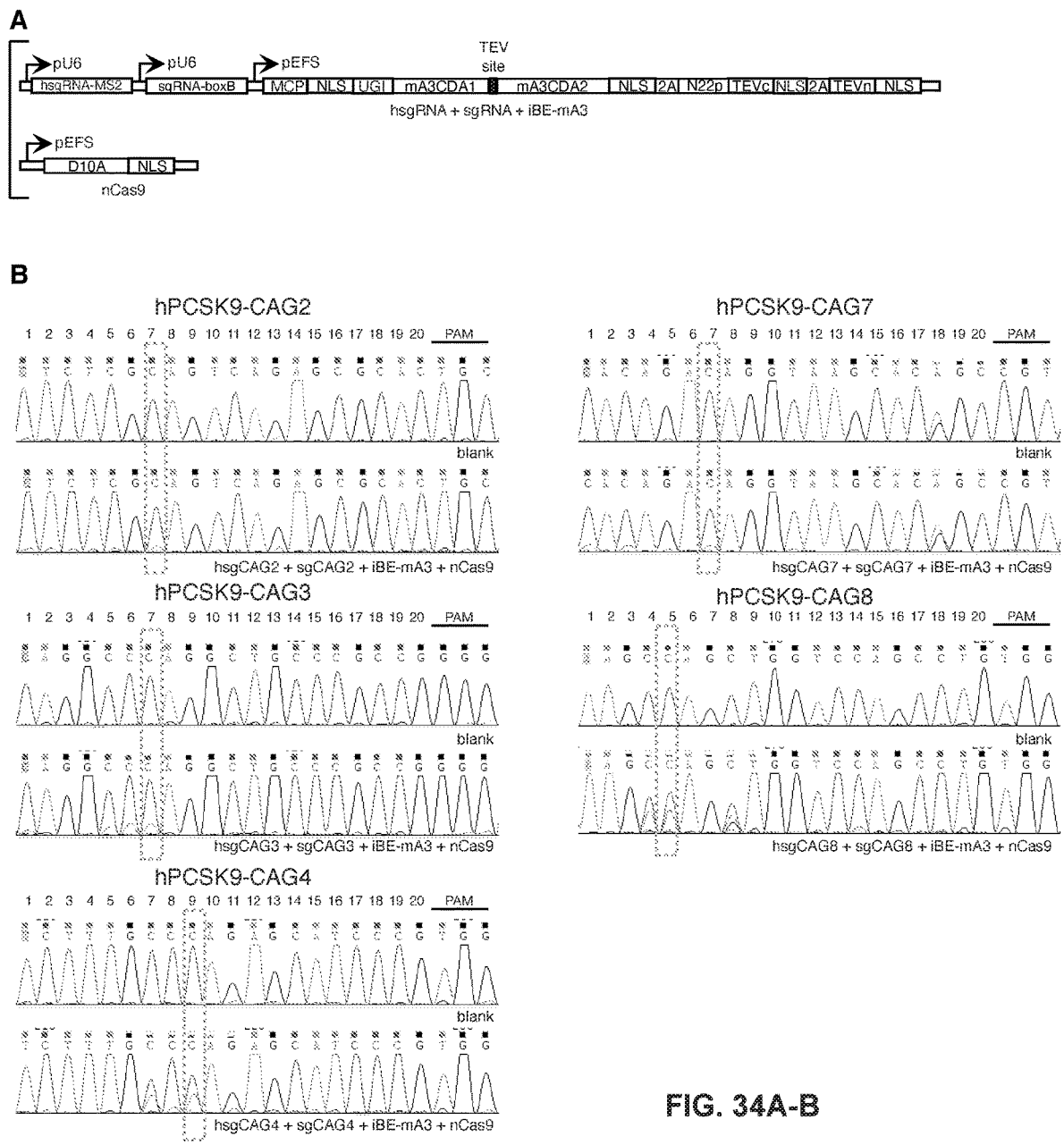
FIG. 34A-B

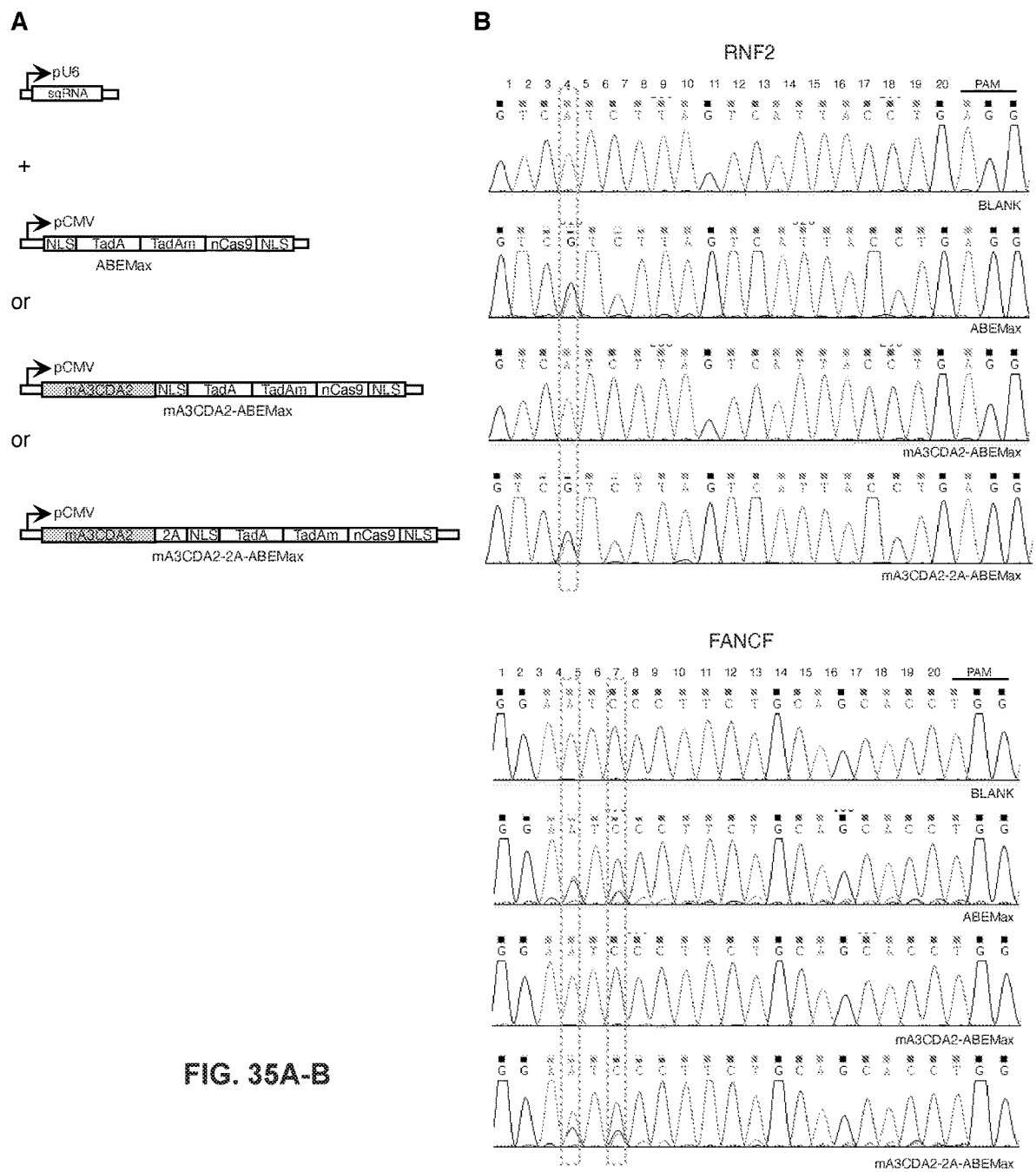
FIG. 35A-B

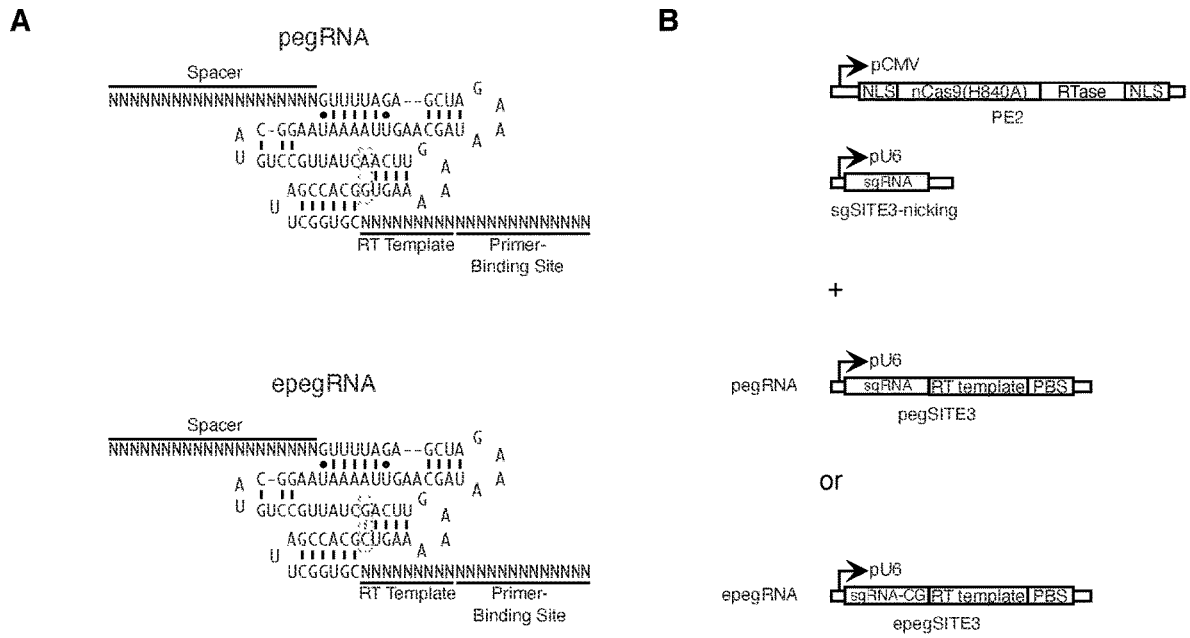
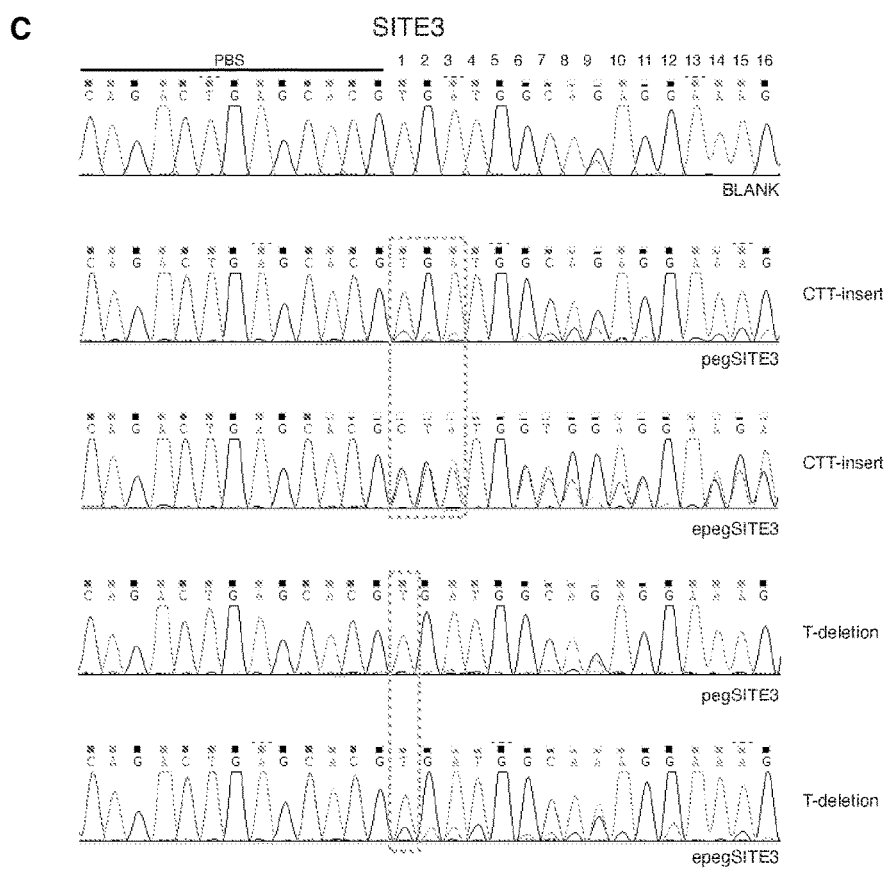
FIG. 36A-C

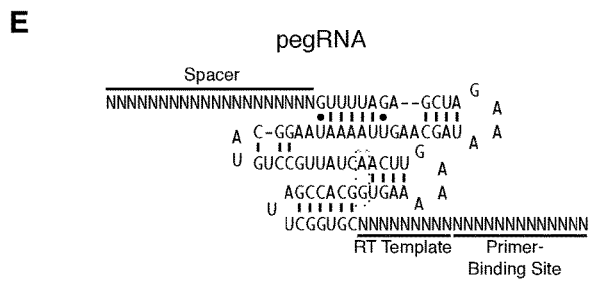
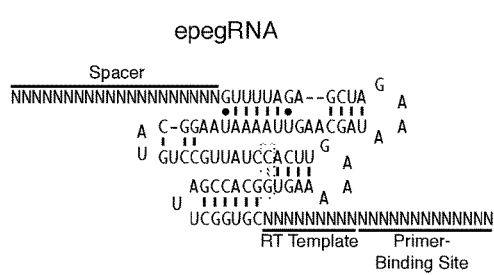
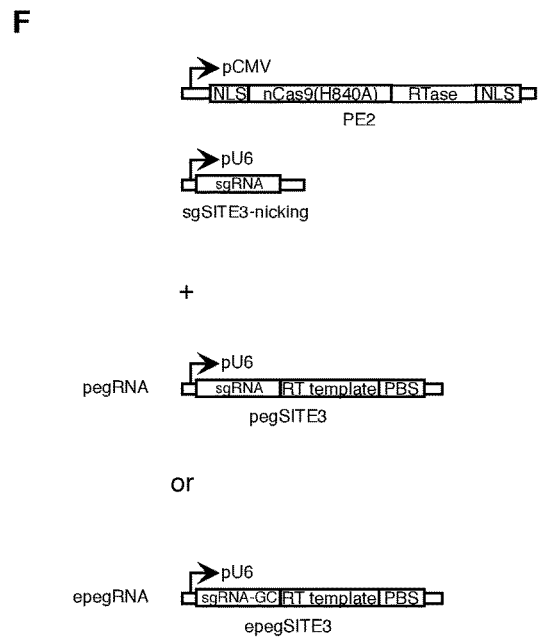
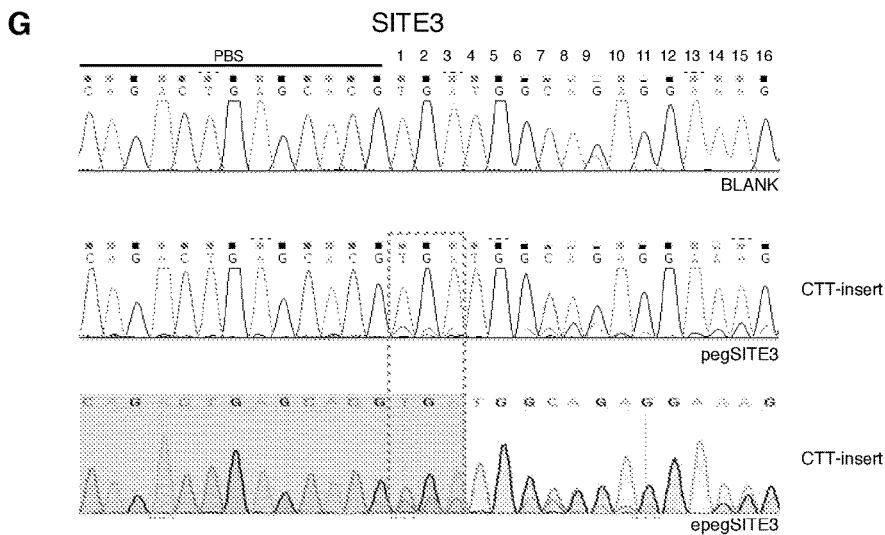
FIG. 36E-G

A
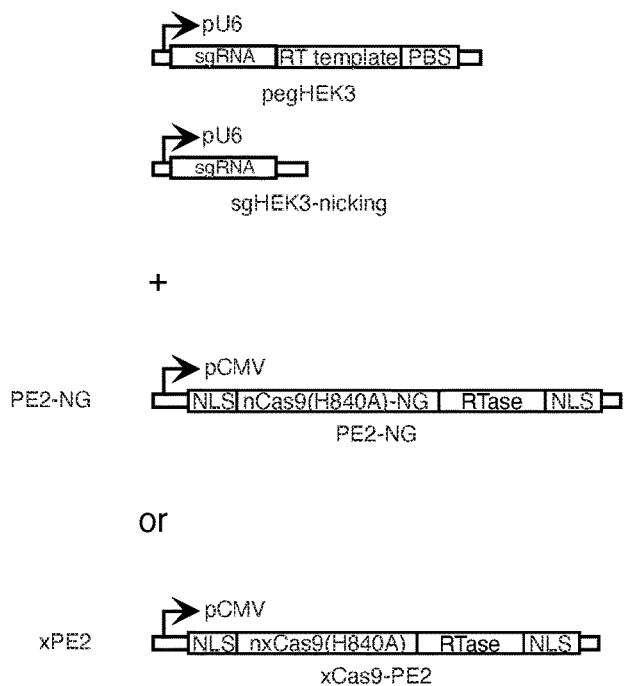
B
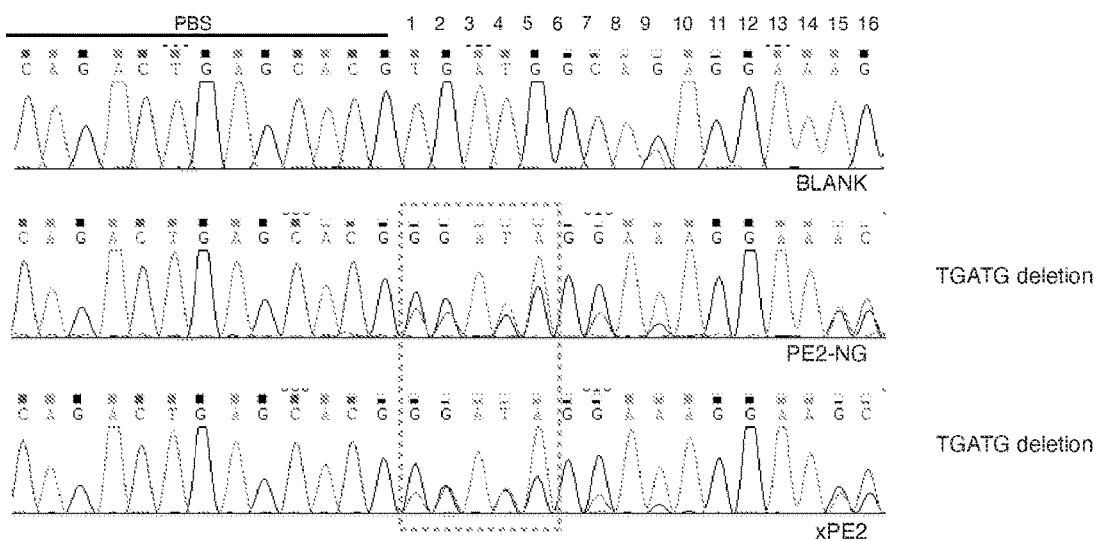
FIG. 37A-B

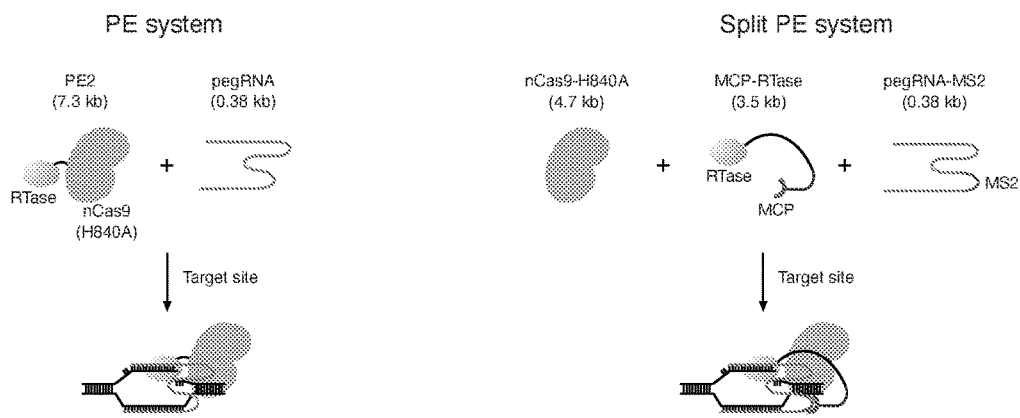
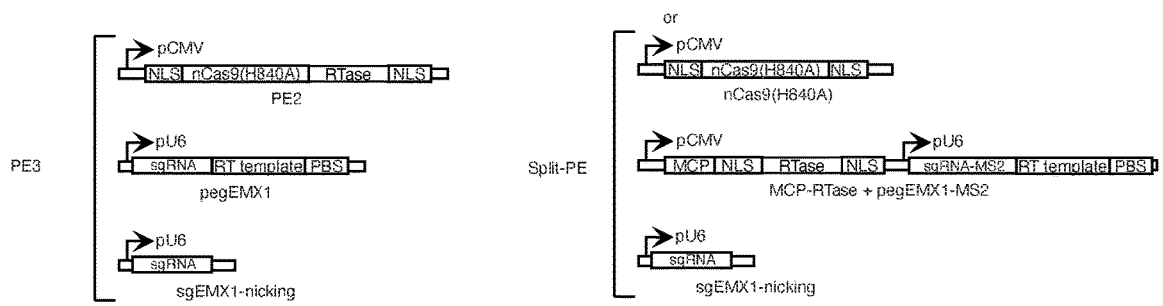
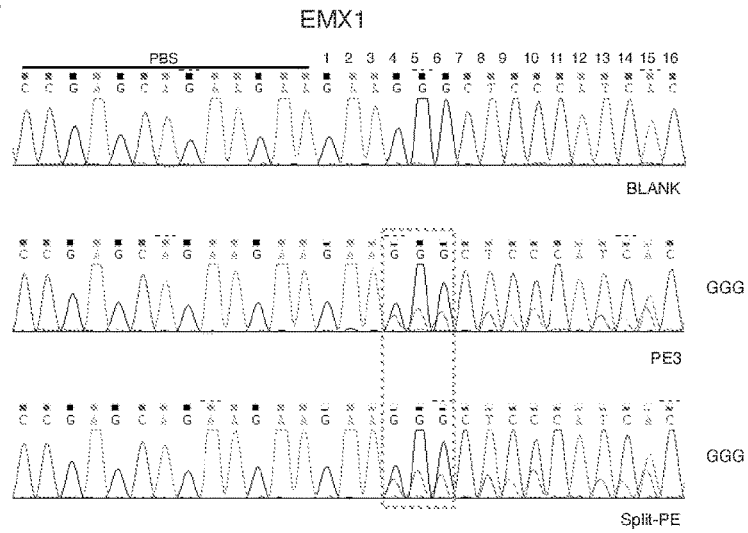
FIG. 38A-C

| | | Section 1 |
|---|---|---|
| | (1) | 1          10          28 |
| Mus musculus A3(282-355) | (1) | SEKGKQHAEILFLDKIRSME---LSQ |
| Mus spicilegus A3(248-321) | (1) | SEKGKQHAEILFLDKIRSME---LSQ |
| Cricetulus longicaudatus A3(249-322) | (1) | SEKGKQHAEILFLDKIRSME---LSQ |
| Mus terricolor A3(248-321) | (1) | SEKGKQHAEILFLEKIRSME---LSQ |
| Mus caroli A3(260-333) | (1) | SEKGKQHAEILFLDKIRSME---LSQ |
| Mus pahari A3(263-336) | (1) | SEKGKQHAEILFLEKIRSME---LSQ |
| Mus shortridgei A3(233-306) | (1) | SEKGKQHAEILFLEKIRSME---LSQ |
| Mus setulosus A3(229-302) | (1) | SEKGKQHAEILFLDKIRSME---LSQ |
| Grammomys surdaster A3(270-344) | (1) | SEKGKPHAEILFLDKMSMEE---LSQ |
| Rattus norvegicus A3(256-328) | (1) | -KKGKQHVEILFLEKMRSME---LSQ |
| Mastomys coucha A3(258-331) | (1) | SEKGRQHAEILFLEKVRSMQ---LSQ |
| Cricetulus griseus A3B(235-307) | (1) | -NKKGKHAEILFIDKMRSLE---LGQ |
| Peromyscus leucopus A3(266-338) | (1) | -NKKGKHAEILFIDKMRSLE---LGQ |
| Mesocricetus auratus A3(268-340) | (1) | -NKKDKHAEILFIDKMRSLE---LCQ |
| Microtus ochrogaster A3B(266-338) | (1) | -NKKGKHAEILFIDKMRSLK---LSQ |
| Nannospalax galili A3(231-302) | (1) | -NKRAKHAEILLIDMKRSME---LGQ |
| Meriones unguiculatus A3(233-305) | (1) | -NKKGRHAEICLIDKMRSLG---LGK |
| Dipodomys ordii A3(256-330) | (1) | -NKKGHHAEIRFIERIRSMGLDPSQD |
| Jaculus jaculus A3(303-374) | (1) | -NKKGKHAEARFVDKMRSMQ---LQH |
| Chinchilla lanigera A3H(86-161) | (1) | SPQKGHHAESRFIKRISMDLDRSKS |
| Heterocephalus glaber A3(277-350) | (1) | --KKGYHAESRFIKRICSMDLQODQS |
| Octodon degus A3(256-329) | (1) | --KKGQHAEIRFIERIHSMALDOARS |
| Urocitellus parryii A3(256-330) | (1) | -NKKGHHAEIRFIKKIRSLDLQOSQN |
| Aotus nancymaae A3H(75-146) | (1) | ----NRHAEICFIDEIKSMGLDKTQC |
| Cebus capucinus imitator A3H(55-126) | (1) | ----NRHAEICFIDKIKSMGLDKTQC |
| Saimiri boliviensis boliviensis A3H(56-125) | (1) | -----AVEICFIDKIASMELDKTQC |
| Homo sapiens A3H(49-123) | (1) | -NKKKCHAEICFINEIKSMGLDETQC |
| Homo sapiens ARP10(48-123) | (1) | ENKKKCHAEICFINEIKSMGLDETQC |
| Pan paniscus A3H(49-123) | (1) | -NKKKCHAEICFINEIKSMGLDETQC |
| Symphalangus syndactylus A3H(49-123) | (1) | -NKKKRHAEIRFINKIKSMGLDETQC |
| Macaca mulatta A3H(49-123) | (1) | -NKKKDHAEIRFINKIKSMGLDETQC |
| Theropithecus gelada A3H(54-128) | (1) | -NKKKEHAEIRFINKIKSMGLDETQC |
| Mandrillus leucophaeus A3H(49-123) | (1) | -NKKKHHAEIHFINKIKSMGLDETQC |
| Bos grunniens A3(74-148) | (1) | -NKKQRHAEIRFIDKINSLDLNPSQS |
| Bubalus bubalis A3(74-148) | (1) | -NKKQRHAEIRFIDKINSLDLNPSQS |
| Odocoileus virginianus texanus A3H(209-283) | (1) | -NKKQRHAEIRFIDKINSLNLDRRQS |
| Sus scrofa A3(51-125) | (1) | -NKKKRHAEIRFIDKINSLNLDQNQC |
| Ceratotherium simum simum A3B(232-306) | (1) | -NKKKRHAEIRFIDKISLGLDRVQS |
| Equus caballus A3H(79-153) | (1) | -NKKKRHAEIRFIDKTNSIGLDQDQS |
| Enhydra lutris kenyoni A3B(243-316) | (1) | --KKKRHAEIRFIDSIRALQLDQSQR |
| Leptonychotes weddellii A3H(50-123) | (1) | --KKKRHAEIRFIDKIKALRLDTSQR |
| Ursus arctos horribilis A3F(552-626) | (1) | -NKKKRHAEIRFIDKIRSLQRDSSQT |
| Panthera leo bleyenberghi A3H(50-124) | (1) | -NKKKRHAEICFIDKIKSLTRDTSQR |
| Panthera tigris sumatrae A3H(50-124) | (1) | -NKKKRHAEICFIDKIKSLTRDTSQR |
| Tupaia belangeri A3(46-120) | (1) | -NKKHRHAEVRFIAKIRSMSLDLDQK |
| Consensus | (1) | NKKK HAEI FIDKIRSM LD  Q |

FIG. 39A

|                                                      |      | Section 2 |
|---|---|---|
|                                                      | (27) | 27       40       52 |
| Mus musculus A3(282-355) | (24) | VTITCYLTWSPCPNCAWQLAAFKRDR |
| Mus spicilegus A3(248-321) | (24) | VTITCYLTWSPCPNCAWQLAAFKRDR |
| Cricetulus longicaudatus A3(249-322) | (24) | VTITCYLTWSPCPNCAWKLAAFKRDR |
| Mus terricolor A3(248-321) | (24) | VTITCYLTWSPCPNCAWQLAAFKKDR |
| Mus caroli A3(260-333) | (24) | VTITCYLTWSPCPNCAWQLAAFKRDR |
| Mus pahari A3(263-336) | (24) | KRITCYLTWSPCPNCAWQLAAFQKDR |
| Mus shortridgei A3(233-306) | (24) | KRITCYLTWSPCPNCAWQLAAFQKDR |
| Mus setulosus A3(229-302) | (24) | VRITCYLTWSPCPNCAWQLETFKKDR |
| Grammomys surdaster A3(270-344) | (25) | VRITCYLTWSPCPNCARQLAAFKKDR |
| Rattus norvegicus A3(256-328) | (23) | VRITCYLTWSPCPNCARQLAAFKKDR |
| Mastomys coucha A3(258-331) | (24) | VRITCYLTWSPCPNCAWQLAAFKMDR |
| Cricetulus griseus A3B(235-307) | (23) | VQITCYLTWSPCPNCAQELAAFKSDR |
| Peromyscus leucopus A3(266-338) | (23) | ARITCYLTWSPCPNCAQELAAFKRDR |
| Mesocricetus auratus A3(268-340) | (23) | VRITCYLTWSPCPNCAQELAAFKRDR |
| Microtus ochrogaster A3B(266-338) | (23) | ERITCYLTWSPCPNCAQELAAFKRDR |
| Nannospalax galili A3(231-302) | (23) | VQITCYITWSPCPTCAQELAAFKQDR |
| Meriones unguiculatus A3(233-305) | (23) | AQITCYLTWSPCRKCAQELATFKKDR |
| Dipodomys ordii A3(256-330) | (26) | YQITCYLTWSPCLDCAFKLAKLKKDF |
| Jaculus jaculus A3(303-374) | (23) | ALITCYLTWSPCLDCSQKLAALKRDH |
| Chinchilla lanigera A3H(86-161) | (27) | RQITCFLTWSPCPSCAQELASFKRAH |
| Heterocephalus glaber A3(277-350) | (25) | YQVTCFLTWSPCPHCAQELVSFKRAH |
| Octodon degus A3(256-329) | (25) | YQITCFLTWSPCPFCAQELASFKQIH |
| Urocitellus parryii A3(256-330) | (26) | YEVTCYLTWSPCPDCAQELVALTRSH |
| Aotus nancymaae A3H(75-146) | (23) | YEVTCYLTWSPCPSCAQKLAAFTKAQ |
| Cebus capucinus imitator A3H(55-126) | (23) | YEVTCYLTWSPCPSCAQRLVAFAKAQ |
| Saimiri boliviensis boliviensis A3H(56-125) | (21) | YDVTCYLTWSPCPSCAQKLAAFAKAQ |
| Homo sapiens A3H(49-123) | (26) | YQVTCYLTWSPCSSCAWELVDFIKAH |
| Homo sapiens A8P10(48-123) | (27) | YQVTCYLTWSPCSSCAWELVDFIKAH |
| Pan paniscus A3H(49-123) | (26) | YQVTCYLTWSPCSSCAWKLVDFIQAH |
| Symphalangus syndactylus A3H(49-123) | (26) | YQVTCYLTWSPCSSCAWELVDFIKAH |
| Macaca mulatta A3H(49-123) | (26) | YQVTCYLTWSPCSSCAGELVDFIKAH |
| Theropithecus gelada A3H(54-128) | (26) | YQVTCYLTWSPCSSCAGELVDFIKAH |
| Mandrillus leucophaeus A3H(49-123) | (26) | YQVTCYLTWSPCSSCARELVDFIKAH |
| Bos grunniens A3(74-148) | (26) | YKIICYITWSPCPNCANELVNFITRH |
| Bubalus bubalis A3(74-148) | (26) | YKIICYITWSPCPNCASELVDFITRH |
| Odocoileus virginianus texanus A3H(209-283) | (26) | YKIICYITWSPCPRCASELVDFITGH |
| Sus scrofa A3(51-125) | (26) | YRIICYVTWSPCHNCAKELVDFISHH |
| Ceratotherium simum simum A3B(232-306) | (26) | YEITCYITWSPCPTCALELVAFTRDY |
| Equus caballus A3H(79-153) | (26) | YEITCYVTWSPCATCACKLIKFTRKT |
| Enhydra lutris kenyoni A3B(243-316) | (25) | FEITCYLTWSPCPTCAKELAMFVCDH |
| Leptonychotes weddellii A3H(50-123) | (25) | FEITCYVTWSPCPTCAKELVAFVRDH |
| Ursus arctos horribilis A3F(552-626) | (26) | FEITCYVTWSPCFTCAEELVAFVRDH |
| Panthera leo bleyenberghi A3H(50-124) | (26) | FEIICYITWSPCPFCAEELVAFVRDH |
| Panthera tigris sumatrae A3H(50-124) | (26) | FEIICYITWSPCPFCAEELVAFVKDH |
| Tupaia belangeri A3(46-120) | (26) | HQLTCYLTWSPCPSCAQELVTFMAES |
| Consensus | (27) | Y ITCYLTWSPCP CA ELAAF KDH |

FIG. 39B

```
                                                                              Section 3
                                              (53) 53          60              77    SEQ ID NO:
             Mus musculus A3(282-355) (50)        PDLILHIYTSRLYFHWKRPFQKGLC     48
              Mus spicilegus A3(248-321) (50)     PDLIPHIYTSRLYFHWKRPFQKGLC     49
          Cricetulus longicaudatus A3(249-322)(50) PDLILHIYTSRLYFHWKRPFQKGLC    50
              Mus terricolor A3(248-321) (50)     PDLILHIYTSRLYFHWKRPFQKGLC     51
                   Mus caroli A3(260-333) (50)    PDLILRIYTSRLYFHWKRPFQKGLC     52
                  Mus pahari A3(263-336) (50)     PDLILHIYTSRLYFHWRRIFQKGLC     53
              Mus shortridgei A3(233-306) (50)    PDLILHIYTSRLYFHWRRIFQKGLC     54
               Mus setulosus A3(229-302) (50)     PDLILHIYTSRLYFHWKRAFQEGLC     55
          Grammomys surdaster A3(270-344) (51)    PGLILRIYTSRLYFYWRKFQKGLC      56
             Rattus norvegicus A3(256-328) (49)   PDLILRIYTSRLYFYWRKKFQKGLC     57
            Mastomys coucha A3(258-331) (50)      PDLILRIYASRLYFHWRRAFQKGLC     58
          Cricetulus griseus A3B(235-307) (49)    PDLVLRIYTSRLYFHWRRRYQEGLC     59
          Peromyscus leucopus A3(266-338) (49)    PDLVLRVYTSRLYFHWRRKYQEGLC     60
         Mesocricetus auratus A3(268-340) (49)    PDLVLRIYTSRLYFHWRRRYQEGLC     61
         Microtus ochrogaster A3B(266-338) (49)   PGLVLRIYASRLYFHWRRKYQEGLC     62
            Nannospalax galili A3(231-302) (49)   PDLVLRIYASRLYFHWKRKFQKGL-     63
        Meriones unguiculatus A3(233-305) (49)    PDLVLRVYASRLYFHWSRKYQQGLC     64
               Dipodomys ordii A3(256-330) (52)   PDLTLRIFTSRLYFHWIRKFQKGL-     65
              Jaculus jaculus A3(303-374) (49)    PGLTLRIFTSRLYFHWVKKFQEGL-     66
            Chinchilla lanigera A3H(86-161) (53)  PHLRFQIFVSRLYFHWERSYQAGL-     67
        Heterocephalus glaber A3(277-350) (51)    PHLRICIFTARLFFHWERSYQEGL-     68
                 Octodon degus A3(256-329) (51)   PRVHLQIFVSRLYFHWERSYQEGL-     69
              Urocitellus parryii A3(256-330) (52) PHVRIRIFTSRLYFHWFWSFQEGL-    70
            Aotus nancymaae A3H(75-146) (49)      VHLNLRIFASRLYTHWRSSYQKGL-     71
         Cebus capucinus imitator A3H(55-126) (49) DHLNLRIFASRLYYHWRRRYREGL-    72
    Saimiri boliviensis boliviensis A3H(56-125) (47) DHLNLRIFASRLYTHWRRSYQKGL-  73
               Homo sapiens A3H(49-123) (52)      DHLNLGIFASRLYTHWCKFQQKGL-     74
              Homo sapiens ARP10(48-123) (53)     DHLNLGIFASRLYTHWCKPQQKGL-     75
                  Pan paniscus A3H(49-123) (52)   DHLNLRIFASRLYTHWCKFQQEGL-     76
      Symphalangus syndactylus A3H(49-123) (52)   DHLNLGIFASRLYTHWCRHQQEGL-     77
              Macaca mulatta A3H(49-123) (52)     RHLNLRIFASRLYYHWRFNYQEGL-     78
        Theropithecus gelada A3H(54-128) (52)     HHLNLRIFASRLYYHWRPNYQEGL-     79
       Mandrillus leucophaeus A3H(49-123) (52)    RHLNLRIFASRLYYHWRFHYQEGL-     80
                Bos grunniens A3(74-148) (52)     NHLKLRIFASRLYFHWIKPFKMGL-     81
                Bubalus bubalis A3(74-146) (52)   DHLDLQIFASRLYFHWIKPFKRGL-     82
      Odocoileus virginianus texanus A3H(209-283) (52) DHLNLQIFASRLYFHWKKPFQRGL- 83
                  Sus scrofa A3(51-125) (52)      HHLSLQLFASRLYFHWVRCYQRGL-     84
      Ceratotherium simum simum A3B(232-306) (52) PHLSLQIFASRLYFHWRHRSIQGL-     85
                Equus caballus A3H(79-153) (52)   PHLSLRIFVSRLYTHWFRQNQQGL-     86
         Enhydra lutris kenyoni A3B(243-316) (51) PHISLRLFASRLYFHWRWKYQEGL-     87
        Leptonychotes weddellii A3H(50-123) (51)  RHISLRLFASRLYFHWLRENKKGL-     88
         Ursus arctos horribilis A3F(552-626) (52) PHVRLRLFASRLYFHWLRKYQEGL-    89
       Panthera leo bleyenberghi A3H(50-124) (52) PHLSLRIFASRLYVHWRWKYQQGL-     90
       Panthera tigris sumatrae A3H(50-124) (52)  PHLSLRIFASRLYVHWRWKYQQGL-     91
                Tupaia belangeri A3(46-120) (52)  RHLNLCVFVSRLYFHWCRDFQQGL-     92
                            Consensus (53)        PHL LRIFASRLYFHWRR  FQ GL
```

FIG. 39C

Section 1

|   | (1) 1        10        20        30        41 |
|---|---|
| Homo sapiens A3B(29-138) | (1) GRSYTWLCYEVKIKRGRSNLLWDTGVFRGQV---------- |
| Gorilla A3B(29-138) | (1) GRSYTWLCYEVKIKRGRSNLLWNTGVFRGQM---------- |
| Pan paniscus A3B(29-138) | (1) GRSYTWLCYEVKIRRGHSNLLWDTGVFRGQM---------- |
| Pan troglodytes A3B(29-138) | (1) GRSYTWLCYEVKIRRGHSNLLWDTGVFRGQM---------- |
| Gorilla A3F(30-127) | (1) -RNTVWLCYEVKTK-GRSRPPLDAKIFRGQV---------- |
| Pan troglodytes A3F(30-137) | (1) -RNTVWLCYEVKTK-GPSRPRLDYKIFRGQV---------- |
| Homo sapiens A3F(30-137) | (1) -RNTVWLCYEVKTK-GPSRPRLDAKIFRGQV---------- |
| Macaca leonina A3F(30-137) | (1) -RNTVWLCYEVKTR-GPSMPTWGTKIFRGQV---------- |
| Macaca nemestrina A3F(30-137) | (1) -RNTVWLCYEVKTR-GPSMPTWGTKIFRGQV---------- |
| Rhinopithecus roxellana A3F(30-137) | (1) -RNTVWLCYEVKTR-GPSMPTWDAKIFRGQV---------- |
| Mandrillus leucophaeus A3F(30-130) | (1) -RNTVWLCYEVKTR-GPSMPTWGTKIFRGQV---------- |
| Macaca mulatta A3F(30-137) | (1) -RNTVWLCYEVKTR-GPSMPTWDTKIFRGQV---------- |
| Theropithecus gelada A3F(30-137) | (1) -RNTVWLCYEVKTR-GPSMPTWGTKIFRGQV---------- |
| Cercocebus atys A3B(29-138) | (1) GRSYTWLCYEVKIRKDPSKLPWYTGVFRGQV---------- |
| Macaca fascicularis A3B(29-138) | (1) GRSYTWLCYEVKIRKDPSKLPWDTGVFRGQV---------- |
| Macaca mulatta A3B(29-138) | (1) GRSYTWLCYEVKIRKDPSKLPWDTGVFRGQV---------- |
| Macaca leonina A3B(29-138) | (1) GRSYTWLCYEVKIRKDPSKLPWDTGVFRGQV---------- |
| Mandrillus leucophaeus A3B(29-138) | (1) GRSYTWLCYEVKIRKDPSKLPWYTGVFRGQV---------- |
| Macaca nemestrina A3B(29-138) | (1) GRSYTWLCYEVKIRKDPSKLPWDTGVFRGQV---------- |
| Rhinopithecus bieti A3F(29-138) | (1) GRSYTWLCYEVKIRKDPSKLPWDTGVFRGQV---------- |
| Rhinopithecus roxellana A3B(29-138) | (1) GRSYTWLCYEVKIRKDPSKLPWDTGVFRGQV---------- |
| Chlorocebus sabaeus A3B(29-138) | (1) GRSYTWLCYEVKIRKDPSKLPWDTGVFRGQM---------- |
| Nomascus leucogenys A3B(30-138) | (1) -RSYTWLCYEVKIRKDPSKLPWDTGVFRGQM---------- |
| Cercocebus atys A3F(29-138) | (1) GRSYTWLCYEVKIKKYPSKLLWDTGVFCGQV---------- |
| Papio anubis A3F(29-138) | (1) GRSYTWLCYEVKIKEDPSKLLWDTGVFCGQV---------- |
| Chlorocebus aethiops A3D(29-150) | (1) GRRYTWLCYEVKIRKDPSKLPWDTGVFPGQVRPKFQSNR-- |
| Chlorocebus sabaeus A3D(29-134) | (1) GRRYTWLCYEVKIRKDPSKLPWDTGVFPGQP---------- |
| Chlorocebus sabaeus A3F(29-150) | (1) GRRYTWLCYEVKIRKDPSKLPWDTGVFPGQVRPKFQSNR-- |
| Erythrocebus patas A3D(29-150) | (1) GRRYTWLCYEVKIRKDPSKLPWDTGVFCGQVRPKFQSNR-- |
| Macaca fascicularis A3D(29-159) | (1) GRSYTWLCYEVKIRKDPSKLPWDTGVFRGQVRPKLQSNRRY |
| Macaca fascicularis A3F(29-138) | (1) GRSYTWLCYEVKIRKDPSKLPWDTGVFRGQV---------- |
| Macaca nemestrina A3D(29-138) | (1) GRSYTWLCYEVKIRKDPSKLPWDTGVFRLQV---------- |
| Macaca leonina A3D(29-138) | (1) GRSYTWLCYEVKIRKDPSKLPWYTGVFRGQV---------- |
| Macaca mulatta A3D(29-138) | (1) GRSYTWLCYEVKIRKDPSKLPWDTGVFRGQV---------- |
| Gorilla A3D(29-150) | (1) GRSYTWLCYEVKIRRGRSNLLWNTGVFRGPVPPKLQSN--- |
| Pan paniscus A3D(29-150) | (1) GRSYTWLCYEVKIRRGCSNLIWDTGVFRGPVLPKLQSN--- |
| Pan troglodytes A3D(29-150) | (1) GRSYTWLCYEVKIKRGCSNLIWDTGVFRGPVLPKLQSN--- |
| Homo sapiens A3D(29-150) | (1) GRSYTWLCYEVKIKRGRSNLLWDTGVFRGPVLPKQSN--- |
| Nomascus leucogenys A3D(29-150) | (1) GRSYTWLCYEVKIRKDPSKLPWDKGVFRQVLPKFQSN--- |
| Saimiri boliviensis A3C(29-138) | (1) GKRYTWLCYEVKIRKDTSKLPWNTGVFRGQVN-------- |
| Saimiri boliviensis A3F(29-138) | (1) GKRYTWLCYEVKIRKDTSKLPWNTGVFRGQVN-------- |
| Piliocolobus tephrosceles A3F(36-145) | (1) GRRYTWLCYEVKIMRDHPKLPWYTGVFRGQV---------- |
| Colobus angolensis palliatus A3F(29-138) | (1) GRRYTWLCYEVKISRDPSKLPWDTGIFRGQV---------- |
| Pongo abelii A3F(30-150) | (1) -RSYTWLCYEVKIRKDPSKLAWDTGVFRGQVLPKLQSN--- |
| Consensus | (1) GRSYTWLCYEVKIRKDPSKLPWDTGVFRGQV |

FIG. 40A

| | | Section 2 |
|---|---|---|
| | (42) 42 50 60 70 82 | |

| | | |
|---|---|---|
| Homo sapiens A3B(29-138) | (32) | ----------YFKPQYHAEMCFLSWFCGNQLPAYKCFQIT |
| Gorilla A3B(29-138) | (32) | ----------YSQPEHHAEMCFLSWFCGNQLPAYKCFQIT |
| Pan paniscus A3B(29-138) | (32) | ----------YSQPEHHAEMYFLSWFCGNQLPAYKCFQIT |
| Pan troglodytes A3B(29-138) | (32) | ----------YSQPEHHAEMCFLSWFCGNQLSAYKCFQIT |
| Gorilla A3F(30-127) | (30) | ----------YFEPQYHAEMCFLSWFCGNQLPAYKCFQIT |
| Pan troglodytes A3F(30-137) | (30) | ----------YFEPQYHAEMCFLSWFCGNQLPAYKCFQIT |
| Homo sapiens A3F(30-137) | (30) | ----------YSQPEHHAEMCFLSWFCGNQLPAYKCFQIT |
| Macaca leonina A3F(30-137) | (30) | ----------CFEPQYHAEMCFLSRFCGNQLPAYKRFQIT |
| Macaca nemestrina A3F(30-137) | (30) | ----------CFEPQYHAEMCFLSRFCGNQLPAYKRFQIT |
| Rhinopithecus roxellana A3F(30-137) | (30) | ----------YFEPQYHAEMCFLSWFCGNQLPAYKRFQIT |
| Mandrillus leucophaeus A3F(30-130) | (30) | ----------YFQPQYHAEMCFLSWFCGNQLPAYERFQIT |
| Macaca mulatta A3F(30-137) | (30) | ----------YSKPEHHAEMCFLSRFCGNQLPAYKRFQIT |
| Theropithecus gelada A3F(30-137) | (30) | ----------YFQPQYHAEMCFLSRFCGNQLPAYKRFQIT |
| Cercocebus atys A3B(29-138) | (32) | ----------YSEPEHHAEMCFLSRFCGNQLPAYKRFQIT |
| Macaca fascicularis A3B(29-138) | (32) | ----------YSKPEHHAEMCFLSRFCGNQLPAYKRFQIT |
| Macaca mulatta A3B(29-138) | (32) | ----------YSKPEHHAEMCFLSRFCGNQLPAYKRFQIT |
| Macaca leonina A3B(29-138) | (32) | ----------YSKPEHHAEMCFLSRFCGNQLPAYKRFQIT |
| Mandrillus leucophaeus A3B(29-138) | (32) | ----------YSFPEHHAEMCFLSRFCGNQLPAYKRFQIT |
| Macaca nemestrina A3B(29-138) | (32) | ----------YSKPEHHAEMCFLSRFCGNQLPAYKRFQIT |
| Rhinopithecus bieti A3F(29-138) | (32) | ----------YSEPEHHAEMYFLSWFCGNQLPAYKRFQIT |
| Rhinopithecus roxellana A3B(29-138) | (32) | ----------YSEPEHHAEMYFLSWFCGNQLPAYERFQIT |
| Chlorocebus sabaeus A3B(29-138) | (32) | ----------YSKPEHHAEMCFLSWFCGNQLPAHKRFQIT |
| Nomascus leucogenys A3B(30-138) | (31) | ----------YFQPEYHAEMCFLSWFCGNQLPAYKRFQIT |
| Cercocebus atys A3F(29-138) | (32) | ----------YFQPQYHAEMCFLSRFCGNQLPAYERFQIT |
| Papio anubis A3F(29-138) | (32) | ----------YFQPQYHAEMCFLSRFCGNQLPAYERFQIT |
| Chlorocebus aethiops A3D(29-150) | (40) | ------RYEVYFQPQYHAEMYFLSWFCGNQLPAYKRFQIT |
| Chlorocebus sabaeus A3D(29-134) | (32) | --------------QYHAEMYFLSWFCGNQLPAYKRFQIT |
| Chlorocebus sabaeus A3F(29-150) | (40) | ------RQEVYFQPQYHAEMYFLSWFCGNQLPAYKRFQIT |
| Erythrocebus patas A3D(29-150) | (40) | ------RYEVYFQPQYHAEMYFLSWFCGNQLPAYKRFQIT |
| Macaca fascicularis A3D(29-159) | (42) | ELSNWECRKVYFQPQYHAEMYFLSWFCGNQLPANKRFQIT |
| Macaca fascicularis A3F(29-138) | (32) | ----------YFQPQYHAEMYFLSWFCGNQLPANKRFQIT |
| Macaca nemestrina A3D(29-138) | (32) | ----------YFQPQYHAEMCFLSWFCGNQLPANKRFQIT |
| Macaca leonina A3D(29-138) | (32) | ----------YFQPQYHAEMCFLSWFCGNQLPANKRFQIT |
| Macaca mulatta A3D(29-138) | (32) | ----------YFQPQYHAEMCFLSWFCGNQLPAYKRFQIT |
| Gorilla A3D(29-150) | (39) | ------HRQEVYFQFENHAEMCFLSWFCGNKLPANRRFQIT |
| Pan paniscus A3D(29-150) | (39) | ------HRQEVYFQFENHAEMCFLSWFCGNKLPANRRFQIT |
| Pan troglodytes A3D(29-150) | (39) | ------HRQEVYFQFENHAEMCFLSWFCGNKLPANRRFQIT |
| Homo sapiens A3D(29-150) | (39) | ------HRQEVYFRFENHAEMCFLSWFCGNKLPANRRFQIT |
| Nomascus leucogenys A3D(29-150) | (39) | ------HRQEVYFQLENHAEMCFLSWFCGNQLPANRRFQIT |
| Saimiri boliviensis A3C(29-138) | (33) | ----------FNPEHHAEMYFLSWFRGKLLPACKRSQIT |
| Saimiri boliviensis A3F(29-138) | (33) | ----------FNPEHHAEMYFLSWFRGFLLPACKRSQIT |
| Piliocolobus tephrosceles A3F(36-145) | (32) | ----------YFEPQNHAEMCFLSWFCGNQLPAYCCQIT |
| Colobus angolensis palliatus A3F(29-138) | (32) | ----------YFEPQYHAEMCFLSWYCGNQLPAYKCFQIT |
| Pongo abelii A3F(30-150) | (38) | ------HRREVYFEPQYHAEMCFLSWFCGNQLSAYERFQIT |
| Consensus | (42) | YFQPQYHAEMCFLSWFCGNQLPAYKRFQIT |

Section 4

| Sequence | | 124 131 | SEQ ID NO: |
|---|---|---|---|
| Homo sapiens A3B(29-138) | (103) | YRRALCRI | 93 |
| Gorilla A3B(29-138) | (103) | YRRALCRI | 94 |
| Pan paniscus A3B(29-138) | (103) | YRRALCRI | 95 |
| Pan troglodytes A3B(29-138) | (103) | YRRALCRI | 96 |
| Gorilla A3F(30-127) | (99) | -------- | 97 |
| Pan troglodytes A3F(30-137) | (101) | YRRALCRI | 98 |
| Homo sapiens A3F(30-137) | (101) | YRRALCRI | 99 |
| Macaca leonina A3F(30-137) | (101) | YRRALCRI | 100 |
| Macaca nemestrina A3F(30-137) | (101) | YRRALCRI | 101 |
| Rhinopithecus roxellana A3F(30-137) | (101) | YRRALCRI | 102 |
| Mandrillus leucophaeus A3F(30-130) | (101) | Y------- | 103 |
| Macaca mulatta A3F(30-137) | (101) | YRRALCRI | 104 |
| Theropithecus gelada A3F(30-137) | (101) | WRRALRRI | 105 |
| Cercocebus atys A3B(29-138) | (103) | WQRALCRI | 106 |
| Macaca fascicularis A3B(29-138) | (103) | WQRALCRI | 107 |
| Macaca mulatta A3B(29-138) | (103) | WQRALCRI | 108 |
| Macaca leonina A3B(29-138) | (103) | WQRALCRI | 109 |
| Mandrillus leucophaeus A3B(29-138) | (103) | WQRALCRI | 110 |
| Macaca nemestrina A3B(29-138) | (103) | WQRALCRI | 111 |
| Rhinopithecus bieti A3F(29-136) | (103) | WRRALCRI | 112 |
| Rhinopithecus roxellana A3B(29-138) | (103) | WRRALCRI | 113 |
| Chlorocebus sabaeus A3B(29-138) | (103) | YRRALCRI | 114 |
| Nomascus leucogenys A3B(30-136) | (102) | WQRALCRI | 115 |
| Cercocebus atys A3F(29-138) | (103) | XRRALRRI | 116 |
| Papio anubis A3F(29-138) | (103) | WRRALRRI | 117 |
| Chlorocebus aethiops A3D(29-150) | (115) | WRRALCRI | 118 |
| Chlorocebus sabaeus A3D(29-134) | (99) | WRRALCRI | 119 |
| Chlorocebus sabaeus A3F(29-150) | (115) | WRRALCRI | 120 |
| Erythrocebus patas A3D(29-150) | (115) | WRRALCRI | 121 |
| Macaca fascicularis A3D(29-159) | (124) | WRRALRPI | 122 |
| Macaca fascicularis A3F(29-136) | (103) | WRRALRRI | 123 |
| Macaca nemestrina A3D(29-138) | (103) | WRRALRPI | 124 |
| Macaca leonina A3D(29-138) | (103) | WRRALRPI | 125 |
| Macaca mulatta A3D(29-138) | (103) | WRRALCRI | 126 |
| Gorilla A3D(29-150) | (115) | WRRVLRRI | 127 |
| Pan paniscus A3D(29-150) | (115) | WRRVLRRI | 128 |
| Pan troglodytes A3D(29-150) | (115) | WRRVLRRI | 129 |
| Homo sapiens A3D(29-150) | (115) | WRWVLLRI | 130 |
| Nomascus leucogenys A3D(29-150) | (115) | WRRALRRI | 131 |
| Saimiri boliviensis A3C(29-138) | (103) | WRRALRKI | 132 |
| Saimiri boliviensis A3F(29-138) | (103) | WRRALRKI | 133 |
| Piliocolobus tephrosceles A3F(36-145) | (103) | WRRALRPI | 134 |
| Colobus angolensis palliatus A3F(29-136) | (103) | YRRALCRI | 135 |
| Pongo abelii A3F(30-150) | (114) | YRGALRRI | |
| Consensus | (124) | WRRALCRL | |

FIG. 40D

INHIBITION OF UNINTENDED MUTATIONS IN GENE EDITING

CROSS-REFERENCE TO RELATED PATENT APPLICATIONS

This application is a U.S. National Stage Application under 35 U.S.C. § 371 of International Application No. PCT/CN2020/074218, filed Feb. 3, 2020, which claims the priority to PCT/CN2019/074577, filed on Feb. 2, 2019, the contents of which are hereby incorporated by reference in their entirety into the present disclosure.

SEQUENCE LISTING

The instant application contains a Sequence Listing which has been submitted electronically in ASCII format and is hereby incorporated by reference in its entirety. Said ASCII copy, created on Apr. 30, 2022, is named 292057SL.txt and is 201,863 bytes in size.

BACKGROUND

Genome editing is a type of genetic engineering in which DNA is inserted, deleted or replaced in the genome of a living organism using engineered nucleases (molecular scissors). Utilizing genome editing tools to genetically manipulate the genome of cells and living organism has broad applications in life sciences researches, biotechnology/agricultural technology development and most importantly pharmaceutical/clinical innovations. For example, genome editing can be used to correct the driver mutations underlying genetic diseases and leading to complete cure of these diseases in living organisms. Genome editing can also be used to engineer the genome of crops, increasing the yield of crops and conferring crops resistance to environmental contamination or pathogen infection. In addition, microbial genome transformation through accurate genome editing is of great significance in the development of renewable bio-energy.

CRISPR/Cas (Clustered regularly interspaced short palindromic repeats/CRISPR-associated protein) system has been the most powerful genomic editing tool since its conception for its unparalleled editing efficiency, convenience and the potential applications in living organisms. Directed by a guide RNA (gRNA), the Cas nuclease can generate DNA double strand breaks (DSBs) at the targeted genomic sites in various cells (both cell lines and cells from living organisms). These DSBs are then repaired by the endogenous DNA repair system, which could be utilized to perform desired genome editing.

In general, two major DNA repair pathways can be activated by DSBs, non-homologous end joining (NHEJ) and homology-directed repair (HDR). NHEJ can introduce random insertions/deletions (indels) in the genomic DNA region around the DSBs, leading to open reading frame (ORF) shift and ultimately gene inactivation. In contrast, when HDR is triggered, the genomic DNA sequence at the target site can be replaced by the sequence of the exogenous donor DNA template through a homologous recombination mechanism, which can result in the correction of genetic mutation. However, the practical efficiency of HDR-mediated gene correction is low (normally <5%) because the occurrence of homologous recombination is both cell type-specific and cell cycle-dependent and NHEJ is triggered more frequently than HDR is. The relatively low efficiency of HDR therefore limited the translation of CRISPR/Cas genome editing tools in the field of precision gene therapy (diseases-driven gene correction).

Base editors (BE), which integrate the CRISPR/Cas system with the APOBEC (apolipoprotein B mRNA editing enzyme, catalytic polypeptide-like) AID (activation-induced cytidine deaminase) family, was recently developed that greatly enhanced the efficiency of CRISPR/Cas-meditated gene correction. Through the fusion with the Cas9 nickase (nCas9) or a catalytically dead Cpf1 (dCpf1 also known as dCas12a), the cytosine (C) deamination activity of APOBEC/AID family members can be purposely directed to the target bases in the genome and to catalyze C to Thymine (T) substitutions at these bases.

However, as APOBEC/AID family members can induce C-to-T base substitution mutations in single-stranded DNA (ssDNA) regions, the specificity of the current base editing system is compromised, thereby limiting the applications, for instance, using BEs to restore the T-to-C mutation that result in human diseases for therapeutic purposes. Hence, creating novel BEs that can specifically edit cytosines in target region but not cause C-to-T mutations in other ssDNA regions is desirable. Such novel BEs will enable us to perform more specific base editing in various living organisms. Importantly, the high specificity of such BEs will promote the potential clinical translation, particularly in the gene therapies that involve restoring disease-related T-to-C mutations.

SUMMARY

The present disclosure, in some embodiments, provides base editors useful for genome editing that cause reduced or even no off-target mutations common to current base editors. In certain embodiments, a nucleobase deaminase inhibitor is cleavably fused to a nucleobase deaminase involved for genome editing. In the presence of the nucleobase deaminase inhibitor, the nucleobase deaminase is unable to (is less able to) react with a nucleotide molecule. At a target editing location, the nucleobase deaminase inhibitor can be cleaved releasing a fully active nucleobase deaminase that can then carry out the editing as desired.

Accordingly, in one embodiment, provided is a fusion protein comprising: a first fragment comprising a nucleobase deaminase or a catalytic domain thereof, a second fragment comprising a nucleobase deaminase inhibitor, and a protease cleavage site between the first fragment and the second fragment.

In some embodiments, the nucleobase deaminase is an adenosine deaminase. In some embodiments, the adenosine deaminase is selected from the group consisting of tRNA-specific adenosine deaminase (TadA), adenosine deaminase tRNA specific 1 (ADAT1), adenosine deaminase tRNA specific 2 (ADAT2), adenosine deaminase tRNA specific 3 (ADAT3), adenosine deaminase RNA specific B1 (ADARB1), adenosine deaminase RNA specific B2 (ADARB2), adenosine monophosphate deaminase 1 (AMPD1), adenosine monophosphate deaminase 2 (AMPD2), adenosine monophosphate deaminase 3 (AMPD3), adenosine deaminase (ADA), adenosine deaminase 2 (ADA2), adenosine deaminase like (ADAL), adenosine deaminase domain containing 1 (ADAD1), adenosine deaminase domain containing 2 (ADAD2), adenosine deaminase RNA specific (ADAR) and adenosine deaminase RNA specific B1 (ADARB1).

In some embodiments, the nucleobase deaminase is a cytidine deaminase. In some embodiments, the cytidine deaminase is selected from the group consisting of APOBEC3B (A3B), APOBEC3C (A3C), APOBEC3D (A3D), APOBEC3F (A3F), APOBEC3G (A3G), APOBEC3H (A3H), APOBEC1 (A1), APOBEC3 (A3), APOBEC2 (A2), APOBEC4 (A4) and AICDA (AID). In some embodiments, the cytidine deaminase is a human or mouse cytidine deaminase. In some embodiments, the catalytic domain is mouse A3 cytidine deaminase domain 1 (CDA1) or human A3B cytidine deaminase domain 2 (CDA2).

In some embodiments, the nucleobase deaminase inhibitor is an inhibitory domain of a nucleobase deaminase. In some embodiments, the nucleobase deaminase inhibitor is an inhibitory domain of a is a cytidine deaminase. In some embodiments, the nucleobase deaminase inhibitor is an inhibitory domain of an adenosine deaminase. In some embodiments, the nucleobase deaminase inhibitor comprises an amino acid sequence selected from SEQ ID NO: 1-2 and Tables 1 and 2 (SEQ ID NO: 48-135), or an amino acid sequence having at least 85% sequence identity to any of the amino acid sequence selected from SEQ ID NO: 1-2 and Tables 1 and 2. In some embodiments, the nucleobase deaminase inhibitor comprises the amino acid sequence of SEQ ID NO:1, amino acids residues AA76-AA149 of SEQ ID NO:1 or the amino acid sequence of SEQ ID NO:2.

In some embodiments, the first fragment further comprises a clustered regularly interspaced short palindromic repeats (CRISPR)-associated (Cas) protein. In some embodiments, the Cas protein is selected from the group consisting of SpCas9, FnCas9, St1Cas9, St3Cas9, NmCas9, SaCas9, AsCpf1, LbCpf1, FnCpf1, VQR SpCas9, EQR SpCas9, VRER SpCas9, xSpCas9, SpCas9-NG, RHA FnCas9, KKH SaCas9, NmeCas9, StCas9, CjCas9, AsCpf1, FnCpf1, SsCpf1, PcCpf1, BpCpf1, CmtCpf1, LiCpf1, PmCpf1, Pb3310Cpf1, Pb4417Cpf1, BsCpf1, EeCpf1, BhCas12b, AkCas12b, EbCas12b, LsCas12b, RfCas13d, LwaCas13a, PspCas13b, PguCas13b, and RanCas13b.

In some embodiments, the protease cleavage site is a protease cleavage site a protease selected from the group consisting of TuMV protease, PPV protease, PVY protease, ZIKV protease and WNV protease.

In some embodiments, the protease cleavage site is a self-cleavage site. In some embodiments, the protease cleavage site is a TEV protease cleavage site. In some embodiments, the fusion protein further comprises a third fragment comprising a TEV protease or a fragment thereof. In some embodiments, the third fragment comprises a TEV protease fragment which alone is not able to cleave the TEV protease cleavage site.

Also provided, in another embodiment, is a fusion protein comprising: a first fragment comprising a cytidine deaminase or a catalytic domain thereof, a clustered regularly interspaced short palindromic repeats (CRISPR)-associated (Cas) protein, and a first TEV protease fragment, a second fragment comprising a cytidine deaminase inhibitor, and a TEV protease cleavage site between the first fragment and the second fragment, wherein the first TEV protease fragment alone is not able to cleave the TEV protease cleavage site.

In some embodiments, the fusion protein further comprises a uracil glycosylase inhibitor (UGI). In some embodiments, the cytidine deaminase inhibitor, the TEV protease cleavage site, the cytidine deaminase or a catalytic domain thereof, the Cas protein, and the first TEV protease fragment are arranged from the N-terminus to the C-terminus. In some embodiments, the first TEV protease fragment is the N-terminal domain (SEQ ID NO:3) or the C-terminal domain (SEQ ID NO:4) of the TEV protease. In some embodiments, the TEV protease cleavage site has the amino acid sequence of SEQ ID NO:5.

Further provided, in one embodiment, is a method for conducting genomic editing in a cell at a target site, comprising introducing to the cell: (a) a fusion protein of the present disclosure, (b) a guide RNA that targets the target site or a crRNA that targets the target site and a tracrRNA, and further comprises a tag sequence, and (c) a second TEV protease fragment coupled to an RNA recognition peptide that is able to bind the tag sequence.

In some embodiments, one or more of the molecules is introduced to the cell by a polynucleotide encoding the molecule. In some embodiments, the first TEV protease fragment and the second TEV protease fragment, when in interaction, are able to cleave the TEV protease cleavage site. In some embodiments, the second TEV protease fragment is fused to the RNA recognition peptide.

In some embodiments, the tag sequence comprises a MS2 sequence (SEQ ID NO:16). In some embodiments, the RNA recognition peptide comprises a MS2 coat protein (MCP, SEQ ID NO:22). In some embodiments, the tag sequence comprises a PP7 sequence (SEQ ID NO:18) and the RNA recognition peptide comprises a PP7 coat protein (PCP, SEQ ID NO: 23), or the tag sequence comprises a boxB sequence (SEQ ID NO:20) and the RNA recognition peptide comprises a boxB coat protein (N22p, SEQ ID NO:24).

Also provided, in one embodiment, is a kit or package for conducting gene editing, comprising: (a) a fusion protein of the present disclosure, and (b) a second TEV protease fragment coupled to an RNA recognition peptide that is able to bind an RNA sequence.

Yet another embodiment provides a fusion protein comprising: a first fragment comprising first cytidine deaminase or a catalytic domain thereof, and a second fragment comprising an inhibitory domain of a second cytidine deaminase, wherein the first cytidine deaminase is same as or different from the second cytidine deaminase.

In another embodiment, a fusion protein is provided comprising a first fragment comprising: a nucleobase deaminase or a catalytic domain thereof, a nucleobase deaminase inhibitor, a first RNA recognition peptide, and a TEV protease cleavage site between the nucleobase deaminase or a catalytic domain thereof and the nucleobase deaminase inhibitor.

In some embodiments, the fusion protein further comprises a second fragment comprising: a TEV protease fragment which alone is not able to cleave the TEV protease cleavage site, and a second RNA recognition peptide. In some embodiments, the fusion protein further comprises a self-cleavage site between the first fragment and the second fragment.

In some embodiments, the fusion protein further comprises a third fragment comprising a second TEV protease fragment, wherein the first TEV protease fragment is able to cleave the TEV protease site in the presence of the second TEV protease fragment. In some embodiments, the fusion protein further comprises a second self-cleavage site between the second fragment and the third fragment, ad upon cleavage of the second self-cleavage site, the fusion protein releases the second TEV protease fragment which is not fused to any RNA recognition peptide.

Also provided, in one embodiment, is a dual guide RNA system, comprising: a target single guide RNA comprising a first spacer having sequence complementarity to a target nucleic acid sequence proximate to a first PAM site, a helper single guide RNA comprising a second spacer having sequence complementarity to a second nucleic acid sequence proximate to a second PAM site, a clustered regularly interspaced short palindromic repeats (CRISPR)-associated (Cas) protein, and a nucleobase deaminase, wherein the second PAM site is from 34 to 91 bases from the first PAM site. In some embodiments, the second spacer is 8-15 bases in length. In some embodiments, the second spacer is 9-12 bases in length.

In one embodiment, provided is guide RNA comprising a scaffold which comprises, from the 5' to 3' direction, a first stem loop portion, a second stem loop portion, a third stem loop portion, and a fourth stem loop portion, wherein the third stem loop comprises five base pairings within. In another embodiment, the present disclosure provides a guide RNA comprising a scaffold derived from SEQ ID NO:31 by introducing a base pairing between the bases at positions 45 and 55. In some embodiments, the scaffold comprises a sequence selected from the group consisting of SEQ ID NO:32-43. In some embodiments, the guide RNA is at least 100, or 120 nucleotides in length.

Another embodiment provides a method for conducting genetic editing in a cell at a target site, comprising introducing to the cell: a first viral particle enclosing a first construct encoding a clustered regularly interspaced short palindromic repeats (CRISPR)-associated (Cas) protein, and a second viral particle enclosing a second construct encoding a reverse-transcriptase fused to an RNA recognition peptide.

In some embodiments, the second construct further encodes a guide RNA comprising an RNA recognition site that the RNA recognition peptide binds to. In some embodiments, the Cas protein is SpCas9-NG (SEQ ID NO:46) or xSpCas9 (SEQ ID NO:47).

Polynucleotides encoding the fusion proteins of the present disclosure, constructs containing the polynucleotides, cells containing the polynucleotides or the constructs, and compositions comprising any of the above are also provided, without limitation.

BRIEF DESCRIPTION OF THE DRAWINGS

FIG. 1A-C: Unintended base substitutions caused by current BEs in Sa-SITE31 ssDNA region. 1A: Schematic diagram illustrating the co-expression of SaD10A nickase and Sa-sgSITE31 to trigger the formation of ssDNA region at Sa-sgSITE31 on-target site. 1B: Schematic diagram illustrating the co-transfection of the plasmid expressing Sa-sgSITE31 and the plasmid expressing SaD10A nickase with the plasmid expressing BE3, the plasmid expressing hA3A-BE3 or an empty vector. 1C: The untended base substitutions caused by BE3 and hA3A-BE3. Dashed boxes represent the locations of untended base substitutions at Sa-sgSITE31 target site. The sequences shown in FIG. 1C, from top to bottom, have the sequences of SEQ ID NO: 204, 204 and 205, respectively.

FIG. 2A-C: Unintended base substitutions caused by current BEs in Sa-SITE42 ssDNA region. 2A: Schematic diagram illustrating the co-expression of SaD10A nickase and Sa-sgSITE42 to trigger the formation of ssDNA region at Sa-sgSITE42 on-target site. 2B: Schematic diagram illustrating the co-transfection of the plasmid expressing Sa-sgSITE42 and the plasmid expressing SaD10A nickase with the plasmid expressing BE3, the plasmid expressing hA3A-BE3 or an empty vector. 2C: The untended base substitutions caused by BE3 and hA3A-BE3. Dashed boxes represent the locations of untended base substitutions at Sa-sgSITE42 target site. The sequences shown in FIG. 2C, from top to bottom, have the sequences of SEQ ID NO: 206, 206 and 207, respectively.

FIG. 3A-C: Unintended base substitutions caused by current BEs in Sa-F1 ssDNA region. 3A: Schematic diagram illustrating the co-expression of SaD10A nickase and Sa-sgF1 to trigger the formation of ssDNA region at Sa-sgF1 on-target site. 3B: Schematic diagram illustrating the co-transfection of the plasmid expressing Sa-sgF1 and the plasmid expressing SaD10A nickase with the plasmid expressing BE3, the plasmid expressing hA3A-BE3 or an empty vector. 3C: The untended base substitutions caused by BE3 and hA3A-BE3. Dashed boxes represent the locations of untended base substitutions at Sa-sgF1 target site. The sequences shown in FIG. 3C have the sequence of SEQ ID NO: 208.

FIG. 4A-C: mA3CDA2 inhibits C-to-T base editing activity in TET1 region. 4A: Schematic diagram illustrating the regions of CDA domains in mA3, rA1 and hA3A. 4B: Schematic diagram illustrating the co-transfection of the plasmid expressing sgTET1 with the plasmid expressing mA3-BE3, the plasmid expressing mA3CDA1-BE3, the plasmid expressing mA3rev-BE3, the plasmid expressing mA3rev-2A-BE3, the plasmid expressing BE3, the plasmid expressing mA3CDA2-BE3, the plasmid expressing mA3CDA2-2A-BE3, the plasmid expressing hA3A-BE3, the plasmid expressing mA3CDA2-hA3A-BE3 or the plasmid expressing mA3CDA2-2A-hA3A-BE3. 4C: mA3CDA2 inhibits C-to-T editing activity of mA3CDA1-BE3, BE3 and hA3A-BE3. Dashed boxes represent the locations of C-to-T base editing at sgTET1 target site. The sequences shown in FIG. 4C, from top to bottom, have the sequences of SEQ ID NO: 209, 209, 209, 209, 209, 209, 209, 209, 209, and 210, respectively.

FIG. 5A-C: mA3CDA2 inhibits C-to-T base editing activity in RNF2 region. 5A: Schematic diagram illustrating the regions of CDA domains in mA3, rA1 and hA3A. 5B: Schematic diagram illustrating the co-transfection of the plasmid expressing sgRNF2 with the plasmid expressing mA3-BE3, the plasmid expressing mA3CDA1-BE3, the plasmid expressing mA3rev-BE3, the plasmid expressing mA3rev-2A-BE3, the plasmid expressing BE3, the plasmid expressing mA3CDA2-BE3, the plasmid expressing mA3CDA2-2A-BE3, the plasmid expressing hA3A-BE3, the plasmid expressing mA3CDA2-hA3A-BE3 or the plasmid expressing mA3CDA2-2A-hA3A-BE3. 5C: mA3CDA2 inhibits C-to-T editing activity of mA3CDA1-BE3, BE3 and hA3A-BE3. Dashed boxes represent the locations of C-to-T base editing at sgRNF2 target site. The sequences shown in FIG. 5C, from top to bottom, have the sequences of SEQ ID NO: 211, 211, 211, 211, 211, 211, 211, 212, 211, and 212, respectively.

FIG. 6A-C: mA3CDA2 inhibits C-to-T base editing activity in SITE3 region. 6A: Schematic diagram illustrating the regions of CDA domains in mA3, rA1 and hA3A. 6B: Schematic diagram illustrating the co-transfection of the plasmid expressing sgSITE3 with the plasmid expressing mA3-BE3, the plasmid expressing mA3CDA1-BE3, the plasmid expressing mA3rev-BE3, the plasmid expressing mA3rev-2A-BE3, the plasmid expressing BE3, the plasmid expressing mA3CDA2-BE3, the plasmid expressing mA3CDA2-2A-BE3, the plasmid expressing hA3A-BE3, the plasmid expressing mA3CDA2-hA3A-BE3 or the plasmid expressing mA3CDA2-2A-hA3A-BE3. 6C: mA3CDA2 inhibits C-to-T editing activity of mA3CDA1-BE3, BE3 and hA3A-BE3. Dashed boxes represent the locations of C-to-T base editing at sgSITE3 target site. The sequences shown in FIG. 6C, from top to bottom, have the sequences of SEQ ID NO: 213, 213, 213, 213, 214, 213, 213, 213, 213, and 213, respectively.

FIG. 7A-C: hA3BCDA1 inhibits C-to-T base editing activity in TET1 region. 7A: Schematic diagram illustrating the regions of CDA domains in hA3B. 7B: Schematic diagram illustrating the co-transfection of the plasmid expressing sgTET1 with the plasmid expressing hA3B-BE3, the plasmid expressing hA3BCDA2-BE3 or the plasmid expressing hA3B-2A-BE3. 7C: hA3BCDA1 inhibits C-to-T editing activity of hA3BCDA2-BE3. Dashed boxes represent the locations of C-to-T base editing at sgTET1 target site. The sequences shown in FIG. 7C have the sequence of SEQ ID NO: 215.

FIG. 8A-C: hA3BCDA1 inhibits C-to-T base editing activity in RNF2 region. 8A: Schematic diagram illustrating the regions of CDA domains in hA3B. 8B: Schematic diagram illustrating the co-transfection of the plasmid expressing sgRNF2 with the plasmid expressing hA3B-BE3, the plasmid expressing hA3BCDA2-BE3 or the plasmid expressing hA3B-2A-BE3. 8C: hA3BCDA1 inhibits C-to-T editing activity of hA3BCDA2-BE3. Dashed boxes represent the locations of C-to-T base editing at sgRNF2 target site. The sequences shown in FIG. 8C, from top to bottom, have the sequences of SEQ ID NO: 216, 217 and 217, respectively.

FIG. 9A-C: hA3BCDA1 inhibits C-to-T base editing activity in SITE3 region. 9A: Schematic diagram illustrating the regions of CDA domains in hA3B. 9B: Schematic diagram illustrating the co-transfection of the plasmid expressing sgSITE3 with the plasmid expressing hA3B-BE3, the plasmid expressing hA3BCDA2-BE3 or the plasmid expressing hA3B-2A-BE3. 9C: hA3BCDA1 inhibits C-to-T editing activity of hA3BCDA2-BE3. Dashed boxes represent the locations of C-to-T base editing at sgSITE3 target site. The sequences shown in FIG. 9C, from top to bottom, have the sequences of SEQ ID NO: 218, 219 and 219, respectively.

FIG. 10A-C: Mapping the split site of mA3 by examining base editing efficiency in FANCF region. 10A: Schematic diagram illustrating the regions of two CDA domains in mA3 and the sites (AA196/AA197, AA207/AA208, AA215/AA216, AA229/AA230, AA237/AA238) used to split mA3. 10B: Schematic diagram illustrating the co-transfection of the plasmid expressing sgFANCF with the plasmid expressing mA3rev-BE3-196, the plasmid expressing mA3rev-2A-BE3-196, the plasmid expressing mA3rev-BE3, the plasmid expressing mA3rev-2A-BE3, the plasmid expressing mA3rev-BE3-215, the plasmid expressing mA3rev-2A-BE3-215, the plasmid expressing mA3rev-BE3-229, the plasmid expressing mA3rev-2A-BE3-229, the plasmid expressing mA3rev-BE3-237 or the plasmid expressing mA3rev-2A-BE3-237. 10C: The splitting sites spanning from AA196/AA197 to AA237/AA238 generally keep C-to-T editing efficiencies. Dashed boxes represent the locations of C-to-T base editing at sgFANCF target site. The sequences shown in FIG. 10C, from top to bottom, have the sequences of SEQ ID NO: 220, 220, 220, 221, 220, 221, 220, 221, 220 and 222, respectively.

FIG. 11A-C: Mapping the split site of mA3 by examining base editing efficiency in SITE2 region. 11A: Schematic diagram illustrating the regions of two CDA domains in mA3 and the sites (AA196/AA197, AA207/AA208, AA215/AA216, AA229/AA230, AA237/AA238) used to split mA3. 11B: Schematic diagram illustrating the co-transfection of the plasmid expressing sgSITE2 with the plasmid expressing mA3rev-BE3-196, the plasmid expressing mA3rev-2A-BE3-196, the plasmid expressing mA3rev-BE3, the plasmid expressing mA3rev-2A-BE3, the plasmid expressing mA3rev-BE3-215, the plasmid expressing mA3rev-2A-BE3-215, the plasmid expressing mA3rev-BE3-229, the plasmid expressing mA3rev-2A-BE3-229, the plasmid expressing mA3rev-BE3-237 or the plasmid expressing mA3rev-2A-BE3-237. 11C: The splitting sites spanning from AA196/AA197 to AA237/AA238 generally keep C-to-T editing efficiencies. Dashed boxes represent the locations of C-to-T base editing at sgSITE2 target site. The sequences shown in FIG. 11C, from top to bottom, have the sequences of SEQ ID NO: 223, 223, 223, 224, 223, 225, 223, 224, 223, and 224, respectively.

FIG. 12A-C: Mapping the split site of mA3 by examining base editing efficiency in SITE4 region. 12A: Schematic diagram illustrating the regions of two CDA domains in mA3 and the sites (AA196/AA197, AA207/AA208, AA215/AA216, AA229/AA230, AA237/AA238) used to split mA3. 12B: Schematic diagram illustrating the co-transfection of the plasmid expressing sgSITE4 with the plasmid expressing mA3rev-BE3-196, the plasmid expressing mA3rev-2A-BE3-196, the plasmid expressing mA3rev-BE3, the plasmid expressing mA3rev-2A-BE3, the plasmid expressing mA3rev-BE3-215, the plasmid expressing mA3rev-2A-BE3-215, the plasmid expressing mA3rev-BE3-229, the plasmid expressing mA3rev-2A-BE3-229, the plasmid expressing mA3rev-BE3-237 or the plasmid expressing mA3rev-2A-BE3-237. 12C: The splitting sites spanning from AA196/AA197 to AA237/AA238 generally keep C-to-T editing efficiencies. Dashed boxes represent the locations of C-to-T base editing at sgSITE4 target site. The sequences shown in FIG. 12C, from top to bottom, have the sequences of SEQ ID NO: 226, 227, 226, 227, 226, 227, 226, 227, 226 and 227, respectively.

FIG. 13A-B: Mapping the minimal region of mA3 that contains the base-editing inhibitory effect in FANCF region. 13A: Schematic diagram illustrating the co-transfection of the plasmid expressing sgFANCF with the plasmid expressing mA3rev-BE3-237, the plasmid expressing mA3rev-BE3-237-Del-255, the plasmid expressing mA3rev-BE3-237-Del-285 or the plasmid expressing mA3rev-BE3-237-Del-333. 13B: The region spanning from AA334 to AA429 of mA3 contains the base-editing inhibitory effect. Dashed boxes represent the locations of C-to-T base editing at sgFANCF target site. The sequences shown in FIG. 13C have the sequence of SEQ ID NO: 228.

FIG. 14A-B: Mapping the minimal region of mA3 that contains the base-editing inhibitory effect in SITE2 region. 14A: Schematic diagram illustrating the co-transfection of the plasmid expressing sgSITE2 with the plasmid expressing mA3rev-BE3-237, the plasmid expressing mA3rev-BE3-237-Del-255, the plasmid expressing mA3rev-BE3-237-Del-285 or the plasmid expressing mA3rev-BE3-237-Del-333. 14B: The region spanning from AA334 to AA429 of mA3 contains the base-editing inhibitory effect. Dashed boxes represent the locations of C-to-T base editing at sgSITE2 target site. The sequences shown in FIG. 14B have the sequence of SEQ ID NO: 229.

FIG. 15A-B: Mapping the minimal region of mA3 that contains the base-editing inhibitory effect in SITE4 region. 15A: Schematic diagram illustrating the co-transfection of the plasmid expressing sgSITE4 with the plasmid expressing mA3rev-BE3-237, the plasmid expressing mA3rev-BE3-237-Del-255, the plasmid expressing mA3rev-BE3-237-Del-285 or the plasmid expressing mA3rev-BE3-237-Del-333. 15B: The region spanning from AA334 to AA429 of mA3 contains the base-editing inhibitory effect. Dashed boxes represent the locations of C-to-T base editing at sgSITE4 target site. The sequences shown in FIG. 15B have the sequence of SEQ ID NO: 230.

FIG. 16A-B: Schematic diagram illustrating the working process of BEsafe and BE3 or hA3A-BE3. 16A: BEsafe induces C-to-T base editing at on-target site and avoids causing mutations in non-relevant ssDNA regions. 16B: BE3 or hA3A-BE3 induces C-to-T base editing at on-target site but causes C-to-T mutations in non-relevant ssDNA regions.

FIG. 17A-D: Comparison of hA3A-BE3 and BEsafe in non-relevant Sa-SITE31 ssDNA region and at TET1 on-target site. 17A: Schematic diagram illustrating the co-expression of SaD10A nickase and Sa-sgSITE31 to trigger the formation of ssDNA region at Sa-sgSITE31 on-target site. 17B: Schematic diagram illustrating the co-transfection of the plasmid expressing Sa-sgSITE31 and the plasmid expressing SaD10A nickase with the plasmid expressing hA3A-BE3 and the plasmid expressing sgTET1, with the plasmid expressing BEsafe and the plasmid expressing MS2-sgTET1 and MCP-TEVc or with the plasmid expressing MCP-TEVc and the plasmid expressing MS2-sgTET1 and BEsafe. 17C: Comparing the untended C-to-T mutation frequencies triggered by hA3A-BE3 and BEsafe in the non-relevant Sa-SITE31 ssDNA region. Dashed boxes represent the locations of untended base substitutions at Sa-sgSITE31 target site. 17D: Comparing the base editing efficiencies of hA3A-BE3 and BEsafe at TET1 site. Dashed boxes represent the locations of C-to-T base editing at sgTET1 target site. The sequences shown in FIG. 17C have the sequence of SEQ ID NO: 231. The sequences shown in FIG. 17D have the sequence of SEQ ID NO: 232.

FIG. 18A-D: Comparison of hA3A-BE3 and BEsafe in non-relevant Sa-SITE32 ssDNA region and at RNF2 on-target site. 18A: Schematic diagram illustrating the co-expression of SaD10A nickase and Sa-sgSITE32 to trigger the formation of ssDNA region at Sa-sgSITE32 on-target site. 18B: Schematic diagram illustrating the co-transfection of the plasmid expressing Sa-sgSITE32 and the plasmid expressing SaD10A nickase with the plasmid expressing hA3A-BE3 and the plasmid expressing sgRNF2, with the plasmid expressing BEsafe and the plasmid expressing MS2-sgRNF2 and MCP-TEVc or with the plasmid expressing MCP-TEVc and the plasmid expressing MS2-sgRNF2 and BEsafe. 18C: Comparing the untended C-to-T mutation frequencies triggered by hA3A-BE3 and BEsafe in the non-relevant Sa-SITE32 ssDNA region. Dashed boxes represent the locations of untended base substitutions at Sa-sgSITE32 target site. 18D: Comparing the base editing efficiencies of hA3A-BE3 and BEsafe at RNF2 site. Dashed boxes represent the locations of C-to-T base editing at sgRNF2 target site. The sequences shown in FIG. 18C have the sequence of SEQ ID NO: 233. The sequences shown in FIG. 18D, from top to bottom, have the sequences of SEQ ID NO: 234, 235 and 234, respectively.

FIG. 19A-D: Comparison of hA3A-BE3 and BEsafe in non-relevant Sa-F1 ssDNA region and at SITE3 on-target site. 19A: Schematic diagram illustrating the co-expression of SaD10A nickase and Sa-sgF1 to trigger the formation of ssDNA region at Sa-sgF1 on-target site. 19B: Schematic diagram illustrating the co-transfection of the plasmid expressing Sa-sgF1 and the plasmid expressing SaD10A nickase with the plasmid expressing hA3A-BE3 and the plasmid expressing sgSITE3, with the plasmid expressing BEsafe and the plasmid expressing MS2-sgSITE3 and MCP-TEVc or with the plasmid expressing MCP-TEVc and the plasmid expressing MS2-sgSITE3 and BEsafe. 19C: Comparing the untended C-to-T mutation frequencies triggered by hA3A-BE3 and BEsafe in the non-relevant Sa-F1 ssDNA region. Dashed boxes represent the locations of untended base substitutions at Sa-sgF1 target site. 19D: Comparing the base editing efficiencies of hA3A-BE3 and BEsafe at SITE3 site. Dashed boxes represent the locations of C-to-T base editing at sgSITE3 target site. The sequences shown in FIG. 19C have the sequence of SEQ ID NO: 236. The sequences shown in FIG. 19D have the sequence of SEQ ID NO: 237.

FIG. 20a-f: Identification of cytidine deaminase inhibitors. 20a: Schematic diagrams illustrate the APOBEC family members that have single- or dual-CDA domains (left) and paired base editors that were constructed with one or two CDAs of dual-domain APOBECs (right). 20b: Editing frequencies induced by the indicated BEs at one representative genomic locus. 20c: Statistical analysis of normalized editing frequencies, setting the ones induced by the single-CDA-containing BEs as 100%. n=78 from three independent experiments at 26 editable cytosine sites shown in (b). 20d: Schematic diagrams illustrate the conjugation of different cytidine deaminase inhibitors (CDIs) to the N-terminus of mA3CDA1-nSpCas9-BE. 20e: Editing frequencies induced by the indicated BEs at one representative genomic locus. 20f: Statistical analysis of normalized editing frequencies, setting the ones induced by the BEs without CDI as 100%. n=57 from three independent experiments at 19 editable cytosine sites shown in (e). (b), (e) Means±s.d. were from three independent experiments. NT, non-transfected control. (c), (f) P value, one-tailed Student's t test. The median and interquartile range (IQR) are shown.

FIG. 21a-f: Conjugation of mA3CDI reduced unintended base editing at sgRNA-independent OTss sites. 21a: Schematic diagrams illustrate that BE3 induces C-to-T mutations but CDI-conjugated iBE1 remains dormant at sgRNA-independent OTss sites. 21b: Comparison of C-to-T editing frequencies induced by BE3 and iBE1 in the ssDNA regions triggered by the nSaCas9-generated SSBs. 21c: Statistical analysis of normalized accumulative editing frequencies at four ssDNA sites shown in (b), setting the ones induced by BE3 as 100%. n=12 from three independent experiments. 21d: Schematic diagrams illustrate that the sgRNA-mediated cleavage of CDI restores the editing activity of iBE at on-target sites. 21e: Comparison of C-to-T editing frequencies induced by BE3 and iBE1 at on-target sites. 21f: Statistical analysis of normalized accumulative editing frequencies at four on-target sites shown in (e), setting the ones induced by BE3 as 100%. n=12 from three independent experiments. (c), (f) Means±s.d. were from three independent experiments. (d), (g) P value, one-tailed Student's t test. The median and interquartile range (IQR) are shown.

FIG. 22a-e: neSpCas9 reduced the unintended editing of iBE1 at OTsg sites. 22a: Schematic diagrams illustrate that iBE1 but not iBE2 induces C-to-T editing at the OTsg sites that are partially complementary to sgRNAs. 22b: Comparison of C-to-T editing frequencies induced by iBE1 and the targeting-specificity-improved iBEs at indicated OTsg sites. 22c: Statistical analysis of normalized accumulative editing frequencies at OTsg sites for two sgRNAs used in (b), setting the ones induced by iBE1 as 100%. n=6 from three independent experiments. 22d: Comparison of C-to-T editing frequencies induced by iBE1 and the targeting-specificity-improved iBEs at on-target sites. 22e: Statistical analysis of normalized accumulative editing frequencies at the six on-target sites shown in (d), setting the ones induced by iBE1 as 100%. n=18 from three independent experiments. (b), (d) Means±s.d. were from three independent experiments. (c), (e) P value, one-tailed Student's t test. The median and interquartile range (IQR) are shown.

FIG. 23a-e: Comparison of the base editing induced by hA3A-BE3 and iBE2. 23a: Comparison of C-to-T editing frequencies induced by hA3A-BE3 and iBE2 at representative OTss, OTsg and on-target sites. 23b-c: Statistical analysis of normalized accumulative editing frequencies at the OTss, OTsg (b) and on-target (c) sites for three sgRNAs used in (a), setting the ones induced by hA3A-BE3 as 100%. n=9 from three independent experiments. 23d: Statistical analysis of the normalized ratios of on-target editing frequencies to the total editing frequencies at OTss and OTsg sites for three sgRNAs used in (a), setting the ones induced by the hA3A-BE3 as 1. n=9 from three independent experiments. 23e: Schematic diagrams illustrate that iBE2 induces specific base editing at on-target sites but not at OTss or OTsg sites, whereas hA3A-BE3 induces base editing at on-target sites and both OTss and OTsg sites. (a) Means±s.d. were from three independent experiments. (b-d) P value, one-tailed Student's t test. The median and IQR are shown.

FIG. 24A-B. Schematic diagram illustrating the working process of isplitBE and regular base editors. 24A: isplitBE induces C-to-T base editing only at on-target site and avoids to cause mutations in non-relevant off-target ssDNA regions (OTss) or at the off-target sites with sequence similarity to the spacer region of sgRNA (OTsg). 24B: BE3 or hA3A-BE3 induces C-to-T base editing at on-target site but causes C-to-T mutations in OTss and OTsg regions.

FIG. 26A-B. C-to-T editing at EMX1-ON, Sa-SITE31-OTss and EMX1-OTsg sites induced by different combinations of nCas9 (D10A), APOBEC cytidine deaminase, cytidine deaminase inhibitor (CDI), uracil DNA glycosylase inhibitor (UGI) and TEV protease. 26A: Schematic diagram illustrating the co-transfection of the plasmid expressing Sa-sgSITE31 and the plasmid expressing SaD10A nickase with the indicated ten pairs of plasmid expressing various base editors. 26B: Comparison of editing efficiencies at EMX1-ON, Sa-SITE31-OTss and EMX1-OTsg sites. isplitBE-rA1 (Pair 9) induced substantial editing at ON site but no editing at OTss or OTsg sites. The sequences shown in FIG. 26B, from top to bottom (and left to right), have the sequences of SEQ ID NO: 238-241, respectively.

FIG. 29A-C. Effect of the distance between helper sgRNA (hsgRNA) and sgRNA on base editing efficiency. 29A: Schematic diagram illustrating the distance between hsgRNA and sgRNA at DNTET1, EMX1 and FANCF sites. 29B: Base editing frequencies induced by the indicated sgRNAs and hsgRNAs. 29C: Summary of the effect of distance between hsgRNA and sgRNA. The range of distance for best base editing efficiency is −91 to −34 bp from the PAM of hsgRNA to the PAM of sgRNA.

FIG. 30A-C. Effect of hsgRNA spacer length on base editing efficiency. 30A: Schematic diagram illustrating the co-transfection of sgRNA and the hsgRNAs with different spacer lengths at DNEMX1, FANCF and V1A sites. 30B: Base editing frequencies induced by the indicated sgRNAs and hsgRNAs at the target sties of hsgRNA and sgRNA. 30C: Statistic analysis of the effects of hsgRNA spacer length. The use of hsgRNA with 10-bp spacer greatly reduce the editing efficiency at hsgRNA target sites but maintain the editing efficiency at sgRNA target sites. The sequences shown in FIG. 30B, from top to bottom (from left to right in each row), have the sequences of SEQ ID NO: 250-255, respectively.

FIG. 32A-C. Comparison of genome-wide C-to-T mutations induced by isplitBE-rA1 and BE3. 32A: mRNA expression levels in wild-type 293FT cells and the APOBEC3 knockout 293FT cells (293FT-A3KO). 32B: Schematic diagram illustrating the procedures to determine genome-wide C-to-T mutations induced by base editors. 32C: On-target editing efficiencies (left) and the number of genome-wide C-to-T mutations induced by Cas9, BE3, hA3A-BE3-Y130F (Y130F) and isplitBE-rA1.

FIG. 33A-C. Comparison of transcriptome-wide C-to-U mutations induced by isplitBE-mA3, BE3 and hA3A-BE3-Y130F (Y130F). 33A: The number of transcriptome-wide C-to-U mutations induced by Cas9, BE3, hA3A-BE3-Y130F (Y130F) and isplitBE-mA3. 33B: RNA C-to-U editing frequencies induced by Cas9, BE3, hA3A-BE3-Y130F (Y130F) and isplitBE-mA3. 33C: Distribution of RNA C-to-U editing induced by BE3 replicate 1 and isplitBE-mA3 replicate 1.

FIG. 34A-D. Stop codon induced by isplitBE-mA3 in human PCSK9 gene. 34A: Schematic diagram illustrating the co-transfection of sgRNA and the hsgRNAs with isplitBE-mA3 and nCas9. 34B-34D: Editing efficiency induced by isplitBE-mA3 at indicated sites. The sequences shown in FIG. 34B, from top to bottom (from left to right in each row), have the sequences of SEQ ID NO: 256-260, respectively. The paired (up and down) sequences shown in FIG. 34C, from top to bottom (from left to right in each row), have the sequences of SEQ ID NO: 261-265, respectively. The paired (up and down) sequences shown in FIG. 34D, from top to bottom (from left to right in each row), have the sequences of SEQ ID NO: 266-270, respectively.

FIG. 35A-B. Inhibiting effect of mA3CDA2 on the editing efficiency of adenine base editor (ABE). 35A: Schematic diagram illustrating the co-transfection of sgRNA and ABE fused with mA3CDA2 or not. 35B: Editing efficiency induced by indicated ABEs at RNF2 and FANCF sites. The sequences shown in FIG. 35B, from top to bottom, have the sequences of SEQ ID NO: 271, 272, 271, 272, 273, 273, 273 and 273, respectively.

FIG. 36A-G. Enhanced prime editing by manipulating prime editing guide RNA (pegRNA). 36A: Schematic diagram illustrating the change of RNA base pairs to increase stem stability of enhanced pegRNA (epegRNA). 36B: Schematic diagram illustrating the co-transfection of PE2, nicking sgRNA with pegRNA or epegRNA-GC. 36C-36D: Comparison of prime editing efficiencies induced with pegRNA and epegRNA-GC. 36E: Schematic diagram illustrating the change of RNA base pairs to increase stem stability of enhanced pegRNA (epegRNA). 36F: Schematic diagram illustrating the co-transfection of PE2, nicking sgRNA with pegRNA or epegRNA-CG. 36G: Comparison of prime editing efficiencies induced with pegRNA and epegRNA-CG. The sequences shown in FIG. 36A, from top to bottom, have the sequences of SEQ ID NO: 274-275, respectively. The sequences shown in FIG. 36C, from top to bottom, have the sequences of SEQ ID NO: 276, 276, 277, 276 and 276, respectively. The sequences shown in FIG. 36D, from top to bottom, have the sequences of SEQ ID NO: 276, 276, 276, 276 and 278, respectively. The sequences shown in FIG. 36E, from top to bottom, have the sequences of SEQ ID NO: 279-280, respectively. The sequences shown in FIG. 36G have the sequence of SEQ ID NO: 276.

FIG. 37A-B. Prime editing system by using PEs containing different Cas9 proteins. 37A: Schematic diagram illustrating the co-transfection of pegRNA, nicking sgRNA with PE2-NG or xPE2. 37B: Prime editing efficiencies induced by PE2-NG and xPE2. The sequences shown in FIG. 37B, from top to bottom, have the sequences of SEQ ID NO: 276, 281 and 282, respectively.

FIG. 38A-C. Split prime editing (split-PE) system. 38A: Schematic diagram illustrating the working process of PE and split-PE systems. 38B: Schematic diagram illustrating the co-transfection of PE and split-PE systems. 38C: Editing efficiency induced by PE and split-PE systems at EMX1 site. The sequences shown in FIG. 38C have the sequence of SEQ ID NO: 283.

FIG. 39A-C. Alignment of mA3CDA2 core region with other cytidine deaminase domains. The sequences shown in FIG. 39A-C, from top to bottom have the sequences of SEQ ID NO: 48-92, respectively.

FIG. 40A-D. Alignment of hA3BCDA1 with other cytidine deaminase domains. The sequences shown in FIG. 39A-C, from top to bottom have the sequences of SEQ ID NO: 93-135, respectively.

DETAILED DESCRIPTION

Definitions

Figure 25:
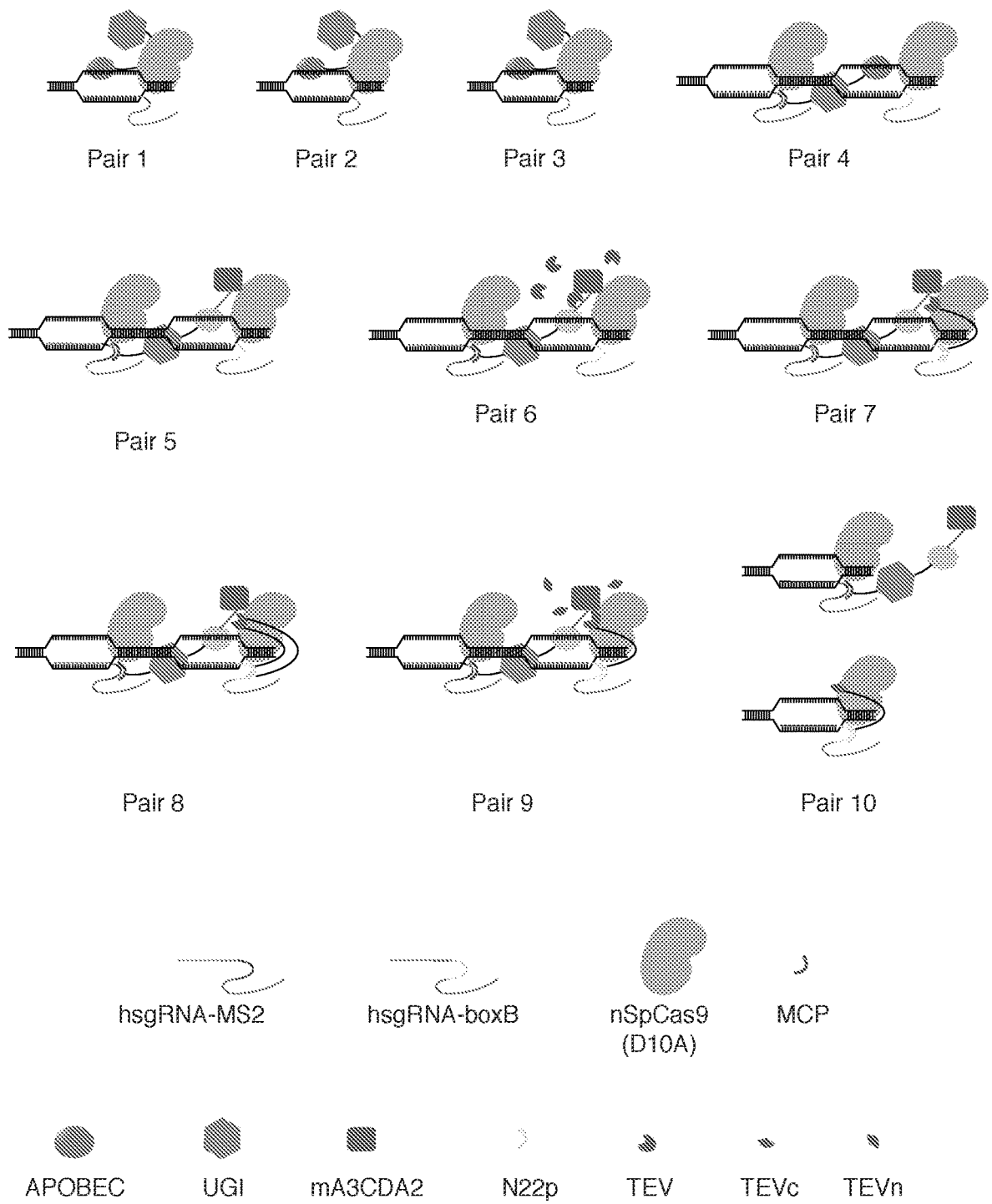
FIG. 25. Schematic diagram illustrating different strategies to remove cytidine deaminase inhibitor (mA3CDA2) at on-target site.

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein", "amino acid chain" or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present disclosure.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters.

The term "an equivalent nucleic acid or polynucleotide" refers to a nucleic acid having a nucleotide sequence having a certain degree of homology, or sequence identity, with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof. Likewise, "an equivalent polypeptide" refers to a polypeptide having a certain degree of homology, or sequence identity, with the amino acid sequence of a reference polypeptide. In some aspects, the sequence identity is at least about 70%, 75%, 80%, 85%, 90%, 95%, 98%, or 99%. In some aspects, the equivalent polypeptide or polynucleotide has one, two, three, four or five addition, deletion, substitution and their combinations thereof as compared to the reference polypeptide or polynucleotide. In some aspects, the equivalent sequence retains the activity (e.g., epitope-binding) or structure (e.g., salt-bridge) of the reference sequence.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

Use of Nucleobase Deaminase Inhibitor to Reduce Random Insertions and Deletions

As shown in the experimental examples and FIG. 1-3, the currently commonly used base editors BE3 and hA3A-BE3 induced C-to-T mutations in off-target single-stranded DNA regions.

It was discovered surprisingly, however, that the use of the mouse APOBEC3 (mA3) in mA3-BE3 (FIGS. 4B, 5B, 6B) generally did not induce C-to-T editing at the tested target sites (FIGS. 4C, 5C, 6C). mA3 has two cytidine deaminase (CDA) domains, CDA1 and CDA2 (FIGS. 4A, 5A, 6A). When the CDA2 domain was removed from the full-length mA3, the resulting base editor mA3CDA1-BE3 (FIGS. 4B, 5B, 6B) induced substantial C-to-T editing (FIGS. 4C, 5C, 6C). These results indicate that the mA3-CDA2 domain is an inhibitor of base editing.

Also surprisingly, the mA3-CDA2 domain not only can inhibit the base editing activity of mA3-CDA1, it can also inhibit other nucleobase deaminases. For instance, when mA3-CDA2 was fused to the N-terminus of each of three active BEs, mA3CDA1-BE3, BE3 and hA3A-BE3, the fusion proteins mA3rev-BE3, mA3-CDA2-BE3 and mA3-CDA2-hA3A-BE3 (FIGS. 4B, 5B, 6B) had clearly reduced base editing efficiencies (FIGS. 4C, 5C, 6C).

Moreover, cleavage of mA3-CDA2 from the fusion proteins restored the base editing efficiency (FIGS. 4C, 5C, 6C), suggesting that the inhibition of mA3-CDA2 is associated with its covalent connection to the BEs.

Like mA3, the human APOBEC3B (hA3B) also has two cytidine deaminase (CDA) domains, CDA1 and CDA2 (FIGS. 7A, 8A, 9A). Incorporation of the full-length hA3B in hA3B-BE3 (FIGS. 7B, 8B, 9B) only induced relatively low levels of C-to-T editing at three tested target sites (FIGS. 7C, 8C, 9C). However, hA3B-CDA2-BE3, which was generated by deleting the hA3B-CDA1 domain (FIGS. 7B, 8B, 9B) induced higher C-to-T editing (FIGS. 7C, 8C, 9C). These results indicate that hA3B-CDA1 is another inhibitor of base editing and the inhibition of hA3B-CDA1 is associated with its covalent connection to the BEs.

Figure 40C:
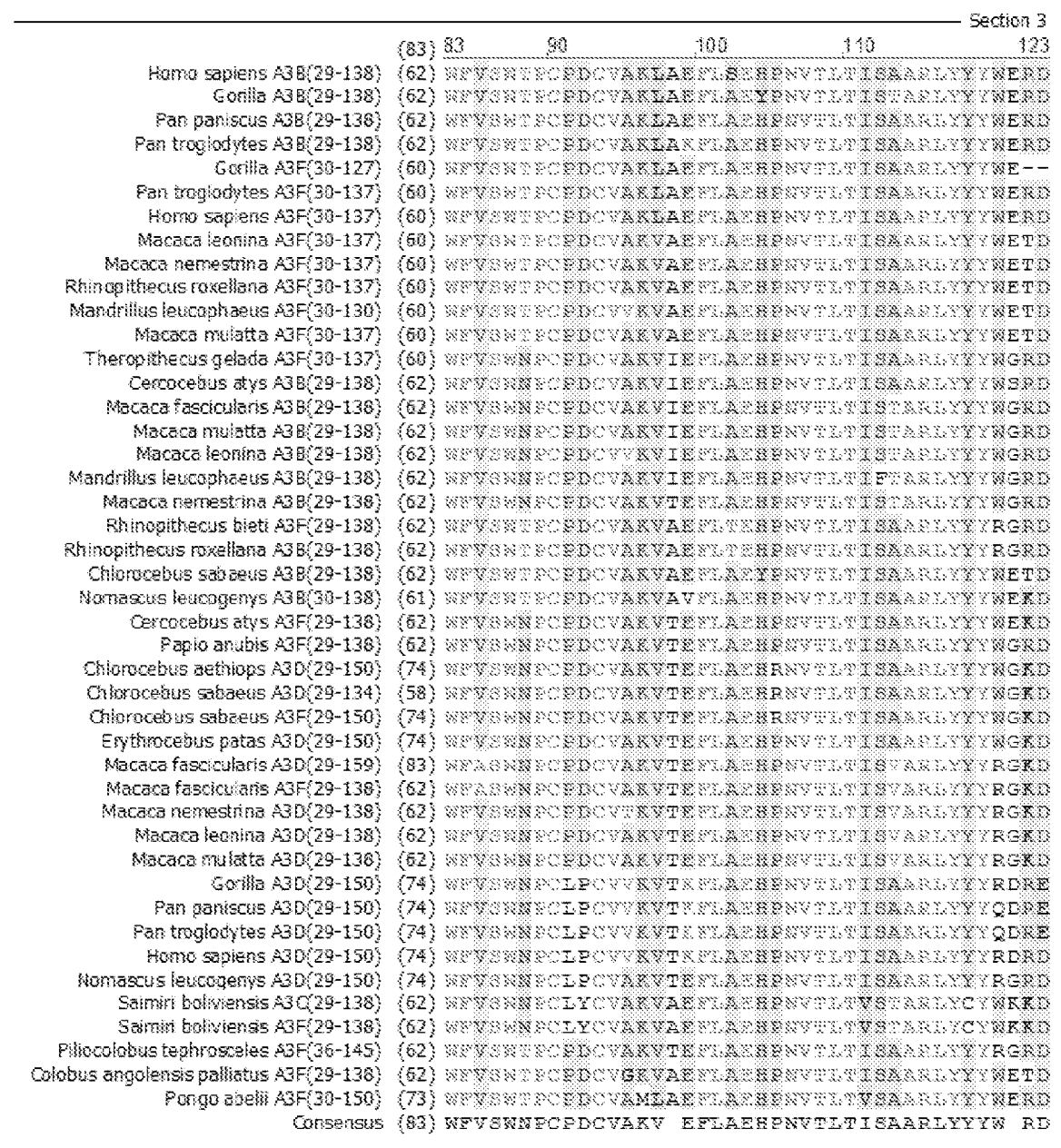

Using the sequences of mA3-CDA2 and hA3B-CDA1, the instant inventors were able to identify additional nucleobase deaminase inhibitors/domains in the protein database. Table 1 shows 44 proteins/domains that have significant sequence homology to mA3-CDA2 core sequence (FIG. 39) and Table 2 shows 43 proteins/domains that have significant sequence homology to hA3B-CDA1 (FIG. 40). All of these proteins and domains, as well as their variants and equivalents, are contemplated to have nucleobase deaminase inhibition activities.

Fusion Proteins

Based on these surprising and expected findings, a fusion protein is designed that can be used to generate a base editor with improved base editing specificity and efficiency. In one embodiment, the present disclosure provides a fusion protein that includes a first fragment comprising a nucleobase deaminase or a catalytic domain thereof, a second fragment comprising a nucleobase deaminase inhibitor, and a protease cleavage site between the first fragment and the second fragment.

A base editor that incorporates such a fusion protein has reduced or even no editing capability and accordingly will generate reduced or no off-target mutations. Upon cleavage of the protease cleavage site and release of the nucleobase deaminase inhibitor from the fusion protein at a target site, the base editor that is at the target site will then be able to edit the target site efficiently.

The term "nucleobase deaminase" as used herein, refers to a group of enzymes that catalyze the hydrolytic deamination of nucleobases such as cytidine, deoxycytidine, adenosine and deoxyadenosine. Non-limiting examples of nucleobase deaminases include cytidine deaminases and adenosine deaminases.

"Cytidine deaminase" refers to enzymes that catalyze the irreversible hydrolytic deamination of cytidine and deoxycytidine to uridine and deoxyuridine, respectively. Cytidine deaminases maintain the cellular pyrimidine pool. A family of cytidine deaminases is APOBEC ("apolipoprotein B mRNA editing enzyme, catalytic polypeptide-like"). Members of this family are C-to-U editing enzymes. Some APOBEC family members have two domains, one domain of APOBEC like proteins is the catalytic domain, while the other domain is a pseudocatalytic domain. More specifically, the catalytic domain is a zinc dependent cytidine deaminase domain and is important for cytidine deamination. RNA editing by APOBEC-1 requires homodimerisation and this complex interacts with RNA binding proteins to form the editosome.

Non-limiting examples of APOBEC proteins include APOBEC1, APOBEC2, APOBEC3A, APOBEC3B, APOBEC3C, APOBEC3D, APOBEC3F, APOBEC3G, APOBEC3H, APOBEC4, and activation-induced (cytidine) deaminase (AID).

Various mutants of the APOBEC proteins are also known that have bring about different editing characteristics for base editors. For instance, for human APOBEC3A, certain mutants (e.g., W98Y, Y130F, Y132D, W104A, D131Y and P134Y) even outperform the wildtype human APOBEC3A in terms of editing efficiency or editing window. Accordingly, the term APOBEC and each of its family member also encompasses variants and mutants that have certain level (e.g., 70%, 75%, 80%, 85%, 90%, 95%, 98%, 99%) of sequence identity to the corresponding wildtype APOBEC protein or the catalytic domain and retain the cytidine deaminating activity. The variants and mutants can be derived with amino acid additions, deletions and/or substitutions. Such substitutions, in some embodiments, are conservative substitutions.

"Adenosine deaminase", also known as adenosine aminohydrolase, or ADA, is an enzyme (EC 3.5.4.4) involved in purine metabolism. It is needed for the breakdown of adenosine from food and for the turnover of nucleic acids in tissues.

Non-limiting examples of adenosine deaminases include tRNA-specific adenosine deaminase (TadA), adenosine deaminase tRNA specific 1 (ADAT1), adenosine deaminase tRNA specific 2 (ADAT2), adenosine deaminase tRNA specific 3 (ADAT3), adenosine deaminase RNA specific B1 (ADARB1), adenosine deaminase RNA specific B2 (ADARB2), adenosine monophosphate deaminase 1 (AMPD1), adenosine monophosphate deaminase 2 (AMPD2), adenosine monophosphate deaminase 3 (AMPD3), adenosine deaminase (ADA), adenosine deaminase 2 (ADA2), adenosine deaminase like (ADAL), adenosine deaminase domain containing 1 (ADAD1), adenosine deaminase domain containing 2 (ADAD2), adenosine deaminase RNA specific (ADAR) and adenosine deaminase RNA specific B1 (ADARB1).

Some of the nucleobase deaminases have a single, catalytic domain, while others also have other domains, such as an inhibitory domain as currently discovered by the instant inventors. In some embodiments, therefore, the first fragment only includes the catalytic domain, such as mA3-CDA1 and hA3B-CDA2. In some embodiments, the first fragment includes at least a catalytic core of the catalytic domain. For instance, as demonstrated in the experimental examples, when mA3-CDA1 was truncated at residues 196/197 the CDA1 domain still retained substantial editing efficiencies (FIG. 10C, 11C, 12C).

The present disclosure tested two nucleobase deaminase inhibitors, mA3-CDA2 and hA3B-CDA1, which are the inhibitory domains of the corresponding nucleobase deaminase. Additional nucleobase deaminase inhibitors and inhibitory domains were also identified in the protein databases (see Tables 1 and 2). Their biological equivalents (e.g., having at least about 80%, 85%, 90%, 95%, 97%, 98%, 99%, 99.5% sequence identity, or having one, two, or three amino acid addition/deletion/substitution, and having nucleobase deaminase inhibitor activity) can also be prepared with known methods in the art, such as conservative amino acid substitutions. A "nucleobase deaminase inhibitor," accordingly, refers to a protein or a protein domain that inhibits the deaminase activity of a nucleobase deaminase. In some embodiments, the second fragment includes at least an inhibitory core of the inhibitory protein/domain. For instance, as demonstrated in the experimental examples, when mA3-CDA2 retained residues 334-429, the CDA2 still had the inhibitory effect of base editing (FIG. 13B, 14B, 15B).

In some embodiments, the fusion protein further includes a clustered regularly interspaced short palindromic repeats (CRISPR)-associated (Cas) protein, optionally in the first fragment, next to the nucleobase deaminase or the catalytic domain thereof.

The term "Cas protein" or "clustered regularly interspaced short palindromic repeats (CRISPR)-associated (Cas) protein" refers to RNA-guided DNA endonuclease enzymes associated with the CRISPR (Clustered Regularly Interspaced Short Palindromic Repeats) adaptive immunity system in *Streptococcus pyogenes*, as well as other bacteria. Cas proteins include Cas9 proteins, Cas12a (Cpf1) proteins, Cas12b (formerly known as C2c1) proteins, Cas13 proteins and various engineered counterparts. Example Cas proteins include SpCas9, FnCas9, St1Cas9, St3Cas9, NmCas9, SaCas9, AsCpf1, LbCpf1, FnCpf1, VQR SpCas9, EQR SpCas9, VRER SpCas9, SpCas9-NG, xSpCas9, RHA FnCas9, KKH SaCas9, NmeCas9, StCas9, CjCas9, AsCpf1, FnCpf1, SsCpf1, PcCpf1, BpCpf1, CmtCpf1, LiCpf1, PmCpf1, Pb3310Cpf1, Pb4417Cpf1, BsCpf1, EeCpf1, BhCas12b, AkCas12b, EbCas12b, LsCas12b, RfCas13d, LwaCas13a, PspCas13b, PguCas13b, RanCas13b and those provided in Table A below.

TABLE A

Example Cas Proteins

| Cas protein types | Cas proteins |
|---|---|
| Cas9 proteins | Cas9 from *Staphylococcus aureus* (SaCas9) |
| | Cas9 from *Neisseria meningitidis* (NmeCas9) |
| | Cas9 from *Streptococcus thermophilus* (StCas9) |
| | Cas9 from *Campylobacter jejuni* (CjCas9) |
| Cas12a (Cpf1) proteins | Cas12a (Cpf1) from *Acidaminococcus* sp BV3L6 (AsCpf1) |
| | Cas12a (Cpf1) from *Francisella novicida* sp BV3L6 (FnCpf1) |
| | Cas12a (Cpf1) from *Smithella* sp SC K08D17 (SsCpf1) |
| | Cas12a (Cpf1) from *Porphyromonas crevioricanis* (PcCpf1) |
| | Cas12a (Cpf1) from *Butyrivibrio proteoclasticus* (BpCpf1) |
| | Cas12a (Cpf1) from *Candidatus Methanoplasma termitum* (CmtCpf1) |
| | Cas12a (Cpf1) from *Leptospira inadai* (LiCpf1) |
| | Cas12a (Cpf1) from *Porphyromonas macacae* (PmCpf1) |
| | Cas12a (Cpf1) from *Peregrinibacteria bacterium* GW2011 WA2 33 10 (Pb3310Cpf1) |
| | Cas12a (Cpf1) from *Parcubacteria bacterium* GW2011 GWC2 44 17 (Pb4417Cpf1) |
| | Cas12a (Cpf1) from *Butyrivibrio* sp. NC3005 (BsCpf1) |
| | Cas12a (Cpf1) from *Eubacterium eligens* (EeCpf1) |
| Cas12b (C2c1) proteins | Cas12b (C2c1) *Bacillus hisashii* (BhCas12b) |
| | Cas12b (C2c1) *Bacillus hisashii* with a gain-of-function mutation (see, e.g., Strecker et al., Nature Communications 10 (article 212) (2019) |
| | Cas12b (C2c1) *Alicyclobacillus kakegawensis* (AkCas12b) |
| | Cas12b (C2c1) *Elusimicrobia bacterium* (EbCas12b) |
| | Cas12b (C2c1) *Laceyella sediminis* (Ls) (LsCas12b) |
| Cas13 proteins | Cas13d from *Ruminococcus flavefaciens* XPD3002 (RfCas13d) |
| | Cas13a from *Leptotrichia wadei* (LwaCas13a) |
| | Cas13b from *Prevotella* sp. P5-125 (PspCas13b) |
| | Cas13b from *Porphyromonas gulae* (PguCas13b) |
| | Cas13b from *Riemerella anatipestifer* (RanCas13b) |
| Engineered Cas proteins | Nickases (mutation in one nuclease domain) |
| | Catalytically inactive mutant (dCas9; mutations in both of the nuclease domains) |
| | Enhanced variants with improved specificity (see, e.g., Chen et al., *Nature*, 550, 407-410 (2017) |

The protease cleavage site between the first fragment and the second fragment can be any known protease cleavage site (peptide) for any proteases. Non-limiting examples of proteases include TEV protease, TuMV protease, PPV protease, PVY protease, ZIKV protease and WNV protease. The protein sequences of example proteases and their corresponding cleavage sites are provided in Table B.

TABLE B

Example Sequences

| Name | Sequence | SEQ ID NO: |
|---|---|---|
| Mouse APOBEC3 cytidine deaminase domain 2 | MSSSTLSNICLTKGLPETRFWVEGRRMDPLSEEEFYSQFYNQRVKHLCY YHRMKPYLCYQLEQFNGQAPLKGCLLSEKGKQHAEILFLDKIRSMELSQ VTITCYLTWSPCPNCAWQLAAFKRDRPDLILHIYTSRLYFHWKRPFQKG LCSLWQSGILVDVMDLPQFTDCWTNFVNPKRPFWPWKGLEIISRRTQRR LRRIKESWGLQDLVNDFGNLQLGPPMS | 1 |
| Human APOBEC3B cytidine deaminase domain 1 | MNPQIRNPMERMYRDTFYDNFENEPILYGRSYTWLCYEVKIKRGRSNLL WDTGVFRGQVYFKPQYHAEMCFLSWFCGNQLPAYKCFQITWFVSWTPCP DCVAKLAEFLSEHPNVTLTISAARLYYYWERDYRRALCRLSQAGARVKI MDYEEFAYCWENFVYNEGQ | 2 |
| TEV protease N-terminal domain | MGESLFKGPRDYNPISSTICHLTNESDGHTTSLYGIGFGPFIITNKHLF RRNNGTLLVQSLHGVFKVKNTTTLQQHLIDGRDMIIIRMPKDFPPFPQK LKFREPQREERICLVTTNFQT | 3 |

TABLE B-continued

Example Sequences

| Name | Sequence | SEQ ID NO: |
|---|---|---|
| TEV protease C-terminal domain | MKSMSSMVSDTSCTFPSSDGIFWKHWIQTKDGQCGSPLVSTRDGFIVGI HSASNFTNTNNYFTSVPKNFMELLTNQEAQQWVSGWRLNADSVLWGGHK VFMVKPEEPFQPVKEATQ | 4 |
| TEV protease cleavage site | ENLYFQS | 5 |
| TuMV protease | MASSNSMFRGLRDYNPISNNICHLTNVSDGASNSLYGVGFGPLILTNRH LFERNNGELVIKSRHGEFVIKNTTQLHLLPIPDRDLLLIRLPKDVPPFP QKLGFRQPEKGERICMVGSNFQTKSITSIVSETSTIMPVENSQFWKHWI STKDGQCGSPMVSTKDGKILGLHSLANFQNSINYFAAFPDDFAEKYLHT IEAHEWVKHWKYNTSAISWGSLNIQASQPSGLFKVSKLISDLDSTAVYA Q | 6 |
| TuMV protease cleavage site | GGCSHQS | 7 |
| PPV protease | MASSKSLFRGLRDYNPIASSICQLNNSSGARQSEMFGLGFGGLIVTNQH LFKRNDGELTIRSHHGEFVVKDTKTLKLLPCKGRDIVIIRLPKDFPPFP RRLQFRTPTTEDRVCLIGSNFQTKSISSTMSETSATYPVDNSHFWKHWI STKDGHCGLPIVSTRDGSILGLHSLANSTNTQNFYAAFPDNFETTYLSN QDNDNWIKQWRYNPDEVCWGSLQLKRDIPQSPFTICKLLTDLDGEFVYT Q | 8 |
| PPV protease cleavage site | QVVVHQSK | 9 |
| PVY protease | MASAKSLMRGLRDFNPIAQTVCRLKVSVEYGASEMYGFGFGAYIVANHH LFRSYNGSMEVQSMHGTFRVKNLHSLSVLPIKGRDIILIKMPKDFPVFP QKLHFRAPTQNERICLVGTNFQEKYASSIITETSTTYNIPGSTFWKHWI ETDNGHCGLPVVSTADGCIVGIHSLANNAHTTNYYSAFDEDFESKYLRT NEHNEWVKSWVYNPDTVLWGPLKLKDSTPKGLFKTTKLVQDLIDHDVVV EQ | 10 |
| PVY protease cleavage site | YDVRHQSR | 11 |
| ZIKV protease | MASDMYIERAGDITWEKDAEVTGNSPRLDVALDESGDFSLVEEDGPPMR EGGGGSGGGGSGALWDVPAPKEVKKGETTDGVYRVMTRRLLGSTQVGVG VMQEGVFHTMWHVTKGAALRSGEGRLDPYWGDVKQDLVSYCGPWKLDAA WDGLSEVQLLAVPPGERARNIQTLPGIFKTKDGDIGAVALDYPAGTSGS PILDKCGRVIGLYGNGVVIKNGSYVSAITQGKREEETPVECFE | 12 |
| ZIKV protease cleavage site | KERKRRGA | 13 |
| WNV protease | MASSTDMWIERTADISWESDAEITGSSERVDVRLDDDGNFQLMNDPGAP WKGGGGSGGGGVLWDTPSPKEYKKGDTTTGVYRIMTRGLLGSYQAGAG VMVEGVFHTLWHTTKGAALMSGEGRLDPYWGSVKEDRLCYGGPWKLQHK WNGQDEVQMIVVEPGKNVKNVQTKPGVFKTPEGEIGAVTLDFPTGTSGS PIVDKNGDVIGLYGNGVIMPNGSYISAIVQGERMDEPIPAGFEPEML | 14 |
| WNV protease cleavage site | KQKKRGGK | 15 |
| MS2 | ACAUGAGGAUCACCCAUGU | 16 |
| sgRNA scaffold with 2 × MS2 | GUUUGAGAGCUAGGCCAACAUGAGGAUCACCCAUGUCUGCAGGGCCUAG CAAGUUCAAAUAAGGCUAGUCCGUUAUCAACUUGGCCACAUGAGGAUC ACCCAUGUCUGCAGGGCCAAGUGGCACCGAGUCGGUGC | 17 |
| PP7 | GGAGCAGACGAUAUGGCGUCGCUCC | 18 |
| sgRNA scaffold with 2 × PP7 | GUUUGAGAGCUACCGGAGCAGACGAUAUGGCGUCGCUCCGGUAGCAAGU UCAAAUAAGGCUAGUCCGUUAUCAACUUGGAGCAGACGAUAUGGCGUCG CUCCAAGUGGCACCGAGUCGGUGC | 19 |
| boxB | GCCCUGAAGAAGGGC | 20 |
| sgRNA scaffold with 2 × boxB | GUUUGAGAGCUAGGGCCCUGAAGAAGGGCCCUAGCAAGUUCAAAUAAGG CUAGUCCGUUAUCAACUUGGGCCCUGAAGAAGGGCCCAAGUGGCACCGA GUCGGUGC | 21 |

TABLE B-continued

Example Sequences

| Name | Sequence | SEQ ID NO: |
|---|---|---|
| MS2 coat protein (MCP) | MASNFTQFVLVDNGGTGDVTVAPSNFANGIAEWISSNSRSQAYKVTCSV RQSSAQNRKYTIKVEVPKGAWRSYLNMELTIPIFATNSDCELIVKAMQG LLKDGNPIPSAIAANSGIY | 22 |
| PP7 coat protein (PCP) | MGSKTIVLSVGEATRTLTEIQSTADRQIFEEKVGPLVGRLRLTASLRQN GAKTAYRVNLKLDQADVVDSGLPKVRYTQVWSHDVTIVANSTEASRKSL YDLTKSLVATSQVEDLVVNLVPLGR | 23 |
| boxB coat protein (N22p) | MGNARTRRRERRAEKQAQWKAAN | 24 |
| UGI | TNLSDIIEKETGKQLVIQESILMLPEEVEEVIGNKPESDILVHTAYDES TDENVMLLTSDAPEYKPWALVIQDSNGENKIKML | 25 |
| P2A | GSGATNFSLLKQAGDVEENPGP | 26 |
| T2A | GSGEGRGSLLTCGDVEENPGP | 27 |
| E2A | GSGQCTNYALLKLAGDVESNPGP | 28 |

In some embodiments, the protease cleavage site is a self-cleaving peptide, such as the 2A peptides. "2A peptides" are 18-22 amino-acid-long viral oligopeptides that mediate "cleavage" of polypeptides during translation in eukaryotic cells. The designation "2A" refers to a specific region of the viral genome and different viral 2As have generally been named after the virus they were derived from. The first discovered 2A was F2A (foot-and-mouth disease virus), after which E2A (equine rhinitis A virus), P2A (porcine teschovirus-1 2A), and T2A (thosea asigna virus 2A) were also identified. A few non-limiting examples of 2A peptides are provided in SEQ ID NO:26-28.

In some embodiments, the protease cleavage site is a cleavage site (e.g., SEQ ID NO:5) for the TEV protease. In some embodiments, the fusion protein further includes a third fragment that includes the TEV protease or a fragment thereof. In some embodiments, the TEV protease fragment in the fusion protein in not active, that is, not able to cleave the TEV cleavage site on its own. However, in the presence of the remaining portion of the TEV protease, this fragment will be able to execute the cleavage. As further described below, such an arrangement provides additional control and flexible of the base editing capabilities. The TEV fragment may be the TEV N-terminal domain (e.g., SEQ ID NO:3) or the TEV C-terminal domain (e.g., SEQ ID NO:4).

Various arrangement of the fragments can be made. Non-limiting examples include, from N-terminal side to C-terminal side:

(1) first fragment (e.g., catalytic domain)—protease cleavage site—second fragment (e.g., inhibitory domain);
(2) first fragment (e.g., catalytic domain and Cas protein)—protease cleavage site—second fragment (e.g., inhibitory domain);
(3) first fragment (e.g., catalytic domain, Cas protein and TEV N-terminal domain)—protease cleavage site (e.g., TEV cleavage site)—second fragment (e.g., inhibitory domain);
(4) second fragment (e.g., inhibitory domain)—protease cleavage site (e.g., TEV cleavage site)—first fragment (e.g., catalytic domain, Cas protein and TEV N-terminal domain); and
(5) second fragment (e.g., inhibitory domain)—protease cleavage site (e.g., TEV cleavage site)—first fragment (e.g., Cas protein, catalytic domain, and TEV C-terminal domain).

In some embodiments, provided are fusion proteins comprising a first fragment comprising first nucleobase deaminase (e.g., cytidine deaminase) or a catalytic domain thereof, and a second fragment comprising an inhibitory domain of a second nucleobase deaminase, wherein the first nucleobase deaminase is different from the second nucleobase deaminase. In some embodiments, each of the first and second nucleobase deaminases is independently selected from the group of human and mouse APOBEC3B (A3B), APOBEC3C (A3C), APOBEC3D (A3D), APOBEC3F (A3F), APOBEC3G (A3G), APOBEC3H (A3H), APOBEC1 (A1), APOBEC3 (A3), APOBEC2 (A2), APOBEC4 (A4) and AICDA (AID).

The fusion proteins may include other fragments, such as uracil DNA glycosylase inhibitor (UGI) and nuclear localization sequences (NLS).

The "Uracil Glycosylase Inhibitor" (UGI), which can be prepared from *Bacillus subtilis* bacteriophage PBS1, is a small protein (9.5 kDa) which inhibits *E. coli* uracil-DNA glycosylase (UDG) as well as UDG from other species. Inhibition of UDG occurs by reversible protein binding with a 1:1 UDG:UGI stoichiometry. UGI is capable of dissociating UDG-DNA complexes. A non-limiting example of UGI is found in *Bacillus* phage AR9 (YP_009283008.1). In some embodiments, the UGI comprises the amino acid sequence of SEQ ID NO:25 or has at least at least 70%, 75%, 80%, 85%, 90% or 95% sequence identity to SEQ ID NO:25 and retains the uracil glycosylase inhibition activity.

The fusion protein, in some embodiments, may include one or more nuclear localization sequences (NLS).

A "nuclear localization signal or sequence" (NLS) is an amino acid sequence that tags a protein for import into the cell nucleus by nuclear transport. Typically, this signal consists of one or more short sequences of positively charged lysines or arginines exposed on the protein surface. Different nuclear localized proteins may share the same NLS. An NLS has the opposite function of a nuclear export signal (NES), which targets proteins out of the nucleus. A non-limiting example of NLS is the internal SV40 nuclear localization sequence (iNLS).

In some embodiments, a peptide linker is optionally provided between each of the fragments in the fusion protein. In some embodiments, the peptide linker has from 1 to 100 amino acid residues (or 3-20, 4-15, without limitation). In some embodiments, at least 10%, 20%, 30%, 40%, 50%, 60%, 70%, 80% or 90% of the amino acid residues of peptide linker are amino acid residues selected from the group consisting of alanine, glycine, cysteine, and serine.

For any fusion protein of the present disclosure, biological equivalents thereof are also provided. In some embodiments, the biological equivalents have at least about 70%, 75%, 80%, 85%, 90%, 95%, 98%, or 99% sequence identity with the reference fusion protein. Preferably, the biological equivalents retained the desired activity of the reference fusion protein. In some embodiments, the biological equivalents are derived by including one, two, three, four, five or more amino acid additions, deletions, substitutions, of the combinations thereof. In some embodiments, the substitution is a conservative amino acid substitution.

A "conservative amino acid substitution" is one in which the amino acid residue is replaced with an amino acid residue having a similar side chain Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably replaced with another amino acid residue from the same side chain family In another embodiment, a string of amino acids can be replaced with a structurally similar string that differs in order and/or composition of side chain family members.

Non-limiting examples of conservative amino acid substitutions are provided in the table below, where a similarity score of 0 or higher indicates conservative substitution between the two amino acids.

TABLE C

Amino Acid Similarity Matrix

| | C | G | P | S | A | T | D | E | N | Q | H | K | R | V | M | I | L | F | Y | W |
|---|---|---|---|---|---|---|---|---|---|---|---|---|---|---|---|---|---|---|---|---|
| W | −8 | −7 | −6 | −2 | −6 | −5 | −7 | −7 | −4 | −5 | −3 | −3 | 2 | −6 | −4 | −5 | −2 | 0 | 0 | 17 |
| Y | 0 | −5 | −5 | −3 | −3 | −3 | −4 | −4 | −2 | −4 | 0 | −4 | −5 | −2 | −2 | −1 | −1 | 7 | 10 | |
| F | −4 | −5 | −5 | −3 | −4 | −3 | −6 | −5 | −4 | −5 | −2 | −5 | −4 | −1 | 0 | 1 | 2 | 9 | | |
| L | −6 | −4 | −3 | −3 | −2 | −2 | −4 | −3 | −3 | −2 | −2 | −3 | −3 | 2 | 4 | 2 | 6 | | | |
| I | −2 | −3 | −2 | −1 | −1 | 0 | −2 | −2 | −2 | −2 | −2 | −2 | −2 | 4 | 2 | 5 | | | | |
| M | −5 | −3 | −2 | −2 | −1 | −1 | −3 | −2 | 0 | −1 | −2 | 0 | 0 | 2 | 6 | | | | | |
| V | −2 | −1 | −1 | −1 | 0 | 0 | −2 | −2 | −2 | −2 | −2 | −2 | −2 | 4 | | | | | | |
| R | −4 | −3 | 0 | 0 | −2 | −1 | −1 | −1 | 0 | 1 | 2 | 3 | 6 | | | | | | | |
| K | −5 | −2 | −1 | 0 | −1 | 0 | 0 | 0 | 1 | 1 | 0 | 5 | | | | | | | | |
| H | −3 | −2 | 0 | −1 | −1 | −1 | 1 | 1 | 2 | 3 | 6 | | | | | | | | | |
| Q | −5 | −1 | 0 | −1 | 0 | −1 | 2 | 2 | 1 | 4 | | | | | | | | | | |
| N | −4 | 0 | −1 | 1 | 0 | 0 | 2 | 1 | 2 | | | | | | | | | | | |
| E | −5 | 0 | −1 | 0 | 0 | 0 | 3 | 4 | | | | | | | | | | | | |
| D | −5 | 1 | −1 | 0 | 0 | 0 | 4 | | | | | | | | | | | | | |
| T | −2 | 0 | 0 | 1 | 1 | 3 | | | | | | | | | | | | | | |
| A | −2 | 1 | 1 | 1 | 2 | | | | | | | | | | | | | | | |
| S | 0 | 1 | 1 | 1 | | | | | | | | | | | | | | | | |
| P | −3 | −1 | 6 | | | | | | | | | | | | | | | | | |
| G | −3 | 5 | | | | | | | | | | | | | | | | | | |
| C | 12 | | | | | | | | | | | | | | | | | | | |

TABLE D

Conservative Amino Acid Substitutions

| For Amino Acid | Substitution With |
|---|---|
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr, L-Ser, D-Ser |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

On-Target Activation of Fusion Proteins

The present disclosure also provides compositions and methods in which a fusion protein of the present disclosure, which includes both a nucleobase deaminase or the catalytic domain thereof and an inhibitor, is activated where its activity is desired. The technology is illustrated in FIG. 16.

In an illustrative configuration, the fusion protein (A) includes (a) a first fragment comprising a nucleobase deaminase (e.g., cytidine deaminase) or a catalytic domain thereof, optionally with a clustered regularly interspaced short palindromic repeats (CRISPR)-associated (Cas) protein, and a first TEV protease fragment, (b) a second fragment comprising a nucleobase deaminase inhibitor, and (c) a TEV protease cleavage site between the first fragment and the second fragment. In some embodiments, wherein the first TEV protease fragment alone is not able to cleave the TEV protease cleavage site.

When the fusion protein is used, in vitro or in vivo, to conduct gene editing in a cell, two additional molecules can be introduced. In one example, one molecule (B) is a single guide RNA (sgRNA) that further incorporates a tag sequence that can be recognized by an RNA recognition peptide. The sgRNA, alternatively, can be replaced by a crRNA that targets the target site and a CRISPR RNA (crRNA) alone, or in combination with a trans-activating CRISPR RNA (tracrRNA). Examples of tag sequences and corresponding RNA recognition peptides include MS2/MS2 coat protein (MCP), PP7/PP7 coat protein (PCP), and boxB/boxB coat protein (N22p), the sequences of which are provided in Table B. The molecule (B) may be provided as a DNA sequence encoding the RNA molecule.

The other additional molecule (C), in some embodiments, includes a second TEV protease fragment coupled to the RNA recognition peptide (e.g., MCP, PCP, N22p). The first TEV fragment and the second TEV fragment, in some embodiments, when present together, are able to cleave a TEV protease site.

Such co-presence can be triggered by the molecule (C) binding to the molecule (B) by virtue of the tag sequence-RNA recognition protein interaction. Meanwhile, the fusion protein (A) and the molecule (B) will be both present at the target genome locus for gene editing. Therefore, the molecule (B) brings both of the TEV protease fragments from the fusion protein (A) and molecule (C) together, which will activate the TEV protease, leading to removal of the nucleobase deaminase inhibitor from the fusion protein and activation of the base editor. It can be readily appreciated that such activation only occurs at the target genome site, not at off-target single-stranded DNA regions. As such, base editing does not occur at the single-stranded DNA regions that sgRNA does not bind to (as demonstrated in FIG. 17-19).

"Guide RNAs" are non coding short RNA sequences which bind to the complementary target DNA sequences. A guide RNA first binds to the Cas enzyme and the gRNA sequence guides the complex via pairing to a specific location on the DNA, where Cas performs its endonuclease activity by cutting the target DNA strand. A "single guide RNA," frequently simply referred to as "guide RNA", refers to synthetic or expressed single guide RNA (sgRNA) that consists of both the crRNA and tracrRNA as a single construct. The tracrRNA portion is responsible for Cas endonuclease activity and the crRNA portion binds to the target specific DNA region. Therefore, the trans activating RNA (tracrRNA, or scaffold region) and crRNA are two key components and are joined by tetraloop which results in formation of sgRNA.

The scaffold of the guide RNA has a stem-loop structure in itself and attaches to the endonuclease enzyme. A typical scaffold has a structure as illustrated in FIG. 36A (upper), which includes, from the 5' to the 3' end, (a) a repeat region, (b) a tetraloop, (c) an anti-repeat that is at least partially complementary to the repeat region, (d) stem loop 1, (e) a linker, (f) stem loop 2, and (g) stem loop 3. The scaffold sequence is generally conserved, but the loops in stem loop 1 and stem loop 3 can have different sequences. More importantly, the loops of tetraloop and stem loop 2 can be entirely replaced with even much longer sequences. Sequences such as RNA tags (e.g., MS2, PP7, boxB) can be inserted here, enabling recognition by the corresponding recognition peptides. Example scaffold sequences are shown below.

TABLE E

Example sgRNA Scaffold Sequences

| SEQ ID NO: | Sequence |
|---|---|
| 29 | GUUUU̲AGAGCUAGAAAUAGCAAGUUA̲AAAUAAGG CU̲AGUCCGUUAUCAACUUGAAAAAGUGGCACCGA G̲UCGGUGC |
| 30 | GUUUU̲AGAGCUAGAAAUAGCAAGUUA̲AAAUAAGG CA̲UGUCCGUUAUCAACUUGAAAAAGUGGCACCGA U̲UCGGUGC |
| 196 | GUUUG̲AGAGCUAGAAAUAGCAAGUUC̲AAAUAAGG CU̲AGUCCGUUAUCAACUUGAAAAAGUGGCACCGA G̲UCGGUGC |

With reference to these example scaffold sequences, the fragment of positions 1-12 (e.g., GUUUUAGAGCUA, SEQ ID NO:197; GUUUGAGAGCUA, SEQ ID NO:198) represents the repeat region, which forms about 8-12 base pairings with the anti-repeat, which includes positions 17-30 (e.g., UAGCAAGUUAAAAU, SEQ ID NO:199). The GAAA loop (SEQ ID NO:200) between them is the tetraloop. As shown in SEQ ID NO:17, this entire loop can be replaced with a MS2 sequence. Stem loop 1 roughly includes positions 31-39 and includes a small loop (e.g., UA, AU, AA, or UU, without limitation). Stem loop 1 generally has 3-4 base parings in the stem. Stem loop 2, including positions 48-61 (e.g., AACUUGAAAAAGUG, SEQ ID NO:201), generally includes 4 base parings in the stem, and a GAAA (SEQ ID NO:200) loop which can be totally replaced. The remaining, positions 62-76 (e.g., GCACCGAGUCGGUGC, SEQ ID NO:202; GCACCGAUUCGGUGC; SEQ ID NO:203) constitute stem loop 3, which generally includes 4 base pairings in the stem. The small loop (U and G here in the example) can be any nucleotide.

Accordingly, the sequence of the scaffold can be expressed as: GUUUN̲AGAGCUAX̲$_1$UAGCAAGUU N̲AAAUAAGGCN̲N̲GUCCGUUAUCAACUUX̲$_2$A AGUGGCACCGAN̲UCGGUGC (SEQ ID NO:31), where N represents any base, and X1 and X2 denotes any nucleotide sequence of a length of 2-50 bases. The terms "guide RNA" and "single guide RNA" encompasses those that include additional sequences, such as MS2, PP7 and boxB, inserted into one or more loops in the RNA.

Various embodiments and examples of nucleobase deaminases, catalytic domains, nucleobase deaminase inhibitors, and Cas proteins are provided in the disclosures. For instance, a nucleobase deaminase can be a cytidine deaminases and adenosine deaminases. Non-limiting examples of cytidine deaminases include APOBEC1, APOBEC2, APOBEC3A, APOBEC3B, APOBEC3C, APOBEC3D, APOBEC3F, APOBEC3G, APOBEC3H, APOBEC4, and activation-induced (cytidine) deaminase.

Non-limiting examples of adenosine deaminases include tRNA-specific adenosine deaminase (TadA), adenosine deaminase tRNA specific 1 (ADAT1), adenosine deaminase tRNA specific 2 (ADAT2), adenosine deaminase tRNA specific 3 (ADAT3), adenosine deaminase RNA specific B1 (ADARB1), adenosine deaminase RNA specific B2 (ADARB2), adenosine monophosphate deaminase 1 (AMPD1), adenosine monophosphate deaminase 2 (AMPD2), adenosine monophosphate deaminase 3 (AMPD3), adenosine deaminase (ADA), adenosine deaminase 2 (ADA2), adenosine deaminase like (ADAL), adenosine deaminase domain containing 1 (ADAD1), adenosine deaminase domain containing 2 (ADAD2), adenosine deaminase RNA specific (ADAR) and adenosine deaminase RNA specific B1 (ADARB1).

Example Cas proteins include SpCas9, FnCas9, St1Cas9, St3Cas9, NmCas9, SaCas9, AsCpf1, LbCpf1, FnCpf1, VQR SpCas9, EQR SpCas9, VRER SpCas9, RHA FnCas9, and KKH SaCas9 and those provided in Table A.

The fusion proteins may include other fragments, such as uracil DNA glycosylase inhibitor (UGI) and nuclear localization sequences (NLS), each of which is discussed herein.

The base editors and base editing methods described in this disclosure can be applied to perform high-specificity and high-efficiency base editing in the genome of various eukaryotes.

The present disclosure provides compositions and methods. Such compositions comprise an effective amount of a fusion protein, and an acceptable carrier. In some embodiments, the composition further includes a guide RNA that has a desired complementarity to a target DNA. Such a composition can be used for base editing in a sample.

The fusion proteins and the compositions can be used for base editing. In one embodiment, a method for editing a target polynucleotide is provided, comprising contacting to the target polynucleotide a fusion protein of the present disclosure and a guide RNA having at least partial sequence complementarity to the target polynucleotide, wherein the editing comprises deamination of a cytosine (C) in the target polynucleotide.

In one embodiment, provided is a method of editing a cytosine on a nucleic acid sequence in a sample. In some embodiments, the method entails contacting the sample a fusion protein of the present disclosure, or a polynucleotide encoding the fusion protein. In some embodiments, further added is a suitable guide RNA. Design of the guide RNA is readily available to the skilled artisan.

The contacting between the fusion protein (and the guide RNA) and the target polynucleotide can be in vitro, in particular in a cell culture. When the contacting is ex vivo, or in vivo, the fusion proteins can exhibit clinical/therapeutic significance. The in vivo contacting may be administration to a live subject, such as a human, an animal, a yeast, a plant, a bacterium, a virus, without limitation.

Configurations of Induced and Split Base Editors

Various configurations of constructs have been tested to implement the induced and split base editor (isplitBE) design (FIG. 24). Among the configuration tested (FIG. 25), Pair 9 of Example 3 exhibited superior editing efficiency and minimized off-target editing (greatly improved specificity). Pair 9 employs a dual sgRNA system, in which a helper sgRNA (hsgRNA) is used to target a site proximate the main target site. Such dual targeting improves specificity (FIG. 32-33).

In configuration Pair 9 (FIG. 25-28), the nucleobase deaminase inhibitor is only released when both sgRNA are bound to the target sequences, ensuring that the nucleobase deaminase does not edit at off-target sites. Configuration Pair 9 includes 6 different molecules, which can be produced from two separate constructs, for instance (FIGS. 26A and 34A).

The first molecule can include just a Cas protein, which has a suitable size for packaging in a common vehicle, AAV. The second molecule includes, among others, a nucleobase deaminase (e.g., APOBEC), a nucleobase deaminase inhibitor (e.g., mA3-CDA2), and an RNA recognition peptide (e.g., MCP). A protease cleavage site (e.g., TEV site) is inserted between the nucleobase deaminase and the nucleobase deaminase inhibitor, which enables removal of the nucleobase deaminase inhibitor at proper timing/location. Optionally, the second molecule further includes a UGI.

The third molecule is a fusion between an inactive portion of the protease (e.g., TEVc) fused to different RNA recognition peptide (e.g., N22p). The fourth molecule is a stand-alone TEVn which, in combination with the first portion, can carry out the protease activity to remove the nucleobase deaminase inhibitor from the second molecule.

The fifth molecule is a helper sgRNA containing an RNA recognition site (e.g., MS2) recognizable by the RNA recognition peptide in the $2^{nd}$ molecule. The sixth molecule is a regular sgRNA that contains an RNA recognition site (e.g., boxB) recognizable by the RNA recognition peptide in the $3^{rd}$ molecule.

At the correct target site in the genome (or RNA), both the hsgRNA and the sgRNA will bind, and each recruits a Cas protein to the binding site. The hsgRNA will also recruit the $2^{nd}$ molecule by virtue of the MS2-MCP binding, and the sgRNA will recruit the $3^{rd}$ molecule by virtue of the boxB-N22p binding. Therefore, the TEVc of the $3^{rd}$ molecule is in contact with the TEV site. Since the standalone TEVn is present in the entire cell, it can also be present here, which ensures that the TEVc is active and cleaves the nucleobase deaminase inhibitor from the nucleobase deaminase in molecule 2, thereby activating the nucleobase deaminase.

It is further discovered that an optimal distance between the hsgRNA binding site and the regular sgRNA binding site is from 34-91 bp (from PAM to PAM), with the hsgRNA on the upstream.

Moreover, even though the proper binding of both hsgRNA and regular sgRNA is required for the intended editing in the target site for regular sgRNA, the editing in the target site for hsgRNA is not desirable. It is discovered herein that when the spacer length of the hsgRNA (spacer is the target complementary region) is from 8-15 bases, such a hsgRNA is still sufficient to provide dual recognition to ensure binding specificity, but greatly reduce the editing in the hsgRNA target site.

In accordance with one embodiment of the disclosure, therefore, provided is a fusion protein comprising a first fragment comprising: a nucleobase deaminase or a catalytic domain thereof, a nucleobase deaminase inhibitor, a first RNA recognition peptide, and a TEV protease cleavage site between the nucleobase deaminase or a catalytic domain thereof and the nucleobase deaminase inhibitor.

In some embodiments, the fusion protein further comprises a second fragment comprising: a TEV protease fragment which alone is not able to cleave the TEV protease cleavage site, and a second RNA recognition peptide. In some embodiments, the fusion protein further comprises a self-cleavage site between the first fragment and the second fragment.

In some embodiments, the fusion protein further comprises a third fragment comprising a second TEV protease fragment, wherein the first TEV protease fragment is able to cleave the TEV protease site in the presence of the second TEV protease fragment. In some embodiments, the fusion protein further comprises a second self-cleavage site between the second fragment and the third fragment, ad upon cleavage of the second self-cleavage site, the fusion protein releases the second TEV protease fragment which is not fused to any RNA recognition peptide.

Also provided, in one embodiment, is a dual guide RNA system, comprising: a target single guide RNA comprising a first spacer having sequence complementarity to a target nucleic acid sequence proximate to a first PAM site, a helper single guide RNA comprising a second spacer having sequence complementarity to a second nucleic acid sequence proximate to a second PAM site, a clustered regularly interspaced short palindromic repeats (CRISPR)-associated (Cas) protein, and a nucleobase deaminase.

In some embodiments, the second PAM site is located within 150 bases, or alternatively within 140, 130, 120, 110, 100, 95, 94, 93, 92, 91, 90, 89, 88, 87, 86, 85, 84, 83, 82, 81, 80, 75 or 70 bases from the second PAM site. In some embodiments, the second PAM site is located at least 10 bases, or alternatively at least 15, 20, 25, 30, 31, 32, 33, 34, 35, 36, 37, 38, 39, 40, 45, 50, 55, or 60 bases from the first PAM. In some embodiments, the second PAM site is upstream from the first PAM site. In some embodiments, the second PAM site is downstream from the first PAM site. In some embodiments, the distance is from 20-100, 25-95, 30-95, 34-95, 34-91, 34-90, 35-90, 40-90, 40-84, 45-85, or 50-80 bases, without limitation.

In some embodiments, the second (helper) spacer is 8-15 bases in length. In some embodiments, the second spacer is 8-14, 8-13, 8-12, 8-11, 8-10, 9-15, 9-14, 9-13, 9-12, 9-11, 9-10, 10-15, 10-14, 10-13, 10-12, 10-11, 11-15, 11-14, 11-13, 11-12, 12-15, 12-14, 12-13, or 13-15 bases in length. The first spacer, by contrast, is at least 16, 17, 18, or 19 bases in length.

Various "split" base editing systems are also described here, which allow the Cas protein and the nucleobase deaminase to be packaged into separate delivery vehicles (e.g., AAV).

In some embodiments, pairs of regular sgRNA and hsgRNA are provided that can mediate efficient editing to generate early stop codons in PCSK9 genes, which can have clinic benefits. Based on the discoveries here, suitable target sites for sgRNA and hsgRNA have been selected for converting a non-stop codon to a stop codon. Take C-to-T/U editing as an example, a non-stop codon can be CAG, CAA or CGA.

Examples of such target sites are illustrated in Table 4. It is readily understood that the sequences in Table 4 are used to show the location of the target. The actual sgRNA and hsgRNA, however, does not need to bind to the entire sequence. In fact, for hsgRNA for instance, a binding of 8-15 nucleotides could well be enough as explained above. Accordingly, the spacer sequence on the hsgRNA can be complementary to a sub-sequence of any shown in Table 4, or even overlap with any of them. The same is true for sgRNA as well, with a preferred spacer length of 18-24 nucleotides, without limitation.

In one embodiment, provided is a pair of helper guide RNA/guide RNA for editing a human PCSK9 nucleic acid sequence, wherein the guide RNA specifically targets a first site on the PCSK9 nucleic acid to enable base editing to convert a non-stop codon to a stop codon, and wherein the helper guide RNA specifically targets a second site on the PCSK9 nucleic acid that is 20 to 100 bases from the first site. In some embodiments, the second site is about 20-100, 25-95, 30-95, 34-95, 34-91, 34-90, 35-90, 40-90, 40-84, 45-85, or 50-80 bases away from the first site.

In some embodiments, the hsgRNA has a spacer that is 8-15 bases in length. In some embodiments, the spacer is 8-14, 8-13, 8-12, 8-11, 8-10, 9-15, 9-14, 9-13, 9-12, 9-11, 9-10, 10-15, 10-14, 10-13, 10-12, 10-11, 11-15, 11-14, 11-13, 11-12, 12-15, 12-14, 12-13, or 13-15 bases in length. In some embodiments, the sgRNA has a spacer that is at least 16, 17, 18, or 19 bases in length.

Spacer sequences for the sgRNA/hsgRNA can be readily designed. For instance, for each target site shown in Table 4, a spacer may be the complementary sequence of the desired length (i.e., complementary to a sub-sequence of any of SEQ ID NO:166-180 or 181-195). Specific examples of pairs of binding sites include, without limitation, SEQ ID NO:166 and 181; SEQ ID NO:167 and 182; SEQ ID NO:168 and 183; SEQ ID NO:169 and 184; SEQ ID NO:170 and 185; SEQ ID NO:171 and 186; SEQ ID NO:172 and 187; SEQ ID NO:173 and 188; SEQ ID NO:174 and 189; SEQ ID NO:175 and 190; SEQ ID NO:176 and 191; SEQ ID NO:177 and 192; SEQ ID NO:178 and 193; SEQ ID NO:179 and 194; and SEQ ID NO:180 and 195.

Example sgRNA/hsgRNA sequences have also been designed and tested. See Table 3. Moreover, polynucleotide sequences encoding the helper guide RNA and guide RNA are also provided.

With such pairs of sgRNA/hsgRNA sequences, methods of inactivating a PSCK9 gene in a cell can be carried out. In some embodiments, the method entails contacting the cell with a pair of helper guide RNA and guide RNA of the present disclosure, a clustered regularly interspaced short palindromic repeats (CRISPR)-associated (Cas) protein, and a nucleobase deaminase. Each of these elements have been further described in the instant disclosure.

Enhanced Prime Editing

Improved prime editing systems are also provided, in some embodiments. In particular, certain prime editing guide RNA (pegRNA) molecules provided herein have improved stability. These pegRNA contain a scaffold that, compared to the conventional guide RNA, has one additional base pairing (see, FIGS. 36A and 36E). Using the standard scaffold (SEQ ID NO:31) at a template, the improved scaffold may have a sequence of any of SEQ ID NO:32-43.

As discussed above, a typical guide RNA scaffold has a structure which includes, from the 5' to the 3' end, (a) a repeat region, (b) a tetraloop, (c) an anti-repeat that is at least partially complementary to the repeat region, (d) stem loop 1, (e) a linker, (f) stem loop 2, and (g) stem loop 3. In other words, the scaffold includes 4 stem loops. The third stem loop (counted from 5' to 3'), also referred to as "Stem loop 2", includes 4 base pairings in the conventional design. In the new design, this stem loop has 5 base pairing.

In one embodiment, provided is a guide RNA comprising a scaffold which comprises, from the 5' to 3' direction, a first stem loop portion, a second stem loop portion, a third stem loop portion, and a fourth stem loop portion, wherein the third stem loop comprises five base pairings within.

The sequence of the scaffold can be expressed as: GUUUNAGAGCUAX1UAGCAAGUUNAAAUAAGGC-NNGUCCGUUAUCAACUUX2A AGUGGCACCGA-NUCGGUGC (SEQ ID NO:31), where N represents any base, and X1 and X2 denotes any nucleotide sequence of a length of 2-50 bases (or 2-40, 3-40, 4-40, 4-30, 2-30, 4-20 bases). Accordingly, in some embodiments, the base pairings comprise one between positions 45 and 55, according to the positions in SEQ ID NO:31. In some embodiments, the scaffold has at least 75%, 80%, 85%, 90%, 95%, 96%, 97%, 98%, or 99% sequence identity to SEQ ID NO:31 and includes give base pairings in the third stem loop.

In one embodiment, therefore, provided is a guide RNA comprising a scaffold derived from SEQ ID NO:31 by introducing a base pairing between the bases at position 45 and position 55, and optionally allowing one, two, three, four, or five base additions, deletions, substitutions, or the combination thereof, as long as it maintains the stem loops structure or the scaffold/guide RNA functionality. In some embodiments, the scaffold comprises a sequence selected from the group consisting of SEQ ID NO:32-43. In some embodiments, the guide RNA is at least 100 nucleotides, or 105, 110, 115, 120, 125, 130, 140 or 150 nucleotides in length. In some embodiments, the guide RNA further includes a spacer (e.g., 8-25 nucleotides), a reverse-transcriptase template, and/or a primer-binding site.

Improved prime editor proteins are also provided, in some embodiments. In one embodiment, the prime editor includes a Cas protein and a reverse-transcriptase linked through a linker tested to optimized for the performance of the prime editor. In one embodiment, the prime editor comprises the amino acid sequence of SEQ ID NO:44. In one embodiment, the prime editor comprises the amino acid sequence of SEQ ID NO:45. Both these prime editors have been tested and shown to exhibit superior editing efficiency and specificity.

Various "split" prime editing systems are also described here, which allow the Cas protein and the reverse transcriptase to be packaged into separate delivery vehicles (e.g., AAV).

With the split prime editing systems, methods for conducting genetic editing in a cell at a target site are also provided. In some embodiments, the method entails introducing to the cell a first viral particle enclosing a first construct encoding a clustered regularly interspaced short palindromic repeats (CRISPR)-associated (Cas) protein, and a second viral particle enclosing a second construct encoding a reverse-transcriptase fused to an RNA recognition peptide. In some embodiments, the second construct further encodes a guide RNA comprising an RNA recognition site that the RNA recognition peptide binds to.

In some embodiments, the second construct further encodes a guide RNA comprising an RNA recognition site that the RNA recognition peptide binds to. In some embodiments, the Cas protein is selected from the group consisting of SpCas9, FnCas9, St1Cas9, St3Cas9, NmCas9, SaCas9, AsCpf1, LbCpf1, FnCpf1, VQR SpCas9, EQR SpCas9, VRER SpCas9, SpCas9-NG, xSpCas9, RHA FnCas9, KKH SaCas9, NmeCas9, StCas9, CjCas9, AsCpf1, FnCpf1, SsCpf1, PcCpf1, BpCpf1, CmtCpf1, LiCpf1, PmCpf1, Pb3310Cpf1, Pb4417Cpf1, BsCpf1, EeCpf1, BhCas12b, AkCas12b, EbCas12b, LsCas12b, RfCas13d, LwaCas13a, PspCas13b, PguCas13b, and RanCas13b. In some embodiments, the Cas protein is SpCas9-NG or xSpCas9.

Non-limiting examples of reverse-transcriptases include human immunodeficiency virus (HIV) reverse-transcriptase, moloney murine leukemia virus (MMLV) reverse-transcriptase and avian myeloblastosis virus (AMV) reverse-transcriptase

EXAMPLES

Example 1. Fusion Base Editors with Reduced Off-Target Editing Activity

Single-guide RNAs (sgRNAs) and base editors (BEs) mentioned in the examples are for SpCas9, unless specifically pointed out, e.g., the sgRNA for SaCas9 (Sa-sgRNAs). To test whether the current base editing system can induce C-to-T mutations in ssDNA regions, we used SaD10A nickase and Sa-sgRNA to make a DNA single-stranded break (SSB), which can trigger end recession to generate a ssDNA region. (FIGS. 1A, 2A and 3A). We co-transfected SaD10A, Sa-sgRNA (Sa-sgSITE31, Sa-sgSITE42 and Sa-sgF1) with two published BEs, i.e., BE3 and hA3A-BE3 or an empty vector (FIGS. 1B, 2B and 3B) and determine the mutagenesis around the ssDNA regions triggered by SaD10A. At three tested sites (Sa-SITE31, Sa-SITE42 and Sa-F1) the expression of BE3 or hA3A-BE3 induced C-to-T mutations, whereas the expression of an empty vector did not (FIGS. 1C, 2C and 3C). These results indicated that the current base editors, which contain catalytically active cytidine deaminases, indeed cause unintended mutations in non-relevant ssDNA regions (FIGS. 1, 2 and 3).

To inhibit the activity of cytidine deaminase at non-relevant sites, e.g., ssDNA regions, we proposed to fuse base editors with a base editing inhibitor. Mouse APOBEC3 (mA3) comprises two cytidine deaminase (CDA) domains (CDA1 and CDA2, FIGS. 4A, 5A, 6A) and the use of full-length mA3 in mA3-BE3 (FIGS. 4B, 5B, 6B) did not induce C-to-T editing at three tested target sites (FIGS. 4C, 5C, 6C). However, mA3CDA1-BE3, which is generated by deleting mA3CDA2 from mA3-BE3 (FIGS. 4B, 5B, 6B), induced substantial C-to-T editing (FIGS. 4C, 5C, 6C). These results suggest that mA3CDA2 is a natural inhibitor of base editing. Thus, we added mA3CDA2 to the N-terminus of three active BEs, i.e., mA3CDA1-BE3, BE3 and hA3A-BE3, to generate mA3rev-BE3, mA3CDA2-BE3 and mA3CDA2-hA3A-BE3 (FIGS. 4B, 5B, 6B). As we expected, the adding of mA3CDA2 to the N-terminus clearly reduced the base editing efficiencies (FIGS. 4C, 5C, 6C).

Next, we considered whether the cleavage of mA3CDA2 can restore the base editing efficiency. 2A self-cleavage peptides were inserted between mA3CDA2 and the rest part of BE in mA3rev-BE3, mA3CDA2-BE3 and mA3CDA2-hA3A-BE3 to generate mA3rev-2A-BE3, mA3CDA2-2A-BE3 and mA3CDA2-2A-hA3A-BE3 (FIGS. 4B, 5B, 6B). Correspondingly, the base editing efficiencies restored in mA3rev-2A-BE3, mA3CDA2-2A-BE3 and mA3CDA2-2A-hA3A-BE3 (FIGS. 4C, 5C, 6C), indicating that the inhibition of mA3CDA2 depends on its covalent connection to BEs. We also searched protein database for the domains similar to mA3CDA2 core sequence and found at least 44 proteins have the similar domains (Table 1).

Human APOBEC3B (hA3B) also comprises two cytidine deaminase (CDA) domains (CDA1 and CDA2, FIGS. 7A, 8A, 9A) and the use of full-length hA3B in hA3B-BE3 (FIGS. 7B, 8B, 9B) only induced relatively low levels of C-to-T editing at three tested target sites (FIGS. 7C, 8C, 9C). However, hA3BCDA2-BE3, which is generated by deleting hA3BCDA1 from hA3B-BE3 (FIGS. 7B, 8B, 9B), induced higher C-to-T editing (FIGS. 7C, 8C, 9C). In addition, 2A self-cleavage peptides were inserted between hA3BCDA1 and hA3BCDA2 to generate hA3B-2A-BE3 (FIGS. 7B, 8B, 9B), which induces higher C-to-T editing efficiencies than hA3B-BE3 (FIGS. 7C, 8C, 9C). These results indicate that hA3BCDA1 is another inhibitor of base editing and the inhibition of hA3BCDA1 depends on its covalent connection to BEs. We also searched protein database for the domains similar to hA3BCDA1 and found at least 43 proteins have the similar domains (Table 2).

Next, we planned to use mA3 to develop novel BEs. The two BEs, mA3rev-BE3 and mA3rev-2A-BE3, were made by splitting mA3 between amino acid (AA)207 and AA208 and then we determined where to split mA3CDA2 can keep the highest editing efficiency (FIGS. 10A, 11A, 12A). As mA3CDA1 ends at amino acid (AA)154 and mA3CDA2 starts from AA238, we split mA3CDA2 at AA196/AA197, AA215/AA216, AA229/AA230 and AA237/AA238 to generate mA3rev-BE3-196, mA3rev-2A-BE3-196, mA3rev-BE3-215, mA3rev-2A-BE3-215, mA3rev-BE3-229, mA3rev-2A-BE3-229, mA3rev-BE3-237, and mA3rev-2A-BE3-237 (FIGS. 10B, 11B, 12B). Although the splitting of mA3 at AA207/AA208 and AA215/AA216 keeps the highest editing efficiencies, the results also showed that the splitting sites spanning from AA196/AA197 to AA237/AA238 generally keep substantial editing efficiencies (FIGS. 10C, 11C, 12C).

Furthermore, we tried to determine the minimal region of mA3 that has a base editing inhibitory effect. We deleted various N-terminal parts of mA3CDA2 in mA3rev-BE-237 to develop mA3rev-BE-237-Del-255, mA3rev-BE-237-Del-285 and mA3rev-BE-237-Del-333, which contains the AA256-AA429, AA286-AA429 and AA334-AA429 parts of mA3 as the base editing inhibitor respectively (FIGS. 13A, 14A, 15A). By comparing with mA3rev-BE-237, which contains the AA238-AA429 part of mA3, mA3rev-BE-237-Del-255, mA3rev-BE-237-Del-285 and mA3rev-BE-237-Del-333 showed similar editing efficiencies (FIGS. 13B, 14B, 15B). These results indicated that the AA334-AA429 part of mA3 still has the inhibitory effect of base editing.

In order to develop base editors that do not cause C-to-T mutation in non-relevant ssDNA regions, we replaced the 2A self-cleavage site with a cleavage site of TEV protease in mA3rev-2A-BE3 and then fused the N-terminal part of TEV protease (TEVn) [Gray et al., 2010, Cell, doi: 10.1016/j.cell.2010.07.014] to the C-terminus of mA3rev-2A-BE3 with another TEV cleavage site. The newly developed BE is named BEsafe. In addition, we put one MS2 loop into the sgRNA to generate MS2-sgRNA [Ma et al., 2016, Nature Biotechnology, doi: 10.1038/nbt.3526] and then fused the C-terminal part of TEV protease (TEVc) with MS2 coat protein (MCP), which can bind to MS2 loop (FIG. 16A). When BEsafe, MS2-sgRNA and MCP-TEVc were co-expressed, the TEVn fused in BEsafe and the TEVc of MCP-TEVc that can be recruited by MS2-sgRNA would associate and restore the protease activity at on-target site. The subsequent cleavages at TEV sites would remove mA3CDA2 and TEVn from the N- and C-terminus of BEsafe and the resulted mA3CDA1-BE3 can induce efficient base editing at on-target site (FIG. 16A). On contrary, the BEsafe would not induce C-to-T mutations in non-relevant ssDNA regions because the cytidine deaminase activity of mA3CDA1 is inhibited by mA3CDA2 (FIG. 16B).

We then compared the performance of BEsafe and hA3A-BE3 at on-target sites and non-relevant ssDNA regions (FIGS. 17, 18, 19). We co-transfected the plasmid expressing Sa-sgRNA and SaD10A, which can trigger ssDNA formation at Sa-sgRNA target sites (FIGS. 17A, 18A, 19A), with the hA3A-BE3 expression plasmid and the sgRNA expression plasmid, with the BEsafe expression plasmid and the plasmid expressing MS2-sgRNA and MCP-TEVc or with the MCP-TEVc expression plasmid and the plasmid expressing MS2-sgRNA and BEsafe (FIGS. 17B, 18B, 19B). We examined the C-to-T mutation frequencies in non-relevant ssDNA regions (Sa-sgRNA on-target sites, orthogonal to those of SpCas9) (FIGS. 17C, 18C, 19C) and the base editing efficiencies at sgRNA on-target sites of hA3A-BE3 and BEsafe, both of which are SpCas9-derived (FIGS. 17D, 18D, 19D). We found that BEsafe did not cause any C-to-T mutation in the non-relevant ssDNA regions (Sa-sgRNA on-target sites) but hA3A-BE3 caused obvious mutations (FIGS. 17C, 18C, 19C). At sgRNA on-target sites, BEsafe induced base editing comparable to hA3A-BE3, while the expression of both MS2-sgRNA and BEsafe from one single plasmid yielded higher base editing efficiencies than the expression of only BEsafe from one plasmid did (FIGS. 17D, 18D, 19D).

The base editors and base editing method described in this invention could be applied to perform high-specificity and high-efficiency base editing in the genome of various eukaryotes.

For the first time, a base editing system was established to avoid causing C-to-T mutations in non-relevant ssDNA regions and to induce efficient base editing at on-target sites. The BEsafe base editing system and the accompanying methods disclosed in this invention could be utilized to perform highly specific base editing that cannot be implemented by the currently existing BEs as the cytidine deaminases in current BEs can cause unintended mutations in non-relevant ssDNA regions. Importantly, the high specificity and efficiency of this BEsafe base editing system will promote the potential clinical translation, especially in the gene therapies that involve restoring disease-related mutations.

TABLE 1 mA3CDA2 Core Sequence Related Domains

| Name | Sequence | SEQ ID NO: |
|---|---|---|
| Mouse APOBEC3 cytidine deaminase domain 2 core (AA282-AA355) | SEKGKQHAEILFLDKIRSMELSQVTITCYLTWSPCPNCAWQLAAFKRDRP DLILHIYTSRLYFHWKRPFQKGLC | 48 |
| Mus spicilegus A3 (AA248-AA321) | SEKGKQHAEILFLDKIRSMELSQVTITCYLTWSPCPNCAWQLAAFKRDRP DLIPHIYTSRLYFHWKRPFQKGLC | 49 |
| Cricetulus longicaudatus A3 (AA249-AA322) | SEKGKQHAEILFLDKIRSMELSQVTITCYLTWSPCPNCAWRLAAFKRDRP DLILHIYTSRLYFHWKRPFQKGLC | 50 |
| Mus terricolor A3 (AA248-AA321) | SEKGKQHAEILFLNKIRSMELSQVTITCYLTWSPCPNCAWQLAAFKKDRP DLILHIYTSRLYFHWKRPFQKGLC | 51 |
| Mus caroli A3 (AA260-AA333) | SKKGKQHAEILFLDKIRSMELSQVTITCYLTWSPCPNCAWQLAAFKRDHP DLILHIYTSRLYFHWKRPFQKGLC | 52 |
| Mus pahari A3 (AA263-AA336) | SKKGKQHAEILFLEKIRSMELSQMRITCYLTWSPCPNCAWQLAAFQKDRP DLILHIYTSRLYFHWRRIFQKGLC | 53 |
| Mus shortridgei A3 (AA233-AA306) | SKKGKQHAEILFLEKIRSMELSQMRITCYLTWSPCPNCAWQLAAFQKDRP DLILHIYTSRLYFHWRRIFQKGLC | 54 |

TABLE 1-continued mA3CDA2 Core Sequence Related Domains

| Name | Sequence | SEQ ID NO: |
|---|---|---|
| *Mus setulosus* A3 (AA29-AA302) | SKKGKQHAEILFLDKIRSMELSQVRITCYLTWSPCPNCAWQLETFKKDRP DLILHIYTSRLYFHWKRAFQEGLC | 55 |
| *Grammomys surdaster* A3 (AA270-AA344) | SKKGKPHAEILFLDKMWSMEELSQVRITCYLTWSPCPNCARQLAAFKKDH PGLILRIYTSRLYFYWRRKFQKGLC | 56 |
| *Rattus norvegicus* A3 (AA256-AA328) | KKGEQHVEILFLEKMRSMELSQVRITCYLTWSPCPNCARQLAAFKKDHPD LILRIYTSRLYFYWRKKFQKGLC | 57 |
| *Mastomys coucha* A3 (AA258-AA331) | SKKGRQHAEILFLEKVRSMQLSQVRITCYLTWSPCPNCAWQLAAFKMDHP DLILRIYASRLYFHWRRAFQKGLC | 58 |
| *Cricetulus griseus* A3B (AA235-AA307) | NKKGKHAEILFIDEMRSLELGQVQITCYLTWSPCPNCAQELAAFKSDHPD LVLRIYTSRLYFHWRRKYQEGLC | 59 |
| *Peromyscus leucopus* A3 (AA266-AA338) | NKKGKHAEILFIDEMRSLELGQARITCYLTWSPCPNCAQKLAAFKKDHPD LVLRVYTSRLYFHWRRKYQEGLC | 60 |
| *Mesocricetus auratus* A3 (AA268-AA340) | NKKDKHAEILFIDKMRSLELCQVRITCYLTWSPCPNCAQELAAFKKDHPD LVLRIYTSRLYFHWRRKYQEGLC | 61 |
| *Microtus ochrogaster* A3B (AA266-AA338) | NKKGKHAEILFIDEMRSLKLSQERITCYLTWSPCPNCAQELAAFKRDHPG LVLRIYASRLYFHWRRKYQEGLC | 62 |
| *Nannospalax galili* A3 (AA231-AA302) | NKRAKHAEILLIDMMRSMELGQVQITCYITWSPCPTCAQELAAFKQDHPD LVLRIYASRLYFHWKRKFQKGL | 63 |
| *Meriones unguiculatus* A3 (AA233-AA305) | NKKGRHAEICLIDEMRSLGLGKAQITCYLTWSPCRKCAQELATFKKDHPD LVLRVYASRLYFHWSRKYQQGLC | 64 |
| *Dipodomys ordii* A3 (AA256-AA330) | NKKGHHAEIRFIERIRSMGLDPSQDYQITCYLTWSPCLDCAFKLAKLKKD FPRLTLRIFTSRLYFHWIRKFQKGL | 65 |
| *Jaculus jaculus* A3 (AA303-AA374) | NKKGKHAEARFVDKMRSMQLDHALITCYLTWSPCLDCSQKLAALKRDHPG LTLRIFTSRLYFHWVKKFQEGL | 66 |
| *Chinchilla lanigera* A3H (AA86-AA161) | SPQKGHHAESRFIKRISSMDLDRSRSYQITCFLTWSPCPSCAQELASFKR AHPHLRFQIFVSRLYFHWKRSYQAGL | 67 |
| *Heterocephalus glaber* A3 (AA277-AA350) | KKGYHAESRFIKRICSMDLGQDQSYQVTCFLTWSPCPHCAQELVSFKRAH PHLRLQIFTARLFFHWKRSYQEGL | 68 |
| *Octodon degus* A3 (AA256-AA329) | KKGQHAEIRFIERIHSMALDQARSYQITCFLTWSPCPFCAQELASFKSTH PRVHLQIFVSRLYFHWKRSYQEGL | 69 |
| *Urocitellus parryii* A3 (AA256-AA330) | NKKGHHAEIRFIKKIRSLDLDQSQNYEVTCYLTWSPCPDCAQELVALTRS HPHVRLRLFTSRLYFHWFWSFQEGL | 70 |
| *Aotus nancymaae* A3H (AA75-AA146) | NRHAEICFIDEIESMGLDKTQCYEVTCYLTWSPCPSCAQKLAAFTKAQVH LNLRIFASRLYYHWRSSYQKGL | 71 |
| *Cebus capucinus imitator* A3H (AA55-AA126) | NRHAEICFIDEIESMGLDKTQCYEVTCYLTWSPCPSCAQKLVAFAKAQDH LNLRIFASRLYYHWRRRYKEGL | 72 |
| *Saimiri boliviensis boliviensis* A3H (AA56-AA125) | HVEICFIDKIASMELDKTQCYDVTCYLTWSPCPSCAQKLAAFAKAQDHLN LRIFASRLYYHWRRSYQKGL | 73 |
| *Homo sapiens* A3H (AA49-AA123) | NKKKCHAEICFINEIKSMGLDETQCYQVTCYLTWSPCSSCAWELVDFIKA HDHLNLGIFASRLYYHWCKPQQKGL | 74 |
| *Homo sapiens* ARP10 (AA48-AA123) | ENKKKCHAEICFINEIKSMGLDETQCYQVTCYLTWSPCSSCAWELVDFIK AHDHLNLGIFASRLYYHWCKPQQKGL | 75 |
| *Pan paniscus* A3H (AA49-AA123) | NKKKCHAEICFINEIKSMGLDETQCYQVTCYLTWSPCSSCAWKLVDFIQA HDHLNLRIFASRLYYHWCKPQQEGL | 76 |

TABLE 1-continued mA3CDA2 Core Sequence Related Domains

| Name | Sequence | SEQ ID NO: |
|---|---|---|
| *Symphalangus syndactylus* A3H (AA49-AA123) | NKKKRHAEIRFINKIKSMGLDETQCYQVTCYLTWSPCPSCAWELVDFIKA HDHLNLGIFASRLYYHWCRHQQEGL | 77 |
| *Macaca mulatta* A3H (AA49-AA123) | NKKKDHAEIRFINKIKSMGLDETQCYQVTCYLTWSPCPSCAGELVDFIKA HRHLNLRIFASRLYYHWRPNYQEGL | 78 |
| *Theropithecus gelada* A3H (AA54-AA128) | NKKKEHAEIRFINKIKSMGLDETQCYQVTCYLTWSPCPSCAGKLVDFIKA HHHLNLRIFASRLYYHWRPNYQEGL | 79 |
| *Mandrillus leucophaeus* A3H (AA49-AA123) | NKKKHHAEIHFINKIKSMGLDETQCYQVTCYLTWSPCPSCARELVDFIKA HRHLNLRIFASRLYYHWRPHYQEGL | 80 |
| *Bos grunniens* A3 (AA74-AA148) | NKKQRHAEIRFIDKINSLDLNPSQSYKIICYITWSPCPNCANELVNFITR NNHLKLEIFASRLYFHWIKPFKMGL | 81 |
| *Bubalus bubalis* A3 (AA74-AA148) | NKKQRHAEIRFIDKINSLDLNPSQSYKIICYITWSPCPNCASELVDFITR NDHLDLQIFASRLYFHWIKPFKRGL | 82 |
| *Odocoileus virginianus texanus* A3H (AA209-AA283) | NKKQRHAEIRFIDKINSLNLDRRQSYKIICYITWSPCPRCASELVDFITG NDHLNLQIFASRLYFHWKKPFQRGL | 83 |
| *Sus scrofa* A3 (AA51-AA125) | NKKKRHAEIRFIDKINSLNLDQNQCYRIICYVTWSPCHNCAKELVDFISN RHHLSLQLFASRLYFHWVRCYQRGL | 84 |
| *Ceratotherium simum simum* A3B (AA232-AA306) | NKKKRHAEIRFIDKIKSLGLDRVQSYEITCYITWSPCPTCALELVAFTRD YPRLSLQIFASRLYFHWRRRSIQGL | 85 |
| *Equus caballus* A3H (AA79-AA153) | NKKKRHAEIRFIDKINSLGLDQDQSYEITCYVTWSPCATCACKLIKFTRK FPNLSLRIFVSRLYYHWFRQNQQGL | 86 |
| *Enhydra lutris kenyoni* A3B (AA243-AA316) | KKKRHAEIRFIDSIRALQLDQSQRFEITCYLTWSPCPTCAKELAMFVQDH PHISLRLFASRLYFHWRWKYQEGL | 87 |
| *Leptonychotes weddellii* A3H (AA50-AA123) | KKKRHAEIRFIDNIKALRLDTSQRFEITCYVTWSPCPTCAKELVAFVRDH RHISLRLFASRLYFHWLRENKKGL | 88 |
| *Ursus arctos horribilis* A3F (AA552-AA626) | NKKKRHAEIRFIDKIRSLQRDSSQTFEITCYVTWSPCFTCAEELVAFVRD HPHVRLRLFASRLYFHWLRKYQEGL | 89 |
| *Panthera leo bleyenberghi* A3H (AA50-AA124) | NKKKRHAEICFIDKIKSLTRDTSQRFEIICYITWSPCPFCAEELVAFVKD NPHLSLRIFASRLYVHWRWKYQQGL | 90 |
| *Panthera tigris sumatrae* A3H (AA50-AA124) | NKKKRHAEICFIDKIKSLTRDTSQRFEIICYITWSPCPFCAEELVAFVKD NPHLSLRIFASRLYVHWRWKYQQGL | 91 |
| *Tupaia belangeri* A3 (AA46-AA120) | NKKHRHAEVRFIAKIRSMSLDLDQKHQLTCYLTWSPCPSCAQELVTFMAE SRHLNLQVFVSRLYFHWQRDFQQGL | 92 |

TABLE 2 hA3BCDA1-Related Domains

| Name | Sequence | SEQ ID NO: |
|---|---|---|
| Gorilla A3B (AA29-AA138) | GRSYNWLCYEVKIKRGRSNLLWNTGVFRGQMYSQPEHHAEMCFLSWFCGN QLPAYKCFQITWFVSWTPCPDCVAKLAEFLAEYPNVTLTISTARLYYWE RDYRRALCRL | 93 |
| *Pan paniscus* A3B (AA29-AA138) | GRSYTWLCYEVKIRRGHSNLLWDTGVFRGQMYSQPEHHAEMYFLSWFCGN QLPAYKCFQITWFVSWTPCPDCVAKLAEFLAEHPNVTLTISAARLYYWE RDYRRALCRL | 94 |

TABLE 2-continued hA3BCDA1-Related Domains

| Name | Sequence | SEQ ID NO: |
|---|---|---|
| Pan troglodytes A3B (AA29-AA138) | GRSYTWLCYEVKIRRGHSNLLWDTGVFRGQMYSQPEHHAEMCFLSWFCGN QLSAYKCFQITWFVSWTPCPDCVAKLAKFLAEHPNVTLTISAARLYYYWE RDYRRALCRL | 95 |
| Gorilla A3F (AA30-AA137) | RNTVWLCYEVKTKGPSRPPLDAKIFRGQVYFEPQYHAEMCFLSWFCGNQL PAYKCFQITWFVSWTPCPDCVAKLAEFLAEHPNVTLTISAARLYYYWE | 96 |
| Pan troglodytes A3F (AA30-AA137) | RNTVWLCYEVKTKGPSRPRLDTKIFRGQVYFEPQYHAEMCFLSWFCGNQL PAYKCFQITWFVSWTPCPDCVAKLAEFLAEHPNVTLTISAARLYYYWERD YRRALCRL | 97 |
| Human sapiens A3F (AA30-AA137) | RNTVWLCYEVKTKGPSRPRLDAKIFRGQVYSQPEHHAEMCFLSWFCGNQL PAYKCFQITWFVSWTPCPDCVAKLAEFLAEHPNVTLTISAARLYYYWERD YRRALCRL | 98 |
| Macaca leonine A3F (AA30-AA137) | RNTVWLCYEVKTRGPSMPTWGTKIFRGQVCFEPQYHAEMCFLSRFCGNQL PAYKRFQITWFVSWTPCPDCVAKVAEFLAEHPNVTLTISAARLYYYWETD YRRALCRL | 99 |
| Macaca nemestrina A3F (AA30-AA137) | RNTVWLCYEVKTRGPSMPTWGTKIFRGQVCFEPQYHAEMCFLSRFCGNQL PAYKRFQITWFVSWTPCPDCVAKVAEFLAEHPNVTLTISAARLYYYWETD YRRALCRL | 100 |
| Rhinopithecus roxellana A3F (AA30-AA137) | RNTVWLCYEVKTRGPSMPTWGAKIFRGQVYFEPQYHAEMCFLSWFCGNQL PAYKRFQITWFVSWTPCPDCVAKVAEFLAEHPNVTLTISAARLYYYWETD YRRALCRL | 101 |
| Mandrillus leucophaeus A3F (AA30-AA130) | RNTVWLCYKVKTRGPSMPTWGTKIFRGQVYFQPQYHAEMCFLSWFCGNQL PAYKRFQITWFVSWTPCPDCVVKVAEFLAEHPNVTLTISAARLYYYWETD Y | 102 |
| Macaca mulatta A3F (AA30-AA137) | RNTVWLCYEVKTRGPSMPTWDTKIFRGQVYSKPEHHAEMCFLSRFCGNQL PAYKRFQITWFVSWTPCPDCVAKVAEFLAEHPNVTLTISAARLYYYWETD YRRALCRL | 103 |
| Theropithecus gelada A3F (AA30-AA137) | RNTVWLCYEVKTRGPSMPTWGTKIFRGQVYFQPQYHAEMCFLSRFCGNQL PAYKRFQITWFVSWNPCPDCVAKVIEFLAEHPNVTLTISAARLYYYWGRD WRRALRRL | 104 |
| Cercocebus atys A3B (AA29-AA138) | GRSYTWLCYEVKIRKDPSKLPWYTGVFRGQVYSKPEHHAEMCFLSRFCGN QLPAYKRFQITWFVSWNPCPDCVAKVIEFLAEHPNVTLTISAARLYYYWS RDWQRALCRL | 105 |
| Macaca fascicularis A3B (AA29-AA138) | GRSYTWLCYEVKIRKDPSKLPWDTGVFRGQVYSKPEHHAEMCFLSRFCGN QLPAYKRFQITWFVSWNPCPDCVAKVIEFLAEHPNVTLTISTARLYYYWG RDWQRALCRL | 106 |
| Macaca mulatta A3B (AA29-AA138) | GRSYTWLCYEVKIRKDPSKLPWDTGVFRGQVYSKPEHHAEMCFLSRFCGN QLPAYKRFQITWFVSWNPCPDCVAKVIEFLAEHPNVTLTISTARLYYYWG RDWQRALCRL | 107 |
| Macaca leonina A3B (AA29-AA138) | GRSYTWLCYEVKIRKDPSKLPWDTGVFRGQVYSKPEHHAEMCFLSRFCGN QLPAYKRFQITWFVSWNPCPDCVVKVIEFLAEHPNVTLTISTARLYYYWG RDWQRALCRL | 108 |
| Mandrillus leucophaeus A3B (AA29-AA138) | GRSYTWLCYEVKIRKDPSKLPWYTGVFRGQVYSKPEHHAEMCFLSRFCGN QLPAYKRFQITWFVSWNPCPDCVAKVIEFLAEHPNVTLTIFTARLYYYWG RDWQRALCRL | 109 |
| Macaca nemestrina A3B (AA29-AA138) | GRSYTWLCYEVKIRKDPSKLPWDTGVFRGQVYSKPEHHAEMCFLSRFCGN QLPAYKRFQITWFVSWNPCPDCVAKVTEFLAEHPNVTLTISTARLYYYWG RDWQRALCRL | 110 |
| Rhinopithecus bieti A3F (AA29-AA138) | GRSYTWLCYEVKIRKDPSKLPWDTGVFRGQVYSEPEHHAEMYFLSWFCGN QLPAYKRFQITWFVSWTPCPDCVAKVAEFLTEHPNVTLTISAARLYYYRG RDWRRALCRL | 111 |
| Rhinopithecus roxellana A3B (AA29-AA138) | GRSYTWLCYEVKIRKDPSKLPWDTGVFRGQVYSEPEHHAEMYFLSWFCGN QLPAYKRFQITWFVSWTPCPDCVAKVAEFLTEHPNVTLTISAARLYYYRG RDWRRALCRL | 112 |
| Chlorocebus sabaeus A3B (AA29-AA138) | GRSYTWLCYEVKIRKDPSKLPWDTGVFRGQMYSKPEHHAEMCFLSWFCGN QLPAHKRFQITWFVSWTPCPDCVAKVAEFLAEYPNVTLTISAARLYYYWE TDYRRALCRL | 113 |

TABLE 2-continued hA3BCDA1-Related Domains

| Name | Sequence | SEQ ID NO: |
|---|---|---|
| Nomascus leucogenys A3B (AA30-AA138) | RSYTWLCYEVKIRKDPSKLPWDTGVFRGQMYFQPEYHAEMCFLSWFCGNQ LPAYKRFQITWFVSWTPCPDCVAKVAVFLAEHPNVTLTISAARLYYYWEK DWQRALCRL | 114 |
| Cercocebus atys A3F (AA29-AA138) | GRSYTWLCYEVKIKKYPSKLLWDTGVFQGQVYFQPQYHAEMCFLSRFCGN QLPAYKRFQITWFVSWNPCPDCVAKVTEFLAEHPNVTLTISAARLYYYWE KDXRRALRRL | 115 |
| Papio anubis A3F (AA29-AA138) | GRSYTWLCYEVKIKEDPSKLLWDTGVFQGQVYFQPQYHAEMCFLSRFCGN QLPAYKRFQITWFVSWNPCPDCVAKVTEFLAEHPNVTLTISAARLYYYWG RDWRRALRRL | 116 |
| Chlorocebus aethiops A3D (AA29-AA150) | GRRYTWLCYEVKIKKDPSKLPWDTGVFPGQVRPKFQSNRRYEVYFQPQYH AEMYFLSWFCGNQLPAYKHFQITWFVSWNPCPDCVAKVTEFLAEHRNVTL TISAARLYYYWGKDWRRALCRL | 117 |
| Chlorocebus sabaeus A3D (AA29-AA134) | GRRYTWLCYEVKIKKDPSKLPWDTGVFPGQPQYHAEMYFLSWFCGNQLPA YKHFQITWFVSWNPCPDCVAKVTEFLAEHRNVTLTISAARLYYYWGKDWR RALCRL | 118 |
| Chlorocebus sabaeus A3F (AA29-AA150) | GRRYTWLCYEVKIKKDPSKLPWDTGVFPGQVRPKFQSNRRQKVYFQPQYH AEMYFLSWFCGNQLPAYKHFQITWFVSWNPCPDCVAKVTEFLAEHRNVTL TISAARLYYYWGKDWRRALCRL | 119 |
| Erythrocebus patas A3D (AA29-AA150) | GRRYTWLCYEVKIKKDPSKLPWDTGVFQGQVRPKFQSNRRYEVYFQPQYH AEMCFLSWFCGNQLPAYKHFQITWFVSWNPCPDCVAKVTEFLAEHPNVTL TISAARLYYYWGKDWRRALCRL | 120 |
| Macaca fascicularis A3D (AA29-AA159) | GRSYTWLCYEVKIRKDPSKLPWDTGVFRGQVRPKLQSNRRYELSNWECRK RVYFQPQYHAEMYFLSWFCGNQLPANKRFQITWFASWNPCPDCVAKVTEF LAEHPNVTLTISVARLYYYRGKDWRRALRRL | 121 |
| Macaca fascicularis A3F (AA29-AA138) | GRSYTWLCYEVKIRKDPSKLPWDTGVFRGQVYFQPQYHAEMYFLSWFCGN QLPANKRFQITWFASWNPCPDCVAKVTEFLAEHPNVTLTISVARLYYYRG KDWRRALRRL | 122 |
| Macaca nemestrina A3D (AA29-AA138) | GRSYTWLCYEVKIRKDPSKLPWDTGVFRDQVYFQPQYHAEMCFLSWFCGN QLPANKRFQITWFVSWNPCPDCVTKVTEFLAEHPNVTLTISVARLYYYRG KDWRRALRRL | 123 |
| Macaca leonina A3D (AA29-AA138) | GRSYTWLCYEVKIRKDPSKLPWYTGVFRGQVYFQPQYHAEMCFLSWFCGN QLPANKRFQITWFVSWNPCPDCVAKVTEFLAEHPNVTLTISVARLYYYRG KDWRRALRRL | 124 |
| Macaca mulatta A3D (AA29-AA138) | GRSYTWLCYEVKIRKDPSKLPWDTGVFRGQVYFQPQYHAEMCFLSWFCGN QLPAYKRFQITWFVSWNPCPDCVAKVTEFLAEHPNVTLTISVARLYYYRG KDWRRALCRL | 125 |
| Gorilla A3D (AA29-AA150) | GRSYTWLCYEVKIRRGSSNLLWNTGVFRGPVPPKLQSNHRQEVYFQFENH AEMCFLSWFCGNRLPANRRFQITWFVSWNPCLPCVVKVTKFLAEHPNVTL TISAARLYYYRDREWRRVLRRL | 126 |
| Pan paniscus A3D (AA29-AA150) | GRSYTWLCYEVKIKRGCSNLIWDTGVFRGPVLPKLQSNHRQEVYFQFENH AEMCFFSWFCGNRLPANRRFQITWFVSWNPCLPCVVKVTKFLAEHPNVTL TISAARLYYYQDREWRRVLRRL | 127 |
| Pan troglodytes A3D (AA29-AA150) | GRSYTWLCYEVKIKRGCSNLIWDTGVFRGPVLPKLQSNHRQEVYFQFENH AEMCFFSWFCGNRLPANRRFQITWFVSWNPCLPCVVKVTKFLAEHPNVTL TISAARLYYYQDREWRRVLRRL | 128 |
| Homo sapiens A3D (AA29-AA150) | GRSYTWLCYEVKIKRGRSNLLWDTGVFRGPVLPKRQSNHRQEVYFRFENH AEMCFLSWFCGNRLPANRRFQITWFVSWNPCLPCVVKVTKFLAEHPNVTL TISAARLYYYRDRDWRWVLLRL | 129 |
| Nomascus leucogenys A3D (AA29-AA150) | GRSYTWLCYEVKIRKDPSKLPWDKGVFRGQVLPKFQSNHRQEVYFQLENH AEMCFLSWFCGNQLPANRRFQITWFVSWNPCLPCVAKVTEFLAEHPNVTL TISAARLYYYRGRDWRRALRRL | 130 |
| Saimiri boliviensis A3C (AA29-AA138) | GKKYTWLCYEVKIKKDTSKLPWNTGVFRGQVNFNPEHHAEMYFLSWFRGK LLPACKRSQITWFVSWNPCLYCVAKVAEFLAEHPNVTLTVSTARLYCYWK KDWRRALRKL | 131 |
| Saimiri boliviensis A3F (AA29-AA138) | GKKYTWLCYEVKIKKDTSKLPWNTGVFRGQVNFNPEHHAEMYFLSWFRGK LLPACKRSQITWFVSWNPCLYCVAKVAEFLAEHPNVTLTVSTARLYCYWK KDWRRALRKL | 132 |

TABLE 2-continued hA3BCDA1-Related Domains

| Name | Sequence | SEQ ID NO: |
|---|---|---|
| Piliocolobus tephrosceles A3F (AA36-AA145) | GRRYTWLCYEVKIMKDHSKLPWYTGVFRGQVYFEPQNHAEMCFLSWFCGN QLPAYECCQITWFVSWTPCPDCVAKVTEFLAEHPNVTLTISAARLYYYRG RDWRRALRRL | 133 |
| Colobus angolensis palliatus A3F (AA29-AA138) | GRRYTWLCYEVKISKDPSKLPWDTGIFRGQVYFEPQYHAEMCFLSWYCGN QLPAYKCFQITWFVSWTPCPDCVGKVAEFLAEHPNVTLTISAARLYYYWE TDYRRALCRL | 134 |
| Pongo abelii A3F (AA30-AA150) | RNYTWLCYEVKIRKDPSKLAWDTGVFRGQVLPKLQSNHRREVYFEPQYHA EMCFLSWFCGNQLSAYERFQITWFVSWTPCPDCVAMLAEFLAEHPNVTLT VSAARLYYYWERDYRGALRRL | 135 |

Example 2. Further Assessment of Inhibitor-Conjugated Base Editors

This example developed an efficient method to demonstrate that the APOBEC moiety of base editors (BEs) directly induced mutations at off-target single-stranded DNA (OTss) sites in an sgRNA-independent manner By testing a series of APOBEC proteins with two cytidine deaminase (CDA) domains, we identified that the catalytically-inactive CDA domains of certain dual-domain APOBECs function as cytidine deaminase inhibitors (CDIs). By taking advantage of this finding and the concept of split-TEV protease, an induced base editor (iBE) by sgRNA-guided cleavage of CDI was developed, which links a nSpCas9-BE and a CDI with a TEV cleavage site. At sgRNA-independent OTss sites, iBE1 remained dormant owing to the covalently linked CDI. Whereas, at on-target sites, iBE1 was activated by sgRNA-guided TEV cleavage of CDI, resulting in efficient base editing. By using 'enhanced specificity' SpCas9 nickase, iBE2 was further developed to reduce unintended OTsg mutations. Due to its minimum off-target effects and uncompromised on-target editing efficiency, the editing specificity of iBEs was significantly higher than that of the previously-reported BEs. Thus, the iBE system described in this example provides a new layer of regulation for the specificity of current base editing system and secures its application against off-target mutations.

Methods

Cell Culture and Transfection

HEK293FT cells from ATCC were maintained in DMEM (10566, Gibco/Thermo Fisher Scientific)+10% FBS (16000-044, Gibco/Thermo Fisher Scientific) and regularly tested to exclude mycoplasma contamination.

For base editing in genomic DNA, HEK293FT cells were seeded in a 24-well plate at a density of $1.1 \times 10^5$ per well and transfected with 250 μl serum-free Opti-MEM that contained 5.35 μl LIPOFECTAMINE LTX (Life, Invitrogen), 2.14 μl LIPOFECTAMINE plus (Life, Invitrogen), 1 μg pCMV-BE3 (or hA3B-BE3, hA3BCDA2-nSpCas9-BE, hA3D-BE3, hA3DCDA2-nSpCas9-BE, hA3F-BE3, hA3FCDA2-nSpCas9-BE, hA3G-BE3, hA3GCDA2-nSpCas9-BE, mA3-BE3, mA3CDA1-nSpCas9-BE, mA3CDA2-mA3CDA1-nSpCas9-BE, hA3FCDA1-mA3CDA1-nSpCas9-BE, hA3BCDA1-mA3CDA1-nSpCas9-BE, mA3CDA2-rA1-nSpCas9-BE, hA3FCDA1-rA1-nSpCas9-BE, hA3BCDA1-rA1-nSpCas9-BE, hA3A-BE3, mA3CDA2-hA3A-nSpCas9-BE, hA3FCDA1-hA3A-nSpCas9-BE, hA3BCDA1-hA3A-nSpCas9-BE, mA3CDA2F1-mA3CDA1-nSpCas9-BE, mA3CDA2F2-mA3CDA1-nSpCas9-BE, mA3CDA2F3-mA3CDA1-nSpCas9-BE, mA3CDA1-T2A-mA3CDA1-nSpCas9-BE, EGFP-mA3CDA1-nSpCas9-BE, EGFP-T2A-mA3CDA1-nSpCas9-BE, mA3CDA1-T2A-rA1-nSpCas9-BE, EGFP-rA1-nSpCas9-BE, EGFP-T2A-rA1-nSpCas9-BE, mA3CDA1-T2A-hA3A-nSpCas9-BE, EGFP-hA3A-nSpCas9-BE, EGFP-T2A-hA3A-nSpCas9-BE, pCMV-dSpCas9, iBE1, iBE2, mA3CDA1-TS-mA3CDA1-nSpCas9HF1-BE-NTEV or mA3CDA1-TS-mA3CDA1-nHypaSpCas9-BE-NTEV) expression vector, 0.64 μg sgRNA expression vector without or with 0.5 μg Sa-sg-SaD10A expression vector. After 24 hr, puromycin (ant-pr-1, InvivoGen) was added to the medium at the final concentration of 4 μg/ml. After another 48 hr, the genomic DNA was extracted from the cells with QuickExtract™ DNA Extraction Solution (QE09050, Epicentre) for subsequent sequencing analysis.

DNA Library Preparation and Sequencing

Target genomic sequences were PCR amplified by high-fidelity DNA polymerase PrimeSTAR HS (Clonetech) with primer sets flanking examined sgRNA target sites. Indexed DNA libraries were prepared by using the TruSeq ChIP Sample Preparation Kit (Illumina) with minor modifications. Briefly, the PCR products amplified from genomic DNA regions were fragmented by Covaris 5220. The fragmented DNAs were then PCR amplified by using the TruSeq ChIP Sample Preparation Kit (Illumina) After quantitated with Qubit High-Sensitivity DNA kit (Invitrogen), PCR products with different tags were pooled together for deep sequencing by using the Illumina Hiseq X10 (2×150) or NextSeq 500 (2×150) at CAS-MPG Partner Institute for Computational Biology Omics Core, Shanghai, China. Raw read qualities were evaluated by FastQC. For paired-end sequencing, only R1 reads were used. Adaptor sequences and read sequences on both ends with Phred quality score lower than 30 were trimmed. Trimmed reads were then mapped with the BWA-MEM algorithm (BWA v0.7.17) to target sequences. After piled up with samtools (v1.9), base substitutions were further calculated.

Base Substitution Calculation

Base substitutions were selected at each position of the examined sgRNA target sites that were mapped with at least 1000 independent reads, and obvious base substitutions were only observed at the targeted base editing sites. Base substitution frequencies were calculated by dividing base substitution reads by total reads. For each sgRNA, the ratio of C-to-T base substitution over indel was calculated by dividing the sum of C-to-T base substitution frequencies at all editing sites by the indel frequency of 50-bp region around sgRNA target site (from upstream eight nucleotides to the target site to downstream 19 nucleotides to PAM sites).

Results

Cytosine or adenine base editors (CBEs/BEs or ABEs) that fuse native cytidine deaminases or in vitro evolved adenosine deaminases with CRISPR-Cas9 have been developed to induce targeted C-to-T or adenine to guanine (A-to-G) conversions with high efficiencies. Because BEs use catalytically dead Cas9 (dCas9) protein or Cas9 nickase (nCas9) to direct their binding to genomic DNA, unintended base substitutions were expected to be induced at OTsg sites that are partially complementary to sgRNA. In this scenario, the use of high-fidelity Cas9 in BEs can reduce these OTsg mutations. Meanwhile, since free APOBECs can induce unexpected C-to-T mutations in single-stranded DNA (ssDNA) regions, the APOBEC moiety of BEs may directly trigger unexpected mutations at OTss sites. In other words, the off-target mutations induced by BEs may also occur at OTss sites independent of the guidance of sgRNA; however, OTss mutations were not revealed due to the lack of a quantitative and reproducible way for detection.

This example set up an efficient method to quantitatively evaluate BE-induced OTss mutations by co-expressing *S. aureus* and *S. pyogenes* Cas9 orthologs (CESSCO). In CESSCO, the expression of nSaCas9/Sa-sgRNA pairs generated DNA single-strand breaks (SSBs) at specific genomic loci and led to the formation of a genomic ssDNA region in a programmable way. At the same time, co-expressed BE3 in the absence of sgRNA (sgRNA means Sp-sgRNA hereafter) was used to examine whether sgRNA-independent C-to-T base substitutions can be induced by BE3 alone in the ssDNA regions generated around nSaCas9/Sa-sgRNA-introduced SSBs. After deep-sequencing the genomic regions targeted by nSaCas9/Sa-sgRNA, it was clearly shown that C-to-T mutations at OTss sites were induced by the rat APOBEC1 (rA1)-containing BE3 but not by dSpCas9 in the absence of sgRNA, confirming that OTss mutations are caused by the APOBEC moiety of BEs in an sgRNA-independent manner This example then sought to reduce OTss mutations by exploiting members of APOBEC family suitable for highly-specific BE construction. Most of commonly used BEs were constructed with single domain APOBECs, such as rA1 in BE3, but not with dual-domain APOBECs. Usually, in APOBECs with two CDA domains, one is catalytically active, while the other one is catalytically inactive, which plays a regulatory role on the cytidine deamination activity and thus may be suited for constructing highly-specific BEs with reduced OTss effects. To attempt this possibility, we constructed and compared the C-to-T editing efficiencies of ten paired BEs, which have either one catalytically active CDA domain or two CDA domains of five dual-domain APOBECs (FIG. 20a), i.e., human APOBEC3B (hA3B), human APOBEC3D (hA3D), human APOBEC3F (hA3F), human APOBEC3G (hA3G) and mouse APOBEC3 (mA3).

As revealed in FIG. 20b,c, the BEs constructed with certain APOBECs (hA3B, hA3F and mA3) containing two CDA domains induced significantly lower editing efficiencies than their paired BEs having only the active CDA domain. This result shows that the catalytically inactive CDA domains from these dual-domain APOBECs, i.e., hA3B, hA3F and mA3, exhibit an inhibitory function on their corresponding active CDA domains.

To examine whether the inhibitory function is general, we covalently linked the catalytically inactive CDA domains of mA3, hA3F or hA3B individually to the N-terminus of mA3CDA1-nSpCas9-BE (FIG. 20d) and two other commonly used BEs, i.e., BE3 and hA3A-BE3. All these catalytically inactive CDA domains showed broad-spectrum inhibitory effects on all tested BEs, and among them, the CDA2 of mA3 (mA3CDA2) manifested the strongest inhibitory effect (FIG. 20e,f). Detailed mapping analysis further revealed that residues 282-355 of mA3CDA2 exhibited an inhibitory effect similar to that of full-length mA3CDA2. Collectively, these results showed that the catalytically-inactive domains of certain dual-domain APOBECs indeed exhibit general inhibitory effects on cytidine deaminase activity, and we thus defined them as cytidine deaminase inhibitors (CDI).

Next, we sought to test whether the cleavage of mA3CDI (mA3CDA2) from its covalently-linked BEs can restore their base editing capacity. We used self-cleaving peptides (T2A) to link mA3CDI and mA3CDA1-nSpCas9-BE for examination. After self-cleavage of mA3CDI, the editing efficiency of mA3CDI-T2A-mA3CDA1-nSpCas9-BE was regained to the levels similar to EGFP-mA3CDA1-nSpCas9-BE or EGFP-T2A-mA3CDA1-nSpCas9-BE, ~10-fold higher than that of the non-cleavable-mA3CDI fused BE. The self-cleavage of mA3CDI from BE3 and hA3A-BE3 also enhanced their editing efficiencies, albeit to different extents.

These results served as a critical proof-of-concept for developing an iBE system for precise base editing with low OTss mutations. iBE1 was constructed by using TEV protease cleavage site (TS) to link three critical modules, i.e., mA3CDI, mA3CDA1-nSpCas9-BE and the N-terminal half of TEV protease (NTEV) (FIG. 21a). In theory, due to the covalent linkage of a CDI, iBE1 remains dormant when it binds to OTss sites by its APOBEC moiety (FIG. 21a). Notably, NTEV itself is inactive but forms a functional TEV protease only when the C-terminal half (CTEV) is recruited. Thus, iBE1 can be guided by its CRISPR-Cas moiety to perform efficient base editing at on-target sites where the CDI is cleaved by the sgRNA-induced assembly of functional TEV protease (FIG. 21d).

After being expressed in cells, iBE1 remained dormant in the sgRNA-independent OTss regions as expected (FIG. 21b) and induced much lower (~20%) level of C-to-T mutations compared to BE3 (FIG. 21c). At on-target sites, the RNA binding protein (MCP)-fused CTEV can be recruited by the MS2-fused sgRNA (FIG. 21d), which leads to the removal of mA3CDI from iBE1 and therefore enables efficient base editing. The comparison of on-target editing efficiency induced by BE3 and iBE1 across multiple genomic loci (FIG. 21e) demonstrated that iBE1 induced on-target base editing at a similar level as BE3 did (FIG. 21f, ~80% of BE3). Together, this example shows that we have developed an iBE system, which catalyzes efficient base editing at on-target sites with suppressed OTss mutations, through the manipulation of CDI.

As Cas9 has been known to induce unintended editing at OTsg sites that have partial sequence complementarity to the sgRNA, we also aimed to further reduce OTsg mutations by replacing the unmodified nSpCas9 in iBE1 with its engineered versions that have improved targeting specificity (FIG. 22a). We tested three engineered versions of nSpCas9, i.e., neSpCas9, nSpCas9HF1 and nHypaSpCas9, and found that using either of these targeting-specificity-improved Cas9 proteins greatly reduced OTsg mutations (FIG. 22b,c). Meanwhile, the use of neSpCas9 did not compromise the on-target editing efficiencies, whereas the use of the other two decreased the on-target editing efficiencies (FIG. 22d,e). In this scenario, we set to replace nSpCas9 with neSpCas9 to construct iBE2.

As an early developed BE, the editing efficiency of BE3 is restricted under certain conditions and additional BEs with improved editing efficiencies were developed later, e.g., AncBE4max or hA3A-BE3. hA3A-BE3 is a highly active BE in various contexts and we thus compared the performance of iBE2 to that of hA3A-BE3, in terms of editing efficiency and specificity (FIG. 23a). Although the average on-target editing frequency of iBE2 was ~50% of hA3A-BE3 (FIG. 23a,c), the C-to-T mutations induced by iBE2 at OTss and OTsg sites were close to the background level, while hA3A-BE3 induced substantial mutations at these off-target sites (FIG. 23a,b). Taken together, the average editing specificity of iBE2 was ~40-fold higher than that of hA3A-BE3 (FIG. 23d).

In this example, we first developed an efficient method (CESSCO) to quantitatively evaluate sgRNA-independent OTss mutations and confirmed that the BEs with a regular APOBEC-nCas9 backbone indeed induced OTss mutations in an sgRNA-independent manner (FIG. 21a, 21b, 23a, 23b). Consistent with our findings, recent whole genome sequencing studies also showed that BE3 induced substantial off-target mutations in mice and rice plants, assumedly also in an sgRNA-independent manner Importantly, we took advantage of our discovery of CDIs to develop iBEs, which remain dormant at OTss sites due to the covalent linkage of CDI but can be activated by sgRNA-mediated cleavage of CDI at on-target sites (FIG. 21a,d). iBEs induced a significantly low level of unintended mutations in sgRNA-independent ssDNA regions, while it performed on-target editing efficiently (FIG. 21b,c,e,f).

By substituting nSpCas9 with the specificity-improved enSpCas9, highly-specific iBE2 was developed to further reduce unintended editing at OTsg sites (FIGS. 22 and 23e). The iBE system is compatible with the BEs having different Cas moieties and the engineered BEs with improved performance, and does not change the characteristics of constructed BEs, such as editing window. In addition, since there are abundant members within APOBEC family, other CDIs may be identified in the future, which would further enrich the repertoire of CDI-conjugated iBE system. As both editing precision and efficiency is essential for base editors, especially in their therapeutic applications, the iBE system developed here will bring a new layer of regulation for the specificity of current base editing system and secure its application against off-target mutations.

Example 3. Testing of Different Configurations of Induced and Split Base Editors This example tested a number of different configurations of molecules for implementing the induced and split base editor (isplitBE) system.

The working process of isplitBE is illustrated in FIG. 24A, as comparison to the conventional BEs as shown in FIG. 24B. In the illustrated isplitBE system, a nCas9-D10A construction is packaged in an AAV vehicle. A typical AAV vehicle has a 4.7 kb capacity, and the nCas9 construct is about 4.7 kb in length. Another AVV vehicle can package the nucleic acids (about 4.4 kb in total length) for encoding: (a) a fusion protein that includes MCP, UGI, APOBEC, a TEV recognition site (TEV site), and mA3CDA2; (b) a fusion protein with TEVc and N22p; (c) a standalone TEVn, (d) a helper sgRNA (hsgRNA) with a MS2 tag, and (e) another sgRNA with a boxB tag.

At a target site (ON, left lower branch), each of the hsgRNA and sgRNA binds to two adjacent sites on a target DNA, and the MCP- and N22p-containing fusion proteins bind to the MS2 tag and boxB tag of the hsgRNA and sgRNA, respectively. Due to proximity of TEVc (in the presence of free TEVn) and the TEV site, the TEVc/TEVn cleaves the TEV site, removing the mA3CDA2 from the APOBEC. Without the attached mA3CDA2, the APOBEC can highly efficiently carry out the desired editing.

At off-target sites, which may be a non-specific binding site (OTss, lower middle branch) or a site that only binds one of the guide RNAs, the TEVc/TEVn complex is not recruited to the TEV site-containing fusion protein, and thus the APOBEC cannot be activated. By contrast, in the conventional BE system (FIG. 24B), the APOBEC is already active and can cause C-to-T editing whenever it is recruited to a single-stranded nucleotide sequence.

Ten different configurations (Pairs 1-10), as illustrated in FIG. 25, were prepared and tested. For instance, as shown in FIG. 26A, Pair 1 included two constructs, the first of which contained rA1 fused to nCas9-D10A (spD10A), along with a UGI and an NLS, and the second of which contained a sgRNA targeting EMX1. Pair 2 is similar to Pair 1 but rA1 was replaced by hA3A. Pair 3 is also similar and used a mutant hA3A instead (Y130F).

In Pair 4, the rA1 and the nCas9 proteins were placed on different constructs. rA1 was further fused to an MCP protein which recognizes a MS2 tag on the helper sgRNA. In Pair 5, a mA3CDA2 was further fused to the rA1, via a TEV recognition site (black solid box). In Pair 6, a TEV protein was further fused, through a self-cleavage site 2A, to the rA1-mA3CDA2 fusion. Self cleavage of 2A would release the TEV from the fusion protein.

Pair 7 is different from Pair 6 by fusing the TEV to a N22p protein, which would recognize the boxB tag on the sgRNA. In Pair 8, the TEV protein was divided into TEVn and TEVc, separated by the 2A self cleavage site. In Pair 9, only the TEVc was fused to a N22p while the TEVn was free of any RNA tag-binding proteins. In Pair 10, the helper sgRNA targeted GFP, rather than a nearby site.

Figure 26B:
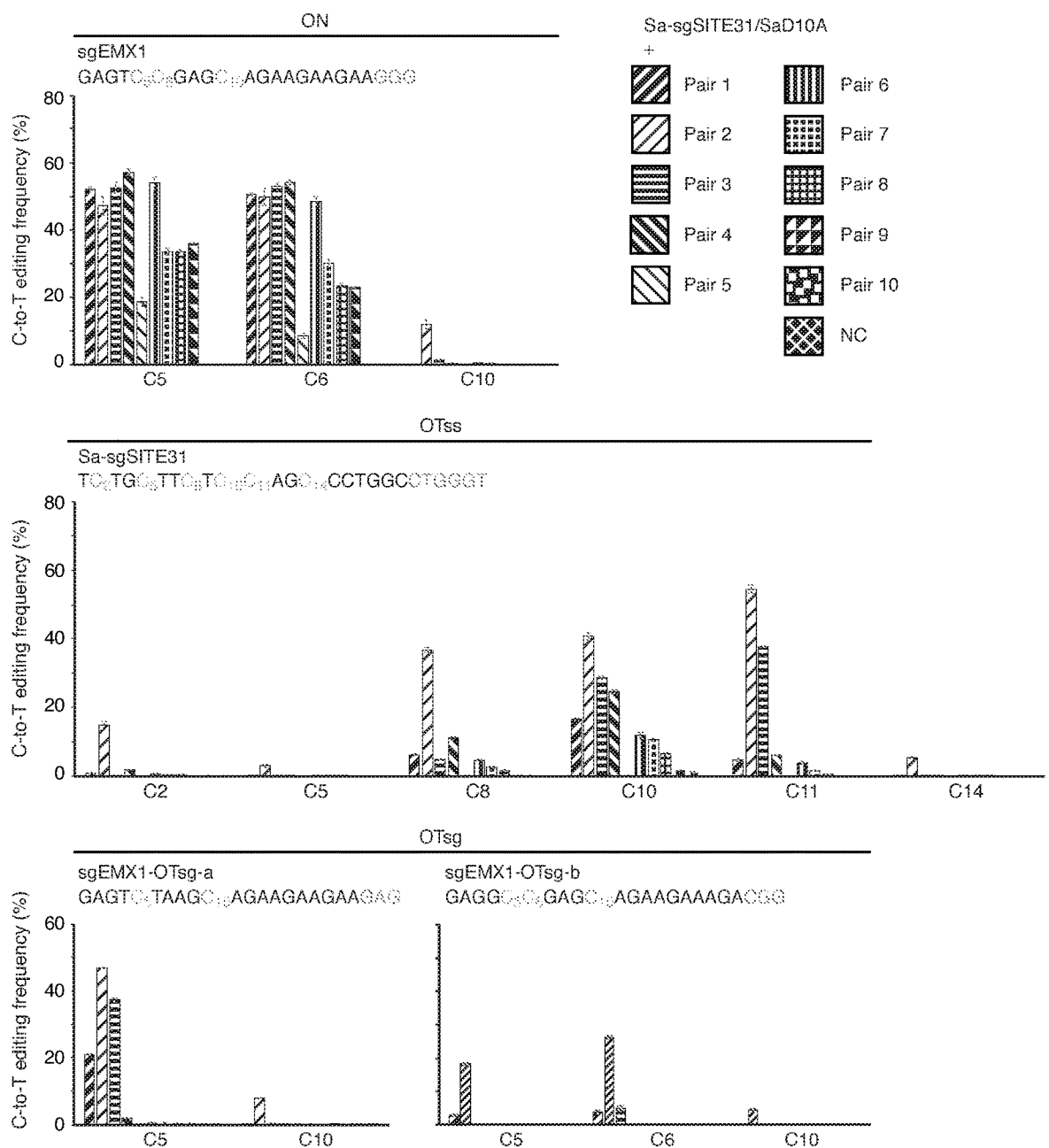

The constructs in FIG. 26A were designed for C-to-T editing at target site EMX1-ON, and the off-target editing at Sa-SITE31-OTss and EMX1-OTsg sites is examined as well. The testing results are shown in FIG. 26B. isplitBE-rA1 (Pair 9) induced substantial editing at ON site but no editing at OTss or OTsg sites.

Figure 27A:
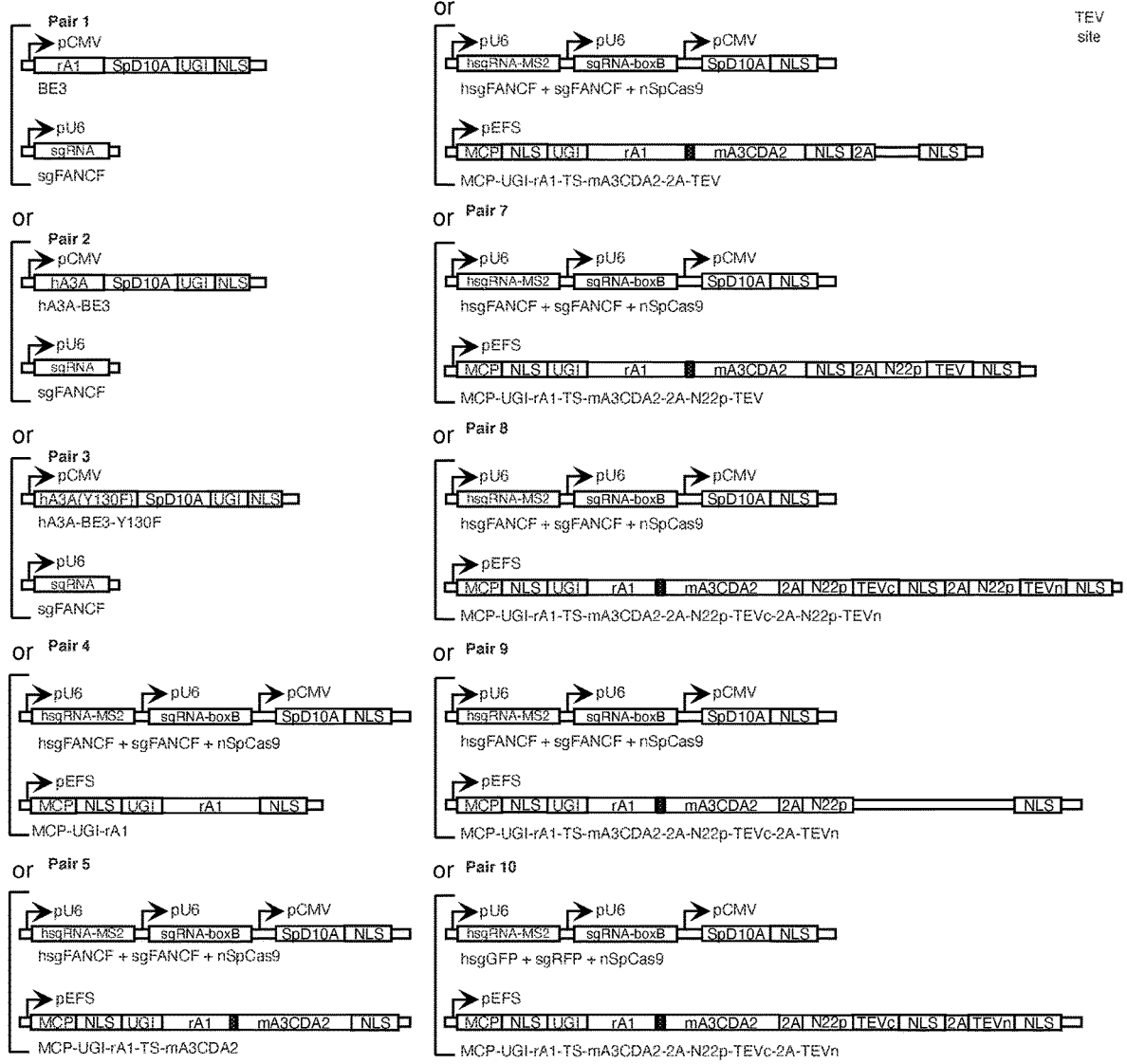
FIG. 27A-B. C-to-T editing at FANCF-ON, Sa-VEGFA-7-OTss and FANCF-OTsg sites induced by different combinations of nCas9 (D10A), APOBEC cytidine deaminase, cytidine deaminase inhibitor (CDI), uracil DNA glycosylase inhibitor (UGI) and TEV protease. 27A: Schematic diagram illustrating the co-transfection of the plasmid expressing Sa-sgVEGFA-7 and the plasmid expressing SaD10A nickase with the indicated ten pairs of plasmid expressing various base editors. 27B: Comparison of editing efficiencies at FANCF-ON, Sa-VEGFA-7-OTss and FANCF-OTsg sites. isplitBE-rA1 (Pair 9) induced substantial editing at ON site but no editing at OTss or OTsg sites. The sequences shown in FIG. 27B, from top to bottom, have the sequences of SEQ ID NO: 242-245, respectively.
Figure 27B:
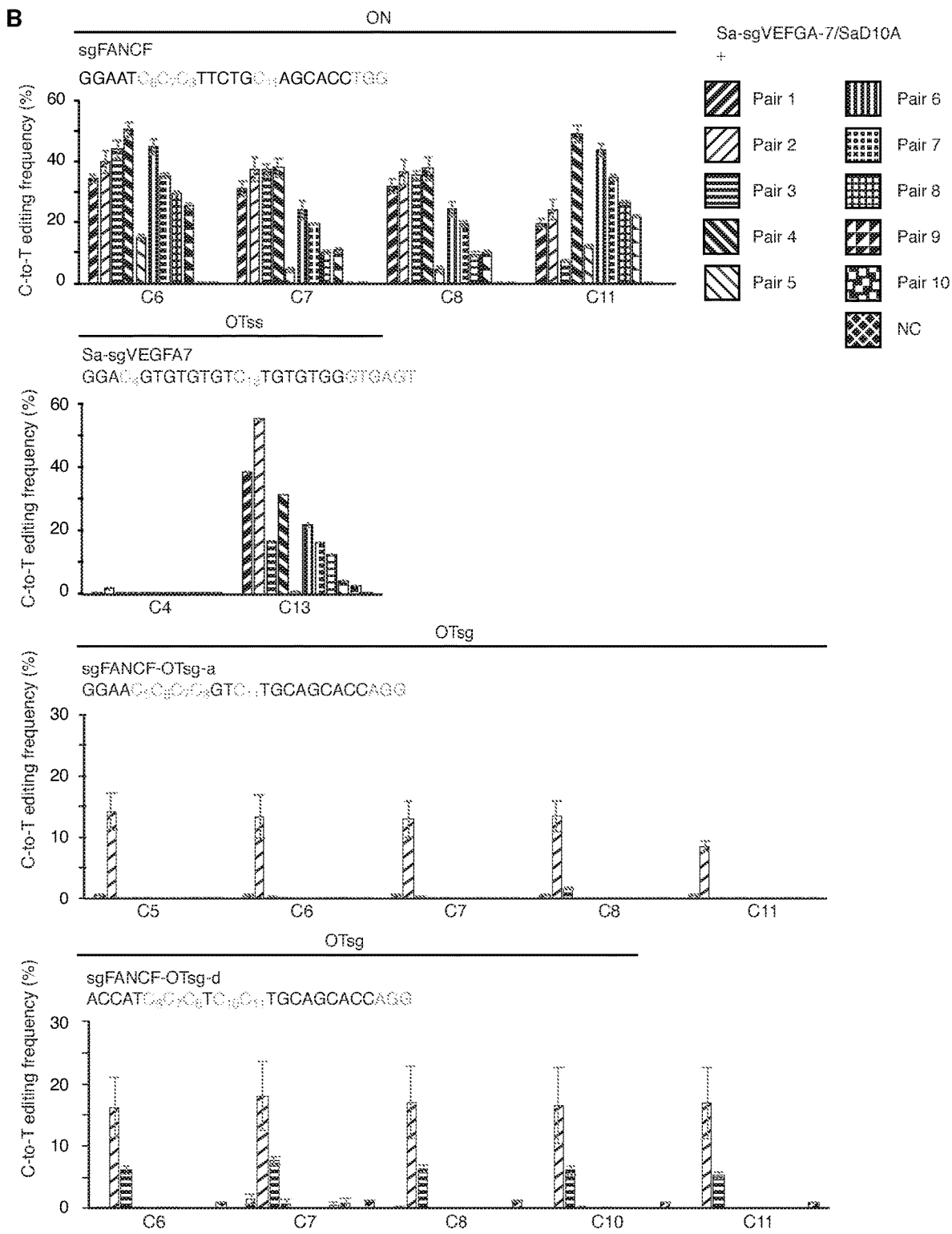

Likewise, all of these configurations were tested with the FANCF-ON, Sa-VEGFA-7-OTss and FANCF-OTsg sites (see schematic diagram in FIG. 27A). FIG. 27B shows the comparison of editing efficiencies for different base editors at FANCF-ON, Sa-VEGFA-7-OTss and FANCF-OTsg sites. Again, isplitBE-rA1 (Pair 9) induced substantial editing at ON site but no editing at OTss or OTsg sites.

Figure 28A:
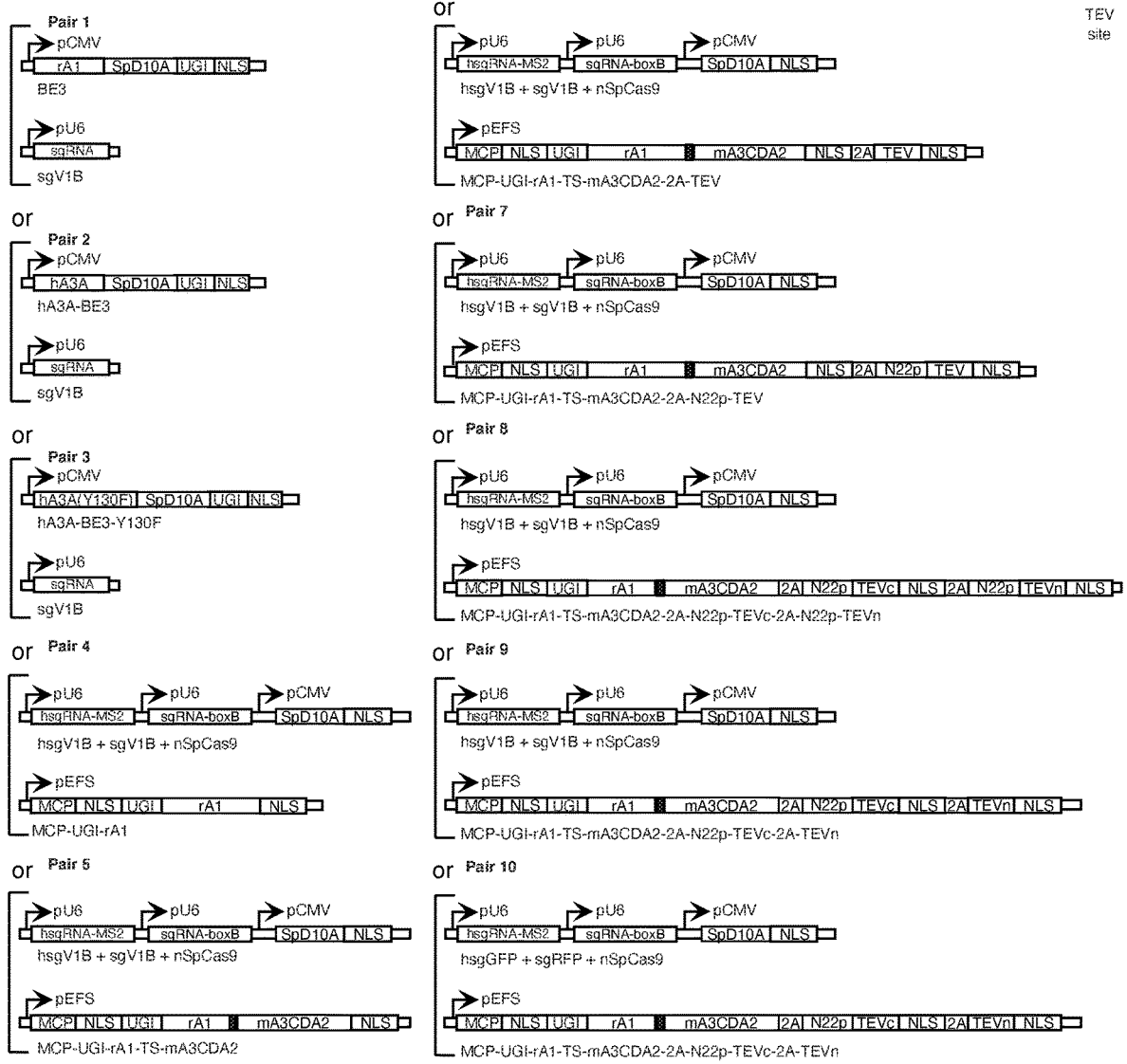
FIG. 28A-B. C-to-T editing at V1B-ON, Sa-SITE42-OTss and V1B-OTsg sites induced by different combinations of nCas9 (D10A), APOBEC cytidine deaminase, cytidine deaminase inhibitor (CDI), uracil DNA glycosylase inhibitor (UGI) and TEV protease. 28A: Schematic diagram illustrating the co-transfection of the plasmid expressing Sa-sgSITE42 and the plasmid expressing SaD10A nickase with the indicated ten pairs of plasmid expressing various base editors. 28B: Comparison of editing efficiencies at V1B-ON, Sa-SITE42-OTss and V1B-OTsg sites. isplitBE-rA1 (Pair 9) induced substantial editing at ON site but no editing at OTss or OTsg sites. The sequences shown in FIG. 28B, from top to bottom, have the sequences of SEQ ID NO: 246-249, respectively.
Figure 28B:
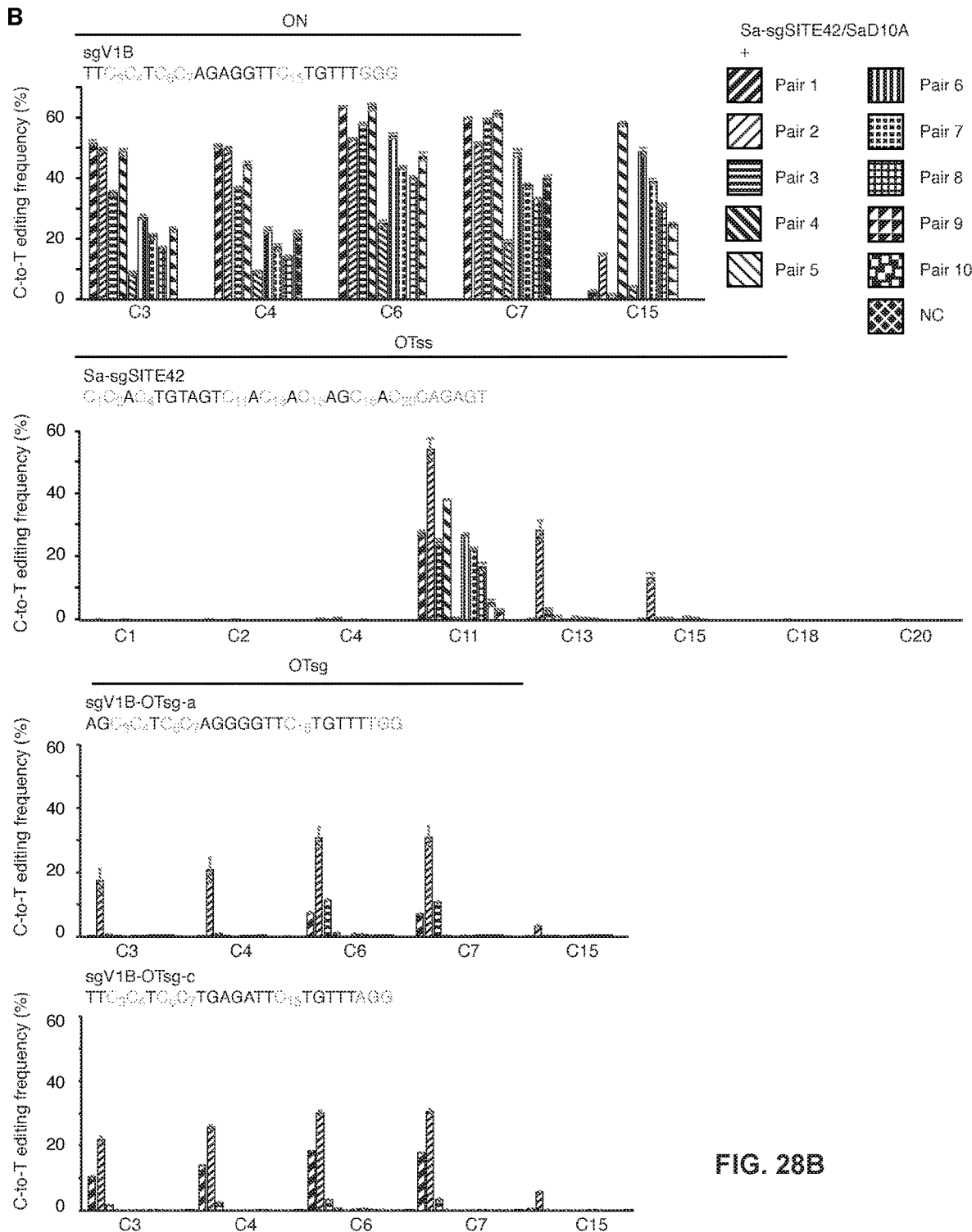

A further testing was done with the V1B-ON, Sa-SITE42-OTss and V1B-OTsg sites (see schematic diagram in FIG. 28A). Again, as shown in FIG. 28B, isplitBE-rA1 (Pair 9) induced substantial editing at ON site but no editing at OTss or OTsg sites.

Example 4. Tuning of Parameters in the isplitBE Systems

Out of the 10 tested configurations, Pair 9 exhibited the best performance in terms of editing specificity. Pair 9 employs two sgRNA, a helper sgRNA (hsgRNA) and a regular sgRNA. The dual use of sgRNA further enhances specificity as it requires that both target sites are in proximity from each other.

In a first assay of this example, the optimal distance between the two target sites was assessed. A schematic diagram is presented in FIG. 29A illustrating the distance between hsgRNA and sgRNA at DNTET1, EMX1 and FANCF sites. FIG. 29B shows the base editing frequencies induced by the indicated sgRNAs and hsgRNAs. The summary of FIG. 29C shows the effect of distance between hsgRNA and sgRNA. Based on the summary, the optimal range of distance for best base editing efficiency is −91 to −34 bp from the PAM of hsgRNA to the PAM of sgRNA.

The second assay tested the effect of hsgRNA spacer length on base editing efficiency and precision. FIG. 30A presents a schematic diagram illustrating the co-transfection of sgRNA and the hsgRNAs with different spacer lengths at DNEMX1, FANCF and V1A sites. FIG. 30B shows the base editing frequencies induced by the indicated sgRNAs and hsgRNAs at the target sties of hsgRNA and sgRNA. The statistic analysis in FIG. 30C shows the effects of hsgRNA spacer length. As shown, the use of hsgRNA with 10-nt spacer greatly reduced the editing efficiency at hsgRNA target sites but maintained the editing efficiency at sgRNA target sites. Accordingly, a spacer of 9-15 nt in the helper sgRNA sequence can be a good range to ensure efficient editing at the sgRNA target site, while minimizing the editing at the hsgRNA target site.

Example 5. Genome- and Transcriptome-wide Evaluation

Figure 31:
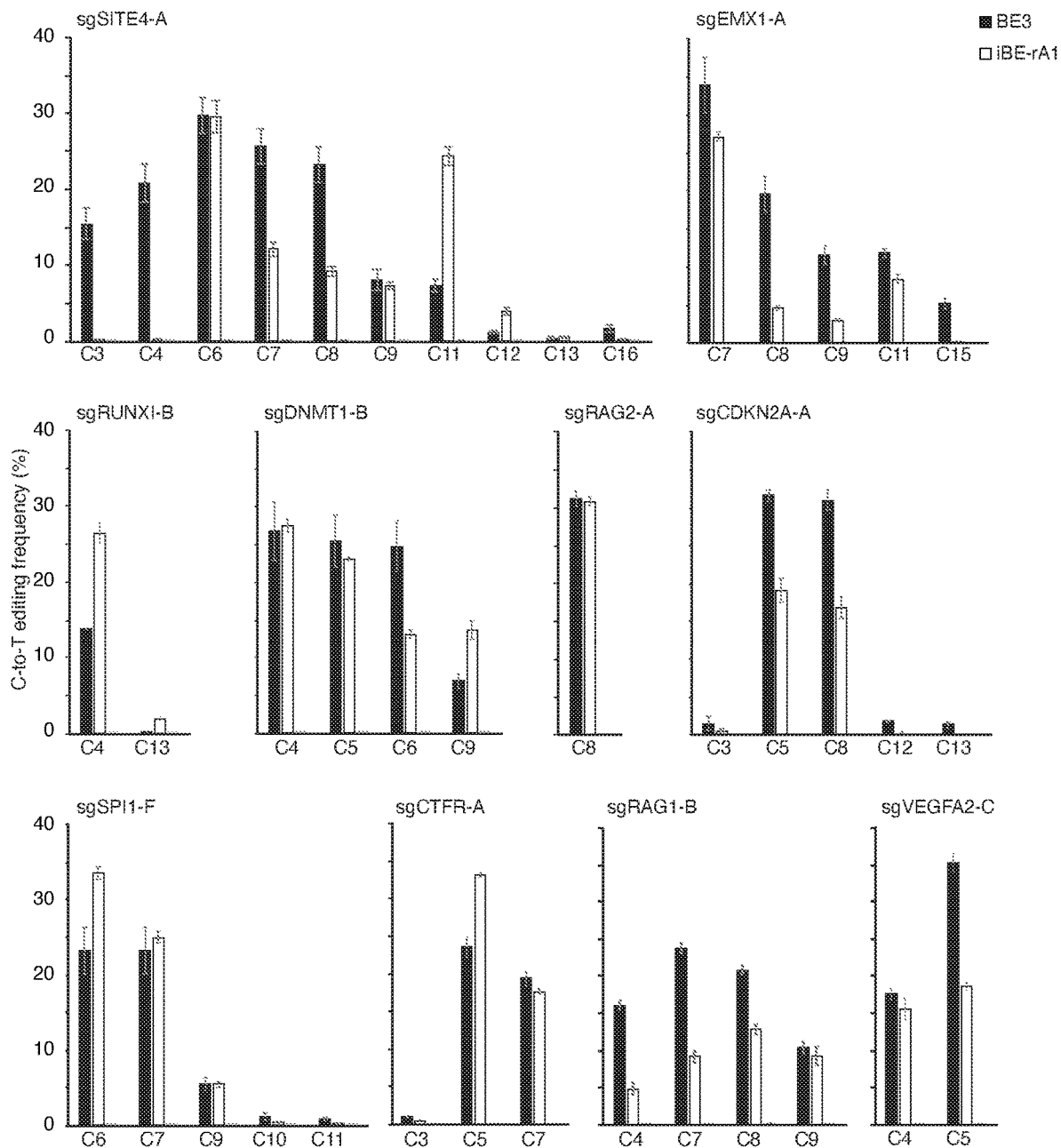
FIG. 31. Comparison of editing efficiency of isplitBE-rA1 and BE3. Editing frequencies induced by indicated base editors at different target sties.

The overall efficiency of the isplitBE system was compared to the conventional BE3. The results are shown in FIG. 31 (editing frequencies induced by indicated base editors at different target sties). There is no apparent sacrifice of efficiency even when the isplitBE had greatly improved specificity.

Normal cells have a background level of C-to-T mutations attributable to their endogenous APOBEC3 activities. To obtain a more accurate measurement of off-target C-to-T mutations, an APOBEC3 knockout 293FT cell line (293FT-A3KO) was used. FIG. 32A shows the mRNA expression levels in wild-type 293FT cells and the APOBEC3 knockout 293FT cells. FIG. 32B presents a schematic diagram illustrating the procedures to determine genome-wide C-to-T mutations induced by base editors, and the testing results are shown in FIG. 32C (on-target editing efficiencies (left) and the number of genome-wide C-to-T mutations induced by Cas9, BE3, hA3A-BE3-Y130F (Y130F) and isplitBE-rA1). While BE3 and Y130F both had fairly high off-target edits, isplitBE-rA1's off-target editing rate is close to the background (Cas9 only).

This example then compared transcriptome-wide C-to-U mutations induced by isplitBE-mA3, BE3 and hA3A-BE3-Y130F (Y130F). The numbers of transcriptome-wide C-to-T(U) mutations induced by Cas9, BE3, hA3A-BE3-Y130F (Y130F) and isplitBE-mA3 are shown in FIG. 33A. FIG. 33B shows RNA C-to-U editing frequencies induced by Cas9, BE3, hA3A-BE3-Y130F (Y130F) and isplitBE-mA3. FIG. 33C shows distribution of RNA C-to-U editing induced by BE3 replicate 1 and isplitBE-mA3 replicate 1. Again, isplitBE induced much lower C-to-U editing than BE3.

Example 6. PCSK9 Knockouts

Proprotein convertase subtilisin/kexin type 9 (PCSK9) is an enzyme encoded by the PCSK9 gene in humans on chromosome 1. It is the 9th member of the proprotein convertase family of proteins that activate other proteins. PCSK9 is inactive when first synthesized, because a section of peptide chains blocks their activity; proprotein convertases remove that section to activate the enzyme. The PCSK9 gene contains one of 27 loci associated with increased risk of coronary artery disease.

PCSK9 is ubiquitously expressed in many tissues and cell types. PCSK9 binds to the receptor for low-density lipoprotein particles (LDL), which typically transport 3,000 to 6,000 fat molecules (including cholesterol) per particle, within extracellular fluid. The LDL receptor (LDLR), on liver and other cell membranes, binds and initiates ingestion of LDL-particles from extracellular fluid into cells, thus reducing LDL particle concentrations. If PCSK9 is blocked, more LDLRs are recycled and are present on the surface of cells to remove LDL-particles from the extracellular fluid. Therefore, blocking PCSK9 can lower blood LDL-particle concentrations.

This example tested an approach to inactivate PCSK9 by introducing stop codons through base editing using the present technology. The sequences of the sgRNA/hsgRNA used are shown in Table 3, and the target sites on PCSK9 are shown in Table 4.

Figure 34C:
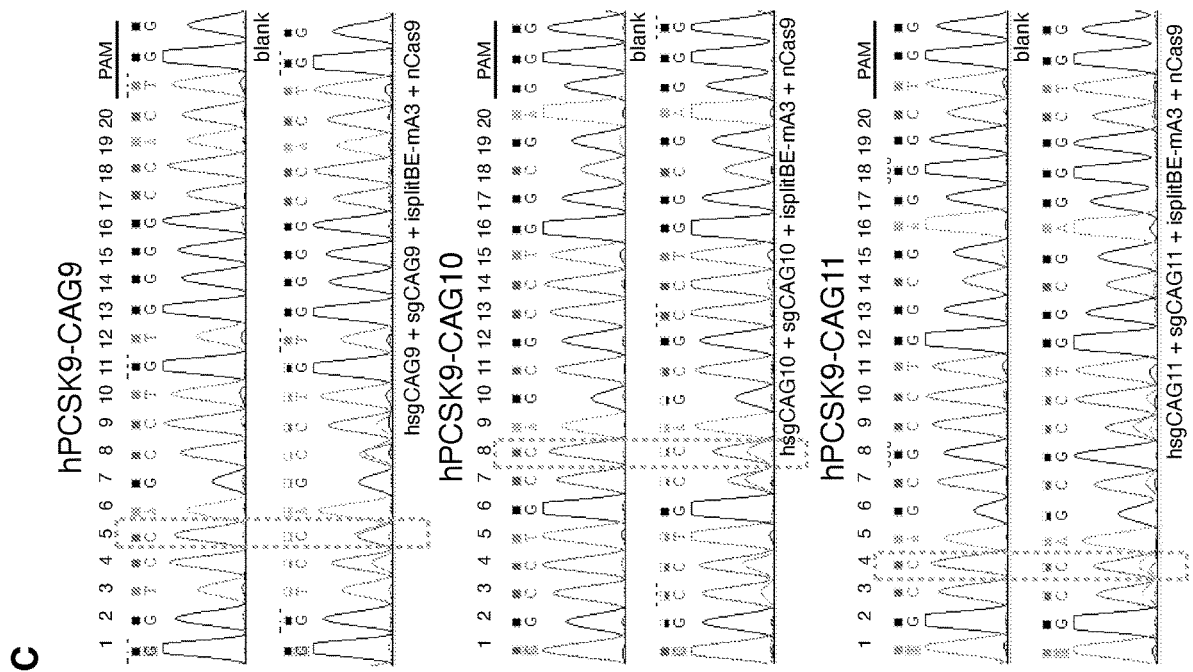
Figure 34D:
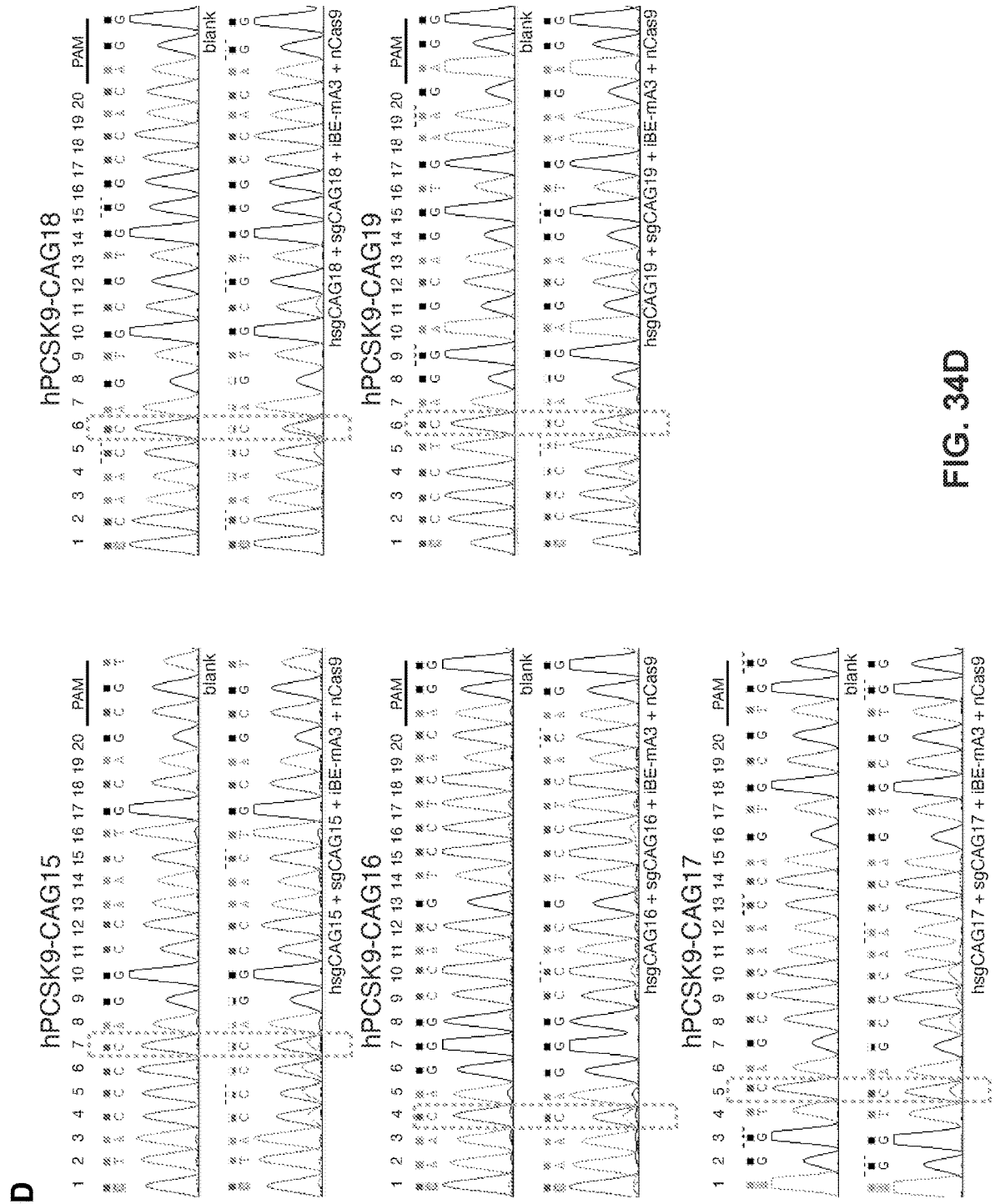

The numbers of stop codons generated by base editing were measured for the human PCSK9 gene. FIG. 34A presents a schematic diagram illustrating the co-transfection of sgRNA and the hsgRNAs with isplitBE-mA3 and nCas9. Editing efficiencies induced by isplitBE-mA3 at indicated sites are shown in FIG. 34B-D. These results demonstrate the high efficiency and specificity of the method.

TABLE 3

Regular sgRNA and hsgRNA scaffolds and target sites in PCSK9 genes

| Name | Sequence | SEQ ID NO: |
| --- | --- | --- |
| hsgCAG2-MS2 | GAGGUUGCCUGGCACCUACGGUUUGAGAGCUAGGCCAACAUGAGGAUCACCCAU<br>GUCUGCAGGGCCUAGCAAGUUCAAAUAAGGCUAGUCCGUUAUCAACUUGAAAAA<br>GUGGCACCGAGUCGGUGC | 136 |
| hsgCAG3-MS2 | GAGACCCACCUCUCGCAGUCGUUUGAGAGCUAGGCCAACAUGAGGAUCACCCAU<br>GUCUGCAGGGCCUAGCAAGUUCAAAUAAGGCUAGUCCGUUAUCAACUUGAAAAA<br>GUGGCACCGAGUCGGUGC | 137 |
| hsgCAG4-MS2 | GCCCCAUGUCGACUACAUCGGUUUGAGAGCUAGGCCAACAUGAGGAUCACCCAU<br>GUCUGCAGGGCCUAGCAAGUUCAAAUAAGGCUAGUCCGUUAUCAACUUGAAAAA<br>GUGGCACCGAGUCGGUGC | 138 |
| hsgCAG7-MS2 | AUGGUCACCGACUUCGAGAAGUUUGAGAGCUAGGCCAACAUGAGGAUCACCCAU<br>GUCUGCAGGGCCUAGCAAGUUCAAAUAAGGCUAGUCCGUUAUCAACUUGAAAAA<br>GUGGCACCGAGUCGGUGC | 139 |

TABLE 3-continued

Regular sgRNA and hsgRNA scaffolds and target sites in PCSK9 genes

| Name | Sequence | SEQ ID NO: |
|---|---|---|
| hsgCAG8-MS2 | ACCUUGGCUUUGUUCCUCCCGUUUGAGAGCUAGGCCAACAUGAGGAUCACCCAUGUCUGCAGGGCCUAGCAAGUUCAAAUAAGGCUAGUCCGUUAUCAACUUGAAAAAGUGGCACCGAGUCGGUGC | 140 |
| hsgCAG9-MS2 | GGCUUUGUUCCUCCCAGGCCGUUUGAGAGCUAGGCCAACAUGAGGAUCACCCAUGUCUGCAGGGCCUAGCAAGUUCAAAUAAGGCUAGUCCGUUAUCAACUUGAAAAAGUGGCACCGAGUCGGUGC | 141 |
| hsgCAG10-MS2 | GUGGUGCUGCUGCCCCUGGCGUUUGAGAGCUAGGCCAACAUGAGGAUCACCCAUGUCUGCAGGGCCUAGCAAGUUCAAAUAAGGCUAGUCCGUUAUCAACUUGAAAAAGUGGCACCGAGUCGGUGC | 142 |
| hsgCAG11-MS2 | UGCUGCUGCCCCUGGCGGGUGUUUGAGAGCUAGGCCAACAUGAGGAUCACCCAUGUCUGCAGGGCCUAGCAAGUUCAAAUAAGGCUAGUCCGUUAUCAACUUGAAAAAGUGGCACCGAGUCGGUGC | 143 |
| hsgCAG12-MS2 | ACCCACCUCCUCACCUUUCCGUUUGAGAGCUAGGCCAACAUGAGGAUCACCCAUGUCUGCAGGGCCUAGCAAGUUCAAAUAAGGCUAGUCCGUUAUCAACUUGAAAAAGUGGCACCGAGUCGGUGC | 144 |
| hsgCAG14-MS2 | AGCGACUGCAGCACCUGCUUGUUUGAGAGCUAGGCCAACAUGAGGAUCACCCAUGUCUGCAGGGCCUAGCAAGUUCAAAUAAGGCUAGUCCGUUAUCAACUUGAAAAAGUGGCACCGAGUCGGUGC | 145 |
| hsgCAG15-MS2 | AACGCUUUUGGGGGUGAGGGGUUUGAGAGCUAGGCCAACAUGAGGAUCACCCAUGUCUGCAGGGCCUAGCAAGUUCAAAUAAGGCUAGUCCGUUAUCAACUUGAAAAAGUGGCACCGAGUCGGUGC | 146 |
| hsgCAG16-MS2 | CCACACAGCUCCACCAGCUGGUUUGAGAGCUAGGCCAACAUGAGGAUCACCCAUGUCUGCAGGGCCUAGCAAGUUCAAAUAAGGCUAGUCCGUUAUCAACUUGAAAAAGUGGCACCGAGUCGGUGC | 147 |
| hsgCAG17-MS2 | CACUGGGAGGUGGAGGACCUGUUUGAGAGCUAGGCCAACAUGAGGAUCACCCAUGUCUGCAGGGCCUAGCAAGUUCAAAUAAGGCUAGUCCGUUAUCAACUUGAAAAAGUGGCACCGAGUCGGUGC | 148 |
| hsgCAG18-MS2 | CCCACAAGCCGCCUGUGCUGGUUUGAGAGCUAGGCCAACAUGAGGAUCACCCAUGUCUGCAGGGCCUAGCAAGUUCAAAUAAGGCUAGUCCGUUAUCAACUUGAAAAAGUGGCACCGAGUCGGUGC | 149 |
| hsgCAG19-MS2 | AGGUCUGGAAUGCAAAGUCAGUUUGAGAGCUAGGCCAACAUGAGGAUCACCCAUGUCUGCAGGGCCUAGCAAGUUCAAAUAAGGCUAGUCCGUUAUCAACUUGAAAAAGUGGCACCGAGUCGGUGC | 150 |
| sgCAG2-boxB | CUCUCGCAGUCAGAGCGCACGUUUGAGAGCUAGGGCCCUGAAGAAGGGCCCUAGCAAGUUCAAAUAAGGCUAGUCCGUUAUCAACUUGGGCCCUGAAGAAGGGCCCAAGUGGCACCGAGUCGGUGC | 151 |
| sgCAG3-boxB | CAGGCCCAGGCUGCCCGCCGGUUUGAGAGCUAGGGCCCUGAAGAAGGGCCCUAGCAAGUUCAAAUAAGGCUAGUCCGUUAUCAACUUGGGCCCUGAAGAAGGGCCCAAGUGGCACCGAGUCGGUGC | 152 |
| sgCAG4-boxB | UCUUUGCCCAGAGCAUCCCGGUUUGAGAGCUAGGGCCCUGAAGAAGGGCCCUAGCAAGUUCAAAUAAGGCUAGUCCGUUAUCAACUUGGGCCCUGAAGAAGGGCCCAAGUGGCACCGAGUCGGUGC | 153 |
| sgCAG7-boxB | CACAGACAGGUAAGCACGGCGUUUGAGAGCUAGGGCCCUGAAGAAGGGCCCUAGCAAGUUCAAAUAAGGCUAGUCCGUUAUCAACUUGGGCCCUGAAGAAGGGCCCAAGUGGCACCGAGUCGGUGC | 154 |
| sgCAG8-boxB | AAGCCAGCUGGUCCAGCCUGGUUUGAGAGCUAGGGCCCUGAAGAAGGGCCCUAGCAAGUUCAAAUAAGGCUAGUCCGUUAUCAACUUGGGCCCUGAAGAAGGGCCCAAGUGGCACCGAGUCGGUGC | 155 |
| sgCAG9-boxB | GGUCCAGCCUGUGGGGCCACGUUUGAGAGCUAGGGCCCUGAAGAAGGGCCCUAGCAAGUUCAAAUAAGGCUAGUCCGUUAUCAACUUGGGCCCUGAAGAAGGGCCCAAGUGGCACCGAGUCGGUGC | 156 |
| sgCAG10-boxB | CGCCUGCCAGCGCCUGGCGAGUUUGAGAGCUAGGGCCCUGAAGAAGGGCCCUAGCAAGUUCAAAUAAGGCUAGUCCGUUAUCAACUUGGGCCCUGAAGAAGGGCCCAAGUGGCACCGAGUCGGUGC | 157 |
| sgCAG11-boxB | UGCCAGCGCCUGGCGAGGGCGUUUGAGAGCUAGGGCCCUGAAGAAGGGCCCUAGCAAGUUCAAAUAAGGCUAGUCCGUUAUCAACUUGGGCCCUGAAGAAGGGCCCAAGUGGCACCGAGUCGGUGC | 158 |

TABLE 3-continued

Regular sgRNA and hsgRNA scaffolds and target sites in PCSK9 genes

| Name | Sequence | SEQ ID NO: |
|---|---|---|
| sgCAG12-boxB | AAGACCAGCCGGUGACCCUGGUUUGAGAGCUAGGGCCCUGAAGAAGGGCCCUAGCAAGUUCAAAUAAGGCUAGUCCGUUAUCAACUUGGGCCCUGAAGAAGGGCCCAAGUGGCACCGAGUCGGUGC | 159 |
| sgCAG14-boxB | AUCACAGGCUGCUGCCCACGGUUUGAGAGCUAGGGCCCUGAAGAAGGGCCCUAGCAAGUUCAAAUAAGGCUAGUCCGUUAUCAACUUGGGCCCUGAAGAAGGGCCCAAGUGGCACCGAGUCGGUGC | 160 |
| sgCAG15-boxB | CUACCCCAGGCCAACUGCAGGUUUGAGAGCUAGGGCCCUGAAGAAGGGCCCUAGCAAGUUCAAAUAAGGCUAGUCCGUUAUCAACUUGGGCCCUGAAGAAGGGCCCAAGUGGCACCGAGUCGGUGC | 161 |
| sgCAG16-boxB | CAACAGGGCCACGUCCUCACGUUUGAGAGCUAGGGCCCUGAAGAAGGGCCCUAGCAAGUUCAAAUAAGGCUAGUCCGUUAUCAACUUGGGCCCUGAAGAAGGGCCCAAGUGGCACCGAGUCGGUGC | 162 |
| sgCAG17-boxB | AGGUCAGCCCAACCAGUGCGGUUUGAGAGCUAGGGCCCUGAAGAAGGGCCCUAGCAAGUUCAAAUAAGGCUAGUCCGUUAUCAACUUGGGCCCUGAAGAAGGGCCCAAGUGGCACCGAGUCGGUGC | 163 |
| sgCAG18-boxB | CCAACCAGUGCGUGGGCCACGUUUGAGAGCUAGGGCCCUGAAGAAGGGCCCUAGCAAGUUCAAAUAAGGCUAGUCCGUUAUCAACUUGGGCCCUGAAGAAGGGCCCAAGUGGCACCGAGUCGGUGC | 164 |
| sgCAG19-boxB | CCCCUCAGGAGCAGGUGAAGGUUUGAGAGCUAGGGCCCUGAAGAAGGGCCCUAGCAAGUUCAAAUAAGGCUAGUCCGUUAUCAACUUGGGCCCUGAAGAAGGGCCCAAGUGGCACCGAGUCGGUGC | 165 |

TABLE 4

Target sites in PCSK9 genes

| Name | Sequence | SEQ ID NO: |
|---|---|---|
| hsgCAG2 | GAGGTTGCCTGGCACCTACGTGG | 166 |
| hsgCAG3 | GAGACCCACCTCTCGCAGTCAGA | 167 |
| hsgCAG4 | GCCCCATGTCGACTACATCGAGG | 168 |
| hsgCAG7 | ATGGTCACCGACTTCGAGAATGT | 169 |
| hsgCAG8 | ACCTTGGCTTTGTTCCTCCCAGG | 170 |
| hsgCAG9 | GGCTTTGTTCCTCCCAGGCCTGG | 171 |
| hsgCAG10 | GTGGTGCTGCTGCCCCTGGCGGG | 172 |
| hsgCAG11 | TGCTGCTGCCCCTGGCGGGTGGG | 173 |
| hsgCAG12 | ACCCACCTCCTCACCTTTCCAGG | 174 |
| hsgCAG14 | AGCGACTGCAGCACCTGCTTTGT | 175 |
| hsgCAG15 | AACGCTTTTGGGGGTGAGGGTGT | 176 |
| hsgCAG16 | CCACACAGCTCCACCAGCTGAGG | 177 |
| hsgCAG17 | CACTGGGAGGTGGAGGACCTTGG | 178 |
| hsgCAG18 | CCCACAAGCCGCCTGTGCTGAGG | 179 |
| hsgCAG19 | AGGTCTGGAATGCAAAGTCAAGG | 180 |
| sgCAG2 | CTCTCGCAGTCAGAGCGCACTGC | 181 |
| sgCAG3 | CAGGCCCAGGCTGCCCGCCGGGG | 182 |
| sgCAG4 | TCTTTGCCCAGAGCATCCCGTGG | 183 |
| sgCAG7 | CACAGACAGGTAAGCACGGCCGT | 184 |
| sgCAG8 | AAGCCAGCTGGTCCAGCCTGTGG | 185 |
| sgCAG9 | GGTCCAGCCTGTGGGGCCACTGG | 186 |
| sgCAG10 | CGCCTGCCAGCGCCTGGCGAGGG | 187 |
| sgCAG11 | TGCCAGCGCCTGGCGAGGGCTGG | 188 |
| sgCAG12 | AAGACCAGCCGGTGACCCTGGGG | 189 |
| sgCAG14 | ATCACAGGCTGCTGCCCACGTGG | 190 |
| sgCAG15 | CTACCCCAGGCCAACTGCAGCGT | 191 |
| sgCAG16 | CAACAGGGCCACGTCCTCACAGG | 192 |
| sgCAG17 | AGGTCAGCCCAACCAGTGCGTGG | 193 |
| sgCAG18 | CCAACCAGTGCGTGGGCCACAGG | 194 |
| sgCAG19 | CCCCTCAGGAGCAGGTGAAGAGG | 195 |

Example 7. Applicability of the isplitBE Design in Adenine Base Editors

This example confirms the applicability of the induced and split base editor (isplitBE) design in other types of base editors. The inhibitor used was mA3CDA2 and the editor was adenine base editor (ABE).

A schematic diagram illustrating the co-transfection of sgRNA and ABE fused with mA3CDA2 (or not as control) is shown in FIG. 35A. The editing efficiencies induced by indicated ABEs at RNF2 and FANCF sites are shown in FIG. 35B. With mA3CDA2 attached to the ABE, the editing efficiency was reduced as compared to ABE alone. When the mA3CDA2 was cleaved by 2A, the editing efficiency of ABE was restored, validating the isplitBE approach for ABE.

Example 8. Enhanced Prime Editing

The conventional base editors are limited to base transitions, not base transversions, insertions or deletions. Recently, a primer editing system was proposed, which employs a primer editor (PE) by conjugating a Cas9 nickase with a reverse transcriptase (RTase). The PE system can write genomes with almost any intended changes, including all types of base substitutions, small indels, and their combinations. The overall efficiency and specificity of the PE systems, however, are still limited.

In a first assay, this example tested a new design for the primer editing guide RNA (pegRNA). Conventionally, each guide RNA includes a scaffold. A commonly used scaffold sequence is GUUUAGAGCUAGAAAUAGCAAGUUAAAAUAAGGCUAGUCCGUUAUCAACUU GAAAAAGUGGCACCGAGUCGGUGC (SEQ ID NO:29). Another example is GUUUAGAGCUAGAAAUAGCAAGUUAAAAUAAGGCAUGUCCGUUAUCAACUU GAAAAAGUGGCACCGAUUCGGUGC (SEQ ID NO:30). A more generic consensus sequence is GUUU$\underline{N}$AGAGCUA$\underline{X_1}$UAGCAAGUU$\underline{N}$AAAUAAGGC$\underline{NN}$GUCCGUUAUCAACUU$\underline{X_2}$A AGUGGCACCGA$\underline{N}$UCGGUGC (SEQ ID NO:31), where N represents any base, and X1 and X2 denotes any nucleotide sequence of a length of 2-50 bases.

The scaffold is expected to form a secondary structure (illustrated in FIG. 36A, SEQ ID NO:30) due to its internal complementary sequences. A typical sgRNA used in base editors is about 96 nt in length which includes a spacer that is about 20 nt in length and binds to the target site. In a pegRNA, a reverse-transcription template and a primer-binding site are further added to the 3' end of the scaffold. Surprisingly, it is discovered herein that the original scaffold is not stable enough in the context of the pegRNA.

A new scaffold was therefore prepared, which forms a new pairing between positions 48 (e.g., A in SEQ ID NO:30) and 61 (e.g., G in SEQ ID NO:30). In the examples shown in FIGS. 36A and 36E, the new scaffold has G and C or C and G instead (SEQ ID NO:36, 37). This and additional example mutant scaffolds are shown in Table 5 below.

TABLE 5

Sequences of Guide RNA Scaffolds

| Description | Guide RNA Scaffold | SEQ ID NO: |
|---|---|---|
| Original | GUUUNAGAGCUA-X1-UAGCAAGUUNAAAUAAGGCNNGUCCGUUAUCAAC UU-X2-AAGUGGCACCGANUCGGUGC | 31 |
| New 1 | GUUUNAGAGCUA-X1-UAGCAAGUUNAAAUAAGGCNNGUCCGUUAUCGAC UU-X2-AAGUCGCACCGANUCGGUGC | 32 |
| New 2 | GUUUNAGAGCUA-X1-UAGCAAGUUNAAAUAAGGCNNGUCCGUUAUCCAC UU-X2-AAGUGGCACCGANUCGGUGC | 33 |
| New 3 | GUUUNAGAGCUA-X1-UAGCAAGUUNAAAUAAGGCNNGUCCGUUAUCAAC UU-X2-AAGUUGCACCGANUCGGUGC | 34 |
| New 4 | GUUUNAGAGCUA-X1-UAGCAAGUUNAAAUAAGGCNNGUCCGUUAUCUAC UU-X2-AAGUAGCACCGANUCGGUGC | 35 |
| Original 2 | GUUUUAGAGCUAGAAAUAGCAAGUUAAAAUAAGGCAUGUCCGUUAUCAAC UUGAAAAAGUGGCACCGAUUCGGUGC | 30 |
| New 5 | GUUUUAGAGCUAGAAAUAGCAAGUUAAAAUAAGGCAUGUCCGUUAUCGAC UUGAAAAAGUCGCACCGAUUCGGUGC | 36 |
| New 6 | GUUUUAGAGCUAGAAAUAGCAAGUUAAAAUAAGGCAUGUCCGUUAUCCAC UUGAAAAAGUGGCACCGAUUCGGUGC | 37 |
| New 7 | GUUUUAGAGCUAGAAAUAGCAAGUUAAAAUAAGGCAUGUCCGUUAUCAAC UUGAAAAAGUUGCACCGAUUCGGUGC | 38 |
| New 8 | GUUUUAGAGCUAGAAAUAGCAAGUUAAAAUAAGGCAUGUCCGUUAUCUAC UUGAAAAAGUAGCACCGAUUCGGUGC | 39 |
| Original 3 | GUUUUAGAGCUAGAAAUAGCAAGUUAAAAUAAGGCUAGUCCGUUAUCAAC UUGAAAAAGUGGCACCGAGUCGGUGC | 29 |
| New 9 | GUUUUAGAGCUAGAAAUAGCAAGUUAAAAUAAGGCUAGUCCGUUAUCGAC UUGAAAAAGUCGCACCGAGUCGGUGC | 40 |
| New 10 | GUUUUAGAGCUAGAAAUAGCAAGUUAAAAUAAGGCUAGUCCGUUAUCCAC UUGAAAAAGUGGCACCGAGUCGGUGC | 41 |
| New 11 | GUUUUAGAGCUAGAAAUAGCAAGUUAAAAUAAGGCUAGUCCGUUAUCAAC UUGAAAAAGUUGCACCGAGUCGGUGC | 42 |
| New 12 | GUUUUAGAGCUAGAAAUAGCAAGUUAAAAUAAGGCUAGUCCGUUAUCUAC UUGAAAAAGUAGCACCGAGUCGGUGC | 43 |

Figure 36D:
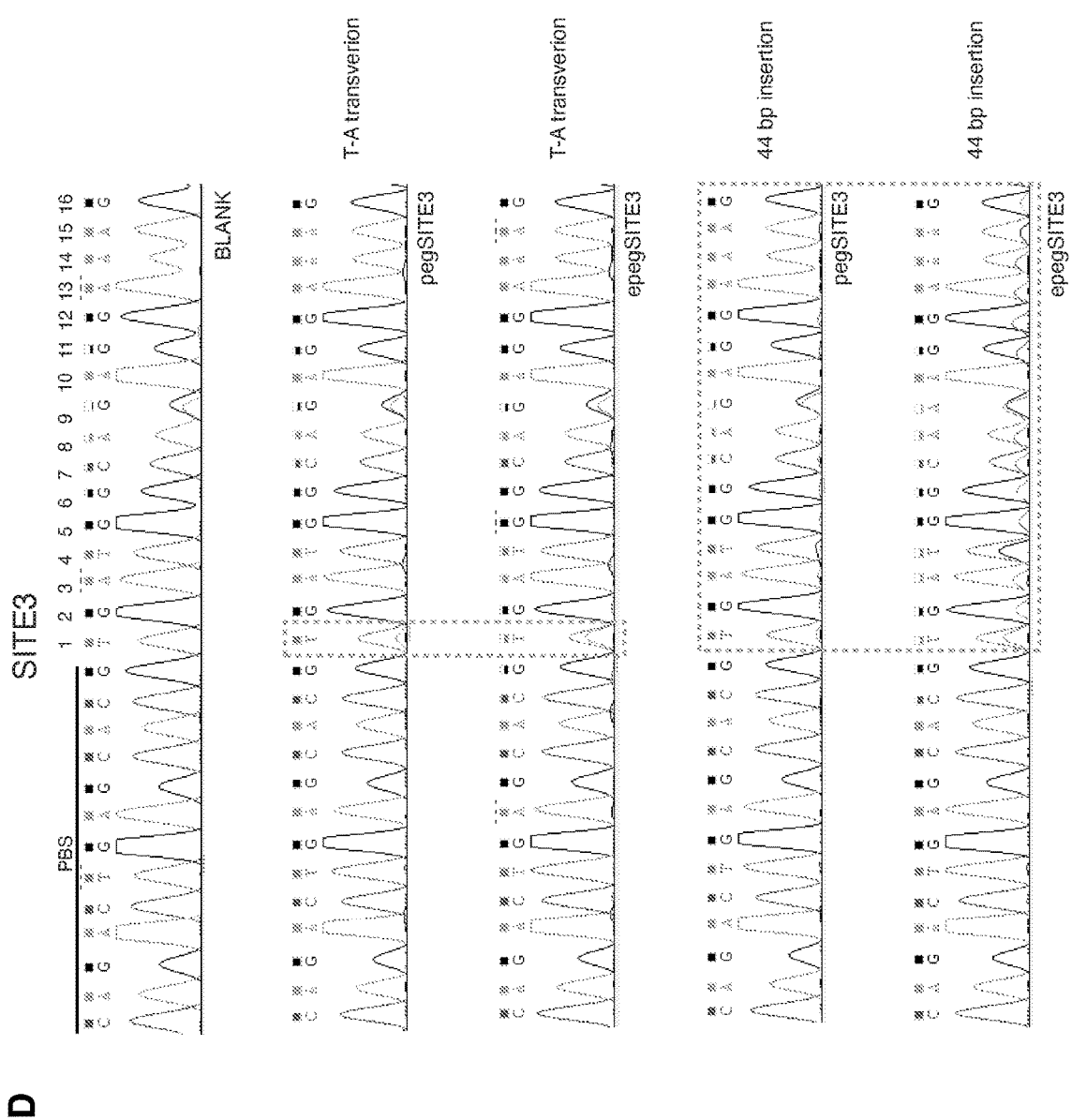

Constructs for testing the conventional pegRNA and the newly designed, enhanced pegRNA (epegRNA) were prepare as shown in FIGS. 36B and 36F for PE2, and the testing results are shown in FIGS. 36C-36D and 36G. Comparison of prime editing efficiencies induced with pegRNA and epegRNA. The epegRNA, with greatly improved stem stability, exhibited much higher editing efficiency than pegRNA across the board.

Likewise, according to the schematic diagram in FIG. 37A, co-transfection of pegRNA, nicking sgRNA with PE2-NG (SEQ ID NO:132) or xPE2 (SEQ ID NO:133) was made to test the editing efficiency for TGATG deletion. The results are shown in FIG. 37B. PE2-NG has an engineered Cas9 that can recognize relaxed NG PAMs (see, e.g., Nishimasu et al., Science 361, 1259-62 (2018)). xPE2 has an engineered Cas9 that can recognize relaxed NG, GAA and GAT PAMs (see, e.g., Hu et al., Nature 556, 57-63 (2018)). The sequences of PE2-NG (SEQ ID NO:44), xPE2 (SEQ ID NO:45), SpCas9-NG (SEQ ID NO:46), and xSpCas9 (SEQ ID NO:47) are shown in Table 6 below.

TABLE 6

Cas and PE sequences

| Name | Sequence | SEQ ID NO: |
|---|---|---|
| PE2-NG | MDKKYSIGLDIGTNSVGWAVITDEYKVPSKKFKVLGNTDRHSIKKNLIGALLFDSGETAEAT RLKRTARRRYTRRKNRICYLQEIFSNEMAKVDDSFFHRLEESFLVEEDKKHERHPIFGNIVD EVAYHEKYPTIYHLRKKLVDSTDKADLRLIYLALAHMIKFRGHFLIEGDLNPDNSDVDKLFI QLVQTYNQLFEENPINASGVDAKAILSARLSKSRRLENLIAQLPGEKKNGLFGNLIALSLGL TPNFKSNFDLAEDAKLQLSKDTYDDDLDNLLAQIGDQYADLFLAAKNLSDAILLSDILRVNT EITKAPLSASMIKRYDEHHQDLTLLKALVRQQLPEKYKEIFFDQSKNGYAGYIDGGASQEEF YKFIKPILEKMDGTEELLVKLNREDLLRKQRTFDNGSIPHQIHLGELHAILRRQEDFYPFLK DNREKIEKILTFRIPYYVGPLARGNSRFAWMTRKSEETITPWNFEEVVDKGASAQSFIERMT NFDKNLPNEKVLPKHSLLYEYFTVYNELTKVKYVTEGMRKPAFLSGEQKKAIVDLLFKTNRK VTVKQLKEDYFKKIECFDSVEISGVEDRFNASLGTYHDLLKIIKDKDFLDNEENEDILEDIV LTLTLFEDREMIEERLKTYAHLFDDKVMKQLKRRRYTGWGRLSRKLINGIRDKQSGKTILDF LKSDGFANRNFMQLIHDDSLTFKEDIQKAQVSGQGDSLHEHIANLAGSPAIKKGILQTVKVV DELVKVMGRHKPENIVIEMARENQTTQKGQKNSRERMKRIEEGIKELGSQILKEHPVENTQL QNEKLYLYYLQNGRDMYVDQELDINRLSDYDVDAIVPQSFLKDDSIDNKVLTRSDKNRGKSD NVPSEEVVKKMKNYWRQLLNAKLITQRKFDNLTKAERGGLSELDKAGFIKRQLVETRQITKH VAQILDSRMNTKYDENDKLIREVKVITLKSKLVSDFRKDFQFYKVREINNYHHAHDAYLNAV VGTALIKKYPKLESEFVYGDYKVYDVRKMIAKSEQEIGKATAKYFFYSNIMNFFKTEITLAN GEIRKRPLIETNGETGEIVWDKGRDFATVRKVLSMPQVNIVKKTEVQTGGFSKESIRPKRNS DKLIARKKDWDPKKYGGFVSPTVAYSVLVVAKVEKGKSKKLKSVKELLGITIMERSSFEKNP IDFLEAKGYKEVKKDLIIKLPKYSLFELENGRKRMLASARFLQKGNELALPSKYVNFLYLAS HYEKLKGSPEDNEQKQLFVEQHKHYLDEIIEQISEFSKRVILADANLDKVLSAYNKHRDKPI REQAENIIHLFTLTNLGAPRAFKYFDTTIDRKVYRSTKEVLDATLIHQSITGLYETRIDLSQ LGGDGTSGGSSGGSSGSETPGTSESATPESSGGSSGGSSTLNIEDEYRLHETSKEPDVSLGS TWLSDFPQAWAETGGMGLAVRQAPLIIPLKATSTPVSIKQYPMSQEARLGIKPHIQRLLDQG ILVPCQSPWNTPLLPVKKPGTNDYRPVQDLREVNKRVEDIHPTVPNPYNLLSGLPPSHQWYT VLDLKDAFFCLRLHPTSQPLFAFEWRDPEMGISGQLTWTRLPQGFKNSPTLFNEALHRDLAD FRIQHPDLILLQYVDDLLLAATSELDCQQGTRALLQTLGNLGYRASAKKAQICQKQVKYLGY LLKEGQRWLTEARKETVMGQPTPKTPRQLREFLGKAGFCRLFIPGFAEMAAPLYPLTKPGTL FNWGPDQQKAYQEIKQALLTAPALGLPDLTKPFELFVDEKQGYAKGVLTQKLGPWRRPVAYL SKKLDPVAAGWPPCLRMVAAIAVLTKDAGKLTMGQPLVILAPHAVEALVKQPPDRWLSNARM THYQALLLDTDRVQFGPVVALNPATLLPLPEEGLQHNCLDILAEAHGTRPDLTDQPLPDADH TWYTDGSSLLQEGQRKAGAAVTTETEVIWAKALPAGTSAQRAELIALTQALKMAEGKKLNVY TDSRYAFATAHIHGEIYRRRGWLTSEGKEIKNKDEILALLKALFLPKRLSIIHCPGHQKGHS AEARGNRMADQAARKAAITETPDTSTLLIENSSP | 44 |
| xPE2 | MDKKYSIGLDIGTNSVGWAVITDEYKVPSKKFKVLGNTDRHSIKKNLIGALLFDSGETAEAT RLKRTARRRYTRRKNRICYLQEIFSNEMAKVDDSFFHRLEESFLVEEDKKHERHPIFGNIVD EVAYHEKYPTIYHLRKKLVDSTDKADLRLIYLALAHMIKFRGHFLIEGDLNPDNSDVDKLFI QLVQTYNQLFEENPINASGVDAKAILSARLSKSRRLENLIAQLPGEKKNGLFGNLIALSLGL TPNFKSNFDLAEDTKLQLSKDTYDDDLDNLLAQIGDQYADLFLAAKNLSDAILLSDILRVNT EITKAPLSASMIKLYDEHHQDLTLLKALVRQQLPEKYKEIFFDQSKNGYAGYIDGGASQEEF YKFIKPILEKMDGTEELLVKLNREDLLRKQRTFDNGIIPHQIHLGELHAILRRQEDFYPFLK DNREKIEKILTFRIPYYVGPLARGNSRFAWMTRKSEETITPWNFEKVVDKGASAQSFIERMT NFDKNLPNEKVLPKHSLLYEYFTVYNELTKVKYVTEGMRKPAFLSGDQKKAIVDLLFKTNRK VTVKQLKEDYFKKIECFDSVEISGVEDRFNASLGTYHDLLKIIKDKDFLDNEENEDILEDIV LTLTLFEDREMIEERLKTYAHLFDDKVMKQLKRRRYTGWGRLSRKLINGIRDKQSGKTILDF LKSDGFANRNFIQLIHDDSLTFKEDIQKAQVSGQGDSLHEHIANLAGSPAIKKGILQTVKVV DELVKVMGRHKPENIVIEMARENQTTQKGQKNSRERMKRIEEGIKELGSQILKEHPVENTQL QNEKLYLYYLQNGRDMYVDQELDINRLSDYDVDAIVPQSFLKDDSIDNKVLTRSDKNRGKSD NVPSEEVVKKMKNYWRQLLNAKLITQRKFDNLTKAERGGLSELDKAGFIKRQLVETRQITKH VAQILDSRMNTKYDENDKLIREVKVITLKSKLVSDFRKDFQFYKVREINNYHHAHDAYLNAV VGTALIKKYPKLESEFVYGDYKVYDVRKMIAKSEQEIGKATAKYFFYSNIMNFFKTEITLAN GEIRKRPLIETNGETGEIVWDKGRDFATVRKVLSMPQVNIVKKTEVQTGGFSKESILPKRNS DKLIARKKDWDPKKYGGFDSPTVAYSVLVVAKVEKGKSKKLKSVKELLGITIMERSSFEKNP IDFLEAKGYKEVKKDLIIKLPKYSLFELENGRKRMLASAGVLQKGNELALPSKYVNFLYLAS HYEKLKGSPEDNEQKQLFVEQHKHYLDEIIEQISEFSKRVILADANLDKVLSAYNKHRDKPI REQAENIIHLFTLTNLGAPAAFKYFDTTIDRKRYTSTKEVLDATLIHQSITGLYETRIDLSQ LGGDGTSGGSSGGSSGSETPGTSESATPESSGGSSGGSSTLNIEDEYRLHETSKEPDVSLGS TWLSDFPQAWAETGGMGLAVRQAPLIIPLKATSTPVSIKQYPMSQEARLGIKPHIQRLLDQG ILVPCQSPWNTPLLPVKKPGTNDYRPVQDLREVNKRVEDIHPTVPNPYNLLSGLPPSHQWYT VLDLKDAFFCLRLHPTSQPLFAFEWRDPEMGISGQLTWTRLPQGFKNSPTLFNEALHRDLAD FRIQHPDLILLQYVDDLLLAATSELDCQQGTRALLQTLGNLGYRASAKKAQICQKQVKYLGY | 45 |

TABLE 6-continued

Cas and PE sequences

| Name | Sequence | SEQ ID NO: |
|---|---|---|
|  | LLKEGQRWLTEARKETVMGQPTPKTPRQLREFLGKAGFCRLFIPGFAEMAAPLYPLTKPGTL FNWGPDQQKAYQEIKQALLTAPALGLPDLTKPFELFVDEKQGYAKGVLTQKLGPWRRPVAYL SKKLDPVAAGWPPCLRMVAAIAVLTKDAGKLTMGQPLVILAPHAVEALVKQPPDRWLSNARM THYQALLLDTDRVQFGPVVALNPATLLPLPEEGLQHNCLDILAEAHGTRPDLTDQPLPDADH TWYTDGSSLLQEGQRKAGAAVTTETEVIWAKALPAGTSAQRAELIALTQALKMAEGKKLNVY TDSRYAFATAHIHGEIYRRRGWLTSEGKEIKNKDEILALLKALFLPKRLSIIHCPGHQKGHS AEARGNRMADQAARKAAITETPDTSTLLIENSSP |  |
| SpCas9-NG | MDKKYSIGLDIGTNSVGWAVITDEYKVPSKKFKVLGNTDRHSIKKNLIGALLFDSGETAEAT RLKRTARRRYTRRKNRICYLQEIFSNEMAKVDDSFFHRLEESFLVEEDKKHERHPIFGNIVD EVAYHEKYPTIYHLRKKLVDSTDKADLRLIYLALAHMIKFRGHFLIEGDLNPDNSDVDKLFI QLVQTYNQLFEENPINASGVDAKAILSARLSKSRRLENLIAQLPGEKKNGLFGNLIALSLGL TPNFKSNFDLAEDAKLQLSKDTYDDDLDNLLAQIGDQYADLFLAAKNLSDAILLSDILRVNT EITKAPLSASMIKRYDEHHQDLTLLKALVRQQLPEKYKEIFFDQSKNGYAGYIDGGASQEEF YKFIKPILEKMDGTEELLVKLNREDLLRKQRTFDNGSIPHQIHLGELHAILRRQEDFYPFLK DNREKIEKILTFRIPYYVGPLARGNSRFAWMTRKSEETITPWNFEEVVDKGASAQSFIERMT NFDKNLPNEKVLPKHSLLYEYFTVYNELTKVKYVTEGMRKPAFLSGEQKKAIVDLLFKTNRK VTVKQLKEDYFKKIECFDSVEISGVEDRFNASLGTYHDLLKIIKDKDFLDNEENEDILEDIV LTLTLFEDREMIEERLKTYAHLFDDKVMKQLKRRRYTGWGRLSRKLINGIRDKQSGKTILDF LKSDGFANRNFMQLIHDDSLTFKEDIQKAQVSGQGDSLHEHIANLAGSPAIKKGILQTVKVV DELVKVMGRHKPENIVIEMARENQTTQKGQKNSRERMKRIEEGIKELGSQILKEHPVENTQL QNEKLYLYYLQNGRDMYVDQELDINRLSDYDVDHIVPQSFLKDDSIDNKVLTRSDKNRGKSD NVPSEEVVKKMKNYWRQLLNAKLITQRKFDNLTKAERGGLSELDKAGFIKRQLVETRQITKH VAQILDSRMNTKYDENDKLIREVKVITLKSKLVSDFRKDFQFYKVREINNYHHAHDAYLNAV VGTALIKKYPKLESEFVYGDYKVYDVRKMIAKSEQEIGKATAKYFFYSNIMNFFKTEITLAN GEIRKRPLIETNGETGEIVWDKGRDFATVRKVLSMPQVNIVKKTEVQTGGFSKESIRPKRNS DKLIARKKDWDPKKYGGFVSPTVAYSVLVVAKVEKGKSKKLKSVKELLGITIMERSSFEKNP IDFLEAKGYKEVKKDLIIKLPKYSLFELENGRKRMLASARFLQKGNELALPSKYVNFLYLAS HYEKLKGSPEDNEQKQLFVEQHKHYLDEIIEQISEFSKRVILADANLDKVLSAYNKHRDKPI REQAENIIHLFTLTNLGAPRAFKYFDTTIDRKVYRSTKEVLDATLIHQSITGLYETRIDLSQ LGGD | 46 |
| xSpCas9 | MDKKYSIGLDIGTNSVGWAVITDEYKVPSKKFKVLGNTDRHSIKKNLIGALLFDSGETAEAT RLKRTARRRYTRRKNRICYLQEIFSNEMAKVDDSFFHRLEESFLVEEDKKHERHPIFGNIVD EVAYHEKYPTIYHLRKKLVDSTDKADLRLIYLALAHMIKFRGHFLIEGDLNPDNSDVDKLFI QLVQTYNQLFEENPINASGVDAKAILSARLSKSRRLENLIAQLPGEKKNGLFGNLIALSLGL TPNFKSNFDLAEDTKLQLSKDTYDDDLDNLLAQIGDQYADLFLAAKNLSDAILLSDILRVNT EITKAPLSASMIKLYDEHHQDLTLLKALVRQQLPEKYKEIFFDQSKNGYAGYIDGGASQEEF YKFIKPILEKMDGTEELLVKLNREDLLRKQRTFDNGIIPHQIHLGELHAILRRQEDFYPFLK DNREKIEKILTFRIPYYVGPLARGNSRFAWMTRKSEETITPWNFEKVVDKGASAQSFIERMT NFDKNLPNEKVLPKHSLLYEYFTVYNELTKVKYVTEGMRKPAFLSGDQKKAIVDLLFKTNRK VTVKQLKEDYFKKIECFDSVEISGVEDRFNASLGTYHDLLKIIKDKDFLDNEENEDILEDIV LTLTLFEDREMIEERLKTYAHLFDDKVMKQLKRRRYTGWGRLSRKLINGIRDKQSGKTILDF LKSDGFANRNFIQLIHDDSLTFKEDIQKAQVSGQGDSLHEHIANLAGSPAIKKGILQTVKVV DELVKVMGRHKPENIVIEMARENQTTQKGQKNSRERMKRIEEGIKELGSQILKEHPVENTQL QNEKLYLYYLQNGRDMYVDQELDINRLSDYDVDHIVPQSFLKDDSIDNKVLTRSDKNRGKSD NVPSEEVVKKMKNYWRQLLNAKLITQRKFDNLTKAERGGLSELDKAGFIKRQLVETRQITKH VAQILDSRMNTKYDENDKLIREVKVITLKSKLVSDFRKDFQFYKVREINNYHHAHDAYLNAV VGTALIKKYPKLESEFVYGDYKVYDVRKMIAKSEQEIGKATAKYFFYSNIMNFFKTEITLAN GEIRKRPLIETNGETGEIVWDKGRDFATVRKVLSMPQVNIVKKTEVQTGGFSKESILPKRNS DKLIARKKDWDPKKYGGFDSPTVAYSVLVVAKVEKGKSKKLKSVKELLGITIMERSSFEKNP IDFLEAKGYKEVKKDLIIKLPKYSLFELENGRKRMLASAGVLQKGNELALPSKYVNFLYLAS HYEKLKGSPEDNEQKQLFVEQHKHYLDEIIEQISEFSKRVILADANLDKVLSAYNKHRDKPI REQAENIIHLFTLTNLGAPAAFKYFDTTIDRKRYTSTKEVLDATLIHQSITGLYETRIDLSQ LGGD | 47 |

A complete prime editor requires a construct (about 11 kb) that is much larger than what an AAV vehicle can accommodate. Accordingly, a Split PE system was designed and tested. The original PE system is illustrated on the left panel of FIG. 38A, and the newly designed Split PE system is illustrated on the right panel, in which the nickase and the RTase are packaged into different AAV particles. The RTase is fused to an RNA binding protein MCP, and the pegRNA includes a binding site MS2. When taken up into a cell, the RTase can be recruited by the pegRNA, through the MS2-MCP binding, and come in contact with the nickase.

An example co-transfection system is illustrated in FIG. 38B, and the testing results are shown in FIG. 38C, at the EMX1 site.

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference.

What is claimed is:

1. A fusion protein comprising:
   a first fragment comprising a cytidine deaminase or a catalytic domain thereof,
   a second fragment comprising an inhibitor to the cytidine deaminase or catalytic domain thereof, wherein said inhibitor is an inhibitory domain from the cytidine deaminase or from a second cytidine deaminase, and
   a protease cleavage site between the first fragment and the second fragment, wherein protease cleavage site is a protease cleavage site of a protease selected from the group consisting of TEV protease, TuMV protease, PPV protease, PVY protease, ZIKV protease and WNV protease, or is a self-cleavage site.

2. The fusion protein of claim 1, wherein the cytidine deaminase is selected from the group consisting of APOBEC3B (A3B), APOBEC3C (A3C), APOBEC3D (A3D), APOBEC3F (A3F), APOBEC3G (A3G), APOBEC3H (A3H), APOBEC1 (A1), APOBEC3 (A3), APOBEC2 (A2), APOBEC4 (A4) and AICDA (AID).

3. The fusion protein of claim 1, wherein the cytidine deaminase is a human or mouse cytidine deaminase.

4. The fusion protein of claim 3, wherein the catalytic domain is mouse A3 cytidine deaminase domain 1 (CDA1) or human A3B cytidine deaminase domain 2 (CDA2).

5. The fusion protein of claim 1, wherein the inhibitor is an inhibitory domain of a second cytidine deaminase.

6. The fusion protein of claim 1, wherein the inhibitor comprises an amino acid sequence selected from SEQ ID NO: 1-2 and 48-135, or an amino acid sequence having at least 85% sequence identity to any of the amino acid sequence selected from SEQ ID NO: 1-2 and 48-135.

7. The fusion protein of claim 1, wherein the inhibitor comprises the amino acid sequence of SEQ ID NO:1, amino acids residues AA128-AA223 of SEQ ID NO:1 or the amino acid sequence of SEQ ID NO:2.

8. The fusion protein of claim 1, wherein the protease cleavage site is a TEV protease cleavage site.

9. The fusion protein of claim 8, further comprising a third fragment comprising a TEV protease or a fragment thereof.

10. The fusion protein of claim 9, wherein the third fragment comprises a TEV protease fragment which alone is not able to cleave the TEV protease cleavage site.

11. A fusion protein comprising a first fragment comprising:
   a cytidine deaminase or a catalytic domain thereof,
   an inhibitor to the cytidine deaminase or catalytic domain thereof, wherein said inhibitor is an inhibitory domain from a cytidine deaminase,
   a first RNA recognition peptide, and
   a TEV protease cleavage site between the cytidine deaminase or a catalytic domain thereof and the cytidine deaminase inhibitor.

12. A method for editing a nucleic acid, comprising contact the nucleic acid with a fusion protein comprising a first fragment comprising a cytidine deaminase or a catalytic domain thereof, cleavably fused to a second fragment comprising an inhibitor to the cytidine deaminase or catalytic domain thereof, wherein said inhibitor is an inhibitor domain from a cytidine deaminase, and wherein the editing is conducted with a protease that cleaves the second fragment from the first fragment thereby activating the nucleobase deaminase or catalytic domain thereof.

13. The method of claim 12, wherein the first fragment is cleavably fused to the second fragment through a protease cleavage site of a protease selected from the group consisting of TEV protease, TuMV protease, PPV protease, PVY protease, ZIKV protease and WNV protease.

14. The method of claim 12, wherein the inhibitor comprises the amino acid sequence of SEQ ID NO:1, amino acids residues AA128-AA223 of SEQ ID NO:1 or the amino acid sequence of SEQ ID NO:2.

* * * * *

SEQUENCE LISTING

<160> NUMBER OF SEQ ID NOS: 283

<210> SEQ ID NO 1
<211> LENGTH: 223
<212> TYPE: PRT
<213> ORGANISM: Artificial Sequence
<220> FEATURE:
<223> OTHER INFORMATION: Synthetic

<400> SEQUENCE: 1

Met Ser Ser Ser Thr Leu Ser Asn Ile Cys Leu Thr Lys Gly Leu Pro
1               5                   10                  15

Glu Thr Arg Phe Trp Val Glu Gly Arg Arg Met Asp Pro Leu Ser Glu
            20                  25                  30

Glu Glu Phe Tyr Ser Gln Phe Tyr Asn Gln Arg Val Lys His Leu Cys
        35                  40                  45

Tyr Tyr His Arg Met Lys Pro Tyr Leu Cys Tyr Gln Leu Glu Gln Phe
    50                  55                  60

Asn Gly Gln Ala Pro Leu Lys Gly Cys Leu Leu Ser Glu Lys Gly Lys
65                  70                  75                  80

Gln His Ala Glu Ile Leu Phe Leu Asp Lys Ile Arg Ser Met Glu Leu
                85                  90                  95

Ser Gln Val Thr Ile Thr Cys Tyr Leu Thr Trp Ser Pro Cys Pro Asn
            100                 105                 110

Cys Ala Trp Gln Leu Ala Ala Phe Lys Arg Asp Arg Pro Asp Leu Ile
        115                 120                 125

Leu His Ile Tyr Thr Ser Arg Leu Tyr Phe His Trp Lys Arg Pro Phe
    130                 135                 140

Gln Lys Gly Leu Cys Ser Leu Trp Gln Ser Gly Ile Leu Val Asp Val
145                 150                 155                 160

Met Asp Leu Pro Gln Phe Thr Asp Cys Trp Thr Asn Phe Val Asn Pro
                165                 170                 175

Lys Arg Pro Phe Trp Pro Trp Lys Gly Leu Glu Ile Ile Ser Arg Arg
            180                 185                 190

Thr Gln Arg Arg Leu Arg Arg Ile Lys Glu Ser Trp Gly Leu Gln Asp
        195                 200                 205

Leu Val Asn Asp Phe Gly Asn Leu Gln Leu Gly Pro Pro Met Ser
    210                 215                 220

<210> SEQ ID NO 2
<211> LENGTH: 166
<212> TYPE: PRT
<213> ORGANISM: Artificial Sequence
<220> FEATURE:
<223> OTHER INFORMATION: Synthetic

<400> SEQUENCE: 2

Met Asn Pro Gln Ile Arg Asn Pro Met Glu Arg Met Tyr Arg Asp Thr
1               5                   10                  15

Phe Tyr Asp Asn Phe Glu Asn Glu Pro Ile Leu Tyr Gly Arg Ser Tyr
            20                  25                  30

Thr Trp Leu Cys Tyr Glu Val Lys Ile Lys Arg Gly Arg Ser Asn Leu
        35                  40                  45

Leu Trp Asp Thr Gly Val Phe Arg Gly Gln Val Tyr Phe Lys Pro Gln
    50                  55                  60

Tyr His Ala Glu Met Cys Phe Leu Ser Trp Phe Cys Gly Asn Gln Leu
65                  70                  75                  80

```
Pro Ala Tyr Lys Cys Phe Gln Ile Thr Trp Phe Val Ser Trp Thr Pro
                85                  90                  95

Cys Pro Asp Cys Val Ala Lys Leu Ala Glu Phe Leu Ser Glu His Pro
            100                 105                 110

Asn Val Thr Leu Thr Ile Ser Ala Ala Arg Leu Tyr Tyr Tyr Trp Glu
        115                 120                 125

Arg Asp Tyr Arg Ala Leu Cys Arg Leu Ser Gln Ala Gly Ala Arg
    130                 135                 140

Val Lys Ile Met Asp Tyr Glu Glu Phe Ala Tyr Cys Trp Glu Asn Phe
145                 150                 155                 160

Val Tyr Asn Glu Gly Gln
                165

<210> SEQ ID NO 3
<211> LENGTH: 119
<212> TYPE: PRT
<213> ORGANISM: Artificial Sequence
<220> FEATURE:
<223> OTHER INFORMATION: Synthetic

<400> SEQUENCE: 3

Met Gly Glu Ser Leu Phe Lys Gly Pro Arg Asp Tyr Asn Pro Ile Ser
1               5                   10                  15

Ser Thr Ile Cys His Leu Thr Asn Glu Ser Asp Gly His Thr Thr Ser
            20                  25                  30

Leu Tyr Gly Ile Gly Phe Gly Pro Phe Ile Ile Thr Asn Lys His Leu
        35                  40                  45

Phe Arg Arg Asn Asn Gly Thr Leu Leu Val Gln Ser Leu His Gly Val
    50                  55                  60

Phe Lys Val Lys Asn Thr Thr Thr Leu Gln Gln His Leu Ile Asp Gly
65                  70                  75                  80

Arg Asp Met Ile Ile Ile Arg Met Pro Lys Asp Phe Pro Pro Phe Pro
                85                  90                  95

Gln Lys Leu Lys Phe Arg Glu Pro Gln Arg Glu Glu Arg Ile Cys Leu
            100                 105                 110

Val Thr Thr Asn Phe Gln Thr
        115

<210> SEQ ID NO 4
<211> LENGTH: 116
<212> TYPE: PRT
<213> ORGANISM: Artificial Sequence
<220> FEATURE:
<223> OTHER INFORMATION: Synthetic

<400> SEQUENCE: 4

Met Lys Ser Met Ser Ser Met Val Ser Asp Thr Ser Cys Thr Phe Pro
1               5                   10                  15

Ser Ser Asp Gly Ile Phe Trp Lys His Trp Ile Gln Thr Lys Asp Gly
            20                  25                  30

Gln Cys Gly Ser Pro Leu Val Ser Thr Arg Asp Gly Phe Ile Val Gly
        35                  40                  45

Ile His Ser Ala Ser Asn Phe Thr Asn Thr Asn Tyr Phe Thr Ser
    50                  55                  60

Val Pro Lys Asn Phe Met Glu Leu Leu Thr Asn Gln Glu Ala Gln Gln
65                  70                  75                  80

Trp Val Ser Gly Trp Arg Leu Asn Ala Asp Ser Val Leu Trp Gly Gly
                85                  90                  95
```

```
His Lys Val Phe Met Val Lys Pro Glu Glu Pro Phe Gln Pro Val Lys
            100                 105                 110

Glu Ala Thr Gln
        115

<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

Glu Asn Leu Tyr Phe Gln Ser
1               5

<210> SEQ ID NO 6
<211> LENGTH: 246
<212> TYPE: PRT
<213> ORGANISM: Artificial Sequence
<220> FEATURE:
<223> OTHER INFORMATION: Synthetic

<400> SEQUENCE: 6

Met Ala Ser Ser Asn Ser Met Phe Arg Gly Leu Arg Asp Tyr Asn Pro
1               5                   10                  15

Ile Ser Asn Asn Ile Cys His Leu Thr Asn Val Ser Asp Gly Ala Ser
            20                  25                  30

Asn Ser Leu Tyr Gly Val Gly Phe Gly Pro Leu Ile Leu Thr Asn Arg
        35                  40                  45

His Leu Phe Glu Arg Asn Asn Gly Glu Leu Val Ile Lys Ser Arg His
    50                  55                  60

Gly Glu Phe Val Ile Lys Asn Thr Thr Gln Leu His Leu Leu Pro Ile
65                  70                  75                  80

Pro Asp Arg Asp Leu Leu Leu Ile Arg Leu Pro Lys Asp Val Pro Pro
                85                  90                  95

Phe Pro Gln Lys Leu Gly Phe Arg Gln Pro Glu Lys Gly Glu Arg Ile
            100                 105                 110

Cys Met Val Gly Ser Asn Phe Gln Thr Lys Ser Ile Thr Ser Ile Val
        115                 120                 125

Ser Glu Thr Ser Thr Ile Met Pro Val Glu Asn Ser Gln Phe Trp Lys
    130                 135                 140

His Trp Ile Ser Thr Lys Asp Gly Gln Cys Gly Ser Pro Met Val Ser
145                 150                 155                 160

Thr Lys Asp Gly Lys Ile Leu Gly Leu His Ser Leu Ala Asn Phe Gln
                165                 170                 175

Asn Ser Ile Asn Tyr Phe Ala Ala Phe Pro Asp Asp Phe Ala Glu Lys
            180                 185                 190

Tyr Leu His Thr Ile Glu Ala His Glu Trp Val Lys His Trp Lys Tyr
        195                 200                 205

Asn Thr Ser Ala Ile Ser Trp Gly Ser Leu Asn Ile Gln Ala Ser Gln
    210                 215                 220

Pro Ser Gly Leu Phe Lys Val Ser Lys Leu Ile Ser Asp Leu Asp Ser
225                 230                 235                 240

Thr Ala Val Tyr Ala Gln
                245
```

<210> SEQ ID NO 7
<211> LENGTH: 7
<212> TYPE: PRT
<213> ORGANISM: Artificial Sequence
<220> FEATURE:
<223> OTHER INFORMATION: Synthetic

<400> SEQUENCE: 7

Gly Gly Cys Ser His Gln Ser
1               5

<210> SEQ ID NO 8
<211> LENGTH: 246
<212> TYPE: PRT
<213> ORGANISM: Artificial Sequence
<220> FEATURE:
<223> OTHER INFORMATION: Synthetic

<400> SEQUENCE: 8

Met Ala Ser Ser Lys Ser Leu Phe Arg Gly Leu Arg Asp Tyr Asn Pro
1               5                   10                  15

Ile Ala Ser Ser Ile Cys Gln Leu Asn Asn Ser Ser Gly Ala Arg Gln
            20                  25                  30

Ser Glu Met Phe Gly Leu Gly Phe Gly Gly Leu Ile Val Thr Asn Gln
        35                  40                  45

His Leu Phe Lys Arg Asn Asp Gly Glu Leu Thr Ile Arg Ser His His
    50                  55                  60

Gly Glu Phe Val Val Lys Asp Thr Lys Thr Leu Lys Leu Leu Pro Cys
65                  70                  75                  80

Lys Gly Arg Asp Ile Val Ile Arg Leu Pro Lys Asp Phe Pro Pro
                85                  90                  95

Phe Pro Arg Arg Leu Gln Phe Arg Thr Pro Thr Thr Glu Asp Arg Val
            100                 105                 110

Cys Leu Ile Gly Ser Asn Phe Gln Thr Lys Ser Ile Ser Ser Thr Met
        115                 120                 125

Ser Glu Thr Ser Ala Thr Tyr Pro Val Asp Asn Ser His Phe Trp Lys
    130                 135                 140

His Trp Ile Ser Thr Lys Asp Gly His Cys Gly Leu Pro Ile Val Ser
145                 150                 155                 160

Thr Arg Asp Gly Ser Ile Leu Gly Leu His Ser Leu Ala Asn Ser Thr
                165                 170                 175

Asn Thr Gln Asn Phe Tyr Ala Ala Phe Pro Asp Asn Phe Glu Thr Thr
            180                 185                 190

Tyr Leu Ser Asn Gln Asp Asn Asp Asn Trp Ile Lys Gln Trp Arg Tyr
        195                 200                 205

Asn Pro Asp Glu Val Cys Trp Gly Ser Leu Gln Leu Lys Arg Asp Ile
    210                 215                 220

Pro Gln Ser Pro Phe Thr Ile Cys Lys Leu Leu Thr Asp Leu Asp Gly
225                 230                 235                 240

Glu Phe Val Tyr Thr Gln
                245

<210> SEQ ID NO 9
<211> LENGTH: 8
<212> TYPE: PRT
<213> ORGANISM: Artificial Sequence
<220> FEATURE:
<223> OTHER INFORMATION: Synthetic

<400> SEQUENCE: 9

Gln Val Val His Gln Ser Lys
1               5

<210> SEQ ID NO 10
<211> LENGTH: 247
<212> TYPE: PRT
<213> ORGANISM: Artificial Sequence
<220> FEATURE:
<223> OTHER INFORMATION: Synthetic

<400> SEQUENCE: 10

Met Ala Ser Ala Lys Ser Leu Met Arg Gly Leu Arg Asp Phe Asn Pro
1               5                   10                  15

Ile Ala Gln Thr Val Cys Arg Leu Lys Val Ser Val Glu Tyr Gly Ala
            20                  25                  30

Ser Glu Met Tyr Gly Phe Gly Phe Gly Ala Tyr Ile Val Ala Asn His
        35                  40                  45

His Leu Phe Arg Ser Tyr Asn Gly Ser Met Glu Val Gln Ser Met His
    50                  55                  60

Gly Thr Phe Arg Val Lys Asn Leu His Ser Leu Ser Val Leu Pro Ile
65                  70                  75                  80

Lys Gly Arg Asp Ile Ile Leu Ile Lys Met Pro Lys Asp Phe Pro Val
                85                  90                  95

Phe Pro Gln Lys Leu His Phe Arg Ala Pro Thr Gln Asn Glu Arg Ile
            100                 105                 110

Cys Leu Val Gly Thr Asn Phe Gln Glu Lys Tyr Ala Ser Ser Ile Ile
        115                 120                 125

Thr Glu Thr Ser Thr Thr Tyr Asn Ile Pro Gly Ser Thr Phe Trp Lys
130                 135                 140

His Trp Ile Glu Thr Asp Asn Gly His Cys Gly Leu Pro Val Val Ser
145                 150                 155                 160

Thr Ala Asp Gly Cys Ile Val Gly Ile His Ser Leu Ala Asn Asn Ala
                165                 170                 175

His Thr Thr Asn Tyr Tyr Ser Ala Phe Asp Glu Asp Phe Glu Ser Lys
            180                 185                 190

Tyr Leu Arg Thr Asn Glu His Asn Glu Trp Val Lys Ser Trp Val Tyr
        195                 200                 205

Asn Pro Asp Thr Val Leu Trp Gly Pro Leu Lys Leu Lys Asp Ser Thr
    210                 215                 220

Pro Lys Gly Leu Phe Lys Thr Thr Lys Leu Val Gln Asp Leu Ile Asp
225                 230                 235                 240

His Asp Val Val Val Glu Gln
                245

<210> SEQ ID NO 11
<211> LENGTH: 8
<212> TYPE: PRT
<213> ORGANISM: Artificial Sequence
<220> FEATURE:
<223> OTHER INFORMATION: Synthetic

<400> SEQUENCE: 11

Tyr Asp Val Arg His Gln Ser Arg
1               5

<210> SEQ ID NO 12
<211> LENGTH: 239
<212> TYPE: PRT

<213> ORGANISM: Artificial Sequence
<220> FEATURE:
<223> OTHER INFORMATION: Synthetic

<400> SEQUENCE: 12

Met Ala Ser Asp Met Tyr Ile Glu Arg Ala Gly Asp Ile Thr Trp Glu
1               5                   10                  15

Lys Asp Ala Glu Val Thr Gly Asn Ser Pro Arg Leu Asp Val Ala Leu
            20                  25                  30

Asp Glu Ser Gly Asp Phe Ser Leu Val Glu Glu Asp Gly Pro Pro Met
        35                  40                  45

Arg Glu Gly Gly Gly Ser Gly Gly Gly Ser Gly Ala Leu Trp
50                  55                  60

Asp Val Pro Ala Pro Lys Glu Val Lys Lys Gly Glu Thr Thr Asp Gly
65                  70                  75                  80

Val Tyr Arg Val Met Thr Arg Arg Leu Leu Gly Ser Thr Gln Val Gly
                85                  90                  95

Val Gly Val Met Gln Glu Gly Val Phe His Thr Met Trp His Val Thr
            100                 105                 110

Lys Gly Ala Ala Leu Arg Ser Gly Glu Gly Arg Leu Asp Pro Tyr Trp
        115                 120                 125

Gly Asp Val Lys Gln Asp Leu Val Ser Tyr Cys Gly Pro Trp Lys Leu
    130                 135                 140

Asp Ala Ala Trp Asp Gly Leu Ser Glu Val Gln Leu Leu Ala Val Pro
145                 150                 155                 160

Pro Gly Glu Arg Ala Arg Asn Ile Gln Thr Leu Pro Gly Ile Phe Lys
                165                 170                 175

Thr Lys Asp Gly Asp Ile Gly Ala Val Ala Leu Asp Tyr Pro Ala Gly
            180                 185                 190

Thr Ser Gly Ser Pro Ile Leu Asp Lys Cys Gly Arg Val Ile Gly Leu
        195                 200                 205

Tyr Gly Asn Gly Val Val Ile Lys Asn Gly Ser Tyr Val Ser Ala Ile
    210                 215                 220

Thr Gln Gly Lys Arg Glu Glu Glu Thr Pro Val Glu Cys Phe Glu
225                 230                 235

<210> SEQ ID NO 13
<211> LENGTH: 8
<212> TYPE: PRT
<213> ORGANISM: Artificial Sequence
<220> FEATURE:
<223> OTHER INFORMATION: Synthetic

<400> SEQUENCE: 13

Lys Glu Arg Lys Arg Arg Gly Ala
1               5

<210> SEQ ID NO 14
<211> LENGTH: 243
<212> TYPE: PRT
<213> ORGANISM: Artificial Sequence
<220> FEATURE:
<223> OTHER INFORMATION: Synthetic

<400> SEQUENCE: 14

Met Ala Ser Ser Thr Asp Met Trp Ile Glu Arg Thr Ala Asp Ile Ser
1               5                   10                  15

Trp Glu Ser Asp Ala Glu Ile Thr Gly Ser Ser Glu Arg Val Asp Val
            20                  25                  30

Arg Leu Asp Asp Asp Gly Asn Phe Gln Leu Met Asn Asp Pro Gly Ala
            35                  40                  45

Pro Trp Lys Gly Gly Gly Ser Gly Gly Gly Gly Val Leu Trp
 50                  55                  60

Asp Thr Pro Ser Pro Lys Glu Tyr Lys Lys Gly Asp Thr Thr Thr Gly
 65                  70                  75                  80

Val Tyr Arg Ile Met Thr Arg Gly Leu Leu Gly Ser Tyr Gln Ala Gly
                 85                  90                  95

Ala Gly Val Met Val Glu Gly Val Phe His Thr Leu Trp His Thr Thr
            100                 105                 110

Lys Gly Ala Ala Leu Met Ser Gly Glu Gly Arg Leu Asp Pro Tyr Trp
            115                 120                 125

Gly Ser Val Lys Glu Asp Arg Leu Cys Tyr Gly Gly Pro Trp Lys Leu
130                 135                 140

Gln His Lys Trp Asn Gly Gln Asp Glu Val Gln Met Ile Val Val Glu
145                 150                 155                 160

Pro Gly Lys Asn Val Lys Asn Val Gln Thr Lys Pro Gly Val Phe Lys
                165                 170                 175

Thr Pro Glu Gly Glu Ile Gly Ala Val Thr Leu Asp Phe Pro Thr Gly
            180                 185                 190

Thr Ser Gly Ser Pro Ile Val Asp Lys Asn Gly Asp Val Ile Gly Leu
            195                 200                 205

Tyr Gly Asn Gly Val Ile Met Pro Asn Gly Ser Tyr Ile Ser Ala Ile
            210                 215                 220

Val Gln Gly Glu Arg Met Asp Glu Pro Ile Pro Ala Gly Phe Glu Pro
225                 230                 235                 240

Glu Met Leu

<210> SEQ ID NO 15
<211> LENGTH: 8
<212> TYPE: PRT
<213> ORGANISM: Artificial Sequence
<220> FEATURE:
<223> OTHER INFORMATION: Synthetic

<400> SEQUENCE: 15

Lys Gln Lys Lys Arg Gly Gly Lys
1               5

<210> SEQ ID NO 16
<211> LENGTH: 19
<212> TYPE: RNA
<213> ORGANISM: Artificial Sequence
<220> FEATURE:
<223> OTHER INFORMATION: Synthetic

<400> SEQUENCE: 16
acaugaggau cacccaugu                                                    19

<210> SEQ ID NO 17
<211> LENGTH: 136
<212> TYPE: RNA
<213> ORGANISM: Artificial Sequence
<220> FEATURE:
<223> OTHER INFORMATION: Synthetic

<400> SEQUENCE: 17
guuugagagc uaggccaaca ugaggaucac ccaugucugc agggccuagc aaguucaaau      60

```
aaggcuaguc cguuaucaac uuggccaaca ugaggaucac ccaugucugc agggccaagu    120
ggcaccgagu cggugc                                                   136

<210> SEQ ID NO 18
<211> LENGTH: 25
<212> TYPE: RNA
<213> ORGANISM: Artificial Sequence
<220> FEATURE:
<223> OTHER INFORMATION: Synthetic

<400> SEQUENCE: 18
ggagcagacg auauggcguc gcucc                                          25

<210> SEQ ID NO 19
<211> LENGTH: 122
<212> TYPE: RNA
<213> ORGANISM: Artificial Sequence
<220> FEATURE:
<223> OTHER INFORMATION: Synthetic

<400> SEQUENCE: 19
guuugagagc uaccggagca gacgauaugg cgucgcuccg guagcaaguu caaauaaggc    60
uaguccguua ucaacuugga gcagacgaua uggcgucgcu ccaaguggca ccgagucggu   120
gc                                                                 122

<210> SEQ ID NO 20
<211> LENGTH: 15
<212> TYPE: RNA
<213> ORGANISM: Artificial Sequence
<220> FEATURE:
<223> OTHER INFORMATION: Synthetic

<400> SEQUENCE: 20
gcccugaaga agggc                                                    15

<210> SEQ ID NO 21
<211> LENGTH: 106
<212> TYPE: RNA
<213> ORGANISM: Artificial Sequence
<220> FEATURE:
<223> OTHER INFORMATION: Synthetic

<400> SEQUENCE: 21
guuugagagc uagggcccug aagaagggcc uagcaaguu caaauaaggc uaguccguua     60
ucaacuuggg cccugaagaa gggcccaagu ggcaccgagu cggugc                 106

<210> SEQ ID NO 22
<211> LENGTH: 117
<212> TYPE: PRT
<213> ORGANISM: Artificial Sequence
<220> FEATURE:
<223> OTHER INFORMATION: Synthetic

<400> SEQUENCE: 22

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Ile Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Asn Arg Lys Tyr Thr Ile Lys Val Glu
    50                  55                  60
```

Val Pro Lys Gly Ala Trp Arg Ser Tyr Leu Asn Met Glu Leu Thr Ile
65                  70                  75                  80

Pro Ile Phe Ala Thr Asn Ser Asp Cys Glu Leu Ile Val Lys Ala Met
                85                  90                  95

Gln Gly Leu Leu Lys Asp Gly Asn Pro Ile Pro Ser Ala Ile Ala Ala
            100                 105                 110

Asn Ser Gly Ile Tyr
        115

<210> SEQ ID NO 23
<211> LENGTH: 123
<212> TYPE: PRT
<213> ORGANISM: Artificial Sequence
<220> FEATURE:
<223> OTHER INFORMATION: Synthetic

<400> SEQUENCE: 23

Met Gly Ser Lys Thr Ile Val Leu Ser Val Gly Glu Ala Thr Arg Thr
1               5                   10                  15

Leu Thr Glu Ile Gln Ser Thr Ala Asp Arg Gln Ile Phe Glu Glu Lys
            20                  25                  30

Val Gly Pro Leu Val Gly Arg Leu Arg Leu Thr Ala Ser Leu Arg Gln
        35                  40                  45

Asn Gly Ala Lys Thr Ala Tyr Arg Val Asn Leu Lys Leu Asp Gln Ala
    50                  55                  60

Asp Val Val Asp Ser Gly Leu Pro Lys Val Arg Tyr Thr Gln Val Trp
65                  70                  75                  80

Ser His Asp Val Thr Ile Val Ala Asn Ser Thr Glu Ala Ser Arg Lys
                85                  90                  95

Ser Leu Tyr Asp Leu Thr Lys Ser Leu Val Ala Thr Ser Gln Val Glu
            100                 105                 110

Asp Leu Val Val Asn Leu Val Pro Leu Gly Arg
        115                 120

<210> SEQ ID NO 24
<211> LENGTH: 23
<212> TYPE: PRT
<213> ORGANISM: Artificial Sequence
<220> FEATURE:
<223> OTHER INFORMATION: Synthetic

<400> SEQUENCE: 24

Met Gly Asn Ala Arg Thr Arg Arg Arg Glu Arg Ala Glu Lys Gln
1               5                   10                  15

Ala Gln Trp Lys Ala Ala Asn
            20

<210> SEQ ID NO 25
<211> LENGTH: 83
<212> TYPE: PRT
<213> ORGANISM: Artificial Sequence
<220> FEATURE:
<223> OTHER INFORMATION: Synthetic

<400> SEQUENCE: 25

Thr Asn Leu Ser Asp Ile Ile Glu Lys Glu Thr Gly Lys Gln Leu Val
1               5                   10                  15

Ile Gln Glu Ser Ile Leu Met Leu Pro Glu Glu Val Glu Glu Val Ile
            20                  25                  30

Gly Asn Lys Pro Glu Ser Asp Ile Leu Val His Thr Ala Tyr Asp Glu
            35                  40                  45

Ser Thr Asp Glu Asn Val Met Leu Leu Thr Ser Asp Ala Pro Glu Tyr
    50                  55                  60

Lys Pro Trp Ala Leu Val Ile Gln Asp Ser Asn Gly Glu Asn Lys Ile
65                  70                  75                  80

Lys Met Leu

<210> SEQ ID NO 26
<211> LENGTH: 22
<212> TYPE: PRT
<213> ORGANISM: Artificial Sequence
<220> FEATURE:
<223> OTHER INFORMATION: Synthetic

<400> SEQUENCE: 26

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 27
<211> LENGTH: 21
<212> TYPE: PRT
<213> ORGANISM: Artificial Sequence
<220> FEATURE:
<223> OTHER INFORMATION: Synthetic

<400> SEQUENCE: 27

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 28
<211> LENGTH: 23
<212> TYPE: PRT
<213> ORGANISM: Artificial Sequence
<220> FEATURE:
<223> OTHER INFORMATION: Synthetic

<400> SEQUENCE: 28

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 29
<211> LENGTH: 76
<212> TYPE: RNA
<213> ORGANISM: Artificial Sequence
<220> FEATURE:
<223> OTHER INFORMATION: Synthetic

<400> SEQUENCE: 29
guuuuagagc uagaaauagc aaguuaaaau aaggcuaguc cguuaucaac uugaaaaagu      60
ggcaccgagu cggugc                                                     76

<210> SEQ ID NO 30
<211> LENGTH: 76
<212> TYPE: RNA
<213> ORGANISM: Artificial Sequence
<220> FEATURE:

<223> OTHER INFORMATION: Synthetic

<400> SEQUENCE: 30
guuuuagagc uagaaauagc aaguuaaaau aaggcauguc cguuaucaac uugaaaagu    60 ggcaccgauu cggugc    76

<210> SEQ ID NO 31
<211> LENGTH: 70
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (13)..(13)
<223> OTHER INFORMATION: n is a, c, g, or u
<220> FEATURE:
<221> NAME/KEY: misc_feature
<222> LOCATION: (23)..(23)
<223> OTHER INFORMATION: n is a, c, g, or u
<220> FEATURE:
<221> NAME/KEY: misc_feature
<222> LOCATION: (33)..(34)
<223> OTHER INFORMATION: n is a, c, g, or u
<220> FEATURE:
<221> NAME/KEY: misc_feature
<222> LOCATION: (50)..(50)
<223> OTHER INFORMATION: n is a, c, g, or u
<220> FEATURE:
<221> NAME/KEY: misc_feature
<222> LOCATION: (63)..(63)
<223> OTHER INFORMATION: n is a, c, g, or u

<400> SEQUENCE: 31
guuunagagc uanuagcaag uunaaauaag gcnnguccgu uaucaacuun aaguggcacc    60 ganucggugc    70

<210> SEQ ID NO 32
<211> LENGTH: 70
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (13)..(13)
<223> OTHER INFORMATION: n is a, c, g, or u
<220> FEATURE:
<221> NAME/KEY: misc_feature
<222> LOCATION: (23)..(23)
<223> OTHER INFORMATION: n is a, c, g, or u
<220> FEATURE:
<221> NAME/KEY: misc_feature
<222> LOCATION: (33)..(34)
<223> OTHER INFORMATION: n is a, c, g, or u
<220> FEATURE:
<221> NAME/KEY: misc_feature
<222> LOCATION: (50)..(50)
<223> OTHER INFORMATION: n is a, c, g, or u
<220> FEATURE:
<221> NAME/KEY: misc_feature
<222> LOCATION: (63)..(63)
<223> OTHER INFORMATION: n is a, c, g, or u

<400> SEQUENCE: 32
guuunagagc uanuagcaag uunaaauaag gcnnguccgu uaucgacuun aagucgcacc 60 ganucggugc 70

<210> SEQ ID NO 33
<211> LENGTH: 70
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (13)..(13)
<223> OTHER INFORMATION: n is a, c, g, or u
<220> FEATURE:
<221> NAME/KEY: misc_feature
<222> LOCATION: (23)..(23)
<223> OTHER INFORMATION: n is a, c, g, or u
<220> FEATURE:
<221> NAME/KEY: misc_feature
<222> LOCATION: (33)..(34)
<223> OTHER INFORMATION: n is a, c, g, or u
<220> FEATURE:
<221> NAME/KEY: misc_feature
<222> LOCATION: (50)..(50)
<223> OTHER INFORMATION: n is a, c, g, or u
<220> FEATURE:
<221> NAME/KEY: misc_feature
<222> LOCATION: (63)..(63)
<223> OTHER INFORMATION: n is a, c, g, or u

<400> SEQUENCE: 33
guuunagagc uanuagcaag uunaaauaag gcnnguccgu uauccacuun aaguggcacc 60 ganucggugc 70

<210> SEQ ID NO 34
<211> LENGTH: 70
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (13)..(13)
<223> OTHER INFORMATION: n is a, c, g, or u
<220> FEATURE:
<221> NAME/KEY: misc_feature
<222> LOCATION: (23)..(23)
<223> OTHER INFORMATION: n is a, c, g, or u
<220> FEATURE:
<221> NAME/KEY: misc_feature
<222> LOCATION: (33)..(34)
<223> OTHER INFORMATION: n is a, c, g, or u
<220> FEATURE:
<221> NAME/KEY: misc_feature
<222> LOCATION: (50)..(50)
<223> OTHER INFORMATION: n is a, c, g, or u
<220> FEATURE:
<221> NAME/KEY: misc_feature
<222> LOCATION: (63)..(63)
<223> OTHER INFORMATION: n is a, c, g, or u

<400> SEQUENCE: 34
guuunagagc uanuagcaag uunaaauaag gcnnguccgu uaucaacuun aaguugcacc 60 ganucggugc                                                              70

<210> SEQ ID NO 35
<211> LENGTH: 70
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (13)..(13)
<223> OTHER INFORMATION: n is a, c, g, or u
<220> FEATURE:
<221> NAME/KEY: misc_feature
<222> LOCATION: (23)..(23)
<223> OTHER INFORMATION: n is a, c, g, or u
<220> FEATURE:
<221> NAME/KEY: misc_feature
<222> LOCATION: (33)..(34)
<223> OTHER INFORMATION: n is a, c, g, or u
<220> FEATURE:
<221> NAME/KEY: misc_feature
<222> LOCATION: (50)..(50)
<223> OTHER INFORMATION: n is a, c, g, or u
<220> FEATURE:
<221> NAME/KEY: misc_feature
<222> LOCATION: (63)..(63)
<223> OTHER INFORMATION: n is a, c, g, or u

<400> SEQUENCE: 35
guuunagagc uanuagcaag uunaaauaag gcnnguccgu uaucuacuun aaguagcacc        60 ganucggugc                                                              70

<210> SEQ ID NO 36
<211> LENGTH: 76
<212> TYPE: RNA
<213> ORGANISM: Artificial Sequence
<220> FEATURE:
<223> OTHER INFORMATION: Synthetic

<400> SEQUENCE: 36
guuuuagagc uagaaauagc aaguuaaaau aaggcauguc cguuaucgac uugaaaagu         60 cgcaccgauu cggugc                                                       76

<210> SEQ ID NO 37
<211> LENGTH: 76
<212> TYPE: RNA
<213> ORGANISM: Artificial Sequence
<220> FEATURE:
<223> OTHER INFORMATION: Synthetic

<400> SEQUENCE: 37
guuuuagagc uagaaauagc aaguuaaaau aaggcauguc cguuauccac uugaaaagu         60 ggcaccgauu cggugc                                                       76

<210> SEQ ID NO 38
<211> LENGTH: 76
<212> TYPE: RNA
<213> ORGANISM: Artificial Sequence
<220> FEATURE:
<223> OTHER INFORMATION: Synthetic

<400> SEQUENCE: 38
guuuuagagc uagaaauagc aaguuaaaau aaggcauguc cguuaucaac uugaaaagu         60

```
ugcaccgauu cggugc                                                    76

<210> SEQ ID NO 39
<211> LENGTH: 76
<212> TYPE: RNA
<213> ORGANISM: Artificial Sequence
<220> FEATURE:
<223> OTHER INFORMATION: Synthetic

<400> SEQUENCE: 39
guuuuagagc uagaaauagc aaguuaaaau aaggcauguc cguuaucuac uugaaaagu     60 agcaccgauu cggugc                                                   76

<210> SEQ ID NO 40
<211> LENGTH: 76
<212> TYPE: RNA
<213> ORGANISM: Artificial Sequence
<220> FEATURE:
<223> OTHER INFORMATION: Synthetic

<400> SEQUENCE: 40
guuuuagagc uagaaauagc aaguuaaaau aaggcuaguc cguuaucgac uugaaaagu     60 cgcaccgagu cggugc                                                   76

<210> SEQ ID NO 41
<211> LENGTH: 76
<212> TYPE: RNA
<213> ORGANISM: Artificial Sequence
<220> FEATURE:
<223> OTHER INFORMATION: Synthetic

<400> SEQUENCE: 41
guuuuagagc uagaaauagc aaguuaaaau aaggcuaguc cguuauccac uugaaaagu     60 ggcaccgagu cggugc                                                   76

<210> SEQ ID NO 42
<211> LENGTH: 76
<212> TYPE: RNA
<213> ORGANISM: Artificial Sequence
<220> FEATURE:
<223> OTHER INFORMATION: Synthetic

<400> SEQUENCE: 42
guuuuagagc uagaaauagc aaguuaaaau aaggcuaguc cguuaucaac uugaaaagu     60 ugcaccgagu cggugc                                                   76

<210> SEQ ID NO 43
<211> LENGTH: 76
<212> TYPE: RNA
<213> ORGANISM: Artificial Sequence
<220> FEATURE:
<223> OTHER INFORMATION: Synthetic

<400> SEQUENCE: 43
guuuuagagc uagaaauagc aaguuaaaau aaggcuaguc cguuaucuac uugaaaagu     60 agcaccgagu cggugc                                                   76

<210> SEQ ID NO 44
<211> LENGTH: 2080
<212> TYPE: PRT
<213> ORGANISM: Artificial Sequence
<220> FEATURE:
```

<223> OTHER INFORMATION: Synthetic

<400> SEQUENCE: 44

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400
```

```
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
        435                 440                 445
Pro Tyr Tyr Val Gly Pro Leu Ala Arg Gly Asn Ser Arg Phe Ala Trp
    450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
            500                 505                 510
Leu Leu Tyr Glu Tyr Phe Thr Val Tyr Asn Glu Leu Thr Lys Val Lys
        515                 520                 525
Tyr Val Thr Glu Gly Met Arg Lys Pro Ala Phe Leu Ser Gly Glu Gln
    530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
            580                 585                 590
Thr Tyr His Asp Leu Leu Lys Ile Ile Lys Asp Lys Asp Phe Leu Asp
        595                 600                 605
Asn Glu Glu Asn Glu Asp Ile Leu Glu Asp Ile Val Leu Thr Leu Thr
    610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
            660                 665                 670
Lys Gln Ser Gly Lys Thr Ile Leu Asp Phe Leu Lys Ser Asp Gly Phe
        675                 680                 685
Ala Asn Arg Asn Phe Met Gln Leu Ile His Asp Asp Ser Leu Thr Phe
    690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
            740                 745                 750
Arg His Lys Pro Glu Asn Ile Val Ile Glu Met Ala Arg Glu Asn Gln
        755                 760                 765
Thr Thr Gln Lys Gly Gln Lys Asn Ser Arg Glu Arg Met Lys Arg Ile
    770                 775                 780
Glu Glu Gly Ile Lys Glu Leu Gly Ser Gln Ile Leu Lys Glu His Pro
785                 790                 795                 800
Val Glu Asn Thr Gln Leu Gln Asn Glu Lys Leu Tyr Leu Tyr Tyr Leu
                805                 810                 815
Gln Asn Gly Arg Asp Met Tyr Val Asp Gln Glu Leu Asp Ile Asn Arg
```

-continued

```
                820                 825                 830
Leu Ser Asp Tyr Asp Val Asp Ala Ile Val Pro Gln Ser Phe Leu Lys
            835                 840                 845
Asp Ser Ile Asp Asn Lys Val Leu Thr Arg Ser Asp Lys Asn Arg
850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
                900                 905                 910
Lys Ala Gly Phe Ile Lys Arg Gln Leu Val Glu Thr Arg Gln Ile Thr
            915                 920                 925
Lys His Val Ala Gln Ile Leu Asp Ser Arg Met Asn Thr Lys Tyr Asp
            930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
                980                 985                 990
Val Gly Thr Ala Leu Ile Lys Lys Tyr Pro Lys Leu Glu Ser Glu Phe
            995                 1000                1005
Val Tyr Gly Asp Tyr Lys Val Tyr Asp Val Arg Lys Met Ile Ala
    1010                1015                1020
Lys Ser Glu Gln Glu Ile Gly Lys Ala Thr Ala Lys Tyr Phe Phe
    1025                1030                1035
Tyr Ser Asn Ile Met Asn Phe Phe Lys Thr Glu Ile Thr Leu Ala
    1040                1045                1050
Asn Gly Glu Ile Arg Lys Arg Pro Leu Ile Glu Thr Asn Gly Glu
    1055                1060                1065
Thr Gly Glu Ile Val Trp Asp Lys Gly Arg Asp Phe Ala Thr Val
    1070                1075                1080
Arg Lys Val Leu Ser Met Pro Gln Val Asn Ile Val Lys Lys Thr
    1085                1090                1095
Glu Val Gln Thr Gly Gly Phe Ser Lys Glu Ser Ile Arg Pro Lys
    1100                1105                1110
Arg Asn Ser Asp Lys Leu Ile Ala Arg Lys Lys Asp Trp Asp Pro
    1115                1120                1125
Lys Lys Tyr Gly Gly Phe Val Ser Pro Thr Val Ala Tyr Ser Val
    1130                1135                1140
Leu Val Val Ala Lys Val Glu Lys Gly Lys Ser Lys Lys Leu Lys
    1145                1150                1155
Ser Val Lys Glu Leu Leu Gly Ile Thr Ile Met Glu Arg Ser Ser
    1160                1165                1170
Phe Glu Lys Asn Pro Ile Asp Phe Leu Glu Ala Lys Gly Tyr Lys
    1175                1180                1185
Glu Val Lys Lys Asp Leu Ile Ile Lys Leu Pro Lys Tyr Ser Leu
    1190                1195                1200
Phe Glu Leu Glu Asn Gly Arg Lys Arg Met Leu Ala Ser Ala Arg
    1205                1210                1215
Phe Leu Gln Lys Gly Asn Glu Leu Ala Leu Pro Ser Lys Tyr Val
    1220                1225                1230
```

```
Asn Phe Leu Tyr Leu Ala Ser His Tyr Glu Lys Leu Lys Gly Ser
1235                1240                1245

Pro Glu Asp Asn Glu Gln Lys Gln Leu Phe Val Glu Gln His Lys
1250                1255                1260

His Tyr Leu Asp Glu Ile Ile Glu Gln Ile Ser Glu Phe Ser Lys
1265                1270                1275

Arg Val Ile Leu Ala Asp Ala Asn Leu Asp Lys Val Leu Ser Ala
1280                1285                1290

Tyr Asn Lys His Arg Asp Lys Pro Ile Arg Glu Gln Ala Glu Asn
1295                1300                1305

Ile Ile His Leu Phe Thr Leu Thr Asn Leu Gly Ala Pro Arg Ala
1310                1315                1320

Phe Lys Tyr Phe Asp Thr Thr Ile Asp Arg Lys Val Tyr Arg Ser
1325                1330                1335

Thr Lys Glu Val Leu Asp Ala Thr Leu Ile His Gln Ser Ile Thr
1340                1345                1350

Gly Leu Tyr Glu Thr Arg Ile Asp Leu Ser Gln Leu Gly Gly Asp
1355                1360                1365

Gly Thr Ser Gly Gly Ser Gly Gly Ser Gly Ser Glu Thr
1370                1375                1380

Pro Gly Thr Ser Glu Ser Ala Thr Pro Glu Ser Ser Gly Gly Ser
1385                1390                1395

Ser Gly Gly Ser Ser Thr Leu Asn Ile Glu Asp Glu Tyr Arg Leu
1400                1405                1410

His Glu Thr Ser Lys Glu Pro Asp Val Ser Leu Gly Ser Thr Trp
1415                1420                1425

Leu Ser Asp Phe Pro Gln Ala Trp Ala Glu Thr Gly Gly Met Gly
1430                1435                1440

Leu Ala Val Arg Gln Ala Pro Leu Ile Ile Pro Leu Lys Ala Thr
1445                1450                1455

Ser Thr Pro Val Ser Ile Lys Gln Tyr Pro Met Ser Gln Glu Ala
1460                1465                1470

Arg Leu Gly Ile Lys Pro His Ile Gln Arg Leu Leu Asp Gln Gly
1475                1480                1485

Ile Leu Val Pro Cys Gln Ser Pro Trp Asn Thr Pro Leu Leu Pro
1490                1495                1500

Val Lys Lys Pro Gly Thr Asn Asp Tyr Arg Pro Val Gln Asp Leu
1505                1510                1515

Arg Glu Val Asn Lys Arg Val Glu Asp Ile His Pro Thr Val Pro
1520                1525                1530

Asn Pro Tyr Asn Leu Leu Ser Gly Leu Pro Pro Ser His Gln Trp
1535                1540                1545

Tyr Thr Val Leu Asp Leu Lys Asp Ala Phe Phe Cys Leu Arg Leu
1550                1555                1560

His Pro Thr Ser Gln Pro Leu Phe Ala Phe Glu Trp Arg Asp Pro
1565                1570                1575

Glu Met Gly Ile Ser Gly Gln Leu Thr Trp Thr Arg Leu Pro Gln
1580                1585                1590

Gly Phe Lys Asn Ser Pro Thr Leu Phe Asn Glu Ala Leu His Arg
1595                1600                1605

Asp Leu Ala Asp Phe Arg Ile Gln His Pro Asp Leu Ile Leu Leu
1610                1615                1620
```

```
Gln Tyr Val Asp Asp Leu Leu Leu Ala Ala Thr Ser Glu Leu Asp
    1625                1630                1635

Cys Gln Gln Gly Thr Arg Ala Leu Leu Gln Thr Leu Gly Asn Leu
    1640                1645                1650

Gly Tyr Arg Ala Ser Ala Lys Lys Ala Gln Ile Cys Gln Lys Gln
    1655                1660                1665

Val Lys Tyr Leu Gly Tyr Leu Leu Lys Glu Gly Gln Arg Trp Leu
    1670                1675                1680

Thr Glu Ala Arg Lys Glu Thr Val Met Gly Gln Pro Thr Pro Lys
    1685                1690                1695

Thr Pro Arg Gln Leu Arg Glu Phe Leu Gly Lys Ala Gly Phe Cys
    1700                1705                1710

Arg Leu Phe Ile Pro Gly Phe Ala Glu Met Ala Ala Pro Leu Tyr
    1715                1720                1725

Pro Leu Thr Lys Pro Gly Thr Leu Phe Asn Trp Gly Pro Asp Gln
    1730                1735                1740

Gln Lys Ala Tyr Gln Glu Ile Lys Gln Ala Leu Leu Thr Ala Pro
    1745                1750                1755

Ala Leu Gly Leu Pro Asp Leu Thr Lys Pro Phe Glu Leu Phe Val
    1760                1765                1770

Asp Glu Lys Gln Gly Tyr Ala Lys Gly Val Leu Thr Gln Lys Leu
    1775                1780                1785

Gly Pro Trp Arg Arg Pro Val Ala Tyr Leu Ser Lys Lys Leu Asp
    1790                1795                1800

Pro Val Ala Ala Gly Trp Pro Pro Cys Leu Arg Met Val Ala Ala
    1805                1810                1815

Ile Ala Val Leu Thr Lys Asp Ala Gly Lys Leu Thr Met Gly Gln
    1820                1825                1830

Pro Leu Val Ile Leu Ala Pro His Ala Val Glu Ala Leu Val Lys
    1835                1840                1845

Gln Pro Pro Asp Arg Trp Leu Ser Asn Ala Arg Met Thr His Tyr
    1850                1855                1860

Gln Ala Leu Leu Leu Asp Thr Asp Arg Val Gln Phe Gly Pro Val
    1865                1870                1875

Val Ala Leu Asn Pro Ala Thr Leu Leu Pro Leu Pro Glu Glu Gly
    1880                1885                1890

Leu Gln His Asn Cys Leu Asp Ile Leu Ala Glu Ala His Gly Thr
    1895                1900                1905

Arg Pro Asp Leu Thr Asp Gln Pro Leu Pro Asp Ala Asp His Thr
    1910                1915                1920

Trp Tyr Thr Asp Gly Ser Ser Leu Leu Gln Glu Gly Gln Arg Lys
    1925                1930                1935

Ala Gly Ala Ala Val Thr Thr Glu Thr Glu Val Ile Trp Ala Lys
    1940                1945                1950

Ala Leu Pro Ala Gly Thr Ser Ala Gln Arg Ala Glu Leu Ile Ala
    1955                1960                1965

Leu Thr Gln Ala Leu Lys Met Ala Glu Gly Lys Lys Leu Asn Val
    1970                1975                1980

Tyr Thr Asp Ser Arg Tyr Ala Phe Ala Thr Ala His Ile His Gly
    1985                1990                1995

Glu Ile Tyr Arg Arg Arg Gly Trp Leu Thr Ser Glu Gly Lys Glu
    2000                2005                2010

Ile Lys Asn Lys Asp Glu Ile Leu Ala Leu Leu Lys Ala Leu Phe
```

Leu Pro Lys Arg Leu Ser Ile Ile His Cys Pro Gly His Gln Lys
     2030            2035            2040

Gly His Ser Ala Glu Ala Arg Gly Asn Arg Met Ala Asp Gln Ala
     2045            2050            2055

Ala Arg Lys Ala Ala Ile Thr Glu Thr Pro Asp Thr Ser Thr Leu
     2060            2065            2070

Leu Ile Glu Asn Ser Ser Pro
     2075            2080

<210> SEQ ID NO 45
<211> LENGTH: 2080
<212> TYPE: PRT
<213> ORGANISM: Artificial Sequence
<220> FEATURE:
<223> OTHER INFORMATION: Synthetic

<400> SEQUENCE: 45

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Thr Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp

```
                290             295             300
Ile Leu Arg Val Asn Thr Glu Ile Thr Lys Ala Pro Leu Ser Ala Ser
305             310             315             320

Met Ile Lys Leu Tyr Asp Glu His His Gln Asp Leu Thr Leu Leu Lys
                325             330             335

Ala Leu Val Arg Gln Gln Leu Pro Glu Lys Tyr Lys Glu Ile Phe Phe
                340             345             350

Asp Gln Ser Lys Asn Gly Tyr Ala Gly Tyr Ile Asp Gly Gly Ala Ser
                355             360             365

Gln Glu Glu Phe Tyr Lys Phe Ile Lys Pro Ile Leu Glu Lys Met Asp
                370             375             380

Gly Thr Glu Glu Leu Leu Val Lys Leu Asn Arg Glu Asp Leu Leu Arg
385             390             395             400

Lys Gln Arg Thr Phe Asp Asn Gly Ile Ile Pro His Gln Ile His Leu
                405             410             415

Gly Glu Leu His Ala Ile Leu Arg Arg Gln Glu Asp Phe Tyr Pro Phe
                420             425             430

Leu Lys Asp Asn Arg Glu Lys Ile Glu Lys Ile Leu Thr Phe Arg Ile
                435             440             445

Pro Tyr Tyr Val Gly Pro Leu Ala Arg Gly Asn Ser Arg Phe Ala Trp
                450             455             460

Met Thr Arg Lys Ser Glu Glu Thr Ile Thr Pro Trp Asn Phe Glu Lys
465             470             475             480

Val Val Asp Lys Gly Ala Ser Ala Gln Ser Phe Ile Glu Arg Met Thr
                485             490             495

Asn Phe Asp Lys Asn Leu Pro Asn Glu Lys Val Leu Pro Lys His Ser
                500             505             510

Leu Leu Tyr Glu Tyr Phe Thr Val Tyr Asn Glu Leu Thr Lys Val Lys
                515             520             525

Tyr Val Thr Glu Gly Met Arg Lys Pro Ala Phe Leu Ser Gly Asp Gln
                530             535             540

Lys Lys Ala Ile Val Asp Leu Leu Phe Lys Thr Asn Arg Lys Val Thr
545             550             555             560

Val Lys Gln Leu Lys Glu Asp Tyr Phe Lys Lys Ile Glu Cys Phe Asp
                565             570             575

Ser Val Glu Ile Ser Gly Val Glu Asp Arg Phe Asn Ala Ser Leu Gly
                580             585             590

Thr Tyr His Asp Leu Leu Lys Ile Ile Lys Asp Lys Asp Phe Leu Asp
                595             600             605

Asn Glu Glu Asn Glu Asp Ile Leu Glu Asp Ile Val Leu Thr Leu Thr
610             615             620

Leu Phe Glu Asp Arg Glu Met Ile Glu Glu Arg Leu Lys Thr Tyr Ala
625             630             635             640

His Leu Phe Asp Asp Lys Val Met Lys Gln Leu Lys Arg Arg Arg Tyr
                645             650             655

Thr Gly Trp Gly Arg Leu Ser Arg Lys Leu Ile Asn Gly Ile Arg Asp
                660             665             670

Lys Gln Ser Gly Lys Thr Ile Leu Asp Phe Leu Lys Ser Asp Gly Phe
                675             680             685

Ala Asn Arg Asn Phe Ile Gln Leu Ile His Asp Asp Ser Leu Thr Phe
                690             695             700

Lys Glu Asp Ile Gln Lys Ala Gln Val Ser Gly Gln Gly Asp Ser Leu
705             710             715             720
```

His Glu His Ile Ala Asn Leu Ala Gly Ser Pro Ala Ile Lys Lys Gly
              725                 730                 735

Ile Leu Gln Thr Val Lys Val Val Asp Glu Leu Val Lys Val Met Gly
              740                 745                 750

Arg His Lys Pro Glu Asn Ile Val Ile Glu Met Ala Arg Glu Asn Gln
              755                 760             765

Thr Thr Gln Lys Gly Gln Lys Asn Ser Arg Glu Arg Met Lys Arg Ile
      770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
              805                 810                 815

Gln Asn Gly Arg Asp Met Tyr Val Asp Gln Glu Leu Asp Ile Asn Arg
              820                 825                 830

Leu Ser Asp Tyr Asp Val Asp Ala Ile Val Pro Gln Ser Phe Leu Lys
              835                 840                 845

Asp Asp Ser Ile Asp Asn Lys Val Leu Thr Arg Ser Asp Lys Asn Arg
              850                 855             860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                    885                 890                 895

Phe Asp Asn Leu Thr Lys Ala Glu Arg Gly Gly Leu Ser Glu Leu Asp
              900                 905                 910

Lys Ala Gly Phe Ile Lys Arg Gln Leu Val Glu Thr Arg Gln Ile Thr
              915                 920                 925

Lys His Val Ala Gln Ile Leu Asp Ser Arg Met Asn Thr Lys Tyr Asp
              930                 935             940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                    965                 970                 975

Glu Ile Asn Asn Tyr His His Ala His Asp Ala Tyr Leu Asn Ala Val
              980                 985                 990

Val Gly Thr Ala Leu Ile Lys Lys Tyr Pro Lys Leu Glu Ser Glu Phe
              995                 1000                1005

Val Tyr Gly Asp Tyr Lys Val Tyr Asp Val Arg Lys Met Ile Ala
   1010                 1015                1020

Lys Ser Glu Gln Glu Ile Gly Lys Ala Thr Ala Lys Tyr Phe Phe
   1025                 1030                1035

Tyr Ser Asn Ile Met Asn Phe Phe Lys Thr Glu Ile Thr Leu Ala
   1040                 1045                1050

Asn Gly Glu Ile Arg Lys Arg Pro Leu Ile Glu Thr Asn Gly Glu
   1055                 1060                1065

Thr Gly Glu Ile Val Trp Asp Lys Gly Arg Asp Phe Ala Thr Val
   1070                 1075                1080

Arg Lys Val Leu Ser Met Pro Gln Val Asn Ile Val Lys Lys Thr
   1085                 1090                1095

Glu Val Gln Thr Gly Gly Phe Ser Lys Glu Ser Ile Leu Pro Lys
   1100                 1105                1110

Arg Asn Ser Asp Lys Leu Ile Ala Arg Lys Lys Asp Trp Asp Pro
   1115                 1120                1125

```
Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Val Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

Gly Thr Ser Gly Gly Ser Ser Gly Gly Ser Ser Gly Ser Glu Thr
    1370                1375                1380

Pro Gly Thr Ser Glu Ser Ala Thr Pro Glu Ser Ser Gly Gly Ser
    1385                1390                1395

Ser Gly Gly Ser Ser Thr Leu Asn Ile Glu Asp Glu Tyr Arg Leu
    1400                1405                1410

His Glu Thr Ser Lys Glu Pro Asp Val Ser Leu Gly Ser Thr Trp
    1415                1420                1425

Leu Ser Asp Phe Pro Gln Ala Trp Ala Glu Thr Gly Gly Met Gly
    1430                1435                1440

Leu Ala Val Arg Gln Ala Pro Leu Ile Ile Pro Leu Lys Ala Thr
    1445                1450                1455

Ser Thr Pro Val Ser Ile Lys Gln Tyr Pro Met Ser Gln Glu Ala
    1460                1465                1470

Arg Leu Gly Ile Lys Pro His Ile Gln Arg Leu Leu Asp Gln Gly
    1475                1480                1485

Ile Leu Val Pro Cys Gln Ser Pro Trp Asn Thr Pro Leu Leu Pro
    1490                1495                1500

Val Lys Lys Pro Gly Thr Asn Asp Tyr Arg Pro Val Gln Asp Leu
    1505                1510                1515

Arg Glu Val Asn Lys Arg Val Glu Asp Ile His Pro Thr Val Pro
```

```
            1520                1525                1530

Asn Pro Tyr Asn Leu Leu Ser Gly Leu Pro Ser His Gln Trp
    1535                1540                1545

Tyr Thr Val Leu Asp Leu Lys Asp Ala Phe Phe Cys Leu Arg Leu
    1550                1555                1560

His Pro Thr Ser Gln Pro Leu Phe Ala Phe Glu Trp Arg Asp Pro
    1565                1570                1575

Glu Met Gly Ile Ser Gly Gln Leu Thr Trp Thr Arg Leu Pro Gln
    1580                1585                1590

Gly Phe Lys Asn Ser Pro Thr Leu Phe Asn Glu Ala Leu His Arg
    1595                1600                1605

Asp Leu Ala Asp Phe Arg Ile Gln His Pro Asp Leu Ile Leu Leu
    1610                1615                1620

Gln Tyr Val Asp Asp Leu Leu Leu Ala Ala Thr Ser Glu Leu Asp
    1625                1630                1635

Cys Gln Gln Gly Thr Arg Ala Leu Leu Gln Thr Leu Gly Asn Leu
    1640                1645                1650

Gly Tyr Arg Ala Ser Ala Lys Lys Ala Gln Ile Cys Gln Lys Gln
    1655                1660                1665

Val Lys Tyr Leu Gly Tyr Leu Leu Lys Glu Gly Gln Arg Trp Leu
    1670                1675                1680

Thr Glu Ala Arg Lys Glu Thr Val Met Gly Gln Pro Thr Pro Lys
    1685                1690                1695

Thr Pro Arg Gln Leu Arg Glu Phe Leu Gly Lys Ala Gly Phe Cys
    1700                1705                1710

Arg Leu Phe Ile Pro Gly Phe Ala Glu Met Ala Ala Pro Leu Tyr
    1715                1720                1725

Pro Leu Thr Lys Pro Gly Thr Leu Phe Asn Trp Gly Pro Asp Gln
    1730                1735                1740

Gln Lys Ala Tyr Gln Glu Ile Lys Gln Ala Leu Leu Thr Ala Pro
    1745                1750                1755

Ala Leu Gly Leu Pro Asp Leu Thr Lys Pro Phe Glu Leu Phe Val
    1760                1765                1770

Asp Glu Lys Gln Gly Tyr Ala Lys Gly Val Leu Thr Gln Lys Leu
    1775                1780                1785

Gly Pro Trp Arg Arg Pro Val Ala Tyr Leu Ser Lys Lys Leu Asp
    1790                1795                1800

Pro Val Ala Ala Gly Trp Pro Pro Cys Leu Arg Met Val Ala Ala
    1805                1810                1815

Ile Ala Val Leu Thr Lys Asp Ala Gly Lys Leu Thr Met Gly Gln
    1820                1825                1830

Pro Leu Val Ile Leu Ala Pro His Ala Val Glu Ala Leu Val Lys
    1835                1840                1845

Gln Pro Pro Asp Arg Trp Leu Ser Asn Ala Arg Met Thr His Tyr
    1850                1855                1860

Gln Ala Leu Leu Leu Asp Thr Asp Arg Val Gln Phe Gly Pro Val
    1865                1870                1875

Val Ala Leu Asn Pro Ala Thr Leu Leu Pro Leu Pro Glu Glu Gly
    1880                1885                1890

Leu Gln His Asn Cys Leu Asp Ile Leu Ala Glu Ala His Gly Thr
    1895                1900                1905

Arg Pro Asp Leu Thr Asp Gln Pro Leu Pro Asp Ala Asp His Thr
    1910                1915                1920
```

Trp Tyr Thr Asp Gly Ser Ser Leu Leu Gln Glu Gly Gln Arg Lys
    1925                1930                1935

Ala Gly Ala Ala Val Thr Thr Glu Thr Glu Val Ile Trp Ala Lys
    1940                1945                1950

Ala Leu Pro Ala Gly Thr Ser Ala Gln Arg Ala Glu Leu Ile Ala
    1955                1960                1965

Leu Thr Gln Ala Leu Lys Met Ala Glu Gly Lys Lys Leu Asn Val
    1970                1975                1980

Tyr Thr Asp Ser Arg Tyr Ala Phe Ala Thr Ala His Ile His Gly
    1985                1990                1995

Glu Ile Tyr Arg Arg Gly Trp Leu Thr Ser Glu Gly Lys Glu
    2000                2005                2010

Ile Lys Asn Lys Asp Glu Ile Leu Ala Leu Leu Lys Ala Leu Phe
    2015                2020                2025

Leu Pro Lys Arg Leu Ser Ile Ile His Cys Pro Gly His Gln Lys
    2030                2035                2040

Gly His Ser Ala Glu Ala Arg Gly Asn Arg Met Ala Asp Gln Ala
    2045                2050                2055

Ala Arg Lys Ala Ala Ile Thr Glu Thr Pro Asp Thr Ser Thr Leu
    2060                2065                2070

Leu Ile Glu Asn Ser Ser Pro
    2075                2080

<210> SEQ ID NO 46
<211> LENGTH: 1368
<212> TYPE: PRT
<213> ORGANISM: Artificial Sequence
<220> FEATURE:
<223> OTHER INFORMATION: Synthetic

<400> SEQUENCE: 46

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

```
Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
        370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605
```

```
Asn Glu Glu Asn Glu Asp Ile Leu Glu Asp Ile Val Leu Thr Leu Thr
    610             615             620
Leu Phe Glu Asp Arg Glu Met Ile Glu Arg Leu Lys Thr Tyr Ala
625             630             635             640
His Leu Phe Asp Asp Lys Val Met Lys Gln Leu Lys Arg Arg Tyr
                645             650             655
Thr Gly Trp Gly Arg Leu Ser Arg Lys Leu Ile Asn Gly Ile Arg Asp
        660             665             670
Lys Gln Ser Gly Lys Thr Ile Leu Asp Phe Leu Lys Ser Asp Gly Phe
        675             680             685
Ala Asn Arg Asn Phe Met Gln Leu Ile His Asp Ser Leu Thr Phe
690             695             700
Lys Glu Asp Ile Gln Lys Ala Gln Val Ser Gly Gln Gly Asp Ser Leu
705             710             715             720
His Glu His Ile Ala Asn Leu Ala Gly Ser Pro Ala Ile Lys Lys Gly
            725             730             735
Ile Leu Gln Thr Val Lys Val Val Asp Glu Leu Val Lys Val Met Gly
            740             745             750
Arg His Lys Pro Glu Asn Ile Val Ile Glu Met Ala Arg Glu Asn Gln
        755             760             765
Thr Thr Gln Lys Gly Gln Lys Asn Ser Arg Glu Arg Met Lys Arg Ile
770             775             780
Glu Glu Gly Ile Lys Glu Leu Gly Ser Gln Ile Leu Lys Glu His Pro
785             790             795             800
Val Glu Asn Thr Gln Leu Gln Asn Glu Lys Leu Tyr Leu Tyr Tyr Leu
            805             810             815
Gln Asn Gly Arg Asp Met Tyr Val Asp Gln Glu Leu Asp Ile Asn Arg
            820             825             830
Leu Ser Asp Tyr Asp Val Asp His Ile Val Pro Gln Ser Phe Leu Lys
    835             840             845
Asp Asp Ser Ile Asp Asn Lys Val Leu Thr Arg Ser Asp Lys Asn Arg
    850             855             860
Gly Lys Ser Asp Asn Val Pro Ser Glu Glu Val Val Lys Lys Met Lys
865             870             875             880
Asn Tyr Trp Arg Gln Leu Leu Asn Ala Lys Leu Ile Thr Gln Arg Lys
            885             890             895
Phe Asp Asn Leu Thr Lys Ala Glu Arg Gly Gly Leu Ser Glu Leu Asp
        900             905             910
Lys Ala Gly Phe Ile Lys Arg Gln Leu Val Glu Thr Arg Gln Ile Thr
        915             920             925
Lys His Val Ala Gln Ile Leu Asp Ser Arg Met Asn Thr Lys Tyr Asp
        930             935             940
Glu Asn Asp Lys Leu Ile Arg Glu Val Lys Val Ile Thr Leu Lys Ser
945             950             955             960
Lys Leu Val Ser Asp Phe Arg Lys Asp Phe Gln Phe Tyr Lys Val Arg
            965             970             975
Glu Ile Asn Asn Tyr His His Ala His Asp Ala Tyr Leu Asn Ala Val
            980             985             990
Val Gly Thr Ala Leu Ile Lys Lys Tyr Pro Lys Leu Glu Ser Glu Phe
        995             1000            1005
Val Tyr Gly Asp Tyr Lys Val Tyr Asp Val Arg Lys Met Ile Ala
        1010            1015            1020
Lys Ser Glu Gln Glu Ile Gly Lys Ala Thr Ala Lys Tyr Phe Phe
```

```
            1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
        1085                1090                1095

Glu Val Gln Thr Gly Gly Phe Ser Lys Glu Ser Ile Arg Pro Lys
        1100                1105                1110

Arg Asn Ser Asp Lys Leu Ile Ala Arg Lys Lys Asp Trp Asp Pro
        1115                1120                1125

Lys Lys Tyr Gly Gly Phe Val Ser Pro Thr Val Ala Tyr Ser Val
        1130                1135                1140

Leu Val Val Ala Lys Val Glu Lys Gly Lys Ser Lys Lys Leu Lys
        1145                1150                1155

Ser Val Lys Glu Leu Leu Gly Ile Thr Ile Met Glu Arg Ser Ser
        1160                1165                1170

Phe Glu Lys Asn Pro Ile Asp Phe Leu Glu Ala Lys Gly Tyr Lys
        1175                1180                1185

Glu Val Lys Lys Asp Leu Ile Ile Lys Leu Pro Lys Tyr Ser Leu
        1190                1195                1200

Phe Glu Leu Glu Asn Gly Arg Lys Arg Met Leu Ala Ser Ala Arg
        1205                1210                1215

Phe Leu Gln Lys Gly Asn Glu Leu Ala Leu Pro Ser Lys Tyr Val
        1220                1225                1230

Asn Phe Leu Tyr Leu Ala Ser His Tyr Glu Lys Leu Lys Gly Ser
        1235                1240                1245

Pro Glu Asp Asn Glu Gln Lys Gln Leu Phe Val Glu Gln His Lys
        1250                1255                1260

His Tyr Leu Asp Glu Ile Ile Glu Gln Ile Ser Glu Phe Ser Lys
        1265                1270                1275

Arg Val Ile Leu Ala Asp Ala Asn Leu Asp Lys Val Leu Ser Ala
        1280                1285                1290

Tyr Asn Lys His Arg Asp Lys Pro Ile Arg Glu Gln Ala Glu Asn
        1295                1300                1305

Ile Ile His Leu Phe Thr Leu Thr Asn Leu Gly Ala Pro Arg Ala
        1310                1315                1320

Phe Lys Tyr Phe Asp Thr Thr Ile Asp Arg Lys Val Tyr Arg Ser
        1325                1330                1335

Thr Lys Glu Val Leu Asp Ala Thr Leu Ile His Gln Ser Ile Thr
        1340                1345                1350

Gly Leu Tyr Glu Thr Arg Ile Asp Leu Ser Gln Leu Gly Gly Asp
        1355                1360                1365

<210> SEQ ID NO 47
<211> LENGTH: 1368
<212> TYPE: PRT
<213> ORGANISM: Artificial Sequence
<220> FEATURE:
<223> OTHER INFORMATION: Synthetic

<400> SEQUENCE: 47

Met Asp Lys Lys Tyr Ser Ile Gly Leu Asp Ile Gly Thr Asn Ser Val
```

-continued

```
  1               5                  10                 15
Gly Trp Ala Val Ile Thr Asp Glu Tyr Lys Val Pro Ser Lys Lys Phe
             20                  25                 30
Lys Val Leu Gly Asn Thr Asp Arg His Ser Ile Lys Lys Asn Leu Ile
             35                  40                 45
Gly Ala Leu Leu Phe Asp Ser Gly Glu Thr Ala Glu Ala Thr Arg Leu
             50                  55                 60
Lys Arg Thr Ala Arg Arg Arg Tyr Thr Arg Arg Lys Asn Arg Ile Cys
 65                  70                  75                 80
Tyr Leu Gln Glu Ile Phe Ser Asn Glu Met Ala Lys Val Asp Asp Ser
                 85                  90                 95
Phe Phe His Arg Leu Glu Glu Ser Phe Leu Val Glu Glu Asp Lys Lys
                100                 105                110
His Glu Arg His Pro Ile Phe Gly Asn Ile Val Asp Glu Val Ala Tyr
                115                 120                125
His Glu Lys Tyr Pro Thr Ile Tyr His Leu Arg Lys Lys Leu Val Asp
                130                 135                140
Ser Thr Asp Lys Ala Asp Leu Arg Leu Ile Tyr Leu Ala Leu Ala His
145                 150                 155                160
Met Ile Lys Phe Arg Gly His Phe Leu Ile Glu Gly Asp Leu Asn Pro
                165                 170                175
Asp Asn Ser Asp Val Asp Lys Leu Phe Ile Gln Leu Val Gln Thr Tyr
                180                 185                190
Asn Gln Leu Phe Glu Glu Asn Pro Ile Asn Ala Ser Gly Val Asp Ala
                195                 200                205
Lys Ala Ile Leu Ser Ala Arg Leu Ser Lys Ser Arg Arg Leu Glu Asn
                210                 215                220
Leu Ile Ala Gln Leu Pro Gly Glu Lys Lys Asn Gly Leu Phe Gly Asn
225                 230                 235                240
Leu Ile Ala Leu Ser Leu Gly Leu Thr Pro Asn Phe Lys Ser Asn Phe
                245                 250                255
Asp Leu Ala Glu Asp Thr Lys Leu Gln Leu Ser Lys Asp Thr Tyr Asp
                260                 265                270
Asp Asp Leu Asp Asn Leu Leu Ala Gln Ile Gly Asp Gln Tyr Ala Asp
                275                 280                285
Leu Phe Leu Ala Ala Lys Asn Leu Ser Asp Ala Ile Leu Leu Ser Asp
                290                 295                300
Ile Leu Arg Val Asn Thr Glu Ile Thr Lys Ala Pro Leu Ser Ala Ser
305                 310                 315                320
Met Ile Lys Leu Tyr Asp Glu His His Gln Asp Leu Thr Leu Leu Lys
                325                 330                335
Ala Leu Val Arg Gln Gln Leu Pro Glu Lys Tyr Lys Glu Ile Phe Phe
                340                 345                350
Asp Gln Ser Lys Asn Gly Tyr Ala Gly Tyr Ile Asp Gly Gly Ala Ser
                355                 360                365
Gln Glu Glu Phe Tyr Lys Phe Ile Lys Pro Ile Leu Glu Lys Met Asp
                370                 375                380
Gly Thr Glu Glu Leu Leu Val Lys Leu Asn Arg Glu Asp Leu Leu Arg
385                 390                 395                400
Lys Gln Arg Thr Phe Asp Asn Gly Ile Ile Pro His Gln Ile His Leu
                405                 410                415
Gly Glu Leu His Ala Ile Leu Arg Arg Gln Glu Asp Phe Tyr Pro Phe
                420                 425                430
```

```
Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Lys
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Asp Gln
530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
            675                 680                 685

Ala Asn Arg Asn Phe Ile Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
            835                 840                 845
```

```
Asp Asp Ser Ile Asp Asn Lys Val Leu Thr Arg Ser Asp Lys Asn Arg
    850             855                 860
Gly Lys Ser Asp Asn Val Pro Ser Glu Val Val Lys Lys Met Lys
865             870                 875                 880
Asn Tyr Trp Arg Gln Leu Leu Asn Ala Lys Leu Ile Thr Gln Arg Lys
            885                 890                 895
Phe Asp Asn Leu Thr Lys Ala Glu Arg Gly Gly Leu Ser Glu Leu Asp
                900                 905                 910
Lys Ala Gly Phe Ile Lys Arg Gln Leu Val Glu Thr Arg Gln Ile Thr
                915                 920                 925
Lys His Val Ala Gln Ile Leu Asp Ser Arg Met Asn Thr Lys Tyr Asp
        930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
                980                 985                 990
Val Gly Thr Ala Leu Ile Lys Lys Tyr Pro Lys Leu Glu Ser Glu Phe
            995                 1000                1005
Val Tyr Gly Asp Tyr Lys Val Tyr Asp Val Arg Lys Met Ile Ala
    1010                1015                1020
Lys Ser Glu Gln Glu Ile Gly Lys Ala Thr Ala Lys Tyr Phe Phe
    1025                1030                1035
Tyr Ser Asn Ile Met Asn Phe Phe Lys Thr Glu Ile Thr Leu Ala
    1040                1045                1050
Asn Gly Glu Ile Arg Lys Arg Pro Leu Ile Glu Thr Asn Gly Glu
    1055                1060                1065
Thr Gly Glu Ile Val Trp Asp Lys Gly Arg Asp Phe Ala Thr Val
    1070                1075                1080
Arg Lys Val Leu Ser Met Pro Gln Val Asn Ile Val Lys Lys Thr
    1085                1090                1095
Glu Val Gln Thr Gly Gly Phe Ser Lys Glu Ser Ile Leu Pro Lys
    1100                1105                1110
Arg Asn Ser Asp Lys Leu Ile Ala Arg Lys Lys Asp Trp Asp Pro
    1115                1120                1125
Lys Lys Tyr Gly Gly Phe Asp Ser Pro Thr Val Ala Tyr Ser Val
    1130                1135                1140
Leu Val Val Ala Lys Val Glu Lys Gly Lys Ser Lys Lys Leu Lys
    1145                1150                1155
Ser Val Lys Glu Leu Leu Gly Ile Thr Ile Met Glu Arg Ser Ser
    1160                1165                1170
Phe Glu Lys Asn Pro Ile Asp Phe Leu Glu Ala Lys Gly Tyr Lys
    1175                1180                1185
Glu Val Lys Lys Asp Leu Ile Ile Lys Leu Pro Lys Tyr Ser Leu
    1190                1195                1200
Phe Glu Leu Glu Asn Gly Arg Lys Arg Met Leu Ala Ser Ala Gly
    1205                1210                1215
Val Leu Gln Lys Gly Asn Glu Leu Ala Leu Pro Ser Lys Tyr Val
    1220                1225                1230
Asn Phe Leu Tyr Leu Ala Ser His Tyr Glu Lys Leu Lys Gly Ser
    1235                1240                1245
Pro Glu Asp Asn Glu Gln Lys Gln Leu Phe Val Glu Gln His Lys
```

His Tyr Leu Asp Glu Ile Ile Glu Gln Ile Ser Glu Phe Ser Lys
            1265                1270                1275

Arg Val Ile Leu Ala Asp Ala Asn Leu Asp Lys Val Leu Ser Ala
            1280                1285                1290

Tyr Asn Lys His Arg Asp Lys Pro Ile Arg Glu Gln Ala Glu Asn
            1295                1300                1305

Ile Ile His Leu Phe Thr Leu Thr Asn Leu Gly Ala Pro Ala Ala
            1310                1315                1320

Phe Lys Tyr Phe Asp Thr Thr Ile Asp Arg Lys Arg Tyr Thr Ser
            1325                1330                1335

Thr Lys Glu Val Leu Asp Ala Thr Leu Ile His Gln Ser Ile Thr
            1340                1345                1350

Gly Leu Tyr Glu Thr Arg Ile Asp Leu Ser Gln Leu Gly Gly Asp
            1355                1360                1365

<210> SEQ ID NO 48
<211> LENGTH: 74
<212> TYPE: PRT
<213> ORGANISM: Artificial Sequence
<220> FEATURE:
<223> OTHER INFORMATION: Synthetic

<400> SEQUENCE: 48

Ser Glu Lys Gly Lys Gln His Ala Glu Ile Leu Phe Leu Asp Lys Ile
1               5                   10                  15

Arg Ser Met Glu Leu Ser Gln Val Thr Ile Thr Cys Tyr Leu Thr Trp
            20                  25                  30

Ser Pro Cys Pro Asn Cys Ala Trp Gln Leu Ala Ala Phe Lys Arg Asp
        35                  40                  45

Arg Pro Asp Leu Ile Leu His Ile Tyr Thr Ser Arg Leu Tyr Phe His
    50                  55                  60

Trp Lys Arg Pro Phe Gln Lys Gly Leu Cys
65                  70

<210> SEQ ID NO 49
<211> LENGTH: 74
<212> TYPE: PRT
<213> ORGANISM: Artificial Sequence
<220> FEATURE:
<223> OTHER INFORMATION: Synthetic

<400> SEQUENCE: 49

Ser Glu Lys Gly Lys Gln His Ala Glu Ile Leu Phe Leu Asp Lys Ile
1               5                   10                  15

Arg Ser Met Glu Leu Ser Gln Val Thr Ile Thr Cys Tyr Leu Thr Trp
            20                  25                  30

Ser Pro Cys Pro Asn Cys Ala Trp Gln Leu Ala Ala Phe Lys Arg Asp
        35                  40                  45

Arg Pro Asp Leu Ile Pro His Ile Tyr Thr Ser Arg Leu Tyr Phe His
    50                  55                  60

Trp Lys Arg Pro Phe Gln Lys Gly Leu Cys
65                  70

<210> SEQ ID NO 50
<211> LENGTH: 74
<212> TYPE: PRT
<213> ORGANISM: Artificial Sequence
<220> FEATURE:

<223> OTHER INFORMATION: Synthetic

<400> SEQUENCE: 50

Ser Glu Lys Gly Lys Gln His Ala Glu Ile Leu Phe Leu Asp Lys Ile
1               5                   10                  15

Arg Ser Met Glu Leu Ser Gln Val Thr Ile Thr Cys Tyr Leu Thr Trp
            20                  25                  30

Ser Pro Cys Pro Asn Cys Ala Trp Arg Leu Ala Ala Phe Lys Arg Asp
        35                  40                  45

Arg Pro Asp Leu Ile Leu His Ile Tyr Thr Ser Arg Leu Tyr Phe His
    50                  55                  60

Trp Lys Arg Pro Phe Gln Lys Gly Leu Cys
65                  70

<210> SEQ ID NO 51
<211> LENGTH: 74
<212> TYPE: PRT
<213> ORGANISM: Artificial Sequence
<220> FEATURE:
<223> OTHER INFORMATION: Synthetic

<400> SEQUENCE: 51

Ser Glu Lys Gly Lys Gln His Ala Glu Ile Leu Phe Leu Asn Lys Ile
1               5                   10                  15

Arg Ser Met Glu Leu Ser Gln Val Thr Ile Thr Cys Tyr Leu Thr Trp
            20                  25                  30

Ser Pro Cys Pro Asn Cys Ala Trp Gln Leu Ala Ala Phe Lys Lys Asp
        35                  40                  45

Arg Pro Asp Leu Ile Leu His Ile Tyr Thr Ser Arg Leu Tyr Phe His
    50                  55                  60

Trp Lys Arg Pro Phe Gln Lys Gly Leu Cys
65                  70

<210> SEQ ID NO 52
<211> LENGTH: 74
<212> TYPE: PRT
<213> ORGANISM: Artificial Sequence
<220> FEATURE:
<223> OTHER INFORMATION: Synthetic

<400> SEQUENCE: 52

Ser Lys Lys Gly Lys Gln His Ala Glu Ile Leu Phe Leu Asp Lys Ile
1               5                   10                  15

Arg Ser Met Glu Leu Ser Gln Val Thr Ile Thr Cys Tyr Leu Thr Trp
            20                  25                  30

Ser Pro Cys Pro Asn Cys Ala Trp Gln Leu Ala Ala Phe Lys Arg Asp
        35                  40                  45

His Pro Asp Leu Ile Leu His Ile Tyr Thr Ser Arg Leu Tyr Phe His
    50                  55                  60

Trp Lys Arg Pro Phe Gln Lys Gly Leu Cys
65                  70

<210> SEQ ID NO 53
<211> LENGTH: 74
<212> TYPE: PRT
<213> ORGANISM: Artificial Sequence
<220> FEATURE:
<223> OTHER INFORMATION: Synthetic

<400> SEQUENCE: 53

Ser Lys Lys Gly Lys Gln His Ala Glu Ile Leu Phe Leu Glu Lys Ile
1               5                   10                  15

Arg Ser Met Glu Leu Ser Gln Met Arg Ile Thr Cys Tyr Leu Thr Trp
            20                  25                  30

Ser Pro Cys Pro Asn Cys Ala Trp Gln Leu Ala Ala Phe Gln Lys Asp
        35                  40                  45

Arg Pro Asp Leu Ile Leu His Ile Tyr Thr Ser Arg Leu Tyr Phe His
    50                  55                  60

Trp Arg Arg Ile Phe Gln Lys Gly Leu Cys
65                  70

<210> SEQ ID NO 54
<211> LENGTH: 74
<212> TYPE: PRT
<213> ORGANISM: Artificial Sequence
<220> FEATURE:
<223> OTHER INFORMATION: Synthetic

<400> SEQUENCE: 54

Ser Lys Lys Gly Lys Gln His Ala Glu Ile Leu Phe Leu Glu Lys Ile
1               5                   10                  15

Arg Ser Met Glu Leu Ser Gln Met Arg Ile Thr Cys Tyr Leu Thr Trp
            20                  25                  30

Ser Pro Cys Pro Asn Cys Ala Trp Gln Leu Ala Ala Phe Gln Lys Asp
        35                  40                  45

Arg Pro Asp Leu Ile Leu His Ile Tyr Thr Ser Arg Leu Tyr Phe His
    50                  55                  60

Trp Arg Arg Ile Phe Gln Lys Gly Leu Cys
65                  70

<210> SEQ ID NO 55
<211> LENGTH: 74
<212> TYPE: PRT
<213> ORGANISM: Artificial Sequence
<220> FEATURE:
<223> OTHER INFORMATION: Synthetic

<400> SEQUENCE: 55

Ser Lys Lys Gly Lys Gln His Ala Glu Ile Leu Phe Leu Asp Lys Ile
1               5                   10                  15

Arg Ser Met Glu Leu Ser Gln Val Arg Ile Thr Cys Tyr Leu Thr Trp
            20                  25                  30

Ser Pro Cys Pro Asn Cys Ala Trp Gln Leu Glu Thr Phe Lys Lys Asp
        35                  40                  45

Arg Pro Asp Leu Ile Leu His Ile Tyr Thr Ser Arg Leu Tyr Phe His
    50                  55                  60

Trp Lys Arg Ala Phe Gln Glu Gly Leu Cys
65                  70

<210> SEQ ID NO 56
<211> LENGTH: 75
<212> TYPE: PRT
<213> ORGANISM: Artificial Sequence
<220> FEATURE:
<223> OTHER INFORMATION: Synthetic

<400> SEQUENCE: 56

Ser Lys Lys Gly Lys Pro His Ala Glu Ile Leu Phe Leu Asp Lys Met
1               5                   10                  15

Trp Ser Met Glu Glu Leu Ser Gln Val Arg Ile Thr Cys Tyr Leu Thr

```
                20                  25                  30

Trp Ser Pro Cys Pro Asn Cys Ala Arg Gln Leu Ala Ala Phe Lys Lys
        35                  40                  45

Asp His Pro Gly Leu Ile Leu Arg Ile Tyr Thr Ser Arg Leu Tyr Phe
    50                  55                  60

Tyr Trp Arg Arg Lys Phe Gln Lys Gly Leu Cys
65                  70                  75

<210> SEQ ID NO 57
<211> LENGTH: 73
<212> TYPE: PRT
<213> ORGANISM: Artificial Sequence
<220> FEATURE:
<223> OTHER INFORMATION: Synthetic

<400> SEQUENCE: 57

Lys Lys Gly Glu Gln His Val Glu Ile Leu Phe Leu Glu Lys Met Arg
1               5                   10                  15

Ser Met Glu Leu Ser Gln Val Arg Ile Thr Cys Tyr Leu Thr Trp Ser
            20                  25                  30

Pro Cys Pro Asn Cys Ala Arg Gln Leu Ala Ala Phe Lys Lys Asp His
        35                  40                  45

Pro Asp Leu Ile Leu Arg Ile Tyr Thr Ser Arg Leu Tyr Phe Tyr Trp
    50                  55                  60

Arg Lys Lys Phe Gln Lys Gly Leu Cys
65                  70

<210> SEQ ID NO 58
<211> LENGTH: 74
<212> TYPE: PRT
<213> ORGANISM: Artificial Sequence
<220> FEATURE:
<223> OTHER INFORMATION: Synthetic

<400> SEQUENCE: 58

Ser Lys Lys Gly Arg Gln His Ala Glu Ile Leu Phe Leu Glu Lys Val
1               5                   10                  15

Arg Ser Met Gln Leu Ser Gln Val Arg Ile Thr Cys Tyr Leu Thr Trp
            20                  25                  30

Ser Pro Cys Pro Asn Cys Ala Trp Gln Leu Ala Ala Phe Lys Met Asp
        35                  40                  45

His Pro Asp Leu Ile Leu Arg Ile Tyr Ala Ser Arg Leu Tyr Phe His
    50                  55                  60

Trp Arg Arg Ala Phe Gln Lys Gly Leu Cys
65                  70

<210> SEQ ID NO 59
<211> LENGTH: 73
<212> TYPE: PRT
<213> ORGANISM: Artificial Sequence
<220> FEATURE:
<223> OTHER INFORMATION: Synthetic

<400> SEQUENCE: 59

Asn Lys Lys Gly Lys His Ala Glu Ile Leu Phe Ile Asp Glu Met Arg
1               5                   10                  15

Ser Leu Glu Leu Gly Gln Val Gln Ile Thr Cys Tyr Leu Thr Trp Ser
            20                  25                  30

Pro Cys Pro Asn Cys Ala Gln Glu Leu Ala Ala Phe Lys Ser Asp His
        35                  40                  45
```

```
Pro Asp Leu Val Leu Arg Ile Tyr Thr Ser Arg Leu Tyr Phe His Trp
    50                  55                  60

Arg Arg Lys Tyr Gln Glu Gly Leu Cys
65                  70
```

<210> SEQ ID NO 60
<211> LENGTH: 73
<212> TYPE: PRT
<213> ORGANISM: Artificial Sequence
<220> FEATURE:
<223> OTHER INFORMATION: Synthetic

<400> SEQUENCE: 60

```
Asn Lys Lys Gly Lys His Ala Glu Ile Leu Phe Ile Asp Glu Met Arg
1               5                   10                  15

Ser Leu Glu Leu Gly Gln Ala Arg Ile Thr Cys Tyr Leu Thr Trp Ser
            20                  25                  30

Pro Cys Pro Asn Cys Ala Gln Lys Leu Ala Ala Phe Lys Lys Asp His
        35                  40                  45

Pro Asp Leu Val Leu Arg Val Tyr Thr Ser Arg Leu Tyr Phe His Trp
    50                  55                  60

Arg Arg Lys Tyr Gln Glu Gly Leu Cys
65                  70
```

<210> SEQ ID NO 61
<211> LENGTH: 73
<212> TYPE: PRT
<213> ORGANISM: Artificial Sequence
<220> FEATURE:
<223> OTHER INFORMATION: Synthetic

<400> SEQUENCE: 61

```
Asn Lys Lys Asp Lys His Ala Glu Ile Leu Phe Ile Asp Lys Met Arg
1               5                   10                  15

Ser Leu Glu Leu Cys Gln Val Arg Ile Thr Cys Tyr Leu Thr Trp Ser
            20                  25                  30

Pro Cys Pro Asn Cys Ala Gln Glu Leu Ala Ala Phe Lys Lys Asp His
        35                  40                  45

Pro Asp Leu Val Leu Arg Ile Tyr Thr Ser Arg Leu Tyr Phe His Trp
    50                  55                  60

Arg Arg Lys Tyr Gln Glu Gly Leu Cys
65                  70
```

<210> SEQ ID NO 62
<211> LENGTH: 73
<212> TYPE: PRT
<213> ORGANISM: Artificial Sequence
<220> FEATURE:
<223> OTHER INFORMATION: Synthetic

<400> SEQUENCE: 62

```
Asn Lys Lys Gly Lys His Ala Glu Ile Leu Phe Ile Asp Glu Met Arg
1               5                   10                  15

Ser Leu Lys Leu Ser Gln Glu Arg Ile Thr Cys Tyr Leu Thr Trp Ser
            20                  25                  30

Pro Cys Pro Asn Cys Ala Gln Glu Leu Ala Ala Phe Lys Arg Asp His
        35                  40                  45

Pro Gly Leu Val Leu Arg Ile Tyr Ala Ser Arg Leu Tyr Phe His Trp
    50                  55                  60
```

Arg Arg Lys Tyr Gln Glu Gly Leu Cys
65                  70

<210> SEQ ID NO 63
<211> LENGTH: 72
<212> TYPE: PRT
<213> ORGANISM: Artificial Sequence
<220> FEATURE:
<223> OTHER INFORMATION: Synthetic

<400> SEQUENCE: 63

Asn Lys Arg Ala Lys His Ala Glu Ile Leu Leu Ile Asp Met Met Arg
1               5                   10                  15

Ser Met Glu Leu Gly Gln Val Gln Ile Thr Cys Tyr Ile Thr Trp Ser
                20                  25                  30

Pro Cys Pro Thr Cys Ala Gln Glu Leu Ala Ala Phe Lys Gln Asp His
            35                  40                  45

Pro Asp Leu Val Leu Arg Ile Tyr Ala Ser Arg Leu Tyr Phe His Trp
        50                  55                  60

Lys Arg Lys Phe Gln Lys Gly Leu
65                  70

<210> SEQ ID NO 64
<211> LENGTH: 73
<212> TYPE: PRT
<213> ORGANISM: Artificial Sequence
<220> FEATURE:
<223> OTHER INFORMATION: Synthetic

<400> SEQUENCE: 64

Asn Lys Lys Gly Arg His Ala Glu Ile Cys Leu Ile Asp Glu Met Arg
1               5                   10                  15

Ser Leu Gly Leu Gly Lys Ala Gln Ile Thr Cys Tyr Leu Thr Trp Ser
                20                  25                  30

Pro Cys Arg Lys Cys Ala Gln Glu Leu Ala Thr Phe Lys Lys Asp His
            35                  40                  45

Pro Asp Leu Val Leu Arg Val Tyr Ala Ser Arg Leu Tyr Phe His Trp
        50                  55                  60

Ser Arg Lys Tyr Gln Gln Gly Leu Cys
65                  70

<210> SEQ ID NO 65
<211> LENGTH: 75
<212> TYPE: PRT
<213> ORGANISM: Artificial Sequence
<220> FEATURE:
<223> OTHER INFORMATION: Synthetic

<400> SEQUENCE: 65

Asn Lys Lys Gly His His Ala Glu Ile Arg Phe Ile Glu Arg Ile Arg
1               5                   10                  15

Ser Met Gly Leu Asp Pro Ser Gln Asp Tyr Gln Ile Thr Cys Tyr Leu
                20                  25                  30

Thr Trp Ser Pro Cys Leu Asp Cys Ala Phe Lys Leu Ala Lys Leu Lys
            35                  40                  45

Lys Asp Phe Pro Arg Leu Thr Leu Arg Ile Phe Thr Ser Arg Leu Tyr
        50                  55                  60

Phe His Trp Ile Arg Lys Phe Gln Lys Gly Leu
65                  70                  75

```
<210> SEQ ID NO 66
<211> LENGTH: 72
<212> TYPE: PRT
<213> ORGANISM: Artificial Sequence
<220> FEATURE:
<223> OTHER INFORMATION: Synthetic

<400> SEQUENCE: 66

Asn Lys Lys Gly Lys His Ala Glu Ala Arg Phe Val Asp Lys Met Arg
1               5                   10                  15

Ser Met Gln Leu Asp His Ala Leu Ile Thr Cys Tyr Leu Thr Trp Ser
            20                  25                  30

Pro Cys Leu Asp Cys Ser Gln Lys Leu Ala Ala Leu Lys Arg Asp His
        35                  40                  45

Pro Gly Leu Thr Leu Arg Ile Phe Thr Ser Arg Leu Tyr Phe His Trp
    50                  55                  60

Val Lys Lys Phe Gln Glu Gly Leu
65                  70

<210> SEQ ID NO 67
<211> LENGTH: 76
<212> TYPE: PRT
<213> ORGANISM: Artificial Sequence
<220> FEATURE:
<223> OTHER INFORMATION: Synthetic

<400> SEQUENCE: 67

Ser Pro Gln Lys Gly His His Ala Glu Ser Arg Phe Ile Lys Arg Ile
1               5                   10                  15

Ser Ser Met Asp Leu Asp Arg Ser Arg Ser Tyr Gln Ile Thr Cys Phe
            20                  25                  30

Leu Thr Trp Ser Pro Cys Pro Ser Cys Ala Gln Glu Leu Ala Ser Phe
        35                  40                  45

Lys Arg Ala His Pro His Leu Arg Phe Gln Ile Phe Val Ser Arg Leu
    50                  55                  60

Tyr Phe His Trp Lys Arg Ser Tyr Gln Ala Gly Leu
65                  70                  75

<210> SEQ ID NO 68
<211> LENGTH: 74
<212> TYPE: PRT
<213> ORGANISM: Artificial Sequence
<220> FEATURE:
<223> OTHER INFORMATION: Synthetic

<400> SEQUENCE: 68

Lys Lys Gly Tyr His Ala Glu Ser Arg Phe Ile Lys Arg Ile Cys Ser
1               5                   10                  15

Met Asp Leu Gly Gln Asp Gln Ser Tyr Gln Val Thr Cys Phe Leu Thr
            20                  25                  30

Trp Ser Pro Cys Pro His Cys Ala Gln Glu Leu Val Ser Phe Lys Arg
        35                  40                  45

Ala His Pro His Leu Arg Leu Gln Ile Phe Thr Ala Arg Leu Phe Phe
    50                  55                  60

His Trp Lys Arg Ser Tyr Gln Glu Gly Leu
65                  70

<210> SEQ ID NO 69
<211> LENGTH: 74
<212> TYPE: PRT
<213> ORGANISM: Artificial Sequence
```

```
<220> FEATURE:
<223> OTHER INFORMATION: Synthetic

<400> SEQUENCE: 69

Lys Lys Gly Gln His Ala Glu Ile Arg Phe Ile Glu Arg Ile His Ser
1               5                   10                  15

Met Ala Leu Asp Gln Ala Arg Ser Tyr Gln Ile Thr Cys Phe Leu Thr
                20                  25                  30

Trp Ser Pro Cys Pro Phe Cys Ala Gln Glu Leu Ala Ser Phe Lys Ser
            35                  40                  45

Thr His Pro Arg Val His Leu Gln Ile Phe Val Ser Arg Leu Tyr Phe
        50                  55                  60

His Trp Lys Arg Ser Tyr Gln Glu Gly Leu
65                  70

<210> SEQ ID NO 70
<211> LENGTH: 75
<212> TYPE: PRT
<213> ORGANISM: Artificial Sequence
<220> FEATURE:
<223> OTHER INFORMATION: Synthetic

<400> SEQUENCE: 70

Asn Lys Lys Gly His His Ala Glu Ile Arg Phe Ile Lys Lys Ile Arg
1               5                   10                  15

Ser Leu Asp Leu Asp Gln Ser Gln Asn Tyr Glu Val Thr Cys Tyr Leu
                20                  25                  30

Thr Trp Ser Pro Cys Pro Asp Cys Ala Gln Glu Leu Val Ala Leu Thr
            35                  40                  45

Arg Ser His Pro His Val Arg Leu Arg Leu Phe Thr Ser Arg Leu Tyr
        50                  55                  60

Phe His Trp Phe Trp Ser Phe Gln Glu Gly Leu
65                  70                  75

<210> SEQ ID NO 71
<211> LENGTH: 72
<212> TYPE: PRT
<213> ORGANISM: Artificial Sequence
<220> FEATURE:
<223> OTHER INFORMATION: Synthetic

<400> SEQUENCE: 71

Asn Arg His Ala Glu Ile Cys Phe Ile Asp Glu Ile Glu Ser Met Gly
1               5                   10                  15

Leu Asp Lys Thr Gln Cys Tyr Glu Val Thr Cys Tyr Leu Thr Trp Ser
                20                  25                  30

Pro Cys Pro Ser Cys Ala Gln Lys Leu Ala Ala Phe Thr Lys Ala Gln
            35                  40                  45

Val His Leu Asn Leu Arg Ile Phe Ala Ser Arg Leu Tyr His Trp
        50                  55                  60

Arg Ser Ser Tyr Gln Lys Gly Leu
65                  70

<210> SEQ ID NO 72
<211> LENGTH: 72
<212> TYPE: PRT
<213> ORGANISM: Artificial Sequence
<220> FEATURE:
<223> OTHER INFORMATION: Synthetic

<400> SEQUENCE: 72
```

Asn Arg His Ala Glu Ile Cys Phe Ile Asp Glu Ile Glu Ser Met Gly
1               5                   10                  15

Leu Asp Lys Thr Gln Cys Tyr Glu Val Thr Cys Tyr Leu Thr Trp Ser
            20                  25                  30

Pro Cys Pro Ser Cys Ala Gln Lys Leu Val Ala Phe Ala Lys Ala Gln
        35                  40                  45

Asp His Leu Asn Leu Arg Ile Phe Ala Ser Arg Leu Tyr Tyr His Trp
    50                  55                  60

Arg Arg Arg Tyr Lys Glu Gly Leu
65              70

<210> SEQ ID NO 73
<211> LENGTH: 70
<212> TYPE: PRT
<213> ORGANISM: Artificial Sequence
<220> FEATURE:
<223> OTHER INFORMATION: Synthetic

<400> SEQUENCE: 73

His Val Glu Ile Cys Phe Ile Asp Lys Ile Ala Ser Met Glu Leu Asp
1               5                   10                  15

Lys Thr Gln Cys Tyr Asp Val Thr Cys Tyr Leu Thr Trp Ser Pro Cys
            20                  25                  30

Pro Ser Cys Ala Gln Lys Leu Ala Ala Phe Ala Lys Ala Gln Asp His
        35                  40                  45

Leu Asn Leu Arg Ile Phe Ala Ser Arg Leu Tyr Tyr His Trp Arg Arg
    50                  55                  60

Ser Tyr Gln Lys Gly Leu
65              70

<210> SEQ ID NO 74
<211> LENGTH: 75
<212> TYPE: PRT
<213> ORGANISM: Artificial Sequence
<220> FEATURE:
<223> OTHER INFORMATION: Synthetic

<400> SEQUENCE: 74

Asn Lys Lys Lys Cys His Ala Glu Ile Cys Phe Ile Asn Glu Ile Lys
1               5                   10                  15

Ser Met Gly Leu Asp Glu Thr Gln Cys Tyr Gln Val Thr Cys Tyr Leu
            20                  25                  30

Thr Trp Ser Pro Cys Ser Ser Cys Ala Trp Glu Leu Val Asp Phe Ile
        35                  40                  45

Lys Ala His Asp His Leu Asn Leu Gly Ile Phe Ala Ser Arg Leu Tyr
    50                  55                  60

Tyr His Trp Cys Lys Pro Gln Gln Lys Gly Leu
65              70                  75

<210> SEQ ID NO 75
<211> LENGTH: 76
<212> TYPE: PRT
<213> ORGANISM: Artificial Sequence
<220> FEATURE:
<223> OTHER INFORMATION: Synthetic

<400> SEQUENCE: 75

Glu Asn Lys Lys Lys Cys His Ala Glu Ile Cys Phe Ile Asn Glu Ile
1               5                   10                  15

```
Lys Ser Met Gly Leu Asp Glu Thr Gln Cys Tyr Gln Val Thr Cys Tyr
            20                  25                  30

Leu Thr Trp Ser Pro Cys Ser Ser Cys Ala Trp Glu Leu Val Asp Phe
        35                  40                  45

Ile Lys Ala His Asp His Leu Asn Leu Gly Ile Phe Ala Ser Arg Leu
    50                  55                  60

Tyr Tyr His Trp Cys Lys Pro Gln Gln Lys Gly Leu
65                  70                  75
```

<210> SEQ ID NO 76
<211> LENGTH: 75
<212> TYPE: PRT
<213> ORGANISM: Artificial Sequence
<220> FEATURE:
<223> OTHER INFORMATION: Synthetic

<400> SEQUENCE: 76

```
Asn Lys Lys Lys Cys His Ala Glu Ile Cys Phe Ile Asn Glu Ile Lys
1               5                   10                  15

Ser Met Gly Leu Asp Glu Thr Gln Cys Tyr Gln Val Thr Cys Tyr Leu
            20                  25                  30

Thr Trp Ser Pro Cys Ser Ser Cys Ala Trp Lys Leu Val Asp Phe Ile
        35                  40                  45

Gln Ala His Asp His Leu Asn Leu Arg Ile Phe Ala Ser Arg Leu Tyr
    50                  55                  60

Tyr His Trp Cys Lys Pro Gln Gln Glu Gly Leu
65                  70                  75
```

<210> SEQ ID NO 77
<211> LENGTH: 75
<212> TYPE: PRT
<213> ORGANISM: Artificial Sequence
<220> FEATURE:
<223> OTHER INFORMATION: Synthetic

<400> SEQUENCE: 77

```
Asn Lys Lys Lys Arg His Ala Glu Ile Arg Phe Ile Asn Lys Ile Lys
1               5                   10                  15

Ser Met Gly Leu Asp Glu Thr Gln Cys Tyr Gln Val Thr Cys Tyr Leu
            20                  25                  30

Thr Trp Ser Pro Cys Pro Ser Cys Ala Trp Glu Leu Val Asp Phe Ile
        35                  40                  45

Lys Ala His Asp His Leu Asn Leu Gly Ile Phe Ala Ser Arg Leu Tyr
    50                  55                  60

Tyr His Trp Cys Arg His Gln Gln Glu Gly Leu
65                  70                  75
```

<210> SEQ ID NO 78
<211> LENGTH: 75
<212> TYPE: PRT
<213> ORGANISM: Artificial Sequence
<220> FEATURE:
<223> OTHER INFORMATION: Synthetic

<400> SEQUENCE: 78

```
Asn Lys Lys Lys Asp His Ala Glu Ile Arg Phe Ile Asn Lys Ile Lys
1               5                   10                  15

Ser Met Gly Leu Asp Glu Thr Gln Cys Tyr Gln Val Thr Cys Tyr Leu
            20                  25                  30

Thr Trp Ser Pro Cys Pro Ser Cys Ala Gly Glu Leu Val Asp Phe Ile
```

```
            35                  40                  45
Lys Ala His Arg His Leu Asn Leu Arg Ile Phe Ala Ser Arg Leu Tyr
    50                  55                  60

Tyr His Trp Arg Pro Asn Tyr Gln Glu Gly Leu
65                  70                  75

<210> SEQ ID NO 79
<211> LENGTH: 75
<212> TYPE: PRT
<213> ORGANISM: Artificial Sequence
<220> FEATURE:
<223> OTHER INFORMATION: Synthetic

<400> SEQUENCE: 79

Asn Lys Lys Lys Glu His Ala Glu Ile Arg Phe Ile Asn Lys Ile Lys
1               5                   10                  15

Ser Met Gly Leu Asp Glu Thr Gln Cys Tyr Gln Val Thr Cys Tyr Leu
                20                  25                  30

Thr Trp Ser Pro Cys Pro Ser Cys Ala Gly Lys Leu Val Asp Phe Ile
            35                  40                  45

Lys Ala His His His Leu Asn Leu Arg Ile Phe Ala Ser Arg Leu Tyr
    50                  55                  60

Tyr His Trp Arg Pro Asn Tyr Gln Glu Gly Leu
65                  70                  75

<210> SEQ ID NO 80
<211> LENGTH: 75
<212> TYPE: PRT
<213> ORGANISM: Artificial Sequence
<220> FEATURE:
<223> OTHER INFORMATION: Synthetic

<400> SEQUENCE: 80

Asn Lys Lys Lys His His Ala Glu Ile His Phe Ile Asn Lys Ile Lys
1               5                   10                  15

Ser Met Gly Leu Asp Glu Thr Gln Cys Tyr Gln Val Thr Cys Tyr Leu
                20                  25                  30

Thr Trp Ser Pro Cys Pro Ser Cys Ala Arg Glu Leu Val Asp Phe Ile
            35                  40                  45

Lys Ala His Arg His Leu Asn Leu Arg Ile Phe Ala Ser Arg Leu Tyr
    50                  55                  60

Tyr His Trp Arg Pro His Tyr Gln Glu Gly Leu
65                  70                  75

<210> SEQ ID NO 81
<211> LENGTH: 75
<212> TYPE: PRT
<213> ORGANISM: Artificial Sequence
<220> FEATURE:
<223> OTHER INFORMATION: Synthetic

<400> SEQUENCE: 81

Asn Lys Lys Gln Arg His Ala Glu Ile Arg Phe Ile Asp Lys Ile Asn
1               5                   10                  15

Ser Leu Asp Leu Asn Pro Ser Gln Ser Tyr Lys Ile Ile Cys Tyr Ile
                20                  25                  30

Thr Trp Ser Pro Cys Pro Asn Cys Ala Asn Glu Leu Val Asn Phe Ile
            35                  40                  45

Thr Arg Asn Asn His Leu Lys Leu Glu Ile Phe Ala Ser Arg Leu Tyr
    50                  55                  60
```

```
Phe His Trp Ile Lys Pro Phe Lys Met Gly Leu
65                  70                  75

<210> SEQ ID NO 82
<211> LENGTH: 75
<212> TYPE: PRT
<213> ORGANISM: Artificial Sequence
<220> FEATURE:
<223> OTHER INFORMATION: Synthetic

<400> SEQUENCE: 82

Asn Lys Lys Gln Arg His Ala Glu Ile Arg Phe Ile Asp Lys Ile Asn
1               5                   10                  15

Ser Leu Asp Leu Asn Pro Ser Gln Ser Tyr Lys Ile Ile Cys Tyr Ile
            20                  25                  30

Thr Trp Ser Pro Cys Pro Asn Cys Ala Ser Glu Leu Val Asp Phe Ile
        35                  40                  45

Thr Arg Asn Asp His Leu Asp Leu Gln Ile Phe Ala Ser Arg Leu Tyr
    50                  55                  60

Phe His Trp Ile Lys Pro Phe Lys Arg Gly Leu
65                  70                  75

<210> SEQ ID NO 83
<211> LENGTH: 75
<212> TYPE: PRT
<213> ORGANISM: Artificial Sequence
<220> FEATURE:
<223> OTHER INFORMATION: Synthetic

<400> SEQUENCE: 83

Asn Lys Lys Gln Arg His Ala Glu Ile Arg Phe Ile Asp Lys Ile Asn
1               5                   10                  15

Ser Leu Asn Leu Asp Arg Arg Gln Ser Tyr Lys Ile Ile Cys Tyr Ile
            20                  25                  30

Thr Trp Ser Pro Cys Pro Arg Cys Ala Ser Glu Leu Val Asp Phe Ile
        35                  40                  45

Thr Gly Asn Asp His Leu Asn Leu Gln Ile Phe Ala Ser Arg Leu Tyr
    50                  55                  60

Phe His Trp Lys Lys Pro Phe Gln Arg Gly Leu
65                  70                  75

<210> SEQ ID NO 84
<211> LENGTH: 75
<212> TYPE: PRT
<213> ORGANISM: Artificial Sequence
<220> FEATURE:
<223> OTHER INFORMATION: Synthetic

<400> SEQUENCE: 84

Asn Lys Lys Lys Arg His Ala Glu Ile Arg Phe Ile Asp Lys Ile Asn
1               5                   10                  15

Ser Leu Asn Leu Asp Gln Asn Gln Cys Tyr Arg Ile Ile Cys Tyr Val
            20                  25                  30

Thr Trp Ser Pro Cys His Asn Cys Ala Lys Glu Leu Val Asp Phe Ile
        35                  40                  45

Ser Asn Arg His His Leu Ser Leu Gln Leu Phe Ala Ser Arg Leu Tyr
    50                  55                  60

Phe His Trp Val Arg Cys Tyr Gln Arg Gly Leu
65                  70                  75
```

<210> SEQ ID NO 85
<211> LENGTH: 75
<212> TYPE: PRT
<213> ORGANISM: Artificial Sequence
<220> FEATURE:
<223> OTHER INFORMATION: Synthetic

<400> SEQUENCE: 85

```
Asn Lys Lys Lys Arg His Ala Glu Ile Arg Phe Ile Asp Lys Ile Lys
1               5                   10                  15

Ser Leu Gly Leu Asp Arg Val Gln Ser Tyr Glu Ile Thr Cys Tyr Ile
                20                  25                  30

Thr Trp Ser Pro Cys Pro Thr Cys Ala Leu Glu Leu Val Ala Phe Thr
            35                  40                  45

Arg Asp Tyr Pro Arg Leu Ser Leu Gln Ile Phe Ala Ser Arg Leu Tyr
        50                  55                  60

Phe His Trp Arg Arg Ser Ile Gln Gly Leu
65                  70                  75
```

<210> SEQ ID NO 86
<211> LENGTH: 75
<212> TYPE: PRT
<213> ORGANISM: Artificial Sequence
<220> FEATURE:
<223> OTHER INFORMATION: Synthetic

<400> SEQUENCE: 86

```
Asn Lys Lys Lys Arg His Ala Glu Ile Arg Phe Ile Asp Lys Ile Asn
1               5                   10                  15

Ser Leu Gly Leu Asp Gln Asp Gln Ser Tyr Glu Ile Thr Cys Tyr Val
                20                  25                  30

Thr Trp Ser Pro Cys Ala Thr Cys Ala Cys Lys Leu Ile Lys Phe Thr
            35                  40                  45

Arg Lys Phe Pro Asn Leu Ser Leu Arg Ile Phe Val Ser Arg Leu Tyr
        50                  55                  60

Tyr His Trp Phe Arg Gln Asn Gln Gly Leu
65                  70                  75
```

<210> SEQ ID NO 87
<211> LENGTH: 74
<212> TYPE: PRT
<213> ORGANISM: Artificial Sequence
<220> FEATURE:
<223> OTHER INFORMATION: Synthetic

<400> SEQUENCE: 87

```
Lys Lys Lys Arg His Ala Glu Ile Arg Phe Ile Asp Ser Ile Arg Ala
1               5                   10                  15

Leu Gln Leu Asp Gln Ser Gln Arg Phe Glu Ile Thr Cys Tyr Leu Thr
                20                  25                  30

Trp Ser Pro Cys Pro Thr Cys Ala Lys Glu Leu Ala Met Phe Val Gln
            35                  40                  45

Asp His Pro His Ile Ser Leu Arg Leu Phe Ala Ser Arg Leu Tyr Phe
        50                  55                  60

His Trp Arg Trp Lys Tyr Gln Glu Gly Leu
65                  70
```

<210> SEQ ID NO 88
<211> LENGTH: 74
<212> TYPE: PRT

<213> ORGANISM: Artificial Sequence
<220> FEATURE:
<223> OTHER INFORMATION: Synthetic

<400> SEQUENCE: 88

```
Lys Lys Lys Arg His Ala Glu Ile Arg Phe Ile Asp Asn Ile Lys Ala
1               5                   10                  15

Leu Arg Leu Asp Thr Ser Gln Arg Phe Glu Ile Thr Cys Tyr Val Thr
            20                  25                  30

Trp Ser Pro Cys Pro Thr Cys Ala Lys Glu Leu Val Ala Phe Val Arg
            35                  40                  45

Asp His Arg His Ile Ser Leu Arg Leu Phe Ala Ser Arg Leu Tyr Phe
        50                  55                  60

His Trp Leu Arg Glu Asn Lys Lys Gly Leu
65                  70
```

<210> SEQ ID NO 89
<211> LENGTH: 75
<212> TYPE: PRT
<213> ORGANISM: Artificial Sequence
<220> FEATURE:
<223> OTHER INFORMATION: Synthetic

<400> SEQUENCE: 89

```
Asn Lys Lys Arg His Ala Glu Ile Arg Phe Ile Asp Lys Ile Arg
1               5                   10                  15

Ser Leu Gln Arg Asp Ser Ser Gln Thr Phe Glu Ile Thr Cys Tyr Val
            20                  25                  30

Thr Trp Ser Pro Cys Phe Thr Cys Ala Glu Glu Leu Val Ala Phe Val
            35                  40                  45

Arg Asp His Pro His Val Arg Leu Arg Leu Phe Ala Ser Arg Leu Tyr
        50                  55                  60

Phe His Trp Leu Arg Lys Tyr Gln Glu Gly Leu
65                  70                  75
```

<210> SEQ ID NO 90
<211> LENGTH: 75
<212> TYPE: PRT
<213> ORGANISM: Artificial Sequence
<220> FEATURE:
<223> OTHER INFORMATION: Synthetic

<400> SEQUENCE: 90

```
Asn Lys Lys Arg His Ala Glu Ile Cys Phe Ile Asp Lys Ile Lys
1               5                   10                  15

Ser Leu Thr Arg Asp Thr Ser Gln Arg Phe Glu Ile Ile Cys Tyr Ile
            20                  25                  30

Thr Trp Ser Pro Cys Pro Phe Cys Ala Glu Glu Leu Val Ala Phe Val
            35                  40                  45

Lys Asp Asn Pro His Leu Ser Leu Arg Ile Phe Ala Ser Arg Leu Tyr
        50                  55                  60

Val His Trp Arg Trp Lys Tyr Gln Gln Gly Leu
65                  70                  75
```

<210> SEQ ID NO 91
<211> LENGTH: 75
<212> TYPE: PRT
<213> ORGANISM: Artificial Sequence
<220> FEATURE:
<223> OTHER INFORMATION: Synthetic -continued

<400> SEQUENCE: 91

Asn Lys Lys Lys Arg His Ala Glu Ile Cys Phe Ile Asp Lys Ile Lys
1               5                   10                  15

Ser Leu Thr Arg Asp Thr Ser Gln Arg Phe Glu Ile Ile Cys Tyr Ile
            20                  25                  30

Thr Trp Ser Pro Cys Pro Phe Cys Ala Glu Glu Leu Val Ala Phe Val
            35                  40                  45

Lys Asp Asn Pro His Leu Ser Leu Arg Ile Phe Ala Ser Arg Leu Tyr
    50                  55                  60

Val His Trp Arg Trp Lys Tyr Gln Gln Gly Leu
65                  70                  75

<210> SEQ ID NO 92
<211> LENGTH: 75
<212> TYPE: PRT
<213> ORGANISM: Artificial Sequence
<220> FEATURE:
<223> OTHER INFORMATION: Synthetic

<400> SEQUENCE: 92

Asn Lys Lys His Arg His Ala Glu Val Arg Phe Ile Ala Lys Ile Arg
1               5                   10                  15

Ser Met Ser Leu Asp Leu Asp Gln Lys His Gln Leu Thr Cys Tyr Leu
            20                  25                  30

Thr Trp Ser Pro Cys Pro Ser Cys Ala Gln Glu Leu Val Thr Phe Met
            35                  40                  45

Ala Glu Ser Arg His Leu Asn Leu Gln Val Phe Val Ser Arg Leu Tyr
    50                  55                  60

Phe His Trp Gln Arg Asp Phe Gln Gln Gly Leu
65                  70                  75

<210> SEQ ID NO 93
<211> LENGTH: 110
<212> TYPE: PRT
<213> ORGANISM: Artificial Sequence
<220> FEATURE:
<223> OTHER INFORMATION: Synthetic

<400> SEQUENCE: 93

Gly Arg Ser Tyr Asn Trp Leu Cys Tyr Glu Val Lys Ile Lys Arg Gly
1               5                   10                  15

Arg Ser Asn Leu Leu Trp Asn Thr Gly Val Phe Arg Gly Gln Met Tyr
            20                  25                  30

Ser Gln Pro Glu His His Ala Glu Met Cys Phe Leu Ser Trp Phe Cys
            35                  40                  45

Gly Asn Gln Leu Pro Ala Tyr Lys Cys Phe Gln Ile Thr Trp Phe Val
    50                  55                  60

Ser Trp Thr Pro Cys Pro Asp Cys Val Ala Lys Leu Ala Glu Phe Leu
65                  70                  75                  80

Ala Glu Tyr Pro Asn Val Thr Leu Thr Ile Ser Thr Ala Arg Leu Tyr
                85                  90                  95

Tyr Tyr Trp Glu Arg Asp Tyr Arg Arg Ala Leu Cys Arg Leu
                100                 105                 110

<210> SEQ ID NO 94
<211> LENGTH: 110
<212> TYPE: PRT
<213> ORGANISM: Artificial Sequence
<220> FEATURE:

<223> OTHER INFORMATION: Synthetic

<400> SEQUENCE: 94

Gly Arg Ser Tyr Thr Trp Leu Cys Tyr Glu Val Lys Ile Arg Arg Gly
1               5                   10                  15

His Ser Asn Leu Leu Trp Asp Thr Gly Val Phe Arg Gly Gln Met Tyr
            20                  25                  30

Ser Gln Pro Glu His His Ala Glu Met Tyr Phe Leu Ser Trp Phe Cys
        35                  40                  45

Gly Asn Gln Leu Pro Ala Tyr Lys Cys Phe Gln Ile Thr Trp Phe Val
    50                  55                  60

Ser Trp Thr Pro Cys Pro Asp Cys Val Ala Lys Leu Ala Glu Phe Leu
65                  70                  75                  80

Ala Glu His Pro Asn Val Thr Leu Thr Ile Ser Ala Ala Arg Leu Tyr
            85                  90                  95

Tyr Tyr Trp Glu Arg Asp Tyr Arg Arg Ala Leu Cys Arg Leu
            100                 105                 110

<210> SEQ ID NO 95
<211> LENGTH: 110
<212> TYPE: PRT
<213> ORGANISM: Artificial Sequence
<220> FEATURE:
<223> OTHER INFORMATION: Synthetic

<400> SEQUENCE: 95

Gly Arg Ser Tyr Thr Trp Leu Cys Tyr Glu Val Lys Ile Arg Arg Gly
1               5                   10                  15

His Ser Asn Leu Leu Trp Asp Thr Gly Val Phe Arg Gly Gln Met Tyr
            20                  25                  30

Ser Gln Pro Glu His His Ala Glu Met Cys Phe Leu Ser Trp Phe Cys
        35                  40                  45

Gly Asn Gln Leu Ser Ala Tyr Lys Cys Phe Gln Ile Thr Trp Phe Val
    50                  55                  60

Ser Trp Thr Pro Cys Pro Asp Cys Val Ala Lys Leu Ala Lys Phe Leu
65                  70                  75                  80

Ala Glu His Pro Asn Val Thr Leu Thr Ile Ser Ala Ala Arg Leu Tyr
            85                  90                  95

Tyr Tyr Trp Glu Arg Asp Tyr Arg Arg Ala Leu Cys Arg Leu
            100                 105                 110

<210> SEQ ID NO 96
<211> LENGTH: 98
<212> TYPE: PRT
<213> ORGANISM: Artificial Sequence
<220> FEATURE:
<223> OTHER INFORMATION: Synthetic

<400> SEQUENCE: 96

Arg Asn Thr Val Trp Leu Cys Tyr Glu Val Lys Thr Lys Gly Pro Ser
1               5                   10                  15

Arg Pro Pro Leu Asp Ala Lys Ile Phe Arg Gly Gln Val Tyr Phe Glu
            20                  25                  30

Pro Gln Tyr His Ala Glu Met Cys Phe Leu Ser Trp Phe Cys Gly Asn
        35                  40                  45

Gln Leu Pro Ala Tyr Lys Cys Phe Gln Ile Thr Trp Phe Val Ser Trp
    50                  55                  60

Thr Pro Cys Pro Asp Cys Val Ala Lys Leu Ala Glu Phe Leu Ala Glu

His Pro Asn Val Thr Leu Thr Ile Ser Ala Ala Arg Leu Tyr Tyr Tyr
                85                  90                  95

Trp Glu

<210> SEQ ID NO 97
<211> LENGTH: 108
<212> TYPE: PRT
<213> ORGANISM: Artificial Sequence
<220> FEATURE:
<223> OTHER INFORMATION: Synthetic

<400> SEQUENCE: 97

Arg Asn Thr Val Trp Leu Cys Tyr Glu Val Lys Thr Lys Gly Pro Ser
1               5                   10                  15

Arg Pro Arg Leu Asp Thr Lys Ile Phe Arg Gly Gln Val Tyr Phe Glu
            20                  25                  30

Pro Gln Tyr His Ala Glu Met Cys Phe Leu Ser Trp Phe Cys Gly Asn
        35                  40                  45

Gln Leu Pro Ala Tyr Lys Cys Phe Gln Ile Thr Trp Phe Val Ser Trp
    50                  55                  60

Thr Pro Cys Pro Asp Cys Val Ala Lys Leu Ala Glu Phe Leu Ala Glu
65                  70                  75                  80

His Pro Asn Val Thr Leu Thr Ile Ser Ala Ala Arg Leu Tyr Tyr Tyr
                85                  90                  95

Trp Glu Arg Asp Tyr Arg Arg Ala Leu Cys Arg Leu
            100                 105

<210> SEQ ID NO 98
<211> LENGTH: 108
<212> TYPE: PRT
<213> ORGANISM: Artificial Sequence
<220> FEATURE:
<223> OTHER INFORMATION: Synthetic

<400> SEQUENCE: 98

Arg Asn Thr Val Trp Leu Cys Tyr Glu Val Lys Thr Lys Gly Pro Ser
1               5                   10                  15

Arg Pro Arg Leu Asp Ala Lys Ile Phe Arg Gly Gln Val Tyr Ser Gln
            20                  25                  30

Pro Glu His His Ala Glu Met Cys Phe Leu Ser Trp Phe Cys Gly Asn
        35                  40                  45

Gln Leu Pro Ala Tyr Lys Cys Phe Gln Ile Thr Trp Phe Val Ser Trp
    50                  55                  60

Thr Pro Cys Pro Asp Cys Val Ala Lys Leu Ala Glu Phe Leu Ala Glu
65                  70                  75                  80

His Pro Asn Val Thr Leu Thr Ile Ser Ala Ala Arg Leu Tyr Tyr Tyr
                85                  90                  95

Trp Glu Arg Asp Tyr Arg Arg Ala Leu Cys Arg Leu
            100                 105

<210> SEQ ID NO 99
<211> LENGTH: 108
<212> TYPE: PRT
<213> ORGANISM: Artificial Sequence
<220> FEATURE:
<223> OTHER INFORMATION: Synthetic

<400> SEQUENCE: 99

Arg Asn Thr Val Trp Leu Cys Tyr Glu Val Lys Thr Arg Gly Pro Ser
1               5                   10                  15

Met Pro Thr Trp Gly Thr Lys Ile Phe Arg Gly Gln Val Cys Phe Glu
            20                  25                  30

Pro Gln Tyr His Ala Glu Met Cys Phe Leu Ser Arg Phe Cys Gly Asn
                35                  40                  45

Gln Leu Pro Ala Tyr Lys Arg Phe Gln Ile Thr Trp Phe Val Ser Trp
        50                  55                  60

Thr Pro Cys Pro Asp Cys Val Ala Lys Val Ala Glu Phe Leu Ala Glu
65                  70                  75                  80

His Pro Asn Val Thr Leu Thr Ile Ser Ala Ala Arg Leu Tyr Tyr Tyr
                85                  90                  95

Trp Glu Thr Asp Tyr Arg Arg Ala Leu Cys Arg Leu
                100                 105

<210> SEQ ID NO 100
<211> LENGTH: 108
<212> TYPE: PRT
<213> ORGANISM: Artificial Sequence
<220> FEATURE:
<223> OTHER INFORMATION: Synthetic

<400> SEQUENCE: 100

Arg Asn Thr Val Trp Leu Cys Tyr Glu Val Lys Thr Arg Gly Pro Ser
1               5                   10                  15

Met Pro Thr Trp Gly Thr Lys Ile Phe Arg Gly Gln Val Cys Phe Glu
            20                  25                  30

Pro Gln Tyr His Ala Glu Met Cys Phe Leu Ser Arg Phe Cys Gly Asn
                35                  40                  45

Gln Leu Pro Ala Tyr Lys Arg Phe Gln Ile Thr Trp Phe Val Ser Trp
        50                  55                  60

Thr Pro Cys Pro Asp Cys Val Ala Lys Val Ala Glu Phe Leu Ala Glu
65                  70                  75                  80

His Pro Asn Val Thr Leu Thr Ile Ser Ala Ala Arg Leu Tyr Tyr Tyr
                85                  90                  95

Trp Glu Thr Asp Tyr Arg Arg Ala Leu Cys Arg Leu
                100                 105

<210> SEQ ID NO 101
<211> LENGTH: 108
<212> TYPE: PRT
<213> ORGANISM: Artificial Sequence
<220> FEATURE:
<223> OTHER INFORMATION: Synthetic

<400> SEQUENCE: 101

Arg Asn Thr Val Trp Leu Cys Tyr Glu Val Lys Thr Arg Gly Pro Ser
1               5                   10                  15

Met Pro Thr Trp Gly Ala Lys Ile Phe Arg Gly Gln Val Tyr Phe Glu
            20                  25                  30

Pro Gln Tyr His Ala Glu Met Cys Phe Leu Ser Trp Phe Cys Gly Asn
                35                  40                  45

Gln Leu Pro Ala Tyr Lys Arg Phe Gln Ile Thr Trp Phe Val Ser Trp
        50                  55                  60

Thr Pro Cys Pro Asp Cys Val Ala Lys Val Ala Glu Phe Leu Ala Glu
65                  70                  75                  80

His Pro Asn Val Thr Leu Thr Ile Ser Ala Ala Arg Leu Tyr Tyr Tyr
                85                  90                  95

Trp Glu Thr Asp Tyr Arg Arg Ala Leu Cys Arg Leu
            100                 105

<210> SEQ ID NO 102
<211> LENGTH: 101
<212> TYPE: PRT
<213> ORGANISM: Artificial Sequence
<220> FEATURE:
<223> OTHER INFORMATION: Synthetic

<400> SEQUENCE: 102

Arg Asn Thr Val Trp Leu Cys Tyr Lys Val Lys Thr Arg Gly Pro Ser
1               5                   10                  15

Met Pro Thr Trp Gly Thr Lys Ile Phe Arg Gly Gln Val Tyr Phe Gln
            20                  25                  30

Pro Gln Tyr His Ala Glu Met Cys Phe Leu Ser Trp Phe Cys Gly Asn
        35                  40                  45

Gln Leu Pro Ala Tyr Lys Arg Phe Gln Ile Thr Trp Phe Val Ser Trp
    50                  55                  60

Thr Pro Cys Pro Asp Cys Val Val Lys Val Ala Glu Phe Leu Ala Glu
65                  70                  75                  80

His Pro Asn Val Thr Leu Thr Ile Ser Ala Ala Arg Leu Tyr Tyr Tyr
                85                  90                  95

Trp Glu Thr Asp Tyr
            100

<210> SEQ ID NO 103
<211> LENGTH: 108
<212> TYPE: PRT
<213> ORGANISM: Artificial Sequence
<220> FEATURE:
<223> OTHER INFORMATION: Synthetic

<400> SEQUENCE: 103

Arg Asn Thr Val Trp Leu Cys Tyr Glu Val Lys Thr Arg Gly Pro Ser
1               5                   10                  15

Met Pro Thr Trp Asp Thr Lys Ile Phe Arg Gly Gln Val Tyr Ser Lys
            20                  25                  30

Pro Glu His His Ala Glu Met Cys Phe Leu Ser Arg Phe Cys Gly Asn
        35                  40                  45

Gln Leu Pro Ala Tyr Lys Arg Phe Gln Ile Thr Trp Phe Val Ser Trp
    50                  55                  60

Thr Pro Cys Pro Asp Cys Val Ala Lys Val Ala Glu Phe Leu Ala Glu
65                  70                  75                  80

His Pro Asn Val Thr Leu Thr Ile Ser Ala Ala Arg Leu Tyr Tyr Tyr
                85                  90                  95

Trp Glu Thr Asp Tyr Arg Arg Ala Leu Cys Arg Leu
            100                 105

<210> SEQ ID NO 104
<211> LENGTH: 108
<212> TYPE: PRT
<213> ORGANISM: Artificial Sequence
<220> FEATURE:
<223> OTHER INFORMATION: Synthetic

<400> SEQUENCE: 104

Arg Asn Thr Val Trp Leu Cys Tyr Glu Val Lys Thr Arg Gly Pro Ser
1               5                   10                  15

```
Met Pro Thr Trp Gly Thr Lys Ile Phe Arg Gly Gln Val Tyr Phe Gln
             20                  25                  30

Pro Gln Tyr His Ala Glu Met Cys Phe Leu Ser Arg Phe Cys Gly Asn
             35                  40                  45

Gln Leu Pro Ala Tyr Lys Arg Phe Gln Ile Thr Trp Phe Val Ser Trp
     50                  55                  60

Asn Pro Cys Pro Asp Cys Val Ala Lys Val Ile Glu Phe Leu Ala Glu
 65                  70                  75                  80

His Pro Asn Val Thr Leu Thr Ile Ser Ala Ala Arg Leu Tyr Tyr Tyr
                 85                  90                  95

Trp Gly Arg Asp Trp Arg Arg Ala Leu Arg Arg Leu
                100                 105
```

<210> SEQ ID NO 105
<211> LENGTH: 110
<212> TYPE: PRT
<213> ORGANISM: Artificial Sequence
<220> FEATURE:
<223> OTHER INFORMATION: Synthetic

<400> SEQUENCE: 105

```
Gly Arg Ser Tyr Thr Trp Leu Cys Tyr Glu Val Lys Ile Arg Lys Asp
  1               5                  10                  15

Pro Ser Lys Leu Pro Trp Tyr Thr Gly Val Phe Arg Gly Gln Val Tyr
             20                  25                  30

Ser Lys Pro Glu His His Ala Glu Met Cys Phe Leu Ser Arg Phe Cys
             35                  40                  45

Gly Asn Gln Leu Pro Ala Tyr Lys Arg Phe Gln Ile Thr Trp Phe Val
     50                  55                  60

Ser Trp Asn Pro Cys Pro Asp Cys Val Ala Lys Val Ile Glu Phe Leu
 65                  70                  75                  80

Ala Glu His Pro Asn Val Thr Leu Thr Ile Ser Ala Ala Arg Leu Tyr
                 85                  90                  95

Tyr Tyr Trp Ser Arg Asp Trp Gln Arg Ala Leu Cys Arg Leu
                100                 105                 110
```

<210> SEQ ID NO 106
<211> LENGTH: 110
<212> TYPE: PRT
<213> ORGANISM: Artificial Sequence
<220> FEATURE:
<223> OTHER INFORMATION: Synthetic

<400> SEQUENCE: 106

```
Gly Arg Ser Tyr Thr Trp Leu Cys Tyr Glu Val Lys Ile Arg Lys Asp
  1               5                  10                  15

Pro Ser Lys Leu Pro Trp Asp Thr Gly Val Phe Arg Gly Gln Val Tyr
             20                  25                  30

Ser Lys Pro Glu His His Ala Glu Met Cys Phe Leu Ser Arg Phe Cys
             35                  40                  45

Gly Asn Gln Leu Pro Ala Tyr Lys Arg Phe Gln Ile Thr Trp Phe Val
     50                  55                  60

Ser Trp Asn Pro Cys Pro Asp Cys Val Ala Lys Val Ile Glu Phe Leu
 65                  70                  75                  80

Ala Glu His Pro Asn Val Thr Leu Thr Ile Ser Thr Ala Arg Leu Tyr
                 85                  90                  95

Tyr Tyr Trp Gly Arg Asp Trp Gln Arg Ala Leu Cys Arg Leu
                100                 105                 110
```

<210> SEQ ID NO 107
<211> LENGTH: 110
<212> TYPE: PRT
<213> ORGANISM: Artificial Sequence
<220> FEATURE:
<223> OTHER INFORMATION: Synthetic

<400> SEQUENCE: 107

Gly Arg Ser Tyr Thr Trp Leu Cys Tyr Glu Val Lys Ile Arg Lys Asp
1               5                   10                  15

Pro Ser Lys Leu Pro Trp Asp Thr Gly Val Phe Arg Gly Gln Val Tyr
            20                  25                  30

Ser Lys Pro Glu His His Ala Glu Met Cys Phe Leu Ser Arg Phe Cys
        35                  40                  45

Gly Asn Gln Leu Pro Ala Tyr Lys Arg Phe Gln Ile Thr Trp Phe Val
    50                  55                  60

Ser Trp Asn Pro Cys Pro Asp Cys Val Ala Lys Val Ile Glu Phe Leu
65                  70                  75                  80

Ala Glu His Pro Asn Val Thr Leu Thr Ile Ser Thr Ala Arg Leu Tyr
                85                  90                  95

Tyr Tyr Trp Gly Arg Asp Trp Gln Arg Ala Leu Cys Arg Leu
            100                 105                 110

<210> SEQ ID NO 108
<211> LENGTH: 110
<212> TYPE: PRT
<213> ORGANISM: Artificial Sequence
<220> FEATURE:
<223> OTHER INFORMATION: Synthetic

<400> SEQUENCE: 108

Gly Arg Ser Tyr Thr Trp Leu Cys Tyr Glu Val Lys Ile Arg Lys Asp
1               5                   10                  15

Pro Ser Lys Leu Pro Trp Asp Thr Gly Val Phe Arg Gly Gln Val Tyr
            20                  25                  30

Ser Lys Pro Glu His His Ala Glu Met Cys Phe Leu Ser Arg Phe Cys
        35                  40                  45

Gly Asn Gln Leu Pro Ala Tyr Lys Arg Phe Gln Ile Thr Trp Phe Val
    50                  55                  60

Ser Trp Asn Pro Cys Pro Asp Cys Val Val Lys Val Ile Glu Phe Leu
65                  70                  75                  80

Ala Glu His Pro Asn Val Thr Leu Thr Ile Ser Thr Ala Arg Leu Tyr
                85                  90                  95

Tyr Tyr Trp Gly Arg Asp Trp Gln Arg Ala Leu Cys Arg Leu
            100                 105                 110

<210> SEQ ID NO 109
<211> LENGTH: 110
<212> TYPE: PRT
<213> ORGANISM: Artificial Sequence
<220> FEATURE:
<223> OTHER INFORMATION: Synthetic

<400> SEQUENCE: 109

Gly Arg Ser Tyr Thr Trp Leu Cys Tyr Glu Val Lys Ile Arg Lys Asp
1               5                   10                  15

Pro Ser Lys Leu Pro Trp Tyr Thr Gly Val Phe Arg Gly Gln Val Tyr
            20                  25                  30

```
Ser Lys Pro Glu His His Ala Glu Met Cys Phe Leu Ser Arg Phe Cys
         35                  40                  45

Gly Asn Gln Leu Pro Ala Tyr Lys Arg Phe Gln Ile Thr Trp Phe Val
 50                  55                  60

Ser Trp Asn Pro Cys Pro Asp Cys Val Ala Lys Val Ile Glu Phe Leu
 65                  70                  75                  80

Ala Glu His Pro Asn Val Thr Leu Thr Ile Phe Thr Ala Arg Leu Tyr
                 85                  90                  95

Tyr Tyr Trp Gly Arg Asp Trp Gln Arg Ala Leu Cys Arg Leu
                100                 105                 110

<210> SEQ ID NO 110
<211> LENGTH: 110
<212> TYPE: PRT
<213> ORGANISM: Artificial Sequence
<220> FEATURE:
<223> OTHER INFORMATION: Synthetic

<400> SEQUENCE: 110

Gly Arg Ser Tyr Thr Trp Leu Cys Tyr Glu Val Lys Ile Arg Lys Asp
 1               5                  10                  15

Pro Ser Lys Leu Pro Trp Asp Thr Gly Val Phe Arg Gly Gln Val Tyr
                 20                  25                  30

Ser Lys Pro Glu His His Ala Glu Met Cys Phe Leu Ser Arg Phe Cys
         35                  40                  45

Gly Asn Gln Leu Pro Ala Tyr Lys Arg Phe Gln Ile Thr Trp Phe Val
 50                  55                  60

Ser Trp Asn Pro Cys Pro Asp Cys Val Ala Lys Val Thr Glu Phe Leu
 65                  70                  75                  80

Ala Glu His Pro Asn Val Thr Leu Thr Ile Ser Thr Ala Arg Leu Tyr
                 85                  90                  95

Tyr Tyr Trp Gly Arg Asp Trp Gln Arg Ala Leu Cys Arg Leu
                100                 105                 110

<210> SEQ ID NO 111
<211> LENGTH: 110
<212> TYPE: PRT
<213> ORGANISM: Artificial Sequence
<220> FEATURE:
<223> OTHER INFORMATION: Synthetic

<400> SEQUENCE: 111

Gly Arg Ser Tyr Thr Trp Leu Cys Tyr Glu Val Lys Ile Arg Lys Asp
 1               5                  10                  15

Pro Ser Lys Leu Pro Trp Asp Thr Gly Val Phe Arg Gly Gln Val Tyr
                 20                  25                  30

Ser Glu Pro Glu His His Ala Glu Met Tyr Phe Leu Ser Trp Phe Cys
         35                  40                  45

Gly Asn Gln Leu Pro Ala Tyr Lys Arg Phe Gln Ile Thr Trp Phe Val
 50                  55                  60

Ser Trp Thr Pro Cys Pro Asp Cys Val Ala Lys Val Ala Glu Phe Leu
 65                  70                  75                  80

Thr Glu His Pro Asn Val Thr Leu Thr Ile Ser Ala Ala Arg Leu Tyr
                 85                  90                  95

Tyr Tyr Arg Gly Arg Asp Trp Arg Arg Ala Leu Cys Arg Leu
                100                 105                 110

<210> SEQ ID NO 112
```

<211> LENGTH: 110
<212> TYPE: PRT
<213> ORGANISM: Artificial Sequence
<220> FEATURE:
<223> OTHER INFORMATION: Synthetic

<400> SEQUENCE: 112

Gly Arg Ser Tyr Thr Trp Leu Cys Tyr Glu Val Lys Ile Arg Lys Asp
1               5                   10                  15

Pro Ser Lys Leu Pro Trp Asp Thr Gly Val Phe Arg Gly Gln Val Tyr
            20                  25                  30

Ser Glu Pro Glu His His Ala Glu Met Tyr Phe Leu Ser Trp Phe Cys
        35                  40                  45

Gly Asn Gln Leu Pro Ala Tyr Lys Arg Phe Gln Ile Thr Trp Phe Val
    50                  55                  60

Ser Trp Thr Pro Cys Pro Asp Cys Val Ala Lys Val Ala Glu Phe Leu
65                  70                  75                  80

Thr Glu His Pro Asn Val Thr Leu Thr Ile Ser Ala Ala Arg Leu Tyr
                85                  90                  95

Tyr Tyr Arg Gly Arg Asp Trp Arg Arg Ala Leu Cys Arg Leu
            100                 105                 110

<210> SEQ ID NO 113
<211> LENGTH: 110
<212> TYPE: PRT
<213> ORGANISM: Artificial Sequence
<220> FEATURE:
<223> OTHER INFORMATION: Synthetic

<400> SEQUENCE: 113

Gly Arg Ser Tyr Thr Trp Leu Cys Tyr Glu Val Lys Ile Arg Lys Asp
1               5                   10                  15

Pro Ser Lys Leu Pro Trp Asp Thr Gly Val Phe Arg Gly Gln Met Tyr
            20                  25                  30

Ser Lys Pro Glu His His Ala Glu Met Cys Phe Leu Ser Trp Phe Cys
        35                  40                  45

Gly Asn Gln Leu Pro Ala His Lys Arg Phe Gln Ile Thr Trp Phe Val
    50                  55                  60

Ser Trp Thr Pro Cys Pro Asp Cys Val Ala Lys Val Ala Glu Phe Leu
65                  70                  75                  80

Ala Glu Tyr Pro Asn Val Thr Leu Thr Ile Ser Ala Ala Arg Leu Tyr
                85                  90                  95

Tyr Tyr Trp Glu Thr Asp Tyr Arg Arg Ala Leu Cys Arg Leu
            100                 105                 110

<210> SEQ ID NO 114
<211> LENGTH: 109
<212> TYPE: PRT
<213> ORGANISM: Artificial Sequence
<220> FEATURE:
<223> OTHER INFORMATION: Synthetic

<400> SEQUENCE: 114

Arg Ser Tyr Thr Trp Leu Cys Tyr Glu Val Lys Ile Arg Lys Asp Pro
1               5                   10                  15

Ser Lys Leu Pro Trp Asp Thr Gly Val Phe Arg Gly Gln Met Tyr Phe
            20                  25                  30

Gln Pro Glu Tyr His Ala Glu Met Cys Phe Leu Ser Trp Phe Cys Gly
        35                  40                  45

```
Asn Gln Leu Pro Ala Tyr Lys Arg Phe Gln Ile Thr Trp Phe Val Ser
 50                  55                  60

Trp Thr Pro Cys Pro Asp Cys Val Ala Lys Val Ala Val Phe Leu Ala
 65                  70                  75                  80

Glu His Pro Asn Val Thr Leu Thr Ile Ser Ala Ala Arg Leu Tyr Tyr
                 85                  90                  95

Tyr Trp Glu Lys Asp Trp Gln Arg Ala Leu Cys Arg Leu
                100                 105
```

<210> SEQ ID NO 115
<211> LENGTH: 110
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (103)..(103)
<223> OTHER INFORMATION: Xaa can be any naturally occurring amino acid

<400> SEQUENCE: 115

```
Gly Arg Ser Tyr Thr Trp Leu Cys Tyr Glu Val Lys Ile Lys Lys Tyr
 1               5                  10                  15

Pro Ser Lys Leu Leu Trp Asp Thr Gly Val Phe Gln Gly Gln Val Tyr
                20                  25                  30

Phe Gln Pro Gln Tyr His Ala Glu Met Cys Phe Leu Ser Arg Phe Cys
             35                  40                  45

Gly Asn Gln Leu Pro Ala Tyr Lys Arg Phe Gln Ile Thr Trp Phe Val
 50                  55                  60

Ser Trp Asn Pro Cys Pro Asp Cys Val Ala Lys Val Thr Glu Phe Leu
 65                  70                  75                  80

Ala Glu His Pro Asn Val Thr Leu Thr Ile Ser Ala Ala Arg Leu Tyr
                 85                  90                  95

Tyr Tyr Trp Glu Lys Asp Xaa Arg Arg Ala Leu Arg Arg Leu
                100                 105                 110
```

<210> SEQ ID NO 116
<211> LENGTH: 110
<212> TYPE: PRT
<213> ORGANISM: Artificial Sequence
<220> FEATURE:
<223> OTHER INFORMATION: Synthetic

<400> SEQUENCE: 116

```
Gly Arg Ser Tyr Thr Trp Leu Cys Tyr Glu Val Lys Ile Lys Glu Asp
 1               5                  10                  15

Pro Ser Lys Leu Leu Trp Asp Thr Gly Val Phe Gln Gly Gln Val Tyr
                20                  25                  30

Phe Gln Pro Gln Tyr His Ala Glu Met Cys Phe Leu Ser Arg Phe Cys
             35                  40                  45

Gly Asn Gln Leu Pro Ala Tyr Lys Arg Phe Gln Ile Thr Trp Phe Val
 50                  55                  60

Ser Trp Asn Pro Cys Pro Asp Cys Val Ala Lys Val Thr Glu Phe Leu
 65                  70                  75                  80

Ala Glu His Pro Asn Val Thr Leu Thr Ile Ser Ala Ala Arg Leu Tyr
                 85                  90                  95

Tyr Tyr Trp Gly Arg Asp Trp Arg Arg Ala Leu Arg Arg Leu
                100                 105                 110
```

-continued

```
<210> SEQ ID NO 117
<211> LENGTH: 122
<212> TYPE: PRT
<213> ORGANISM: Artificial Sequence
<220> FEATURE:
<223> OTHER INFORMATION: Synthetic

<400> SEQUENCE: 117

Gly Arg Arg Tyr Thr Trp Leu Cys Tyr Glu Val Lys Ile Lys Lys Asp
1               5                   10                  15

Pro Ser Lys Leu Pro Trp Asp Thr Gly Val Phe Pro Gly Gln Val Arg
            20                  25                  30

Pro Lys Phe Gln Ser Asn Arg Arg Tyr Glu Val Tyr Phe Gln Pro Gln
        35                  40                  45

Tyr His Ala Glu Met Tyr Phe Leu Ser Trp Phe Cys Gly Asn Gln Leu
    50                  55                  60

Pro Ala Tyr Lys His Phe Gln Ile Thr Trp Phe Val Ser Trp Asn Pro
65                  70                  75                  80

Cys Pro Asp Cys Val Ala Lys Val Thr Glu Phe Leu Ala Glu His Arg
                85                  90                  95

Asn Val Thr Leu Thr Ile Ser Ala Ala Arg Leu Tyr Tyr Tyr Trp Gly
            100                 105                 110

Lys Asp Trp Arg Arg Ala Leu Cys Arg Leu
        115                 120

<210> SEQ ID NO 118
<211> LENGTH: 106
<212> TYPE: PRT
<213> ORGANISM: Artificial Sequence
<220> FEATURE:
<223> OTHER INFORMATION: Synthetic

<400> SEQUENCE: 118

Gly Arg Arg Tyr Thr Trp Leu Cys Tyr Glu Val Lys Ile Lys Lys Asp
1               5                   10                  15

Pro Ser Lys Leu Pro Trp Asp Thr Gly Val Phe Pro Gly Gln Pro Gln
            20                  25                  30

Tyr His Ala Glu Met Tyr Phe Leu Ser Trp Phe Cys Gly Asn Gln Leu
        35                  40                  45

Pro Ala Tyr Lys His Phe Gln Ile Thr Trp Phe Val Ser Trp Asn Pro
    50                  55                  60

Cys Pro Asp Cys Val Ala Lys Val Thr Glu Phe Leu Ala Glu His Arg
65                  70                  75                  80

Asn Val Thr Leu Thr Ile Ser Ala Ala Arg Leu Tyr Tyr Tyr Trp Gly
                85                  90                  95

Lys Asp Trp Arg Arg Ala Leu Cys Arg Leu
            100                 105

<210> SEQ ID NO 119
<211> LENGTH: 122
<212> TYPE: PRT
<213> ORGANISM: Artificial Sequence
<220> FEATURE:
<223> OTHER INFORMATION: Synthetic

<400> SEQUENCE: 119

Gly Arg Arg Tyr Thr Trp Leu Cys Tyr Glu Val Lys Ile Lys Lys Asp
1               5                   10                  15

Pro Ser Lys Leu Pro Trp Asp Thr Gly Val Phe Pro Gly Gln Val Arg
            20                  25                  30
```

Pro Lys Phe Gln Ser Asn Arg Arg Gln Lys Val Tyr Phe Gln Pro Gln
             35                  40                  45

Tyr His Ala Glu Met Tyr Phe Leu Ser Trp Phe Cys Gly Asn Gln Leu
     50                  55                  60

Pro Ala Tyr Lys His Phe Gln Ile Thr Trp Phe Val Ser Trp Asn Pro
 65                  70                  75                  80

Cys Pro Asp Cys Val Ala Lys Val Thr Glu Phe Leu Ala Glu His Arg
                 85                  90                  95

Asn Val Thr Leu Thr Ile Ser Ala Ala Arg Leu Tyr Tyr Tyr Trp Gly
                100                 105                 110

Lys Asp Trp Arg Arg Ala Leu Cys Arg Leu
            115                 120

<210> SEQ ID NO 120
<211> LENGTH: 122
<212> TYPE: PRT
<213> ORGANISM: Artificial Sequence
<220> FEATURE:
<223> OTHER INFORMATION: Synthetic

<400> SEQUENCE: 120

Gly Arg Arg Tyr Thr Trp Leu Cys Tyr Glu Val Lys Ile Lys Lys Asp
 1               5                  10                  15

Pro Ser Lys Leu Pro Trp Asp Thr Gly Val Phe Gln Gly Gln Val Arg
             20                  25                  30

Pro Lys Phe Gln Ser Asn Arg Arg Tyr Glu Val Tyr Phe Gln Pro Gln
             35                  40                  45

Tyr His Ala Glu Met Cys Phe Leu Ser Trp Phe Cys Gly Asn Gln Leu
     50                  55                  60

Pro Ala Tyr Lys His Phe Gln Ile Thr Trp Phe Val Ser Trp Asn Pro
 65                  70                  75                  80

Cys Pro Asp Cys Val Ala Lys Val Thr Glu Phe Leu Ala Glu His Pro
                 85                  90                  95

Asn Val Thr Leu Thr Ile Ser Ala Ala Arg Leu Tyr Tyr Tyr Trp Gly
                100                 105                 110

Lys Asp Trp Arg Arg Ala Leu Cys Arg Leu
            115                 120

<210> SEQ ID NO 121
<211> LENGTH: 131
<212> TYPE: PRT
<213> ORGANISM: Artificial Sequence
<220> FEATURE:
<223> OTHER INFORMATION: Synthetic

<400> SEQUENCE: 121

Gly Arg Ser Tyr Thr Trp Leu Cys Tyr Glu Val Lys Ile Arg Lys Asp
 1               5                  10                  15

Pro Ser Lys Leu Pro Trp Asp Thr Gly Val Phe Arg Gly Gln Val Arg
             20                  25                  30

Pro Lys Leu Gln Ser Asn Arg Arg Tyr Glu Leu Ser Asn Trp Glu Cys
             35                  40                  45

Arg Lys Arg Val Tyr Phe Gln Pro Gln Tyr His Ala Glu Met Tyr Phe
         50                  55                  60

Leu Ser Trp Phe Cys Gly Asn Gln Leu Pro Ala Asn Lys Arg Phe Gln
 65                  70                  75                  80

Ile Thr Trp Phe Ala Ser Trp Asn Pro Cys Pro Asp Cys Val Ala Lys

```
                85                  90                  95
Val Thr Glu Phe Leu Ala Glu His Pro Asn Val Thr Leu Thr Ile Ser
            100                 105                 110

Val Ala Arg Leu Tyr Tyr Tyr Arg Gly Lys Asp Trp Arg Arg Ala Leu
            115                 120                 125

Arg Arg Leu
        130

<210> SEQ ID NO 122
<211> LENGTH: 110
<212> TYPE: PRT
<213> ORGANISM: Artificial Sequence
<220> FEATURE:
<223> OTHER INFORMATION: Synthetic

<400> SEQUENCE: 122

Gly Arg Ser Tyr Thr Trp Leu Cys Tyr Glu Val Lys Ile Arg Lys Asp
1               5                   10                  15

Pro Ser Lys Leu Pro Trp Asp Thr Gly Val Phe Arg Gly Gln Val Tyr
            20                  25                  30

Phe Gln Pro Gln Tyr His Ala Glu Met Tyr Phe Leu Ser Trp Phe Cys
        35                  40                  45

Gly Asn Gln Leu Pro Ala Asn Lys Arg Phe Gln Ile Thr Trp Phe Ala
    50                  55                  60

Ser Trp Asn Pro Cys Pro Asp Cys Val Ala Lys Val Thr Glu Phe Leu
65                  70                  75                  80

Ala Glu His Pro Asn Val Thr Leu Thr Ile Ser Val Ala Arg Leu Tyr
                85                  90                  95

Tyr Tyr Arg Gly Lys Asp Trp Arg Arg Ala Leu Arg Arg Leu
            100                 105                 110

<210> SEQ ID NO 123
<211> LENGTH: 110
<212> TYPE: PRT
<213> ORGANISM: Artificial Sequence
<220> FEATURE:
<223> OTHER INFORMATION: Synthetic

<400> SEQUENCE: 123

Gly Arg Ser Tyr Thr Trp Leu Cys Tyr Glu Val Lys Ile Arg Lys Asp
1               5                   10                  15

Pro Ser Lys Leu Pro Trp Asp Thr Gly Val Phe Arg Asp Gln Val Tyr
            20                  25                  30

Phe Gln Pro Gln Tyr His Ala Glu Met Cys Phe Leu Ser Trp Phe Cys
        35                  40                  45

Gly Asn Gln Leu Pro Ala Asn Lys Arg Phe Gln Ile Thr Trp Phe Val
    50                  55                  60

Ser Trp Asn Pro Cys Pro Asp Cys Val Thr Lys Val Thr Glu Phe Leu
65                  70                  75                  80

Ala Glu His Pro Asn Val Thr Leu Thr Ile Ser Val Ala Arg Leu Tyr
                85                  90                  95

Tyr Tyr Arg Gly Lys Asp Trp Arg Arg Ala Leu Arg Arg Leu
            100                 105                 110

<210> SEQ ID NO 124
<211> LENGTH: 110
<212> TYPE: PRT
<213> ORGANISM: Artificial Sequence
<220> FEATURE:
```

<223> OTHER INFORMATION: Synthetic

<400> SEQUENCE: 124

Gly Arg Ser Tyr Thr Trp Leu Cys Tyr Glu Val Lys Ile Arg Lys Asp
1               5                   10                  15

Pro Ser Lys Leu Pro Trp Tyr Thr Gly Val Phe Arg Gly Gln Val Tyr
            20                  25                  30

Phe Gln Pro Gln Tyr His Ala Glu Met Cys Phe Leu Ser Trp Phe Cys
        35                  40                  45

Gly Asn Gln Leu Pro Ala Asn Lys Arg Phe Gln Ile Thr Trp Phe Val
    50                  55                  60

Ser Trp Asn Pro Cys Pro Asp Cys Val Ala Lys Val Thr Glu Phe Leu
65                  70                  75                  80

Ala Glu His Pro Asn Val Thr Leu Thr Ile Ser Val Ala Arg Leu Tyr
                85                  90                  95

Tyr Tyr Arg Gly Lys Asp Trp Arg Arg Ala Leu Arg Arg Leu
            100                 105                 110

<210> SEQ ID NO 125
<211> LENGTH: 110
<212> TYPE: PRT
<213> ORGANISM: Artificial Sequence
<220> FEATURE:
<223> OTHER INFORMATION: Synthetic

<400> SEQUENCE: 125

Gly Arg Ser Tyr Thr Trp Leu Cys Tyr Glu Val Lys Ile Arg Lys Asp
1               5                   10                  15

Pro Ser Lys Leu Pro Trp Asp Thr Gly Val Phe Arg Gly Gln Val Tyr
            20                  25                  30

Phe Gln Pro Gln Tyr His Ala Glu Met Cys Phe Leu Ser Trp Phe Cys
        35                  40                  45

Gly Asn Gln Leu Pro Ala Tyr Lys Arg Phe Gln Ile Thr Trp Phe Val
    50                  55                  60

Ser Trp Asn Pro Cys Pro Asp Cys Val Ala Lys Val Thr Glu Phe Leu
65                  70                  75                  80

Ala Glu His Pro Asn Val Thr Leu Thr Ile Ser Val Ala Arg Leu Tyr
                85                  90                  95

Tyr Tyr Arg Gly Lys Asp Trp Arg Arg Ala Leu Cys Arg Leu
            100                 105                 110

<210> SEQ ID NO 126
<211> LENGTH: 122
<212> TYPE: PRT
<213> ORGANISM: Artificial Sequence
<220> FEATURE:
<223> OTHER INFORMATION: Synthetic

<400> SEQUENCE: 126

Gly Arg Ser Tyr Thr Trp Leu Cys Tyr Glu Val Lys Ile Arg Arg Gly
1               5                   10                  15

Ser Ser Asn Leu Leu Trp Asn Thr Gly Val Phe Arg Gly Pro Val Pro
            20                  25                  30

Pro Lys Leu Gln Ser Asn His Arg Gln Glu Val Tyr Phe Gln Phe Glu
        35                  40                  45

Asn His Ala Glu Met Cys Phe Leu Ser Trp Phe Cys Gly Asn Arg Leu
    50                  55                  60

Pro Ala Asn Arg Arg Phe Gln Ile Thr Trp Phe Val Ser Trp Asn Pro

```
                65                  70                  75                  80
Cys Leu Pro Cys Val Val Lys Val Thr Lys Phe Leu Ala Glu His Pro
                85                  90                  95

Asn Val Thr Leu Thr Ile Ser Ala Ala Arg Leu Tyr Tyr Tyr Arg Asp
                100                 105                 110

Arg Glu Trp Arg Arg Val Leu Arg Arg Leu
                115                 120

<210> SEQ ID NO 127
<211> LENGTH: 122
<212> TYPE: PRT
<213> ORGANISM: Artificial Sequence
<220> FEATURE:
<223> OTHER INFORMATION: Synthetic

<400> SEQUENCE: 127

Gly Arg Ser Tyr Thr Trp Leu Cys Tyr Glu Val Lys Ile Lys Arg Gly
1               5                   10                  15

Cys Ser Asn Leu Ile Trp Asp Thr Gly Val Phe Arg Gly Pro Val Leu
                20                  25                  30

Pro Lys Leu Gln Ser Asn His Arg Gln Glu Val Tyr Phe Gln Phe Glu
                35                  40                  45

Asn His Ala Glu Met Cys Phe Phe Ser Trp Phe Cys Gly Asn Arg Leu
                50                  55                  60

Pro Ala Asn Arg Arg Phe Gln Ile Thr Trp Phe Val Ser Trp Asn Pro
65                  70                  75                  80

Cys Leu Pro Cys Val Val Lys Val Thr Lys Phe Leu Ala Glu His Pro
                85                  90                  95

Asn Val Thr Leu Thr Ile Ser Ala Ala Arg Leu Tyr Tyr Tyr Gln Asp
                100                 105                 110

Arg Glu Trp Arg Arg Val Leu Arg Arg Leu
                115                 120

<210> SEQ ID NO 128
<211> LENGTH: 122
<212> TYPE: PRT
<213> ORGANISM: Artificial Sequence
<220> FEATURE:
<223> OTHER INFORMATION: Synthetic

<400> SEQUENCE: 128

Gly Arg Ser Tyr Thr Trp Leu Cys Tyr Glu Val Lys Ile Lys Arg Gly
1               5                   10                  15

Cys Ser Asn Leu Ile Trp Asp Thr Gly Val Phe Arg Gly Pro Val Leu
                20                  25                  30

Pro Lys Leu Gln Ser Asn His Arg Gln Glu Val Tyr Phe Gln Phe Glu
                35                  40                  45

Asn His Ala Glu Met Cys Phe Phe Ser Trp Phe Cys Gly Asn Arg Leu
                50                  55                  60

Pro Ala Asn Arg Arg Phe Gln Ile Thr Trp Phe Val Ser Trp Asn Pro
65                  70                  75                  80

Cys Leu Pro Cys Val Val Lys Val Thr Lys Phe Leu Ala Glu His Pro
                85                  90                  95

Asn Val Thr Leu Thr Ile Ser Ala Ala Arg Leu Tyr Tyr Tyr Gln Asp
                100                 105                 110

Arg Glu Trp Arg Arg Val Leu Arg Arg Leu
                115                 120
```

<210> SEQ ID NO 129
<211> LENGTH: 122
<212> TYPE: PRT
<213> ORGANISM: Artificial Sequence
<220> FEATURE:
<223> OTHER INFORMATION: Synthetic

<400> SEQUENCE: 129

```
Gly Arg Ser Tyr Thr Trp Leu Cys Tyr Glu Val Lys Ile Lys Arg Gly
1               5                   10                  15

Arg Ser Asn Leu Leu Trp Asp Thr Gly Val Phe Arg Gly Pro Val Leu
            20                  25                  30

Pro Lys Arg Gln Ser Asn His Arg Gln Glu Val Tyr Phe Arg Phe Glu
        35                  40                  45

Asn His Ala Glu Met Cys Phe Leu Ser Trp Phe Cys Gly Asn Arg Leu
    50                  55                  60

Pro Ala Asn Arg Arg Phe Gln Ile Thr Trp Phe Val Ser Trp Asn Pro
65                  70                  75                  80

Cys Leu Pro Cys Val Val Lys Val Thr Lys Phe Leu Ala Glu His Pro
                85                  90                  95

Asn Val Thr Leu Thr Ile Ser Ala Ala Arg Leu Tyr Tyr Tyr Arg Asp
            100                 105                 110

Arg Asp Trp Arg Trp Val Leu Leu Arg Leu
        115                 120
```

<210> SEQ ID NO 130
<211> LENGTH: 122
<212> TYPE: PRT
<213> ORGANISM: Artificial Sequence
<220> FEATURE:
<223> OTHER INFORMATION: Synthetic

<400> SEQUENCE: 130

```
Gly Arg Ser Tyr Thr Trp Leu Cys Tyr Glu Val Lys Ile Arg Lys Asp
1               5                   10                  15

Pro Ser Lys Leu Pro Trp Asp Lys Gly Val Phe Arg Gly Gln Val Leu
            20                  25                  30

Pro Lys Phe Gln Ser Asn His Arg Gln Glu Val Tyr Phe Gln Leu Glu
        35                  40                  45

Asn His Ala Glu Met Cys Phe Leu Ser Trp Phe Cys Gly Asn Gln Leu
    50                  55                  60

Pro Ala Asn Arg Arg Phe Gln Ile Thr Trp Phe Val Ser Trp Asn Pro
65                  70                  75                  80

Cys Leu Pro Cys Val Ala Lys Val Thr Glu Phe Leu Ala Glu His Pro
                85                  90                  95

Asn Val Thr Leu Thr Ile Ser Ala Ala Arg Leu Tyr Tyr Tyr Arg Gly
            100                 105                 110

Arg Asp Trp Arg Arg Ala Leu Arg Arg Leu
        115                 120
```

<210> SEQ ID NO 131
<211> LENGTH: 110
<212> TYPE: PRT
<213> ORGANISM: Artificial Sequence
<220> FEATURE:
<223> OTHER INFORMATION: Synthetic

<400> SEQUENCE: 131

```
Gly Lys Lys Tyr Thr Trp Leu Cys Tyr Glu Val Lys Ile Lys Lys Asp
```

```
                1               5                  10                 15
Thr Ser Lys Leu Pro Trp Asn Thr Gly Val Phe Arg Gly Gln Val Asn
                20                 25                 30

Phe Asn Pro Glu His His Ala Glu Met Tyr Phe Leu Ser Trp Phe Arg
                35                 40                 45

Gly Lys Leu Leu Pro Ala Cys Lys Arg Ser Gln Ile Thr Trp Phe Val
                50                 55                 60

Ser Trp Asn Pro Cys Leu Tyr Cys Val Ala Lys Val Ala Glu Phe Leu
65                  70                 75                 80

Ala Glu His Pro Asn Val Thr Leu Thr Val Ser Thr Ala Arg Leu Tyr
                85                 90                 95

Cys Tyr Trp Lys Lys Asp Trp Arg Arg Ala Leu Arg Lys Leu
                100                105                110

<210> SEQ ID NO 132
<211> LENGTH: 110
<212> TYPE: PRT
<213> ORGANISM: Artificial Sequence
<220> FEATURE:
<223> OTHER INFORMATION: Synthetic

<400> SEQUENCE: 132

Gly Lys Lys Tyr Thr Trp Leu Cys Tyr Glu Val Lys Ile Lys Lys Asp
1               5                  10                 15

Thr Ser Lys Leu Pro Trp Asn Thr Gly Val Phe Arg Gly Gln Val Asn
                20                 25                 30

Phe Asn Pro Glu His His Ala Glu Met Tyr Phe Leu Ser Trp Phe Arg
                35                 40                 45

Gly Lys Leu Leu Pro Ala Cys Lys Arg Ser Gln Ile Thr Trp Phe Val
                50                 55                 60

Ser Trp Asn Pro Cys Leu Tyr Cys Val Ala Lys Val Ala Glu Phe Leu
65                  70                 75                 80

Ala Glu His Pro Asn Val Thr Leu Thr Val Ser Thr Ala Arg Leu Tyr
                85                 90                 95

Cys Tyr Trp Lys Lys Asp Trp Arg Arg Ala Leu Arg Lys Leu
                100                105                110

<210> SEQ ID NO 133
<211> LENGTH: 110
<212> TYPE: PRT
<213> ORGANISM: Artificial Sequence
<220> FEATURE:
<223> OTHER INFORMATION: Synthetic

<400> SEQUENCE: 133

Gly Arg Arg Tyr Thr Trp Leu Cys Tyr Glu Val Lys Ile Met Lys Asp
1               5                  10                 15

His Ser Lys Leu Pro Trp Tyr Thr Gly Val Phe Arg Gly Gln Val Tyr
                20                 25                 30

Phe Glu Pro Gln Asn His Ala Glu Met Cys Phe Leu Ser Trp Phe Cys
                35                 40                 45

Gly Asn Gln Leu Pro Ala Tyr Glu Cys Cys Gln Ile Thr Trp Phe Val
                50                 55                 60

Ser Trp Thr Pro Cys Pro Asp Cys Val Ala Lys Val Thr Glu Phe Leu
65                  70                 75                 80

Ala Glu His Pro Asn Val Thr Leu Thr Ile Ser Ala Ala Arg Leu Tyr
                85                 90                 95
```

Tyr Tyr Arg Gly Arg Asp Trp Arg Arg Ala Leu Arg Arg Leu
       100                 105                 110

<210> SEQ ID NO 134
<211> LENGTH: 110
<212> TYPE: PRT
<213> ORGANISM: Artificial Sequence
<220> FEATURE:
<223> OTHER INFORMATION: Synthetic

<400> SEQUENCE: 134

Gly Arg Arg Tyr Thr Trp Leu Cys Tyr Glu Val Lys Ile Ser Lys Asp
1               5                   10                  15

Pro Ser Lys Leu Pro Trp Asp Thr Gly Ile Phe Arg Gly Gln Val Tyr
            20                  25                  30

Phe Glu Pro Gln Tyr His Ala Glu Met Cys Phe Leu Ser Trp Tyr Cys
        35                  40                  45

Gly Asn Gln Leu Pro Ala Tyr Lys Cys Phe Gln Ile Thr Trp Phe Val
    50                  55                  60

Ser Trp Thr Pro Cys Pro Asp Cys Val Gly Lys Val Ala Glu Phe Leu
65                  70                  75                  80

Ala Glu His Pro Asn Val Thr Leu Thr Ile Ser Ala Ala Arg Leu Tyr
                85                  90                  95

Tyr Tyr Trp Glu Thr Asp Tyr Arg Arg Ala Leu Cys Arg Leu
            100                 105                 110

<210> SEQ ID NO 135
<211> LENGTH: 121
<212> TYPE: PRT
<213> ORGANISM: Artificial Sequence
<220> FEATURE:
<223> OTHER INFORMATION: Synthetic

<400> SEQUENCE: 135

Arg Asn Tyr Thr Trp Leu Cys Tyr Glu Val Lys Ile Arg Lys Asp Pro
1               5                   10                  15

Ser Lys Leu Ala Trp Asp Thr Gly Val Phe Arg Gly Gln Val Leu Pro
            20                  25                  30

Lys Leu Gln Ser Asn His Arg Arg Glu Val Tyr Phe Glu Pro Gln Tyr
        35                  40                  45

His Ala Glu Met Cys Phe Leu Ser Trp Phe Cys Gly Asn Gln Leu Ser
    50                  55                  60

Ala Tyr Glu Arg Phe Gln Ile Thr Trp Phe Val Ser Trp Thr Pro Cys
65                  70                  75                  80

Pro Asp Cys Val Ala Met Leu Ala Glu Phe Leu Ala Glu His Pro Asn
                85                  90                  95

Val Thr Leu Thr Val Ser Ala Ala Arg Leu Tyr Tyr Tyr Trp Glu Arg
            100                 105                 110

Asp Tyr Arg Gly Ala Leu Arg Arg Leu
        115                 120

<210> SEQ ID NO 136
<211> LENGTH: 126
<212> TYPE: RNA
<213> ORGANISM: Artificial Sequence
<220> FEATURE:
<223> OTHER INFORMATION: Synthetic

<400> SEQUENCE: 136
gagguugccu ggcaccuacg guuugagagc uaggccaaca ugaggaucac ccaugucugc    60

```
agggccuagc aaguucaaau aaggcuaguc cguuaucaac uugaaaaagu ggcaccgagu    120
cggugc                                                              126

<210> SEQ ID NO 137
<211> LENGTH: 126
<212> TYPE: RNA
<213> ORGANISM: Artificial Sequence
<220> FEATURE:
<223> OTHER INFORMATION: Synthetic

<400> SEQUENCE: 137
gagacccacc ucucgcaguc guuugagagc uaggccaaca ugaggaucac ccaugucugc    60
agggccuagc aaguucaaau aaggcuaguc cguuaucaac uugaaaaagu ggcaccgagu    120
cggugc                                                              126

<210> SEQ ID NO 138
<211> LENGTH: 126
<212> TYPE: RNA
<213> ORGANISM: Artificial Sequence
<220> FEATURE:
<223> OTHER INFORMATION: Synthetic

<400> SEQUENCE: 138 gcccauguc dacuacaucg guuugagagc uaggccaaca ugaggaucac ccaugucugc    60
agggccuagc aaguucaaau aaggcuaguc cguuaucaac uugaaaaagu ggcaccgagu    120
cggugc                                                              126

<210> SEQ ID NO 139
<211> LENGTH: 126
<212> TYPE: RNA
<213> ORGANISM: Artificial Sequence
<220> FEATURE:
<223> OTHER INFORMATION: Synthetic

<400> SEQUENCE: 139
auggucaccg acuucgagaa guuugagagc uaggccaaca ugaggaucac ccaugucugc    60
agggccuagc aaguucaaau aaggcuaguc cguuaucaac uugaaaaagu ggcaccgagu    120
cggugc                                                              126

<210> SEQ ID NO 140
<211> LENGTH: 126
<212> TYPE: RNA
<213> ORGANISM: Artificial Sequence
<220> FEATURE:
<223> OTHER INFORMATION: Synthetic

<400> SEQUENCE: 140
accuuggcuu uguuccuccc guuugagagc uaggccaaca ugaggaucac ccaugucugc    60
agggccuagc aaguucaaau aaggcuaguc cguuaucaac uugaaaaagu ggcaccgagu    120
cggugc                                                              126

<210> SEQ ID NO 141
<211> LENGTH: 126
<212> TYPE: RNA
<213> ORGANISM: Artificial Sequence
<220> FEATURE:
<223> OTHER INFORMATION: Synthetic

<400> SEQUENCE: 141
```

-continued

```
ggcuuuguuc ucccaggcc guuugagagc uaggccaaca ugaggaucac ccaugucugc      60
agggccuagc aaguucaaau aaggcuaguc cguuaucaac uugaaaaagu ggcaccgagu    120
cggugc                                                               126
```

<210> SEQ ID NO 142
<211> LENGTH: 126
<212> TYPE: RNA
<213> ORGANISM: Artificial Sequence
<220> FEATURE:
<223> OTHER INFORMATION: Synthetic

<400> SEQUENCE: 142

```
guggugcugc ugcccuggc guuugagagc uaggccaaca ugaggaucac ccaugucugc      60
agggccuagc aaguucaaau aaggcuaguc cguuaucaac uugaaaaagu ggcaccgagu    120
cggugc                                                               126
```

<210> SEQ ID NO 143
<211> LENGTH: 126
<212> TYPE: RNA
<213> ORGANISM: Artificial Sequence
<220> FEATURE:
<223> OTHER INFORMATION: Synthetic

<400> SEQUENCE: 143

```
ugcugcugcc ccuggcgggu guuugagagc uaggccaaca ugaggaucac ccaugucugc      60
agggccuagc aaguucaaau aaggcuaguc cguuaucaac uugaaaaagu ggcaccgagu    120
cggugc                                                               126
```

<210> SEQ ID NO 144
<211> LENGTH: 126
<212> TYPE: RNA
<213> ORGANISM: Artificial Sequence
<220> FEATURE:
<223> OTHER INFORMATION: Synthetic

<400> SEQUENCE: 144

```
acccaccucc ucaccuuucc guuugagagc uaggccaaca ugaggaucac ccaugucugc      60
agggccuagc aaguucaaau aaggcuaguc cguuaucaac uugaaaaagu ggcaccgagu    120
cggugc                                                               126
```

<210> SEQ ID NO 145
<211> LENGTH: 126
<212> TYPE: RNA
<213> ORGANISM: Artificial Sequence
<220> FEATURE:
<223> OTHER INFORMATION: Synthetic

<400> SEQUENCE: 145

```
agcgacugca gcaccugcuu guuugagagc uaggccaaca ugaggaucac ccaugucugc      60
agggccuagc aaguucaaau aaggcuaguc cguuaucaac uugaaaaagu ggcaccgagu    120
cggugc                                                               126
```

<210> SEQ ID NO 146
<211> LENGTH: 126
<212> TYPE: RNA
<213> ORGANISM: Artificial Sequence
<220> FEATURE:
<223> OTHER INFORMATION: Synthetic

<400> SEQUENCE: 146

```
aacgcuuuug ggggugaggg guuugagagc uaggccaaca ugaggaucac ccaugucugc      60
agggccuagc aaguucaaau aaggcuaguc cguuaucaac uugaaaaagu ggcaccgagu     120
cggugc                                                               126

<210> SEQ ID NO 147
<211> LENGTH: 126
<212> TYPE: RNA
<213> ORGANISM: Artificial Sequence
<220> FEATURE:
<223> OTHER INFORMATION: Synthetic

<400> SEQUENCE: 147
ccacacagcu ccaccagcug guuugagagc uaggccaaca ugaggaucac ccaugucugc      60
agggccuagc aaguucaaau aaggcuaguc cguuaucaac uugaaaaagu ggcaccgagu     120
cggugc                                                               126

<210> SEQ ID NO 148
<211> LENGTH: 126
<212> TYPE: RNA
<213> ORGANISM: Artificial Sequence
<220> FEATURE:
<223> OTHER INFORMATION: Synthetic

<400> SEQUENCE: 148
cacugggagg uggaggaccu guuugagagc uaggccaaca ugaggaucac ccaugucugc      60
agggccuagc aaguucaaau aaggcuaguc cguuaucaac uugaaaaagu ggcaccgagu     120
cggugc                                                               126

<210> SEQ ID NO 149
<211> LENGTH: 126
<212> TYPE: RNA
<213> ORGANISM: Artificial Sequence
<220> FEATURE:
<223> OTHER INFORMATION: Synthetic

<400> SEQUENCE: 149
cccacaagcc gccugugcug guuugagagc uaggccaaca ugaggaucac ccaugucugc      60
agggccuagc aaguucaaau aaggcuaguc cguuaucaac uugaaaaagu ggcaccgagu     120
cggugc                                                               126

<210> SEQ ID NO 150
<211> LENGTH: 126
<212> TYPE: RNA
<213> ORGANISM: Artificial Sequence
<220> FEATURE:
<223> OTHER INFORMATION: Synthetic

<400> SEQUENCE: 150
aggucuggaa ugcaaaguca guuugagagc uaggccaaca ugaggaucac ccaugucugc      60
agggccuagc aaguucaaau aaggcuaguc cguuaucaac uugaaaaagu ggcaccgagu     120
cggugc                                                               126

<210> SEQ ID NO 151
<211> LENGTH: 126
<212> TYPE: RNA
<213> ORGANISM: Artificial Sequence
<220> FEATURE:
<223> OTHER INFORMATION: Synthetic
```

```
<400> SEQUENCE: 151
cucucgcagu cagagcgcac guuugagagc uagggcccug aagaagggcc cuagcaaguu    60
caaauaaggc uaguccguua ucaacuuggg cccugaagaa gggcccaagu ggcaccgagu   120
cggugc                                                             126

<210> SEQ ID NO 152
<211> LENGTH: 126
<212> TYPE: RNA
<213> ORGANISM: Artificial Sequence
<220> FEATURE:
<223> OTHER INFORMATION: Synthetic

<400> SEQUENCE: 152
caggcccagg cugcccgccg guuugagagc uagggcccug aagaagggcc cuagcaaguu    60
caaauaaggc uaguccguua ucaacuuggg cccugaagaa gggcccaagu ggcaccgagu   120
cggugc                                                             126

<210> SEQ ID NO 153
<211> LENGTH: 126
<212> TYPE: RNA
<213> ORGANISM: Artificial Sequence
<220> FEATURE:
<223> OTHER INFORMATION: Synthetic

<400> SEQUENCE: 153
ucuuugccca gagcaucccg guuugagagc uagggcccug aagaagggcc cuagcaaguu    60
caaauaaggc uaguccguua ucaacuuggg cccugaagaa gggcccaagu ggcaccgagu   120
cggugc                                                             126

<210> SEQ ID NO 154
<211> LENGTH: 126
<212> TYPE: RNA
<213> ORGANISM: Artificial Sequence
<220> FEATURE:
<223> OTHER INFORMATION: Synthetic

<400> SEQUENCE: 154
cacagacagg uaagcacggc guuugagagc uagggcccug aagaagggcc cuagcaaguu    60
caaauaaggc uaguccguua ucaacuuggg cccugaagaa gggcccaagu ggcaccgagu   120
cggugc                                                             126

<210> SEQ ID NO 155
<211> LENGTH: 126
<212> TYPE: RNA
<213> ORGANISM: Artificial Sequence
<220> FEATURE:
<223> OTHER INFORMATION: Synthetic

<400> SEQUENCE: 155
aagccagcug guccagccug guuugagagc uagggcccug aagaagggcc cuagcaaguu    60
caaauaaggc uaguccguua ucaacuuggg cccugaagaa gggcccaagu ggcaccgagu   120
cggugc                                                             126

<210> SEQ ID NO 156
<211> LENGTH: 126
<212> TYPE: RNA
<213> ORGANISM: Artificial Sequence
<220> FEATURE:
<223> OTHER INFORMATION: Synthetic
```

<400> SEQUENCE: 156 ggccagccu gugggccac guuugagagc uagggcccug aagaagggcc cuagcaaguu      60
caaauaaggc uaguccguua ucaacuuggg cccugaagaa gggcccaagu ggcaccgagu    120
cggugc                                                              126

<210> SEQ ID NO 157
<211> LENGTH: 126
<212> TYPE: RNA
<213> ORGANISM: Artificial Sequence
<220> FEATURE:
<223> OTHER INFORMATION: Synthetic

<400> SEQUENCE: 157
cgccugccag cgccuggcga guuugagagc uagggcccug aagaagggcc cuagcaaguu      60
caaauaaggc uaguccguua ucaacuuggg cccugaagaa gggcccaagu ggcaccgagu    120
cggugc                                                              126

<210> SEQ ID NO 158
<211> LENGTH: 126
<212> TYPE: RNA
<213> ORGANISM: Artificial Sequence
<220> FEATURE:
<223> OTHER INFORMATION: Synthetic

<400> SEQUENCE: 158
ugccagcgcc uggcgagggc guuugagagc uagggcccug aagaagggcc cuagcaaguu      60
caaauaaggc uaguccguua ucaacuuggg cccugaagaa gggcccaagu ggcaccgagu    120
cggugc                                                              126

<210> SEQ ID NO 159
<211> LENGTH: 126
<212> TYPE: RNA
<213> ORGANISM: Artificial Sequence
<220> FEATURE:
<223> OTHER INFORMATION: Synthetic

<400> SEQUENCE: 159
aagaccagcc ggugacccug guuugagagc uagggcccug aagaagggcc cuagcaaguu      60
caaauaaggc uaguccguua ucaacuuggg cccugaagaa gggcccaagu ggcaccgagu    120
cggugc                                                              126

<210> SEQ ID NO 160
<211> LENGTH: 126
<212> TYPE: RNA
<213> ORGANISM: Artificial Sequence
<220> FEATURE:
<223> OTHER INFORMATION: Synthetic

<400> SEQUENCE: 160
aucacaggcu gcugcccacg guuugagagc uagggcccug aagaagggcc cuagcaaguu      60
caaauaaggc uaguccguua ucaacuuggg cccugaagaa gggcccaagu ggcaccgagu    120
cggugc                                                              126

<210> SEQ ID NO 161
<211> LENGTH: 126
<212> TYPE: RNA
<213> ORGANISM: Artificial Sequence
<220> FEATURE:

<223> OTHER INFORMATION: Synthetic

<400> SEQUENCE: 161 cuacccagg ccaacugcag guuugagagc uagggcccug aagaagggcc cuagcaaguu      60
caaauaaggc uaguccguua ucaacuuggg cccugaagaa gggcccaagu ggcaccgagu    120
cggugc                                                              126

<210> SEQ ID NO 162
<211> LENGTH: 126
<212> TYPE: RNA
<213> ORGANISM: Artificial Sequence
<220> FEATURE:
<223> OTHER INFORMATION: Synthetic

<400> SEQUENCE: 162
caacagggcc acguccucac guuugagagc uagggcccug aagaagggcc cuagcaaguu      60
caaauaaggc uaguccguua ucaacuuggg cccugaagaa gggcccaagu ggcaccgagu    120
cggugc                                                              126

<210> SEQ ID NO 163
<211> LENGTH: 126
<212> TYPE: RNA
<213> ORGANISM: Artificial Sequence
<220> FEATURE:
<223> OTHER INFORMATION: Synthetic

<400> SEQUENCE: 163
aggucagccc aaccagugcg guuugagagc uagggcccug aagaagggcc cuagcaaguu      60
caaauaaggc uaguccguua ucaacuuggg cccugaagaa gggcccaagu ggcaccgagu    120
cggugc                                                              126

<210> SEQ ID NO 164
<211> LENGTH: 126
<212> TYPE: RNA
<213> ORGANISM: Artificial Sequence
<220> FEATURE:
<223> OTHER INFORMATION: Synthetic

<400> SEQUENCE: 164
ccaaccagug cgugggccac guuugagagc uagggcccug aagaagggcc cuagcaaguu      60
caaauaaggc uaguccguua ucaacuuggg cccugaagaa gggcccaagu ggcaccgagu    120
cggugc                                                              126

<210> SEQ ID NO 165
<211> LENGTH: 126
<212> TYPE: RNA
<213> ORGANISM: Artificial Sequence
<220> FEATURE:
<223> OTHER INFORMATION: Synthetic

<400> SEQUENCE: 165
ccccucagga gcaggugaag guuugagagc uagggcccug aagaagggcc cuagcaaguu      60
caaauaaggc uaguccguua ucaacuuggg cccugaagaa gggcccaagu ggcaccgagu    120
cggugc                                                              126

<210> SEQ ID NO 166
<211> LENGTH: 23
<212> TYPE: DNA
<213> ORGANISM: Artificial Sequence

```
<220> FEATURE:
<223> OTHER INFORMATION: Synthetic

<400> SEQUENCE: 166
gaggttgcct ggcacctacg tgg                                               23

<210> SEQ ID NO 167
<211> LENGTH: 23
<212> TYPE: DNA
<213> ORGANISM: Artificial Sequence
<220> FEATURE:
<223> OTHER INFORMATION: Synthetic

<400> SEQUENCE: 167
gagacccacc tctcgcagtc aga                                               23

<210> SEQ ID NO 168
<211> LENGTH: 23
<212> TYPE: DNA
<213> ORGANISM: Artificial Sequence
<220> FEATURE:
<223> OTHER INFORMATION: Synthetic

<400> SEQUENCE: 168
gccccatgtc gactacatcg agg                                               23

<210> SEQ ID NO 169
<211> LENGTH: 23
<212> TYPE: DNA
<213> ORGANISM: Artificial Sequence
<220> FEATURE:
<223> OTHER INFORMATION: Synthetic

<400> SEQUENCE: 169
atggtcaccg acttcgagaa tgt                                               23

<210> SEQ ID NO 170
<211> LENGTH: 23
<212> TYPE: DNA
<213> ORGANISM: Artificial Sequence
<220> FEATURE:
<223> OTHER INFORMATION: Synthetic

<400> SEQUENCE: 170
accttggctt tgttcctccc agg                                               23

<210> SEQ ID NO 171
<211> LENGTH: 23
<212> TYPE: DNA
<213> ORGANISM: Artificial Sequence
<220> FEATURE:
<223> OTHER INFORMATION: Synthetic

<400> SEQUENCE: 171
ggctttgttc ctcccaggcc tgg                                               23

<210> SEQ ID NO 172
<211> LENGTH: 23
<212> TYPE: DNA
<213> ORGANISM: Artificial Sequence
<220> FEATURE:
<223> OTHER INFORMATION: Synthetic

<400> SEQUENCE: 172
gtggtgctgc tgccctggc ggg                                                23
```

```
<210> SEQ ID NO 173
<211> LENGTH: 23
<212> TYPE: DNA
<213> ORGANISM: Artificial Sequence
<220> FEATURE:
<223> OTHER INFORMATION: Synthetic

<400> SEQUENCE: 173
tgctgctgcc cctggcgggt ggg                                              23

<210> SEQ ID NO 174
<211> LENGTH: 23
<212> TYPE: DNA
<213> ORGANISM: Artificial Sequence
<220> FEATURE:
<223> OTHER INFORMATION: Synthetic

<400> SEQUENCE: 174
acccacctcc tcacctttcc agg                                              23

<210> SEQ ID NO 175
<211> LENGTH: 23
<212> TYPE: DNA
<213> ORGANISM: Artificial Sequence
<220> FEATURE:
<223> OTHER INFORMATION: Synthetic

<400> SEQUENCE: 175
agcgactgca gcacctgctt tgt                                              23

<210> SEQ ID NO 176
<211> LENGTH: 23
<212> TYPE: DNA
<213> ORGANISM: Artificial Sequence
<220> FEATURE:
<223> OTHER INFORMATION: Synthetic

<400> SEQUENCE: 176
aacgcttttg ggggtgaggg tgt                                              23

<210> SEQ ID NO 177
<211> LENGTH: 23
<212> TYPE: DNA
<213> ORGANISM: Artificial Sequence
<220> FEATURE:
<223> OTHER INFORMATION: Synthetic

<400> SEQUENCE: 177
ccacacagct ccaccagctg agg                                              23

<210> SEQ ID NO 178
<211> LENGTH: 23
<212> TYPE: DNA
<213> ORGANISM: Artificial Sequence
<220> FEATURE:
<223> OTHER INFORMATION: Synthetic

<400> SEQUENCE: 178
cactgggagg tggaggacct tgg                                              23

<210> SEQ ID NO 179
<211> LENGTH: 23
<212> TYPE: DNA
<213> ORGANISM: Artificial Sequence
<220> FEATURE:
<223> OTHER INFORMATION: Synthetic
```

```
<400> SEQUENCE: 179
cccacaagcc gcctgtgctg agg                                       23

<210> SEQ ID NO 180
<211> LENGTH: 23
<212> TYPE: DNA
<213> ORGANISM: Artificial Sequence
<220> FEATURE:
<223> OTHER INFORMATION: Synthetic

<400> SEQUENCE: 180
aggtctggaa tgcaaagtca agg                                       23

<210> SEQ ID NO 181
<211> LENGTH: 23
<212> TYPE: DNA
<213> ORGANISM: Artificial Sequence
<220> FEATURE:
<223> OTHER INFORMATION: Synthetic

<400> SEQUENCE: 181
ctctcgcagt cagagcgcac tgc                                       23

<210> SEQ ID NO 182
<211> LENGTH: 23
<212> TYPE: DNA
<213> ORGANISM: Artificial Sequence
<220> FEATURE:
<223> OTHER INFORMATION: Synthetic

<400> SEQUENCE: 182
caggcccagg ctgcccgccg ggg                                       23

<210> SEQ ID NO 183
<211> LENGTH: 23
<212> TYPE: DNA
<213> ORGANISM: Artificial Sequence
<220> FEATURE:
<223> OTHER INFORMATION: Synthetic

<400> SEQUENCE: 183
tctttgccca gagcatcccg tgg                                       23

<210> SEQ ID NO 184
<211> LENGTH: 23
<212> TYPE: DNA
<213> ORGANISM: Artificial Sequence
<220> FEATURE:
<223> OTHER INFORMATION: Synthetic

<400> SEQUENCE: 184
cacagacagg taagcacggc cgt                                       23

<210> SEQ ID NO 185
<211> LENGTH: 23
<212> TYPE: DNA
<213> ORGANISM: Artificial Sequence
<220> FEATURE:
<223> OTHER INFORMATION: Synthetic

<400> SEQUENCE: 185
aagccagctg gtccagcctg tgg                                       23

<210> SEQ ID NO 186
```

```
<211> LENGTH: 23
<212> TYPE: DNA
<213> ORGANISM: Artificial Sequence
<220> FEATURE:
<223> OTHER INFORMATION: Synthetic

<400> SEQUENCE: 186
ggtccagcct gtggggccac tgg                                              23

<210> SEQ ID NO 187
<211> LENGTH: 23
<212> TYPE: DNA
<213> ORGANISM: Artificial Sequence
<220> FEATURE:
<223> OTHER INFORMATION: Synthetic

<400> SEQUENCE: 187
cgcctgccag cgcctggcga ggg                                              23

<210> SEQ ID NO 188
<211> LENGTH: 23
<212> TYPE: DNA
<213> ORGANISM: Artificial Sequence
<220> FEATURE:
<223> OTHER INFORMATION: Synthetic

<400> SEQUENCE: 188
tgccagcgcc tggcgagggc tgg                                              23

<210> SEQ ID NO 189
<211> LENGTH: 23
<212> TYPE: DNA
<213> ORGANISM: Artificial Sequence
<220> FEATURE:
<223> OTHER INFORMATION: Synthetic

<400> SEQUENCE: 189
aagaccagcc ggtgaccctg ggg                                              23

<210> SEQ ID NO 190
<211> LENGTH: 23
<212> TYPE: DNA
<213> ORGANISM: Artificial Sequence
<220> FEATURE:
<223> OTHER INFORMATION: Synthetic

<400> SEQUENCE: 190
atcacaggct gctgcccacg tgg                                              23

<210> SEQ ID NO 191
<211> LENGTH: 23
<212> TYPE: DNA
<213> ORGANISM: Artificial Sequence
<220> FEATURE:
<223> OTHER INFORMATION: Synthetic

<400> SEQUENCE: 191
ctaccccagg ccaactgcag cgt                                              23

<210> SEQ ID NO 192
<211> LENGTH: 23
<212> TYPE: DNA
<213> ORGANISM: Artificial Sequence
<220> FEATURE:
<223> OTHER INFORMATION: Synthetic

<400> SEQUENCE: 192
```

```
caacagggcc acgtcctcac agg                                              23

<210> SEQ ID NO 193
<211> LENGTH: 23
<212> TYPE: DNA
<213> ORGANISM: Artificial Sequence
<220> FEATURE:
<223> OTHER INFORMATION: Synthetic

<400> SEQUENCE: 193
aggtcagccc aaccagtgcg tgg                                              23

<210> SEQ ID NO 194
<211> LENGTH: 23
<212> TYPE: DNA
<213> ORGANISM: Artificial Sequence
<220> FEATURE:
<223> OTHER INFORMATION: Synthetic

<400> SEQUENCE: 194
ccaaccagtg cgtgggccac agg                                              23

<210> SEQ ID NO 195
<211> LENGTH: 23
<212> TYPE: DNA
<213> ORGANISM: Artificial Sequence
<220> FEATURE:
<223> OTHER INFORMATION: Synthetic

<400> SEQUENCE: 195
cccctcagga gcaggtgaag agg                                              23

<210> SEQ ID NO 196
<211> LENGTH: 76
<212> TYPE: RNA
<213> ORGANISM: Artificial Sequence
<220> FEATURE:
<223> OTHER INFORMATION: Synthetic

<400> SEQUENCE: 196
guuugagagc uagaaauagc aaguucaaau aaggcuaguc cguuaucaac uugaaaaagu      60
ggcaccgagu cggugc                                                      76

<210> SEQ ID NO 197
<211> LENGTH: 12
<212> TYPE: RNA
<213> ORGANISM: Artificial Sequence
<220> FEATURE:
<223> OTHER INFORMATION: Synthetic

<400> SEQUENCE: 197
guuuuagagc ua                                                          12

<210> SEQ ID NO 198
<211> LENGTH: 12
<212> TYPE: RNA
<213> ORGANISM: Artificial Sequence
<220> FEATURE:
<223> OTHER INFORMATION: Synthetic

<400> SEQUENCE: 198
guuugagagc ua                                                          12

<210> SEQ ID NO 199
```

```
<211> LENGTH: 14
<212> TYPE: RNA
<213> ORGANISM: Artificial Sequence
<220> FEATURE:
<223> OTHER INFORMATION: Synthetic

<400> SEQUENCE: 199
uagcaaguua aaau                                                      14

<210> SEQ ID NO 200
<211> LENGTH: 10
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(10)
<223> OTHER INFORMATION: N is absent

<400> SEQUENCE: 200 gaaannnnnn                                                           10

<210> SEQ ID NO 201
<211> LENGTH: 14
<212> TYPE: RNA
<213> ORGANISM: Artificial Sequence
<220> FEATURE:
<223> OTHER INFORMATION: Synthetic

<400> SEQUENCE: 201
aacuugaaaa agug                                                      14

<210> SEQ ID NO 202
<211> LENGTH: 15
<212> TYPE: RNA
<213> ORGANISM: Artificial Sequence
<220> FEATURE:
<223> OTHER INFORMATION: Synthetic

<400> SEQUENCE: 202
gcaccgaguc ggugc                                                     15

<210> SEQ ID NO 203
<211> LENGTH: 15
<212> TYPE: RNA
<213> ORGANISM: Artificial Sequence
<220> FEATURE:
<223> OTHER INFORMATION: Synthetic

<400> SEQUENCE: 203
gcaccgauuc ggugc                                                     15

<210> SEQ ID NO 204
<211> LENGTH: 26
<212> TYPE: DNA
<213> ORGANISM: Artificial Sequence
<220> FEATURE:
<223> OTHER INFORMATION: Synthetic

<400> SEQUENCE: 204
tctgcttctc cagccctggc ctgggt                                         26

<210> SEQ ID NO 205
<211> LENGTH: 26
<212> TYPE: DNA
<213> ORGANISM: Artificial Sequence
```

```
<220> FEATURE:
<223> OTHER INFORMATION: Synthetic

<400> SEQUENCE: 205
tctgcttctt cagccctggc ctgggt                                              26

<210> SEQ ID NO 206
<211> LENGTH: 26
<212> TYPE: DNA
<213> ORGANISM: Artificial Sequence
<220> FEATURE:
<223> OTHER INFORMATION: Synthetic

<400> SEQUENCE: 206
ccactgtagt cacacagcac cagagt                                              26

<210> SEQ ID NO 207
<211> LENGTH: 26
<212> TYPE: DNA
<213> ORGANISM: Artificial Sequence
<220> FEATURE:
<223> OTHER INFORMATION: Synthetic

<400> SEQUENCE: 207
ccactgtagt tacacagcac cagagt                                              26

<210> SEQ ID NO 208
<211> LENGTH: 26
<212> TYPE: DNA
<213> ORGANISM: Artificial Sequence
<220> FEATURE:
<223> OTHER INFORMATION: Synthetic

<400> SEQUENCE: 208
gatgttccaa tcagtacgca gagagt                                              26

<210> SEQ ID NO 209
<211> LENGTH: 23
<212> TYPE: DNA
<213> ORGANISM: Artificial Sequence
<220> FEATURE:
<223> OTHER INFORMATION: Synthetic

<400> SEQUENCE: 209
aggaccagcc tgagagagtt ggg                                                 23

<210> SEQ ID NO 210
<211> LENGTH: 23
<212> TYPE: DNA
<213> ORGANISM: Artificial Sequence
<220> FEATURE:
<223> OTHER INFORMATION: Synthetic

<400> SEQUENCE: 210
aggattagcc tgagagagtt ggg                                                 23

<210> SEQ ID NO 211
<211> LENGTH: 23
<212> TYPE: DNA
<213> ORGANISM: Artificial Sequence
<220> FEATURE:
<223> OTHER INFORMATION: Synthetic

<400> SEQUENCE: 211
gtcatcttag tcattacctg agg                                                 23
```

<210> SEQ ID NO 212
<211> LENGTH: 23
<212> TYPE: DNA
<213> ORGANISM: Artificial Sequence
<220> FEATURE:
<223> OTHER INFORMATION: Synthetic

<400> SEQUENCE: 212
gtcattttag tcattacctg agg                                              23

<210> SEQ ID NO 213
<211> LENGTH: 23
<212> TYPE: DNA
<213> ORGANISM: Artificial Sequence
<220> FEATURE:
<223> OTHER INFORMATION: Synthetic

<400> SEQUENCE: 213
ggcccagact gagcacgtga tgg                                              23

<210> SEQ ID NO 214
<211> LENGTH: 23
<212> TYPE: DNA
<213> ORGANISM: Artificial Sequence
<220> FEATURE:
<223> OTHER INFORMATION: Synthetic

<400> SEQUENCE: 214
ggcttagact gagcacgtga tgg                                              23

<210> SEQ ID NO 215
<211> LENGTH: 23
<212> TYPE: DNA
<213> ORGANISM: Artificial Sequence
<220> FEATURE:
<223> OTHER INFORMATION: Synthetic

<400> SEQUENCE: 215
aggaccagcc tgagagagtt ggg                                              23

<210> SEQ ID NO 216
<211> LENGTH: 23
<212> TYPE: DNA
<213> ORGANISM: Artificial Sequence
<220> FEATURE:
<223> OTHER INFORMATION: Synthetic

<400> SEQUENCE: 216
gtcatcttag tcattacctg agg                                              23

<210> SEQ ID NO 217
<211> LENGTH: 23
<212> TYPE: DNA
<213> ORGANISM: Artificial Sequence
<220> FEATURE:
<223> OTHER INFORMATION: Synthetic

<400> SEQUENCE: 217
gtcattttag tcattacctg agg                                              23

<210> SEQ ID NO 218
<211> LENGTH: 23
<212> TYPE: DNA
<213> ORGANISM: Artificial Sequence
<220> FEATURE:
<223> OTHER INFORMATION: Synthetic

```
<400> SEQUENCE: 218
ggctcagact gagcacgtga tgg                                              23

<210> SEQ ID NO 219
<211> LENGTH: 23
<212> TYPE: DNA
<213> ORGANISM: Artificial Sequence
<220> FEATURE:
<223> OTHER INFORMATION: Synthetic

<400> SEQUENCE: 219
ggcttagact gagcacgtga tgg                                              23

<210> SEQ ID NO 220
<211> LENGTH: 23
<212> TYPE: DNA
<213> ORGANISM: Artificial Sequence
<220> FEATURE:
<223> OTHER INFORMATION: Synthetic

<400> SEQUENCE: 220
ggaatccctt ctgcagcacc tgg                                              23

<210> SEQ ID NO 221
<211> LENGTH: 23
<212> TYPE: DNA
<213> ORGANISM: Artificial Sequence
<220> FEATURE:
<223> OTHER INFORMATION: Synthetic

<400> SEQUENCE: 221
ggaatttctt ctgcagcacc tgg                                              23

<210> SEQ ID NO 222
<211> LENGTH: 23
<212> TYPE: DNA
<213> ORGANISM: Artificial Sequence
<220> FEATURE:
<223> OTHER INFORMATION: Synthetic

<400> SEQUENCE: 222
ggaattcctt ctgcagcacc tgg                                              23

<210> SEQ ID NO 223
<211> LENGTH: 23
<212> TYPE: DNA
<213> ORGANISM: Artificial Sequence
<220> FEATURE:
<223> OTHER INFORMATION: Synthetic

<400> SEQUENCE: 223
gaacacaaag catagactgc ggg                                              23

<210> SEQ ID NO 224
<211> LENGTH: 23
<212> TYPE: DNA
<213> ORGANISM: Artificial Sequence
<220> FEATURE:
<223> OTHER INFORMATION: Synthetic

<400> SEQUENCE: 224
gaacataaag catagactgc ggg                                              23

<210> SEQ ID NO 225
```

```
<211> LENGTH: 23
<212> TYPE: DNA
<213> ORGANISM: Artificial Sequence
<220> FEATURE:
<223> OTHER INFORMATION: Synthetic

<400> SEQUENCE: 225
gaatataaag catagactgc ggg                                           23

<210> SEQ ID NO 226
<211> LENGTH: 23
<212> TYPE: DNA
<213> ORGANISM: Artificial Sequence
<220> FEATURE:
<223> OTHER INFORMATION: Synthetic

<400> SEQUENCE: 226
ggcactgcgg ctggaggtgg ggg                                           23

<210> SEQ ID NO 227
<211> LENGTH: 23
<212> TYPE: DNA
<213> ORGANISM: Artificial Sequence
<220> FEATURE:
<223> OTHER INFORMATION: Synthetic

<400> SEQUENCE: 227
ggcattgcgg ctggaggtgg ggg                                           23

<210> SEQ ID NO 228
<211> LENGTH: 23
<212> TYPE: DNA
<213> ORGANISM: Artificial Sequence
<220> FEATURE:
<223> OTHER INFORMATION: Synthetic

<400> SEQUENCE: 228
ggaatccctt ctgcagcacc tgg                                           23

<210> SEQ ID NO 229
<211> LENGTH: 23
<212> TYPE: DNA
<213> ORGANISM: Artificial Sequence
<220> FEATURE:
<223> OTHER INFORMATION: Synthetic

<400> SEQUENCE: 229
gaacacaaag catagactgc ggg                                           23

<210> SEQ ID NO 230
<211> LENGTH: 23
<212> TYPE: DNA
<213> ORGANISM: Artificial Sequence
<220> FEATURE:
<223> OTHER INFORMATION: Synthetic

<400> SEQUENCE: 230
ggcactgcgg ctggaggtgg ggg                                           23

<210> SEQ ID NO 231
<211> LENGTH: 26
<212> TYPE: DNA
<213> ORGANISM: Artificial Sequence
<220> FEATURE:
<223> OTHER INFORMATION: Synthetic

<400> SEQUENCE: 231
```
tctgcttctc cagccctggc ctgggt                                      26

<210> SEQ ID NO 232
<211> LENGTH: 23
<212> TYPE: DNA
<213> ORGANISM: Artificial Sequence
<220> FEATURE:
<223> OTHER INFORMATION: Synthetic

<400> SEQUENCE: 232
aggaccagcc tgagagagtt ggg                                         23

<210> SEQ ID NO 233
<211> LENGTH: 26
<212> TYPE: DNA
<213> ORGANISM: Artificial Sequence
<220> FEATURE:
<223> OTHER INFORMATION: Synthetic

<400> SEQUENCE: 233
acgtgctcag tctgggcccc aaggat                                      26

<210> SEQ ID NO 234
<211> LENGTH: 23
<212> TYPE: DNA
<213> ORGANISM: Artificial Sequence
<220> FEATURE:
<223> OTHER INFORMATION: Synthetic

<400> SEQUENCE: 234
gtcattttag tcattacctg agg                                         23

<210> SEQ ID NO 235
<211> LENGTH: 23
<212> TYPE: DNA
<213> ORGANISM: Artificial Sequence
<220> FEATURE:
<223> OTHER INFORMATION: Synthetic

<400> SEQUENCE: 235
gtcatcttag tcattacctg agg                                         23

<210> SEQ ID NO 236
<211> LENGTH: 26
<212> TYPE: DNA
<213> ORGANISM: Artificial Sequence
<220> FEATURE:
<223> OTHER INFORMATION: Synthetic

<400> SEQUENCE: 236
gatgttccaa tcagtacgca gagagt                                      26

<210> SEQ ID NO 237
<211> LENGTH: 23
<212> TYPE: DNA
<213> ORGANISM: Artificial Sequence
<220> FEATURE:
<223> OTHER INFORMATION: Synthetic

<400> SEQUENCE: 237
ggcccagact gagcacgtga tgg                                         23

<210> SEQ ID NO 238
<211> LENGTH: 23
<212> TYPE: DNA

```
<213> ORGANISM: Artificial Sequence
<220> FEATURE:
<223> OTHER INFORMATION: Synthetic

<400> SEQUENCE: 238
gagtccgagc agaagaagaa ggg                                          23

<210> SEQ ID NO 239
<211> LENGTH: 26
<212> TYPE: DNA
<213> ORGANISM: Artificial Sequence
<220> FEATURE:
<223> OTHER INFORMATION: Synthetic

<400> SEQUENCE: 239
tctgcttctc cagccctggc ctgggt                                       26

<210> SEQ ID NO 240
<211> LENGTH: 23
<212> TYPE: DNA
<213> ORGANISM: Artificial Sequence
<220> FEATURE:
<223> OTHER INFORMATION: Synthetic

<400> SEQUENCE: 240
gagtctaagc agaagaagaa gag                                          23

<210> SEQ ID NO 241
<211> LENGTH: 23
<212> TYPE: DNA
<213> ORGANISM: Artificial Sequence
<220> FEATURE:
<223> OTHER INFORMATION: Synthetic

<400> SEQUENCE: 241
gaggccgagc agaagaaaga cgg                                          23

<210> SEQ ID NO 242
<211> LENGTH: 23
<212> TYPE: DNA
<213> ORGANISM: Artificial Sequence
<220> FEATURE:
<223> OTHER INFORMATION: Synthetic

<400> SEQUENCE: 242 ggaatcccctt ctgcagcacc tgg                                         23

<210> SEQ ID NO 243
<211> LENGTH: 26
<212> TYPE: DNA
<213> ORGANISM: Artificial Sequence
<220> FEATURE:
<223> OTHER INFORMATION: Synthetic

<400> SEQUENCE: 243
ggacgtgtgt gtctgtgtgg gtgagt                                       26

<210> SEQ ID NO 244
<211> LENGTH: 23
<212> TYPE: DNA
<213> ORGANISM: Artificial Sequence
<220> FEATURE:
<223> OTHER INFORMATION: Synthetic

<400> SEQUENCE: 244
ggaaccccgt ctgcagcacc agg                                          23
```

<210> SEQ ID NO 245
<211> LENGTH: 23
<212> TYPE: DNA
<213> ORGANISM: Artificial Sequence
<220> FEATURE:
<223> OTHER INFORMATION: Synthetic

<400> SEQUENCE: 245
accatccctc ctgcagcacc agg                                              23

<210> SEQ ID NO 246
<211> LENGTH: 23
<212> TYPE: DNA
<213> ORGANISM: Artificial Sequence
<220> FEATURE:
<223> OTHER INFORMATION: Synthetic

<400> SEQUENCE: 246
ttcctccaga ggttctgttt ggg                                              23

<210> SEQ ID NO 247
<211> LENGTH: 26
<212> TYPE: DNA
<213> ORGANISM: Artificial Sequence
<220> FEATURE:
<223> OTHER INFORMATION: Synthetic

<400> SEQUENCE: 247
ccactgtagt cacacagcac cagagt                                           26

<210> SEQ ID NO 248
<211> LENGTH: 23
<212> TYPE: DNA
<213> ORGANISM: Artificial Sequence
<220> FEATURE:
<223> OTHER INFORMATION: Synthetic

<400> SEQUENCE: 248
agcctccagg ggttctgttt tgg                                              23

<210> SEQ ID NO 249
<211> LENGTH: 23
<212> TYPE: DNA
<213> ORGANISM: Artificial Sequence
<220> FEATURE:
<223> OTHER INFORMATION: Synthetic

<400> SEQUENCE: 249
ttcctcctga gattctgttt agg                                              23

<210> SEQ ID NO 250
<211> LENGTH: 23
<212> TYPE: DNA
<213> ORGANISM: Artificial Sequence
<220> FEATURE:
<223> OTHER INFORMATION: Synthetic

<400> SEQUENCE: 250
gagtccgagc agaagaagaa ggg                                              23

<210> SEQ ID NO 251
<211> LENGTH: 23
<212> TYPE: DNA
<213> ORGANISM: Artificial Sequence
<220> FEATURE:

<223> OTHER INFORMATION: Synthetic

<400> SEQUENCE: 251
attgccacga agcaggccaa tgg                                              23

<210> SEQ ID NO 252
<211> LENGTH: 23
<212> TYPE: DNA
<213> ORGANISM: Artificial Sequence
<220> FEATURE:
<223> OTHER INFORMATION: Synthetic

<400> SEQUENCE: 252
cgccgtctcc aaggtgaaag cgg                                              23

<210> SEQ ID NO 253
<211> LENGTH: 23
<212> TYPE: DNA
<213> ORGANISM: Artificial Sequence
<220> FEATURE:
<223> OTHER INFORMATION: Synthetic

<400> SEQUENCE: 253
ggaatccctt ctgcagcacc tgg                                              23

<210> SEQ ID NO 254
<211> LENGTH: 23
<212> TYPE: DNA
<213> ORGANISM: Artificial Sequence
<220> FEATURE:
<223> OTHER INFORMATION: Synthetic

<400> SEQUENCE: 254
ctccaccgct ttcccaagag tgg                                              23

<210> SEQ ID NO 255
<211> LENGTH: 23
<212> TYPE: DNA
<213> ORGANISM: Artificial Sequence
<220> FEATURE:
<223> OTHER INFORMATION: Synthetic

<400> SEQUENCE: 255
atcccgtgac tcagaacccc tgg                                              23

<210> SEQ ID NO 256
<211> LENGTH: 23
<212> TYPE: DNA
<213> ORGANISM: Artificial Sequence
<220> FEATURE:
<223> OTHER INFORMATION: Synthetic

<400> SEQUENCE: 256
ctctcgcagt cagagcgcac tgc                                              23

<210> SEQ ID NO 257
<211> LENGTH: 23
<212> TYPE: DNA
<213> ORGANISM: Artificial Sequence
<220> FEATURE:
<223> OTHER INFORMATION: Synthetic

<400> SEQUENCE: 257
caggcccagg ctgcccgccg ggg                                              23

```
<210> SEQ ID NO 258
<211> LENGTH: 23
<212> TYPE: DNA
<213> ORGANISM: Artificial Sequence
<220> FEATURE:
<223> OTHER INFORMATION: Synthetic

<400> SEQUENCE: 258
tctttgccca gagcatcccg tgg                                              23

<210> SEQ ID NO 259
<211> LENGTH: 23
<212> TYPE: DNA
<213> ORGANISM: Artificial Sequence
<220> FEATURE:
<223> OTHER INFORMATION: Synthetic

<400> SEQUENCE: 259
cacagacagg taagcacggc cgt                                              23

<210> SEQ ID NO 260
<211> LENGTH: 23
<212> TYPE: DNA
<213> ORGANISM: Artificial Sequence
<220> FEATURE:
<223> OTHER INFORMATION: Synthetic

<400> SEQUENCE: 260
aagccagctg gtccagcctg tgg                                              23

<210> SEQ ID NO 261
<211> LENGTH: 23
<212> TYPE: DNA
<213> ORGANISM: Artificial Sequence
<220> FEATURE:
<223> OTHER INFORMATION: Synthetic

<400> SEQUENCE: 261
ggtccagcct gtggggccac tgg                                              23

<210> SEQ ID NO 262
<211> LENGTH: 23
<212> TYPE: DNA
<213> ORGANISM: Artificial Sequence
<220> FEATURE:
<223> OTHER INFORMATION: Synthetic

<400> SEQUENCE: 262
cgcctgccag cgcctggcga ggg                                              23

<210> SEQ ID NO 263
<211> LENGTH: 23
<212> TYPE: DNA
<213> ORGANISM: Artificial Sequence
<220> FEATURE:
<223> OTHER INFORMATION: Synthetic

<400> SEQUENCE: 263
tgccagcgcc tggcgagggc tgg                                              23

<210> SEQ ID NO 264
<211> LENGTH: 23
<212> TYPE: DNA
<213> ORGANISM: Artificial Sequence
<220> FEATURE:
<223> OTHER INFORMATION: Synthetic
```

<400> SEQUENCE: 264
aagaccagcc ggtgaccctg ggg                                                23

<210> SEQ ID NO 265
<211> LENGTH: 23
<212> TYPE: DNA
<213> ORGANISM: Artificial Sequence
<220> FEATURE:
<223> OTHER INFORMATION: Synthetic

<400> SEQUENCE: 265
atcacaggct gctgcccacg tgg                                                23

<210> SEQ ID NO 266
<211> LENGTH: 23
<212> TYPE: DNA
<213> ORGANISM: Artificial Sequence
<220> FEATURE:
<223> OTHER INFORMATION: Synthetic

<400> SEQUENCE: 266
ctaccccagg ccaactgcag cgt                                                23

<210> SEQ ID NO 267
<211> LENGTH: 23
<212> TYPE: DNA
<213> ORGANISM: Artificial Sequence
<220> FEATURE:
<223> OTHER INFORMATION: Synthetic

<400> SEQUENCE: 267
caacagggcc acgtcctcac agg                                                23

<210> SEQ ID NO 268
<211> LENGTH: 23
<212> TYPE: DNA
<213> ORGANISM: Artificial Sequence
<220> FEATURE:
<223> OTHER INFORMATION: Synthetic

<400> SEQUENCE: 268
aggtcagccc aaccagtgcg tgg                                                23

<210> SEQ ID NO 269
<211> LENGTH: 23
<212> TYPE: DNA
<213> ORGANISM: Artificial Sequence
<220> FEATURE:
<223> OTHER INFORMATION: Synthetic

<400> SEQUENCE: 269
ccaaccagtg cgtgggccac agg                                                23

<210> SEQ ID NO 270
<211> LENGTH: 23
<212> TYPE: DNA
<213> ORGANISM: Artificial Sequence
<220> FEATURE:
<223> OTHER INFORMATION: Synthetic

<400> SEQUENCE: 270
cccctcagga gcaggtgaag agg                                                23

<210> SEQ ID NO 271
<211> LENGTH: 23

```
<212> TYPE: DNA
<213> ORGANISM: Artificial Sequence
<220> FEATURE:
<223> OTHER INFORMATION: Synthetic

<400> SEQUENCE: 271
gtcatcttag tcattacctg agg                                              23

<210> SEQ ID NO 272
<211> LENGTH: 23
<212> TYPE: DNA
<213> ORGANISM: Artificial Sequence
<220> FEATURE:
<223> OTHER INFORMATION: Synthetic

<400> SEQUENCE: 272
gtcgtcttag tcattacctg agg                                              23

<210> SEQ ID NO 273
<211> LENGTH: 23
<212> TYPE: DNA
<213> ORGANISM: Artificial Sequence
<220> FEATURE:
<223> OTHER INFORMATION: Synthetic

<400> SEQUENCE: 273
ggaatccctt ctgcagcacc tgg                                              23

<210> SEQ ID NO 274
<211> LENGTH: 119
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(119)
<223> OTHER INFORMATION: N can be any base

<400> SEQUENCE: 274
nnnnnnnnnn nnnnnnnnnn guuuuagagc uagaaauagc aaguuaaaau aaggcuaguc       60
cguuaucaac uugaaaaagu gggaccgagu cgguccnnnn nnnnnnnnnn nnnnnnnn        119

<210> SEQ ID NO 275
<211> LENGTH: 119
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(119)
<223> OTHER INFORMATION: N is any base

<400> SEQUENCE: 275
nnnnnnnnnn nnnnnnnnnn guuuuagagc uagaaauagc aaguuaaaau aaggcuaguc       60
cguuaucgac uugaaaaagu cggaccgagu cgguccnnnn nnnnnnnnnn nnnnnnnn        119

<210> SEQ ID NO 276
<211> LENGTH: 29
<212> TYPE: DNA
<213> ORGANISM: Artificial Sequence
<220> FEATURE:
<223> OTHER INFORMATION: Synthetic

<400> SEQUENCE: 276
```
cagactgagc acgtgatggc agaggaaag                29

<210> SEQ ID NO 277
<211> LENGTH: 29
<212> TYPE: DNA
<213> ORGANISM: Artificial Sequence
<220> FEATURE:
<223> OTHER INFORMATION: Synthetic

<400> SEQUENCE: 277
cagactgagc acgctatggc agaggaaga                29

<210> SEQ ID NO 278
<211> LENGTH: 29
<212> TYPE: DNA
<213> ORGANISM: Artificial Sequence
<220> FEATURE:
<223> OTHER INFORMATION: Synthetic

<400> SEQUENCE: 278
cagactgagc acgtgatggc aaaggaaag                29

<210> SEQ ID NO 279
<211> LENGTH: 119
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(119)
<223> OTHER INFORMATION: N is any base

<400> SEQUENCE: 279
nnnnnnnnnn nnnnnnnnnn guuuuagagc uagaaauagc aaguuaaaau aaggcuaguc      60
cguuaucaac uugaaaaagu gggaccgagu cgguccnnnn nnnnnnnnnn nnnnnnnn       119

<210> SEQ ID NO 280
<211> LENGTH: 119
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(119)
<223> OTHER INFORMATION: N is any base

<400> SEQUENCE: 280
nnnnnnnnnn nnnnnnnnnn guuuuagagc uagaaauagc aaguuaaaau aaggcuaguc      60
cguuaucgac uugaaaaagu cggaccgagu cgguccnnnn nnnnnnnnnn nnnnnnnn       119

<210> SEQ ID NO 281
<211> LENGTH: 29
<212> TYPE: DNA
<213> ORGANISM: Artificial Sequence
<220> FEATURE:
<223> OTHER INFORMATION: Synthetic

<400> SEQUENCE: 281
cagactgagc acgggatagg aaaggaaac                29

<210> SEQ ID NO 282
<211> LENGTH: 29
<212> TYPE: DNA
<213> ORGANISM: Artificial Sequence

```
<220> FEATURE:
<223> OTHER INFORMATION: Synthetic

<400> SEQUENCE: 282
cagactgagc acgggatagg aaaggaagc                                       29

<210> SEQ ID NO 283
<211> LENGTH: 29
<212> TYPE: DNA
<213> ORGANISM: Artificial Sequence
<220> FEATURE:
<223> OTHER INFORMATION: Synthetic

<400> SEQUENCE: 283
ccgagcagaa gaagaagggc tcccatcac                                       29
```